United States Patent
Wilson et al.

(10) Patent No.: US 11,692,042 B2
(45) Date of Patent: Jul. 4, 2023

(54) ANTI-CD73 ANTIBODIES AND METHODS OF USE THEREOF

(71) Applicant: Agenus Inc., Lexington, MA (US)

(72) Inventors: Nicholas Stuart Wilson, San Carlos, CA (US); Jeremy Dale Waight, Everett, MA (US); Shawn Michael Jennings, Acton, MA (US); Olga Ignatovich, Cambridge (GB); Emmanuel Cyrille Pascal Briend, Cambridge (GB); Benjamin Maxime Morin, Somerville, MA (US); Oliver Schon, Cambridge (GB); Spencer Campbell, Essex (GB)

(73) Assignee: AGENUS INC., Lexington, MA (US)

( * ) Notice: Subject to any disclaimer, the term of this patent is extended or adjusted under 35 U.S.C. 154(b) by 735 days.

(21) Appl. No.: 16/296,532

(22) Filed: Mar. 8, 2019

(65) Prior Publication Data

US 2019/0352418 A1   Nov. 21, 2019

Related U.S. Application Data

(60) Provisional application No. 62/640,850, filed on Mar. 9, 2018.

(51) Int. Cl.
| | |
|---|---|
| C07K 16/28 | (2006.01) |
| A61P 35/04 | (2006.01) |
| A61P 35/00 | (2006.01) |
| C07K 14/71 | (2006.01) |
| A61K 39/395 | (2006.01) |
| A61K 39/00 | (2006.01) |

(52) U.S. Cl.
CPC .......... *C07K 16/2896* (2013.01); *A61P 35/00* (2018.01); *A61P 35/04* (2018.01); *C07K 14/71* (2013.01); *A61K 2039/505* (2013.01); *C07K 2317/24* (2013.01); *C07K 2317/76* (2013.01); *C07K 2317/92* (2013.01); *C07K 2319/00* (2013.01)

(58) Field of Classification Search
CPC ................ C07K 16/2896; C07K 14/71; C07K 2317/24; C07K 2317/76; C07K 2317/92; C07K 2319/00; C07K 2317/33; C07K 2317/34; C07K 2317/77; C07K 2317/565; A61P 35/04; A61P 35/00; A61K 2039/505

See application file for complete search history.

(56) References Cited

U.S. PATENT DOCUMENTS

| | | |
|---|---|---|
| 5,693,607 A | 12/1997 | Segarini et al. |
| 5,844,099 A | 12/1998 | Stahl et al. |
| 6,001,969 A | 12/1999 | Lin et al. |
| 6,472,179 B2 | 10/2002 | Stahl et al. |
| 6,492,497 B1 | 12/2002 | Thompson et al. |
| 7,060,269 B1 | 6/2006 | Baca et al. |
| 7,148,321 B2 | 12/2006 | Gillies et al. |
| 7,151,169 B2 | 12/2006 | Thompson et al. |
| 7,306,799 B2 | 12/2007 | Wiegand et al. |
| 7,531,173 B2 | 5/2009 | Wiegand et al. |
| 7,612,181 B2 | 11/2009 | Wu et al. |
| 7,723,486 B2 | 5/2010 | Ledbetter et al. |
| 7,786,261 B2 | 8/2010 | De Crescenzo et al. |
| 7,795,389 B2 | 9/2010 | Sun et al. |
| 8,318,135 B2 | 11/2012 | O'Connor-McCourt et al. |
| 8,815,247 B2 | 8/2014 | Govindappa et al. |
| 8,993,524 B2 | 3/2015 | Bedi et al. |
| 9,090,697 B2 | 7/2015 | Sim |
| 9,388,249 B2 | 7/2016 | Sugioka et al. |
| 9,605,080 B2 | 3/2017 | Lonberg et al. |
| 9,611,306 B2 | 4/2017 | Hinck et al. |
| 9,676,863 B2 | 6/2017 | Lo |
| 9,809,637 B2 | 11/2017 | Kumar et al. |
| 9,938,356 B2 | 4/2018 | Hay et al. |
| 9,988,456 B2 | 6/2018 | Govindappa et al. |
| 10,100,129 B2 | 10/2018 | Lonberg et al. |
| 10,584,169 B2 | 3/2020 | Wang et al. |
| 10,766,966 B2 | 9/2020 | Perrot et al. |
| 10,822,426 B2 | 11/2020 | Griffin et al. |
| 2002/0009444 A1 | 1/2002 | Grillo-Lopez |
| 2004/0202658 A1 | 10/2004 | Benyunes |

(Continued)

FOREIGN PATENT DOCUMENTS

| | | |
|---|---|---|
| EP | 0118311 A2 | 9/1984 |
| WO | WO-1998045332 A2 | 10/1998 |

(Continued)

OTHER PUBLICATIONS

Lazar et al. Molecular and Cellular Biology 8:1247-1252, 1988 (Year: 1988).*
Burgess et al., J of Cell Bio. 111:2129-2138, 1990 (Year: 1990).*
Bowie et al. Science, 247:1306-1310, 1990 (Year: 1990).*
Ngo et al., in The Protein Folding Problem and Tertiary Structure Prediction, 1994, Merz, et al., (ed.), Birkhauser, Boston, MA, pp. 433 and 492-495 (Year: 1994).*
Yang S, Zhao J, Sun X. Resistance to anti-VEGF therapy in neovascular age-related macular degeneration: a comprehensive review. Drug Des Devel Ther. 2016;10:1857-1867. Published Jun. 2, 2016. doi:10.2147/DDDT.S97653 (Year: 2016).*

(Continued)

*Primary Examiner* — Hong Sang
*Assistant Examiner* — Sung Min Yoon
(74) *Attorney, Agent, or Firm* — Dechert LLP; Andrew T Wilkins; Kayla L. Metzger

(57) ABSTRACT

The instant disclosure provides antibodies that specifically bind to CD73 (e.g., human CD73) and antagonize CD73 function. Also provided are anti-CD73 antibodies that further comprise a TGFβ-binding moiety or a VEGF-binding moiety. The instant disclosure additionally provides pharmaceutical compositions comprising these antibodies, nucleic acids encoding these antibodies, expression vectors and host cells for making these antibodies, and methods of treating a subject using these antibodies.

22 Claims, 37 Drawing Sheets

Specification includes a Sequence Listing.

(56) References Cited

U.S. PATENT DOCUMENTS

| | | |
|---|---|---|
| 2005/0203022 A1 | 9/2005 | Gotwals et al. |
| 2006/0134111 A1 | 6/2006 | Agarwal |
| 2007/0009518 A1 | 1/2007 | Novobrantseva et al. |
| 2010/0204104 A1 | 8/2010 | Qiu et al. |
| 2011/0008250 A1 | 1/2011 | Curd et al. |
| 2011/0110852 A1 | 5/2011 | Miller et al. |
| 2011/0177070 A1 | 7/2011 | Lofquist et al. |
| 2013/0109645 A1 | 5/2013 | Gahl et al. |
| 2014/0127203 A1 | 5/2014 | Thompson et al. |
| 2015/0225483 A1 | 8/2015 | Lo |
| 2016/0075755 A1 | 3/2016 | Valdes et al. |
| 2016/0287664 A1 | 10/2016 | Yu et al. |
| 2016/0289298 A1 | 10/2016 | Kumar et al. |
| 2016/0318989 A1 | 11/2016 | Dewey et al. |
| 2016/0354403 A1 | 12/2016 | von Andrian et al. |
| 2017/0037100 A1 | 2/2017 | Kumar et al. |
| 2017/0281764 A1 | 10/2017 | Tso et al. |
| 2017/0355770 A1 | 12/2017 | Wang et al. |
| 2018/0009899 A1 | 1/2018 | Griffin et al. |
| 2018/0030144 A1 | 2/2018 | Chanteux et al. |
| 2018/0125973 A1 | 5/2018 | Sachsenmeier et al. |
| 2018/0207273 A1 | 7/2018 | Dranoff et al. |
| 2018/0237536 A1 | 8/2018 | Perrot et al. |
| 2019/0225703 A1 | 7/2019 | Caux et al. |
| 2019/0284293 A1 | 9/2019 | Lonberg et al. |
| 2020/0071404 A1 | 3/2020 | Sato et al. |
| 2020/0148781 A1 | 5/2020 | Zeidler et al. |
| 2020/0231652 A1 | 7/2020 | Zwaagstra et al. |
| 2020/0232974 A1 | 7/2020 | Menetrier-Caux et al. |

FOREIGN PATENT DOCUMENTS

| | | | | |
|---|---|---|---|---|
| WO | WO-2014153424 A1 | 9/2014 | | |
| WO | WO-2016075099 A1 | 5/2016 | | |
| WO | WO-2016081748 A2 | 5/2016 | | |
| WO | WO-2016131950 A1 * | 8/2016 | ......... | C07K 16/2896 |
| WO | WO-2017064043 A1 | 4/2017 | | |
| WO | WO-2017100670 A1 | 6/2017 | | |
| WO | WO-2017118613 A1 | 7/2017 | | |
| WO | WO-2017134592 A1 | 8/2017 | | |
| WO | WO-2017152085 A1 | 9/2017 | | |
| WO | WO-2018013611 A1 | 1/2018 | | |
| WO | WO2019/173692 | 9/2019 | | |

OTHER PUBLICATIONS

Leninger M, Sae Her A, Traaseth NJ. Inducing conformational preference of the membrane protein transporter EmrE through conservative mutations. Elife. Oct. 22, 2019;8:e48909. doi: 10.7554/eLife.48909. PMID: 31637997; PMCID: PMC6805155. (Year: 2019).*
Teixeira AF, Ten Dijke P, Zhu HJ. On-Target Anti-TGF-β Therapies Are Not Succeeding in Clinical Cancer Treatments: What Are Remaining Challenges?. Front Cell Dev Biol. 2020;8:605. Published Jul. 8, 2020 (Year: 2020).*
Allard et al., "Targeting CD73 enhances the antitumor activity of anti-PD-1 and anti-CTLA-4 mAbs," Clin Cancer Res., 19(20): 5626-5635 (2013).
Antonioli et al., "Immunity, inflammation and cancer: A leading role for adenosine," Nat Rev Cancer., 13(12): 842-857 (2013).
Chen and Mellman, "Elements of cancer immunity and the cancer-immune set point," Nature, 541(7637):321-330 (2017).
Ferrari et al., "A Purinergic Trail for Metastases," Trends Pharm Sci., 38(3): 277-290 (2017).
Forte et al., "Inhibition of CD73 improves B cell-mediated antitumor immunity in a mouse model of melanoma," J Immunol., 189(5): 2226-2233 (2012).
Holash et al., "VEGF-Trap: a VEGF blocker with potent antitumor effects," PNAS 99 (17): 11393-98 (2002).
Hugo et al., "Genomic and Transcriptomic Features of Response to Anti-PD-1 Therapy in Metastatic Melanoma," Cell, 165(1): 35-44 (2016).
International Preliminary Report on Patentability received for PCT Patent Application No. PCT/US2019/021313, dated Sep. 15, 2020, 12 Pages.
Knapp et al., "Crystal structure of the human ecto-5'-nucleotidase (CD73): Insights into the regulation of purinergic signaling," Structure 20(12): 2161-2173 (2012).
Kummer et al., "Development and properties of a monoclonal antibody specific for human ecto-5'-nucleotidase," Immunobiol., 166(2):203-211 (1984).
LaMantia K, Conklyn M, Quagliata F, Silber R., "Lymphocyte 5'-Nucleotidase: Absence of Detectable Protein in Chronic Lymphocytitc Leukemia," Blood, 50(4):683-689 (1977).
Loi et al., "CD73 promotes anthracycline resistance and poor prognosis in triple negative breast cancer," Proc Natl Acad Sci U.S.A., 110(27): 11091-11096 (2013).
M. G. Terp et al., "Anti-Human CD73 Monoclonal Antibody Inhibits Metastasis Formation in Human Breast Cancer by Inducing Clustering and Internalization of CD73 Expressed on the Surface of Cancer Cells", J Immunol., 191(8): 4165-4173 (2013).
Massagué, "TGFbeta in Cancer," Cell, 134(2): 215-230 (2008).
Misumi Y, Ogata S, Ohkubo K, Hirose S, Ikehara Y., "Primary structure of human placental 5'-nucleotidase and identification of the glycolipid anchor in the mature form," Eur J Biochem. 191(3): 563-9 (1990).
Neuzillet et al., "Targeting the TGFβ pathway for cancer therapy," Pharmacology & Therapeutics., 147:22-31 (2015).
Oshimori et al., "TGF-β promotes heterogeneity and drug resistance in squamous cell carcinoma," Cell, 160(5): 963-976 (2015).
Ravi et al., "Bifunctional immune checkpoint-targeted antibody-ligand traps that simultaneously disable TGFβ enhance the efficacy of cancer immunotherapy," Nat Commun. 9:741 (2018).
Reinhardt et al., "MAPK signaling and inflammation link melanoma phenotype switching to induction of CD73 during immunotherapy," Can Res., 77(17): 4697-4709 (2017).
Sachsenmeier et al., "Development of a novel ectonucleotidase assay suitable for high-throughput screening," J Biomol Screen., 17(7) :993-8 (2012).
Streicher et al., "'Increased CD73 and reduced IFNG signature expression in relation to response rates to anti-PD-1 (L1) therapies in EGFR-mutant NSCLC,'" Amer Society Clin Oncol., 35(15) suppl (May 20, 2017) 11505-11505. (abstract) ASCO Meeting Library [online] (2017).
Tian and Schiemann, "The TGF-beta paradox in human cancer: An update," Future Oncol., 5(2): 259-271 (2009).
Turcotte et al., "CD73 promotes resistance to HER2/ErbB2 antibody therapy," Cancer Res., 77(20): 5652-5663 (2017).
Vijayan et al., "Targeting immunosuppressive adenosine in cancer," Nat Rev Cancer., 17(12): 709-724 (2017).
Wang et al., "New chimeric antigen receptor design for solid tumors," Front Immunol., 8: 1934 (2017).
Young et al., "Co-inhibition of CD73 and A2AR adenosine signaling improves anti-tumor immune responses," Cancer Cell, 30(3): 391-403 (2016).
Zachowski et al., "Immunological evidence that plasma-membrane 5'-nucleotidase is a transmembrane protein," Biochim Biophys Acta., 644(1): 121-126 (1981).
Zhang et al., "CD73: a novel target for cancer immunotherapy," Cancer Res. 70(16): 6407-6411 (2010).
Zwaagstra et al., "Engineering and therapeutic application of single-chain bivalent TGF-β family traps," Mol Cancer Ther., 11(7): 1477-87 (2012).

* cited by examiner

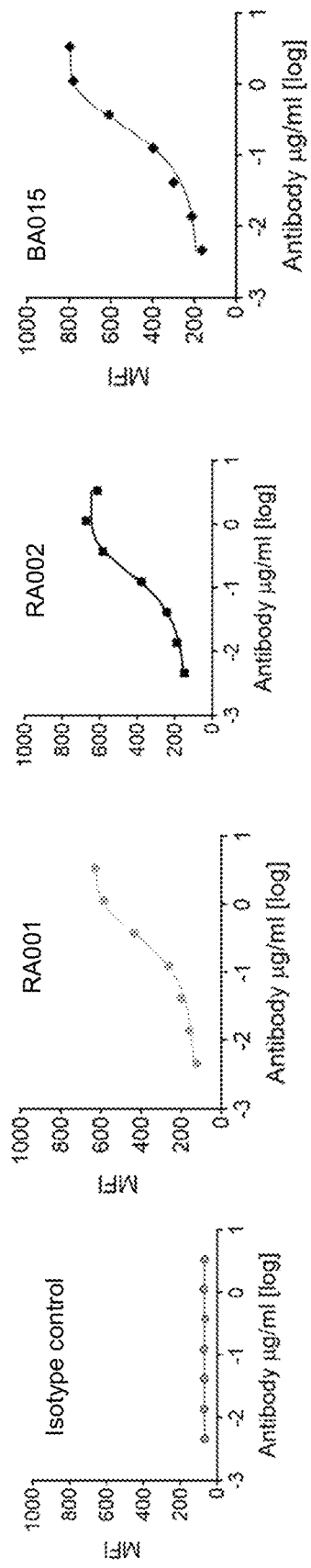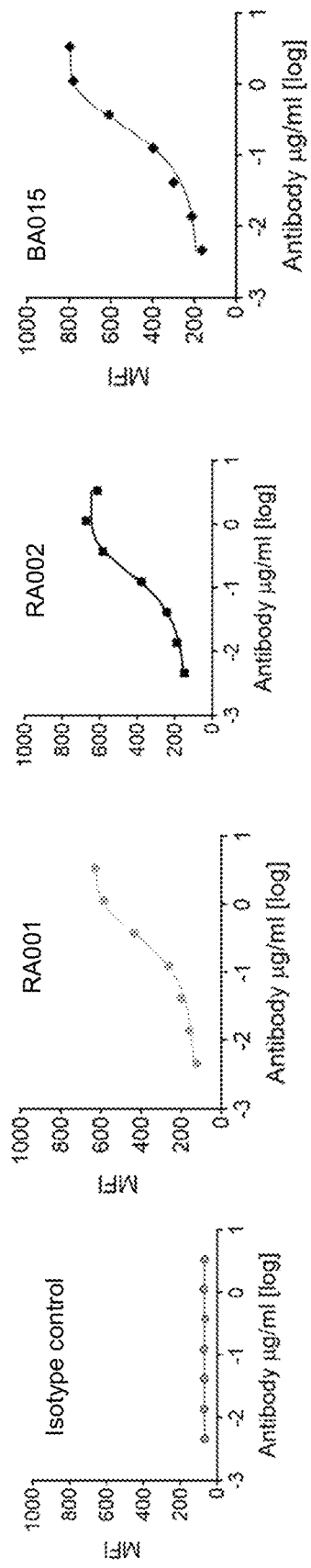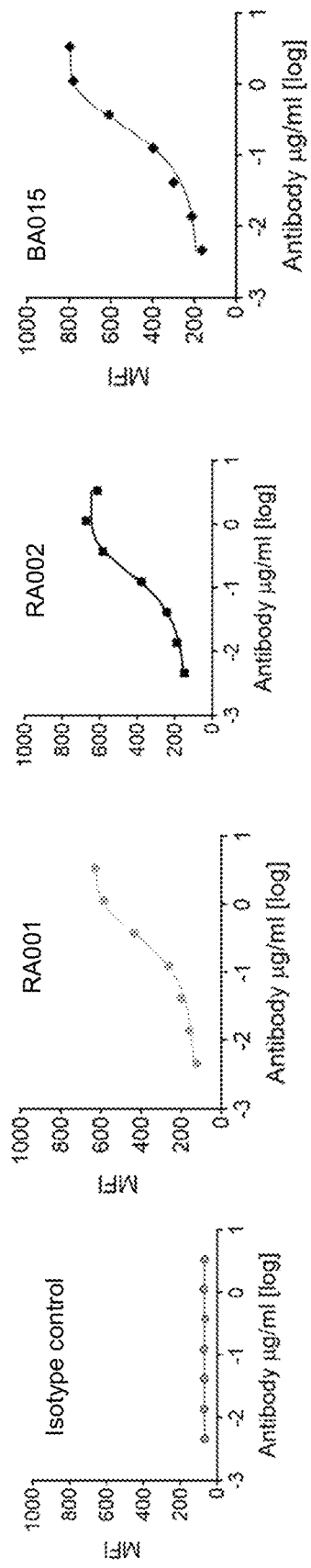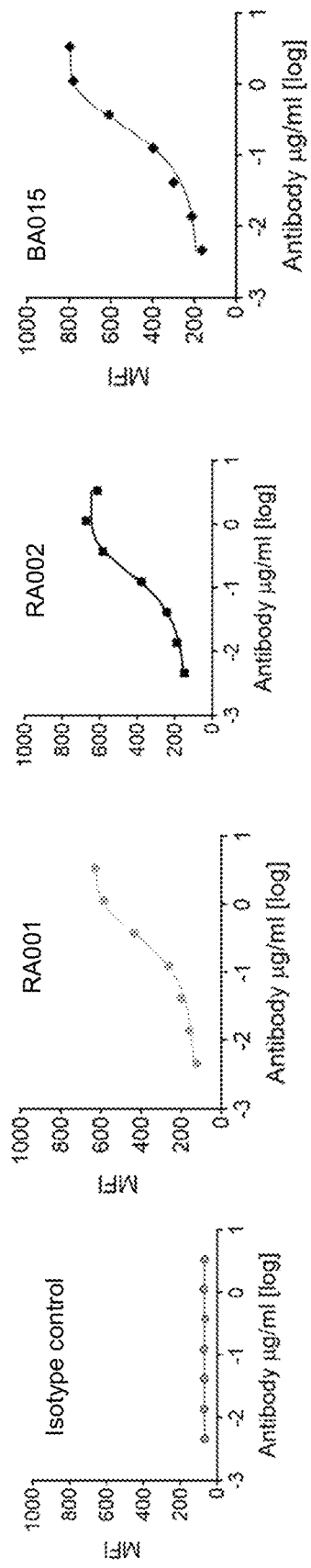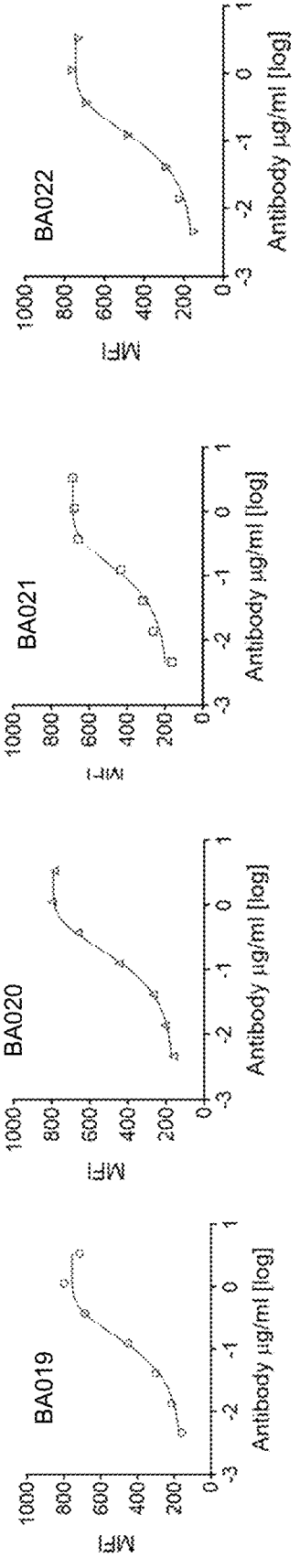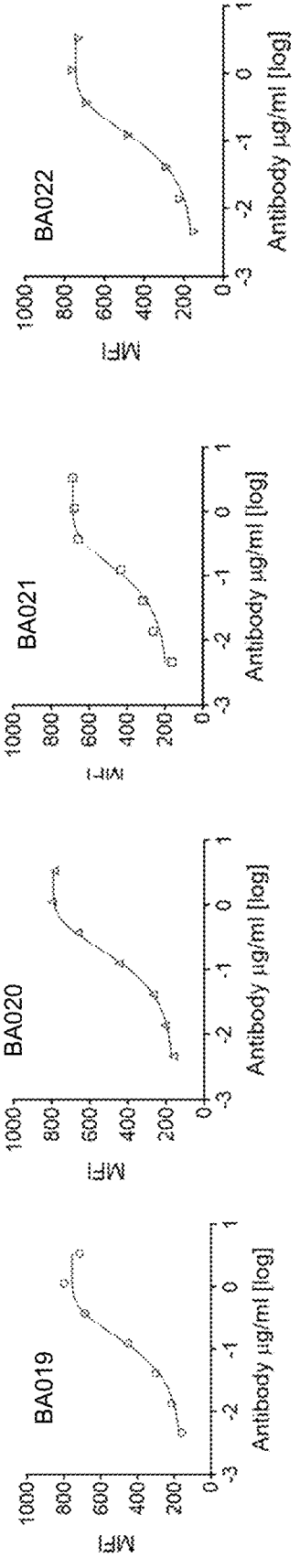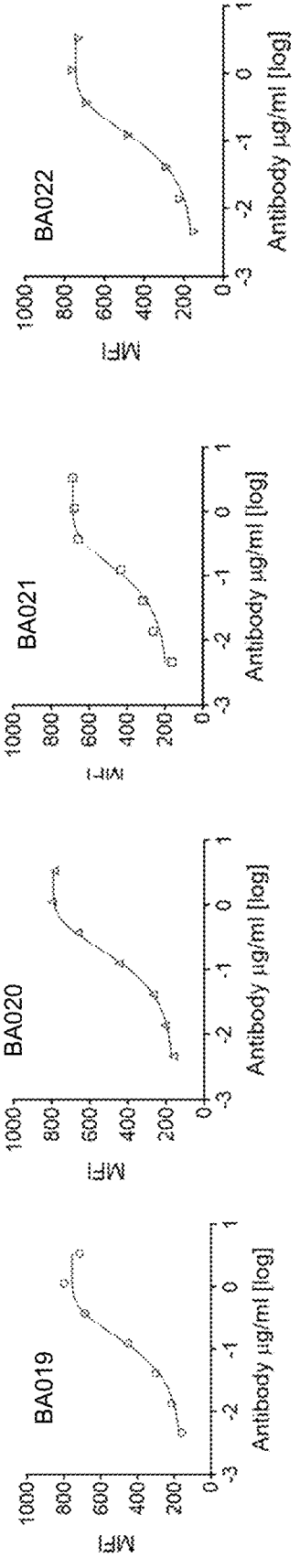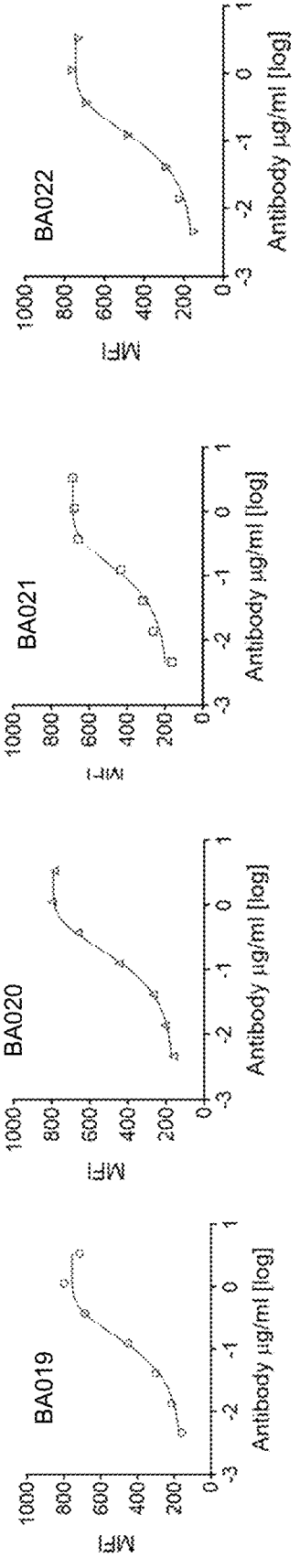

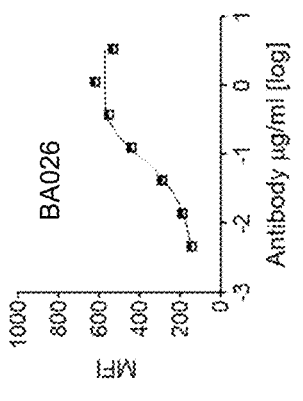
FIG. 4I
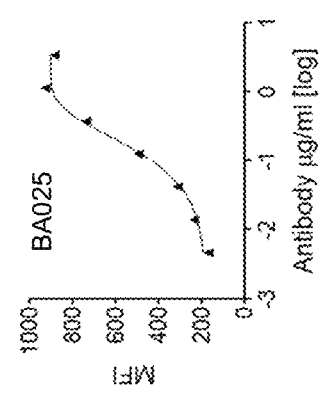
FIG. 4J
FIG. 4K
FIG. 4L
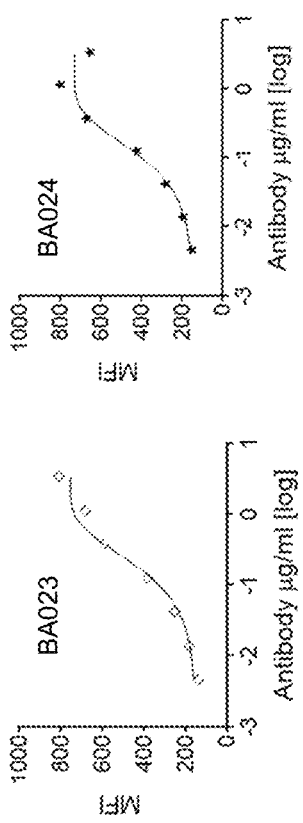
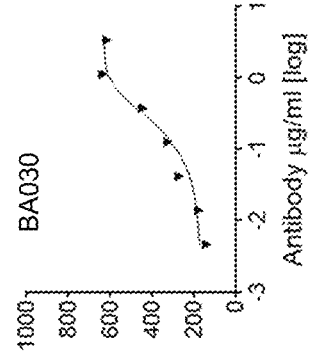
FIG. 4M
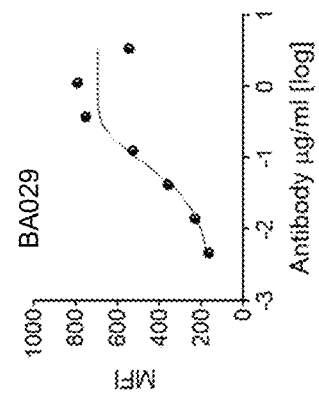
FIG. 4N
FIG. 4O
FIG. 4P

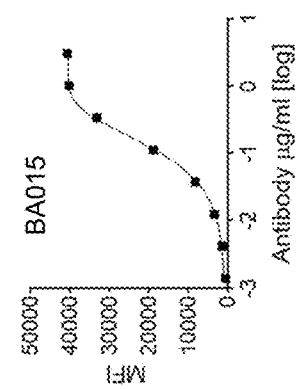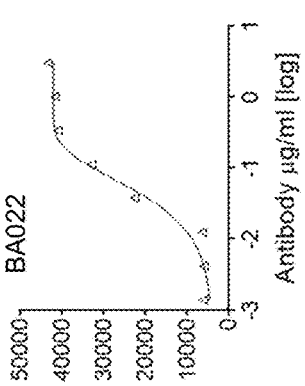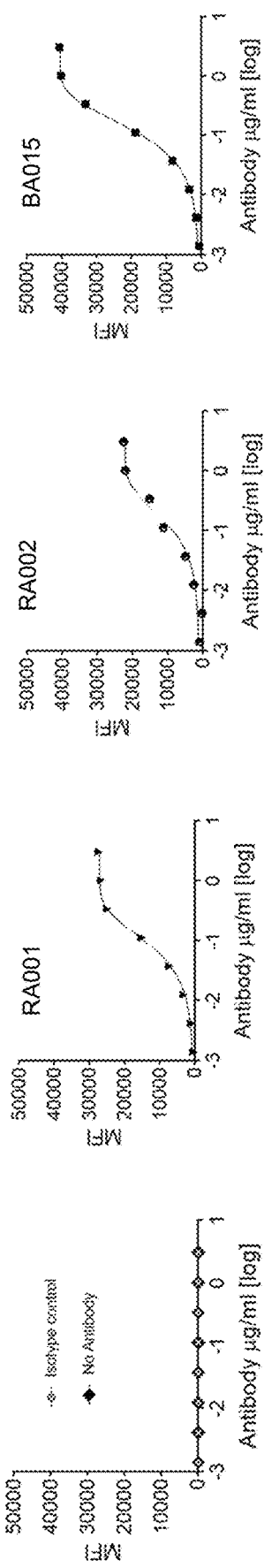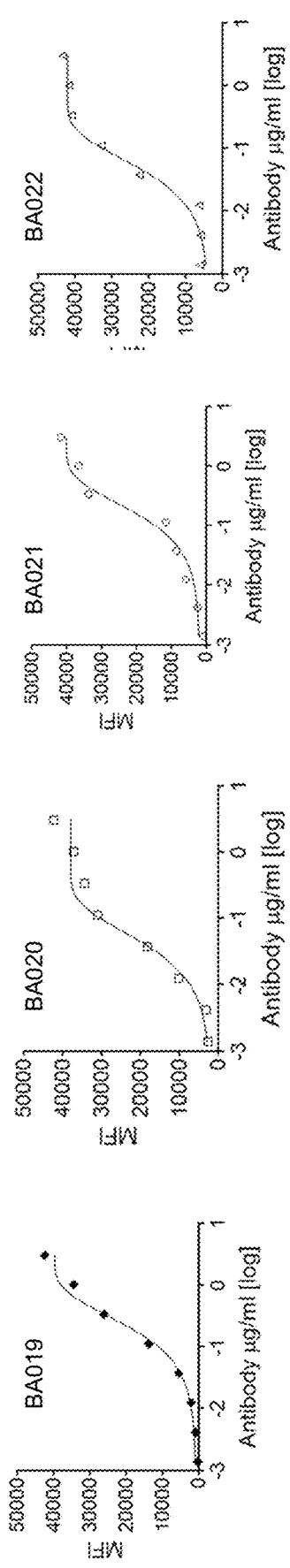

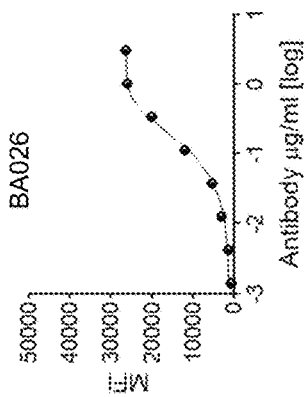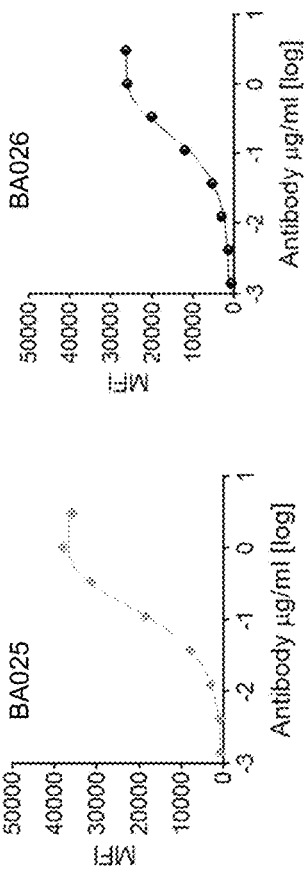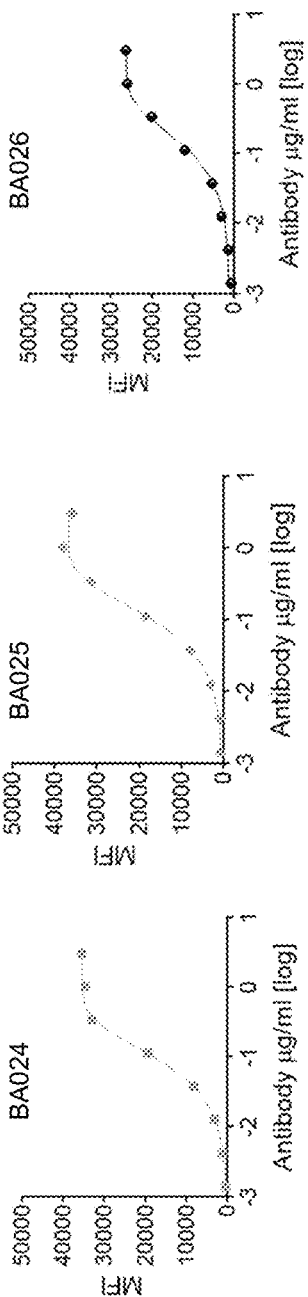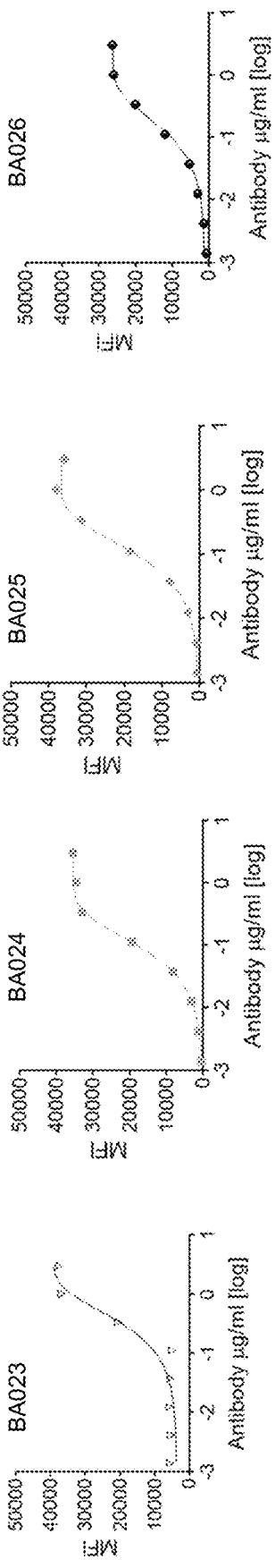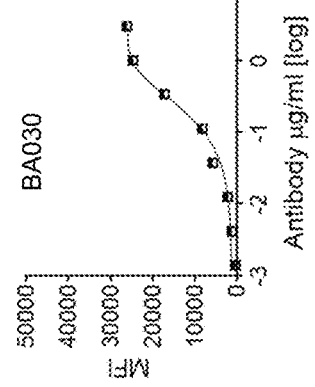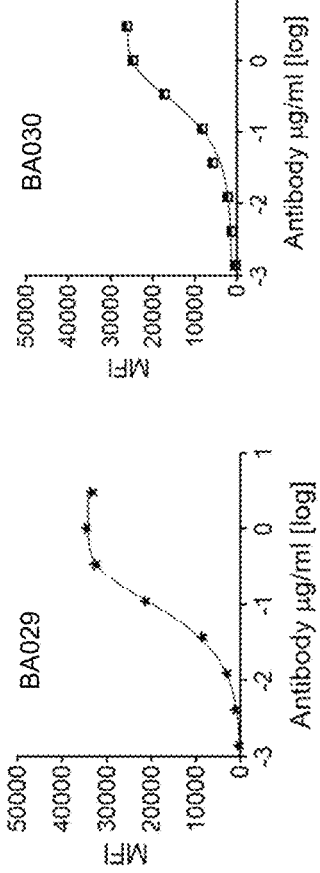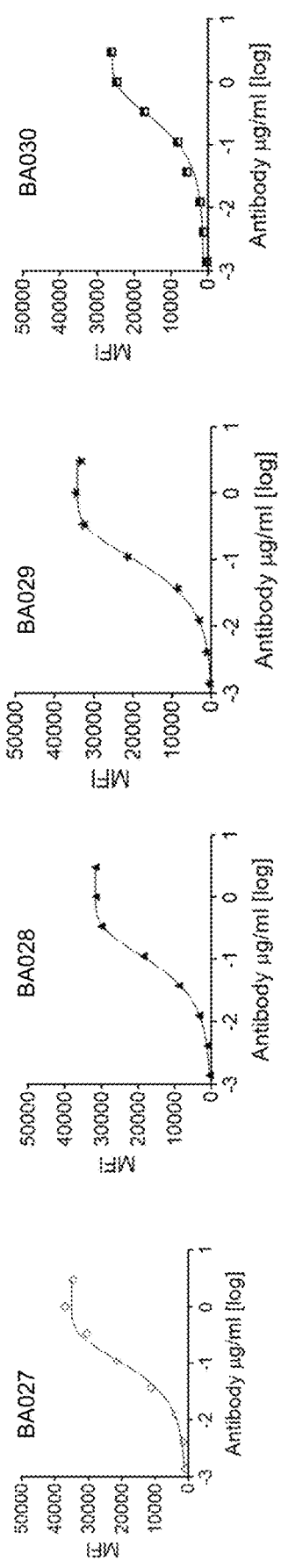

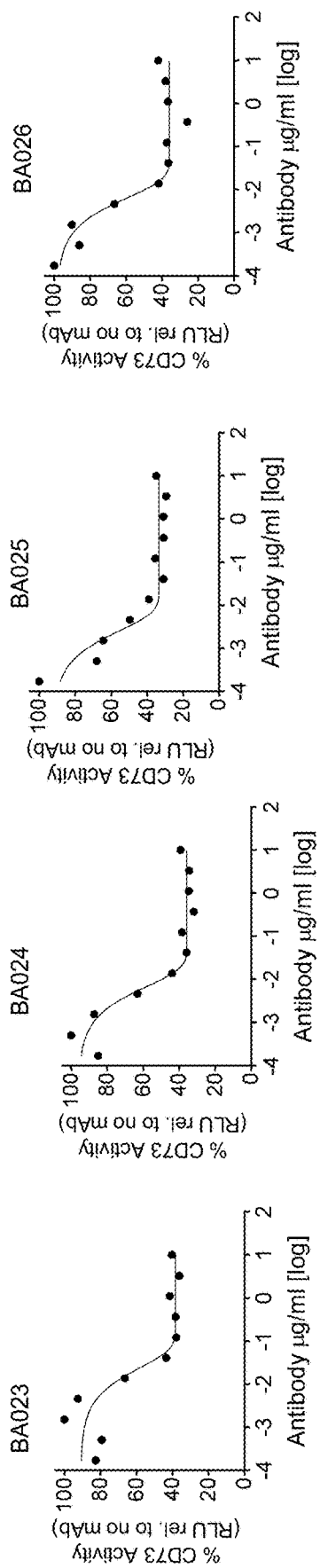
FIG. 6I BA023
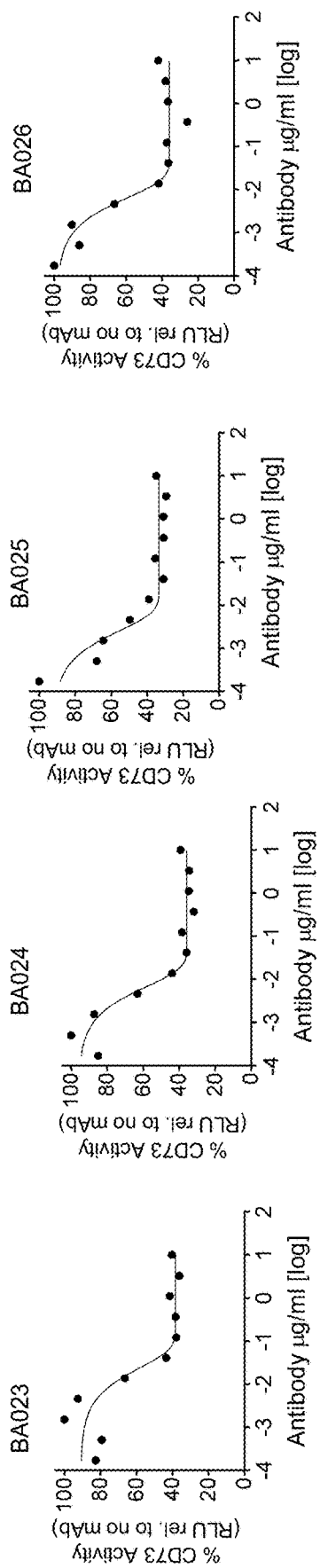
FIG. 6J BA024
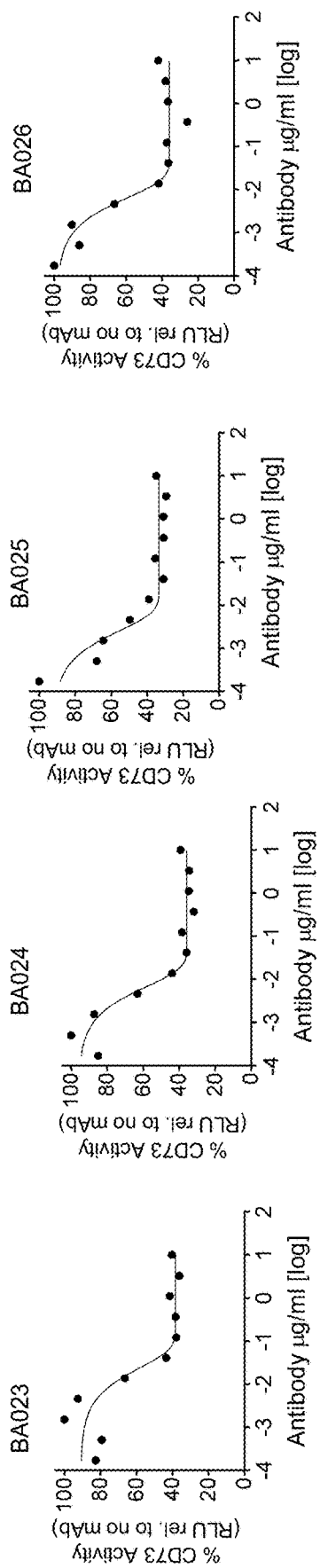
FIG. 6K BA025
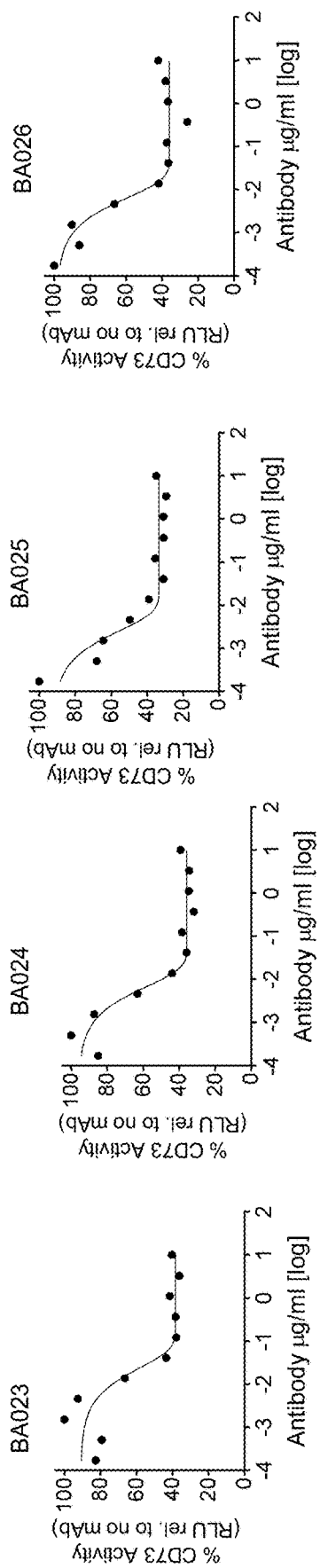
FIG. 6L BA026
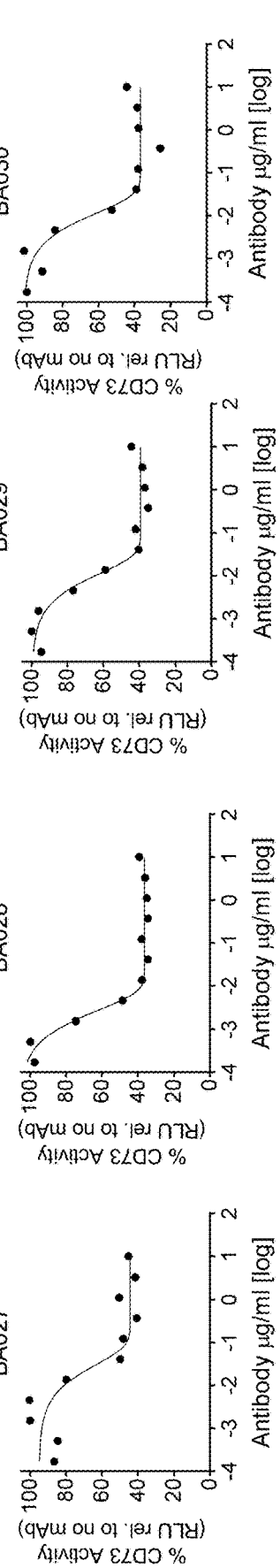
FIG. 6M BA027
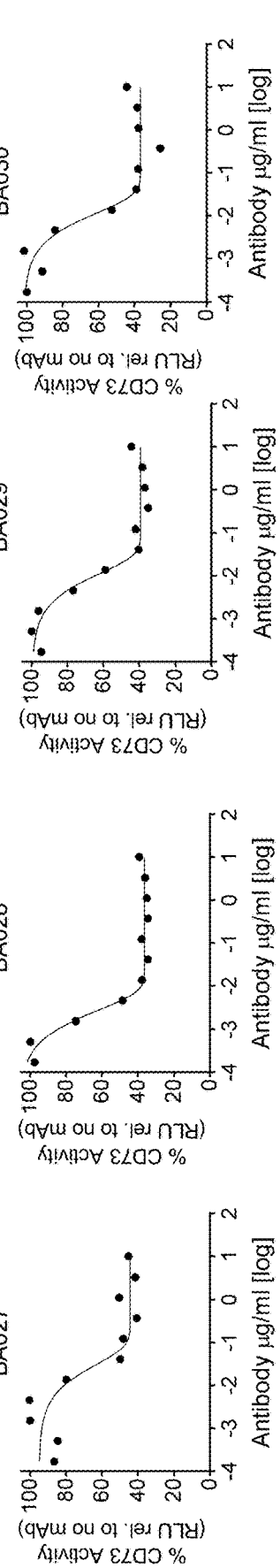
FIG. 6N BA028
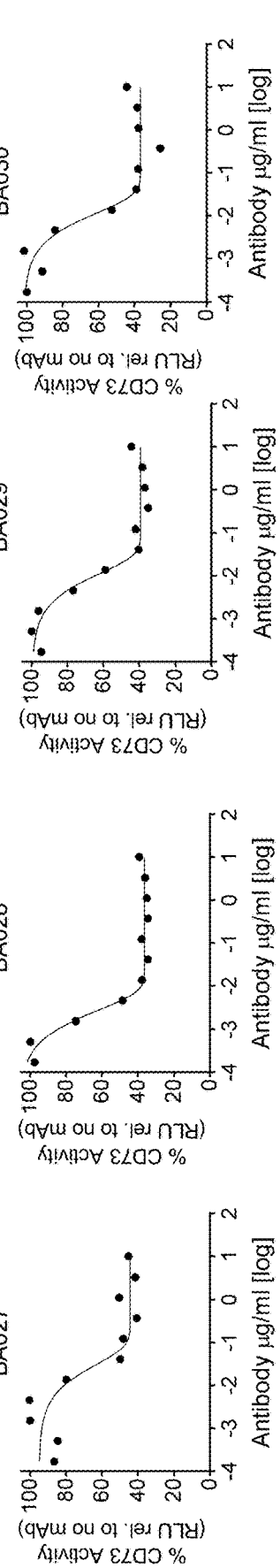
FIG. 6O BA029
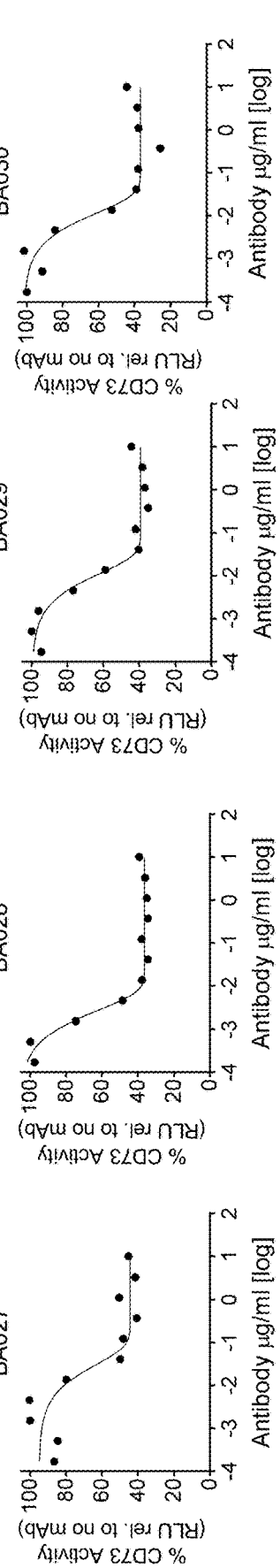
FIG. 6P BA030

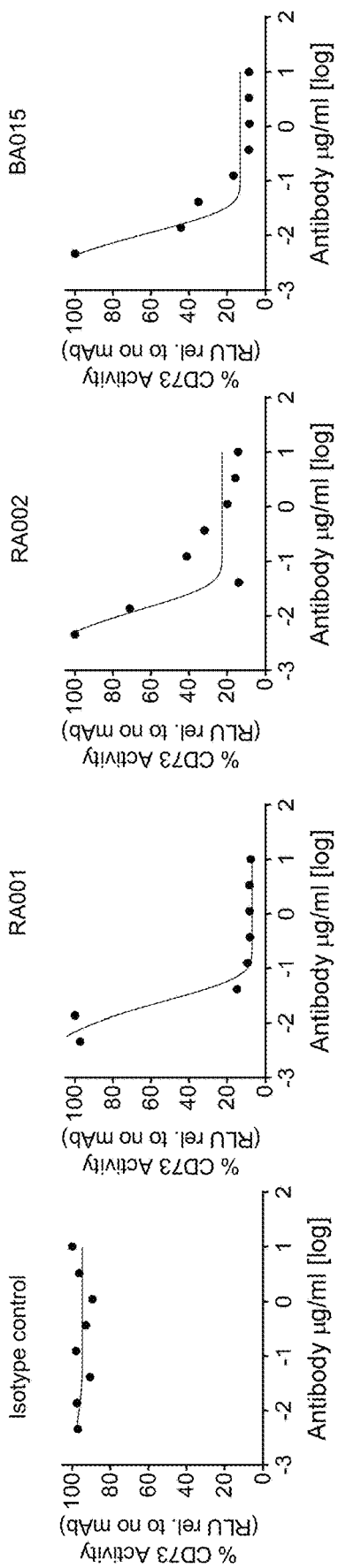
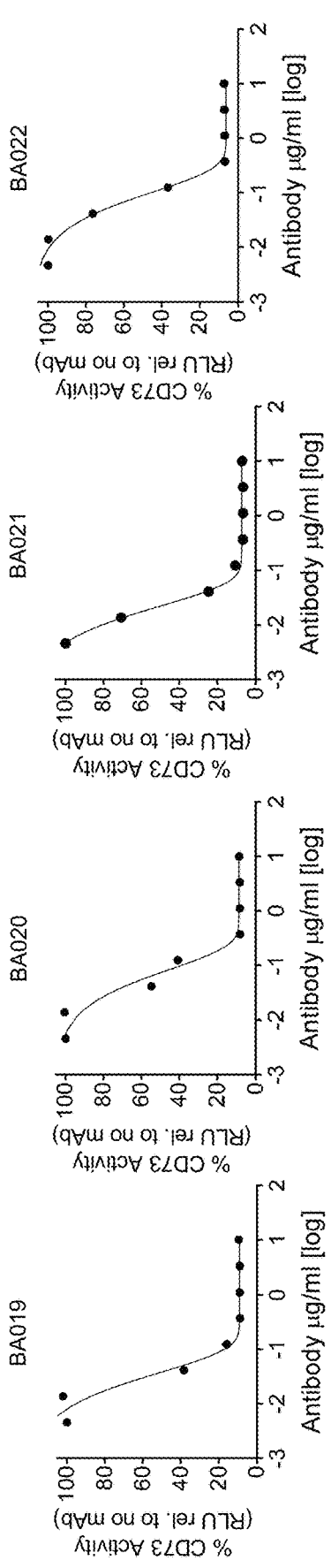

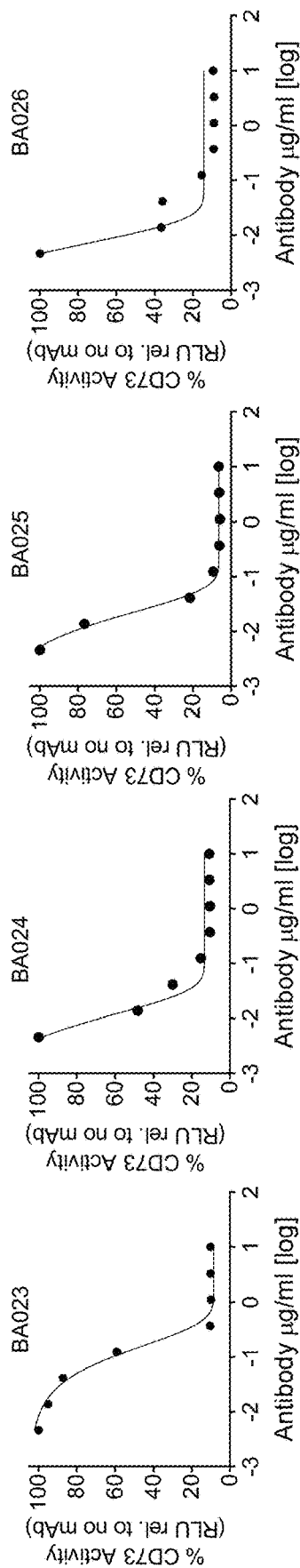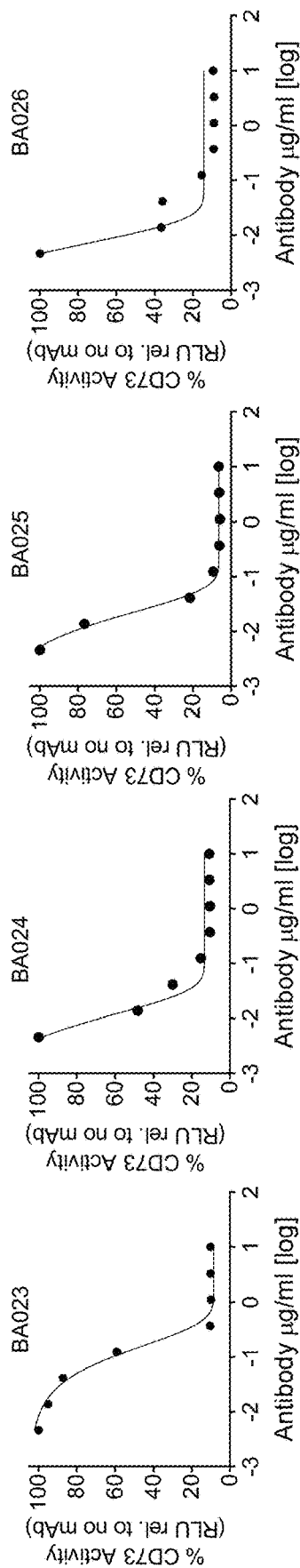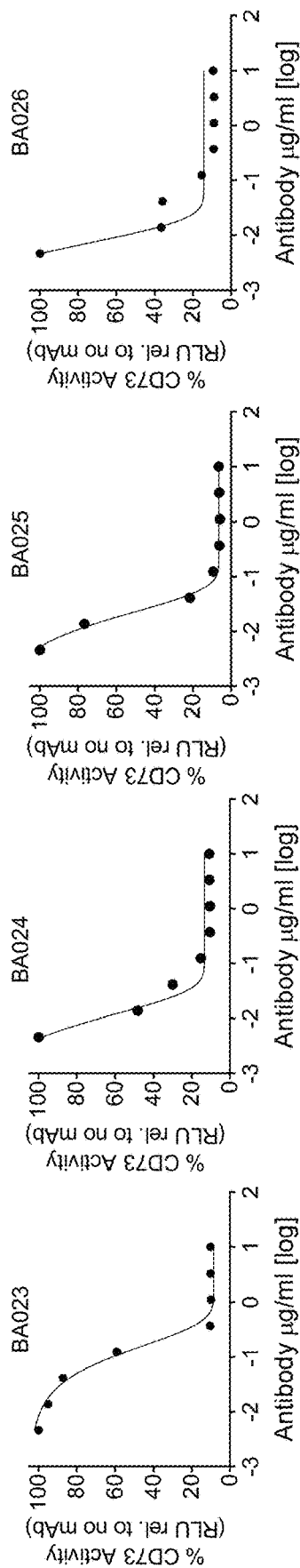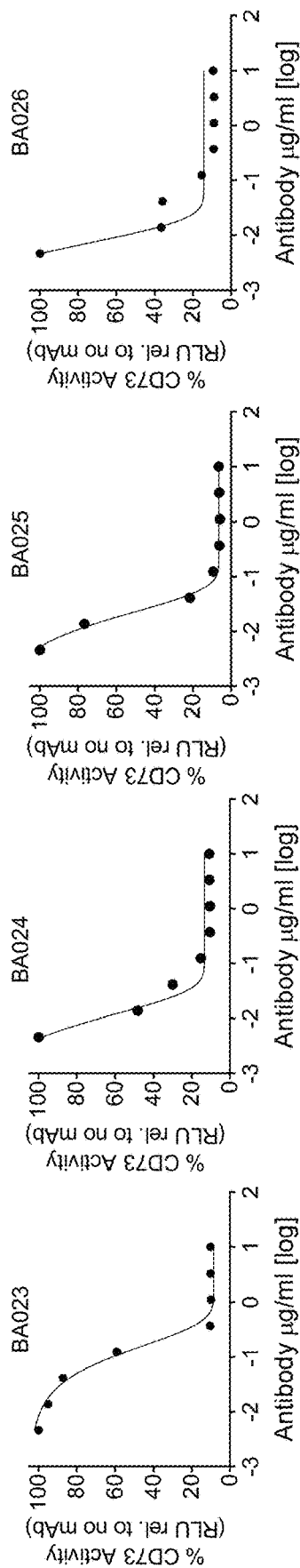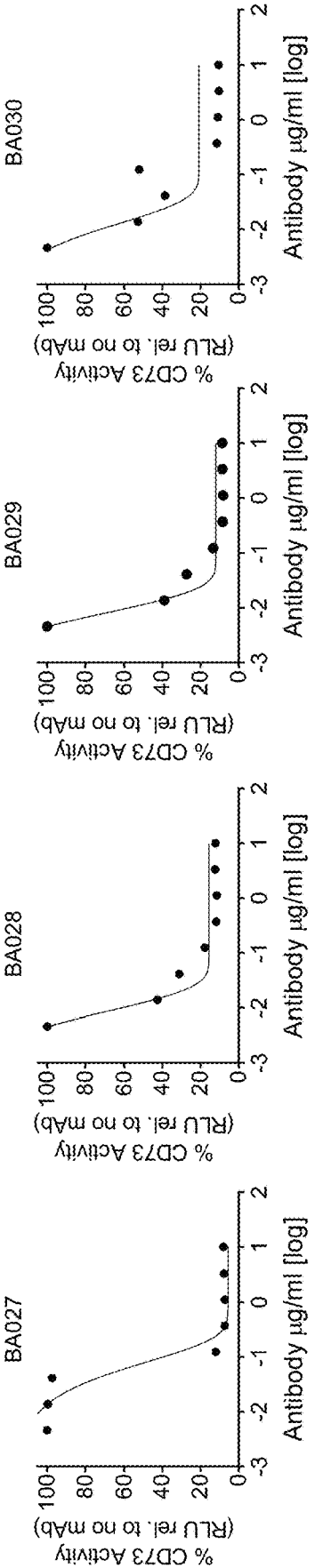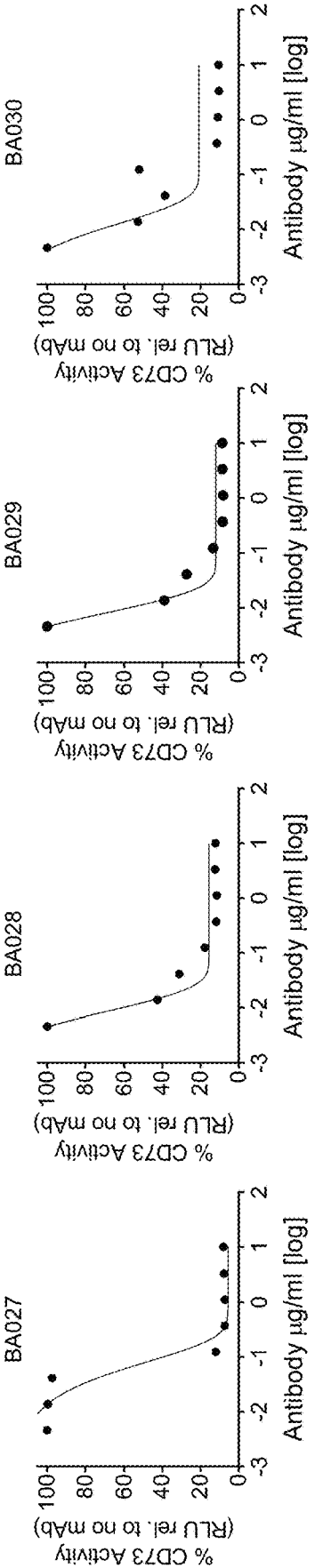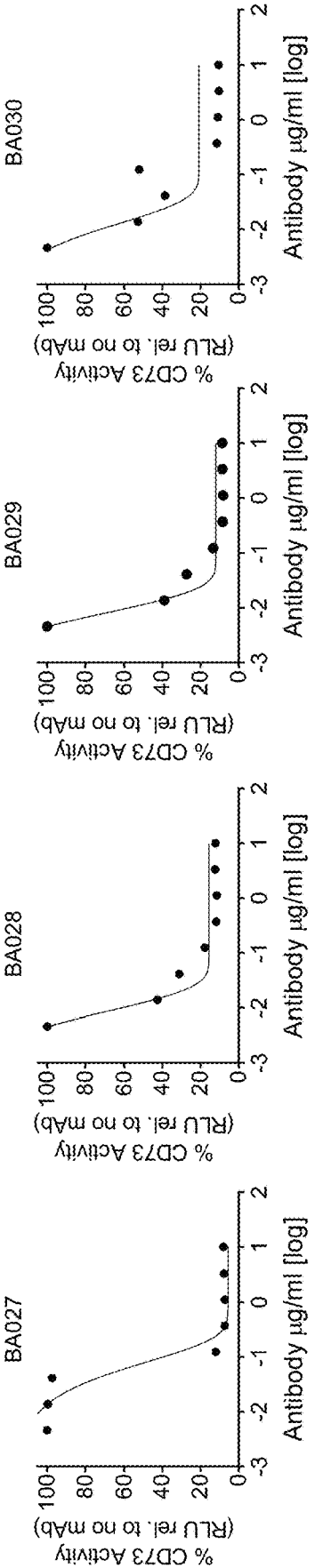

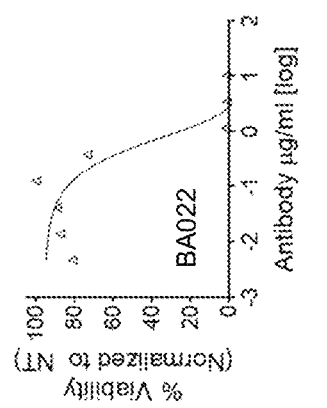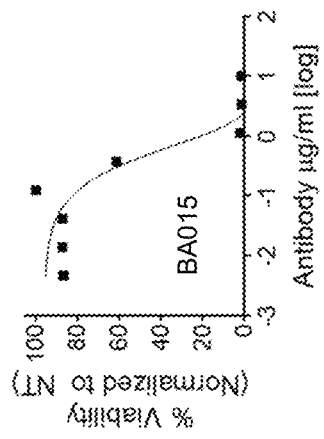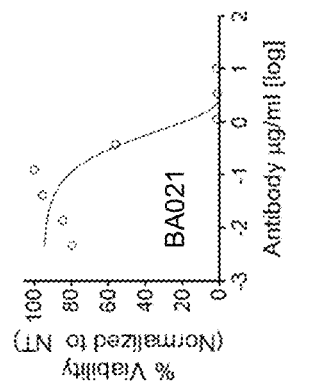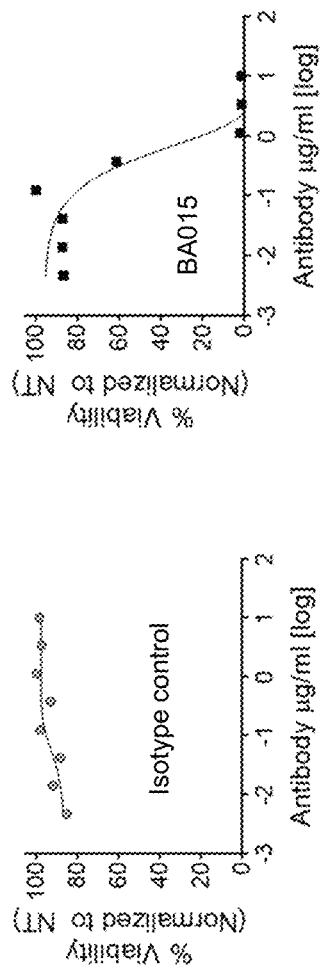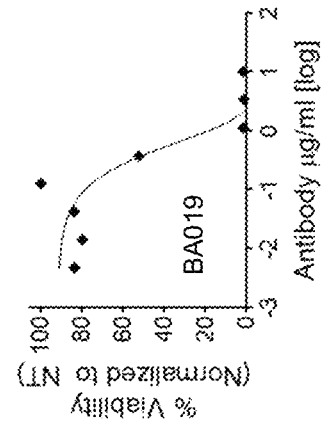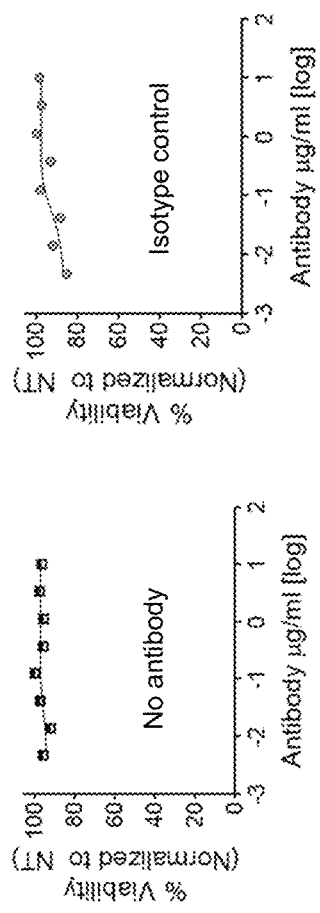

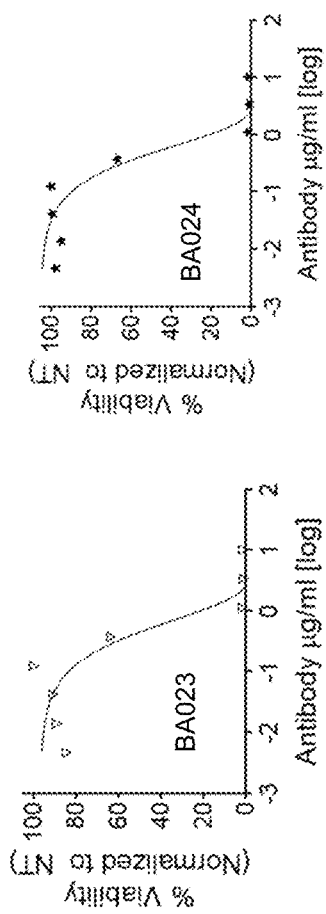
FIG. 8H BA023
FIG. 8I BA024
FIG. 8J BA025
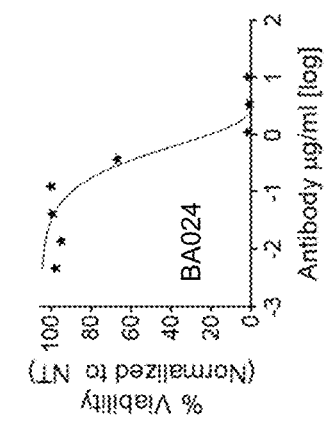
FIG. 8K BA026
FIG. 8L BA027
FIG. 8M BA030

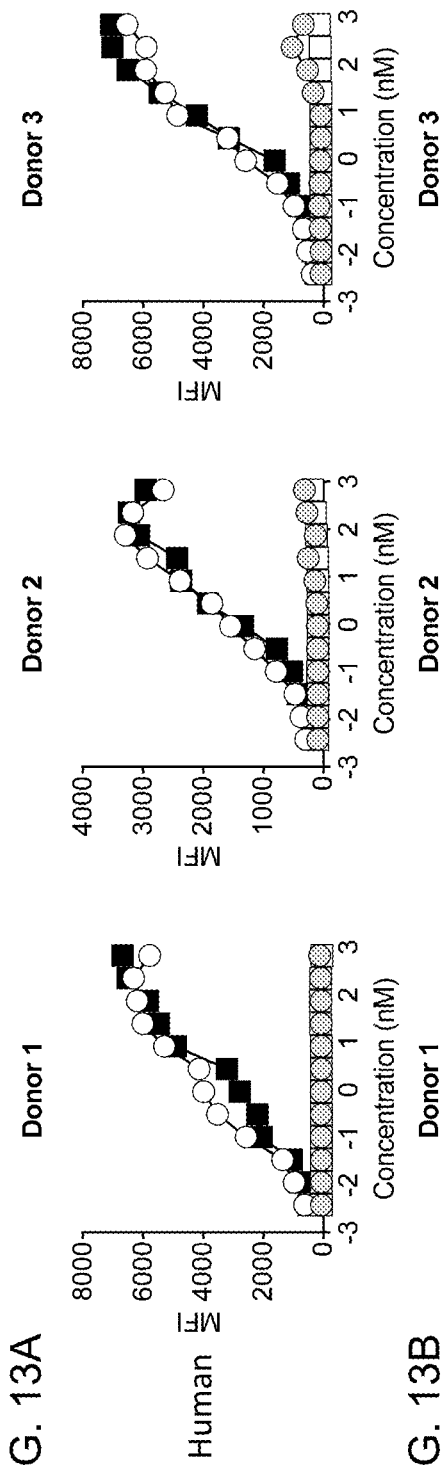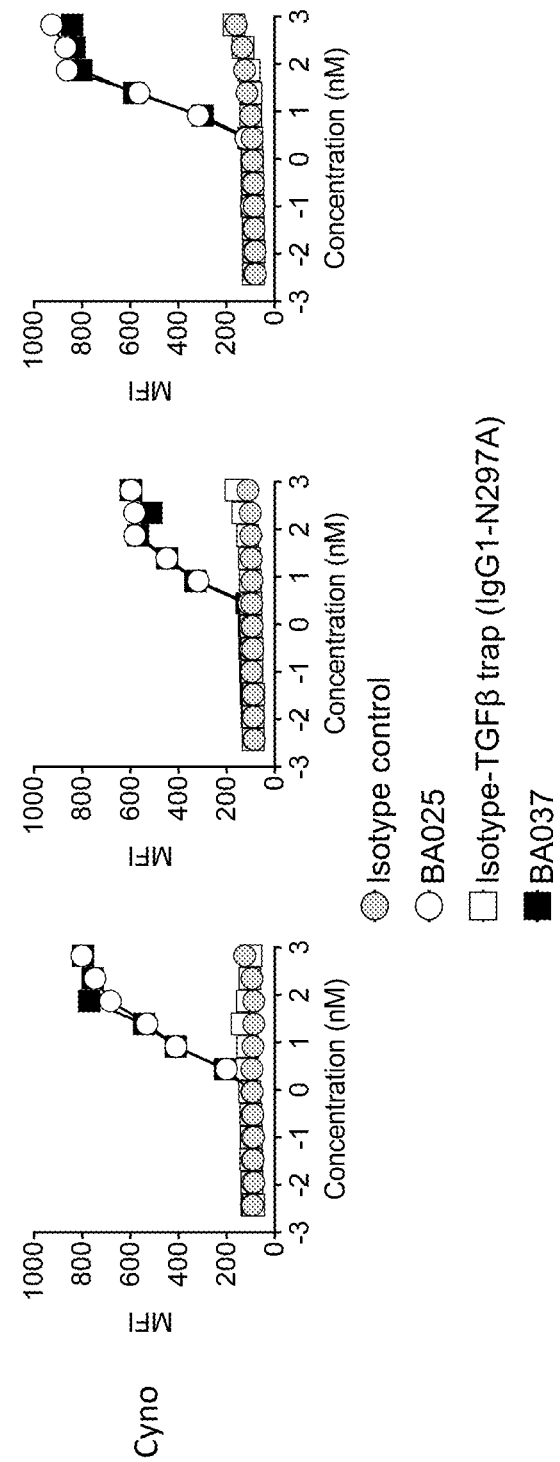
FIG. 13A
FIG. 13B

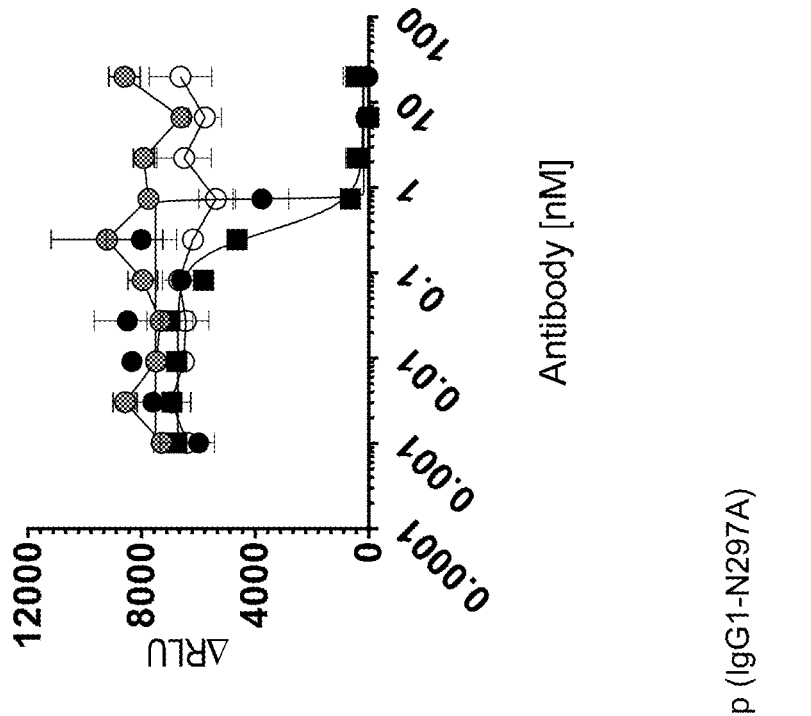
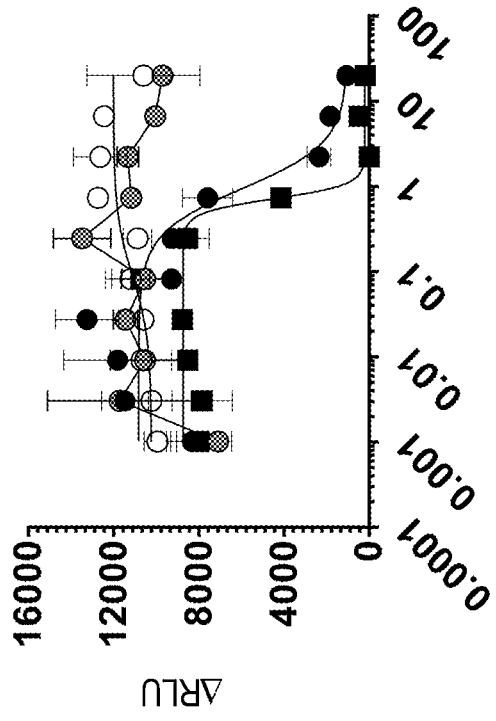
FIG. 14A
FIG. 14B

Human soluble CD73 inhibition by anti-CD73-TGFβ trap

- ○ Isotype control
- ● BA025
- ◐ Isotype-TGFβ trap (IgG1-N297A)
- ■ BA037

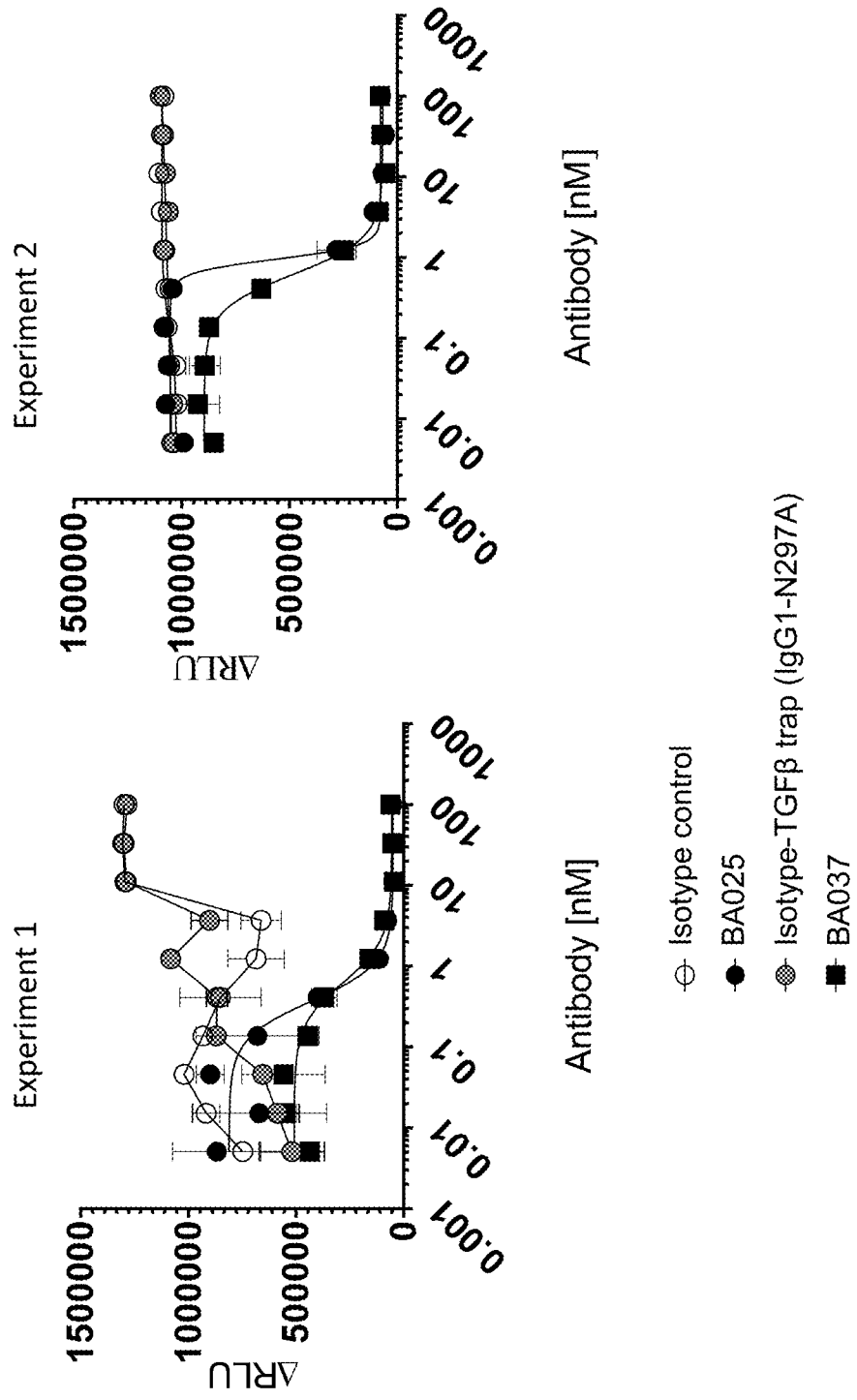

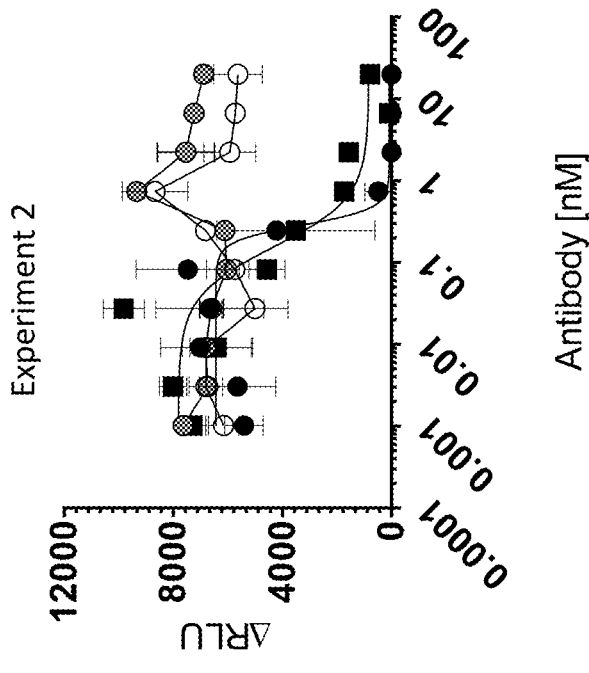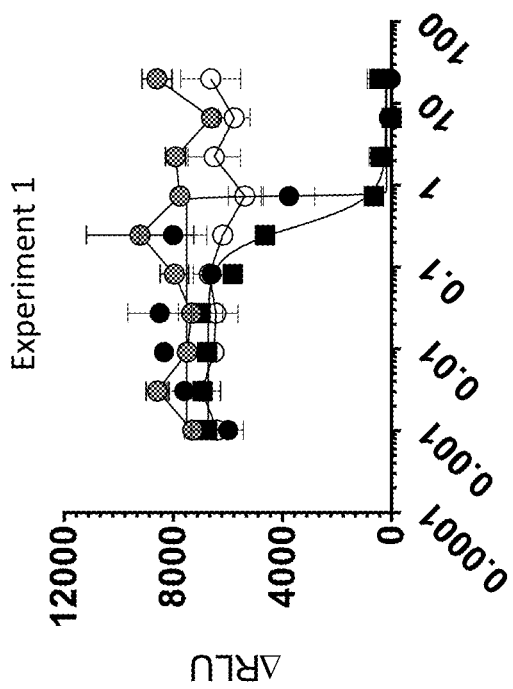
Human cell-expressed CD73 inhibition by anti-CD73-TGFβ trap
FIG. 16A Experiment 1
FIG. 16B Experiment 2
○ Isotype control
● BA025
▨ Isotype-TGFβ trap (IgG1-N297A)
■ BA037

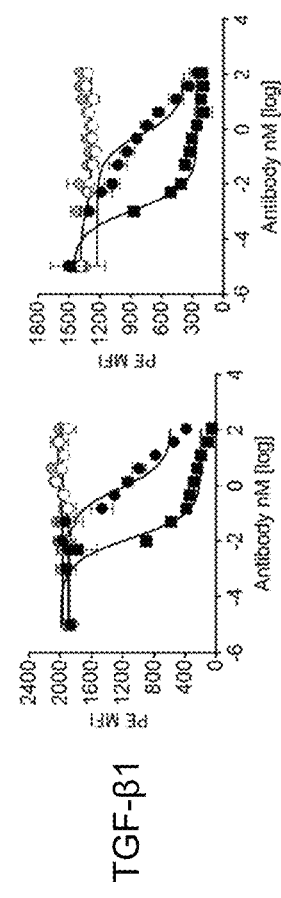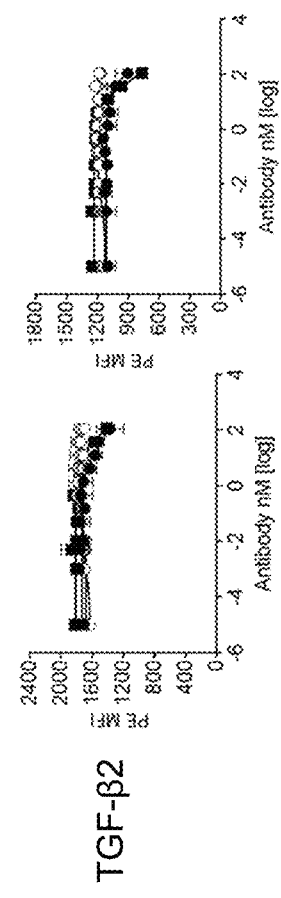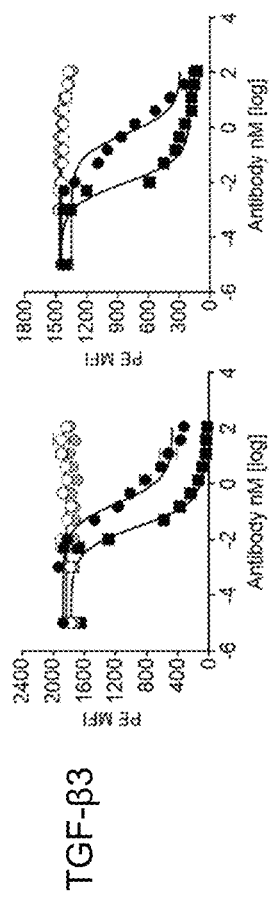

TGFβ inhibition by anti-CD73-TGFβ trap

Experiment 3 – (37°C)

TGF-β1

TGF-β2

TGF-β3

- ● BA037
- ○ BA025
- ◇ Isotype control
- ■ Isotype-TGFβ trap (IgG1-N297A)

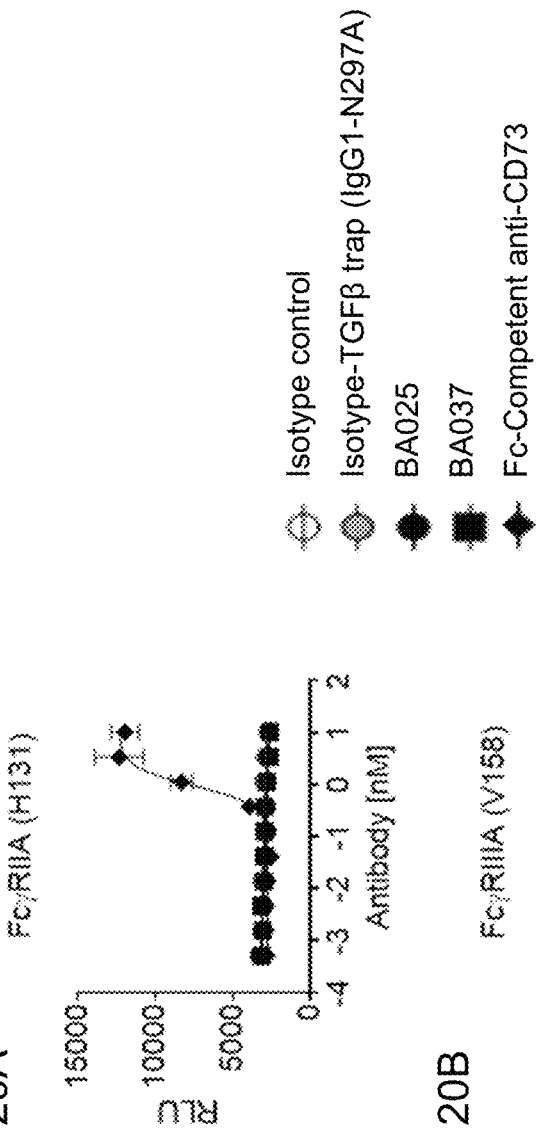
FIG. 20A FcγR Activation by BA037 — FcγRIIA (H131)
FIG. 20B FcγRIIIA (V158)

SEQUENCE LISTING

<160> NUMBER OF SEQ ID NOS: 158

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 1

Asn Tyr Trp Met His
1               5

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Ser Trp Ile Asn
1               5

<210> SEQ ID NO 3
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Ile Tyr Pro Arg Asn Ser Asp Thr Asn Tyr Asn Gln Lys Phe Lys
1               5                   10                  15

Gly

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Ile Tyr Pro Arg Asn Gly Asp Thr Asn Tyr Asn Gly Lys Phe Lys
1               5                   10                  15

Asp

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Arg Ile Tyr Pro Arg Ala Gly Asp Thr Asn Tyr Ala Gly Lys Phe Lys
1               5                   10                  15

Asp

<210> SEQ ID NO 6
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 6

Arg Ile Tyr Pro Arg Ser Gly Asp Thr Asn Tyr Ser Gly Lys Phe Lys
1               5                   10                  15

Asp

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Leu Leu Asp Tyr Ser Met Asp Tyr
1               5

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Ala Ser Gln Asp Ile Ser Asn Tyr Leu Asn
1               5                   10

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Arg Ala Ser Gln Asp Ile Ser Ile Ser Leu Asn
1               5                   10

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Tyr Thr Ser Arg Leu His Ser
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 11

Gln Gln Gly Asn Thr Leu Pro Trp Thr
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Gln Gly Asn Thr Leu Pro Leu Thr
1               5

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (2)..(2)
<223> OTHER INFORMATION: Ser or Tyr
<220> FEATURE:
<221> NAME/KEY: MOD_RES
<222> LOCATION: (4)..(4)
<223> OTHER INFORMATION: Ile or Met
<220> FEATURE:
<221> NAME/KEY: MOD_RES
<222> LOCATION: (5)..(5)
<223> OTHER INFORMATION: Asn or His

<400> SEQUENCE: 13

Xaa Xaa Trp Xaa Xaa
1               5

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Arg or Thr
<220> FEATURE:
<221> NAME/KEY: MOD_RES
<222> LOCATION: (6)..(6)
<223> OTHER INFORMATION: Asn, Ala or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (12)..(12)
<223> OTHER INFORMATION: Asn, Ala or Ser
<220> FEATURE:
<221> NAME/KEY: MOD_RES
```

```
<222> LOCATION: (13)..(13)
<223> OTHER INFORMATION: Gly or Gln
<220> FEATURE:
<221> NAME/KEY: MOD_RES
<222> LOCATION: (17)..(17)
<223> OTHER INFORMATION: Asp or Gly

<400> SEQUENCE: 14

Xaa Ile Tyr Pro Arg Xaa Xaa Asp Thr Asn Tyr Xaa Xaa Lys Phe Lys
1               5                   10                  15

Xaa

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Asn, Ala or Ser
<220> FEATURE:
<221> NAME/KEY: MOD_RES
<222> LOCATION: (12)..(12)
<223> OTHER INFORMATION: Asn, Ala or Ser

<400> SEQUENCE: 15

Arg Ile Tyr Pro Arg Xaa Gly Asp Thr Asn Tyr Xaa Gly Lys Phe Lys
1               5                   10                  15

Asp

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Asn or Ile
<220> FEATURE:
<221> NAME/KEY: MOD_RES
<222> LOCATION: (9)..(9)
<223> OTHER INFORMATION: Tyr or Ser

<400> SEQUENCE: 16

Arg Ala Ser Gln Asp Ile Ser Xaa Xaa Leu Asn
1               5                   10

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Leu or Trp
```

<400> SEQUENCE: 17

Gln Gln Gly Asn Thr Leu Pro Xaa Thr
1               5

<210> SEQ ID NO 18
<211> LENGTH: 98
<212> TYPE: PRT
<213> ORGANISM: Mus musculus

<400> SEQUENCE: 18

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Tyr Ile Tyr Pro Arg Asp Gly Ser Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg

<210> SEQ ID NO 19
<211> LENGTH: 117
<212> TYPE: PRT
<213> ORGANISM: Mus musculus
<220> FEATURE:
<221> NAME/KEY: MOD_RES
<222> LOCATION: (1)..(1)
<223> OTHER INFORMATION: Gln or pyroglutamate

<400> SEQUENCE: 19

Xaa Val Gln Leu Gln Gln Pro Gly Thr Val Leu Ala Arg Pro Gly Ala
1               5                   10                  15

Ser Val Lys Met Ser Cys Lys Thr Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Thr Ile Tyr Pro Arg Asn Ser Asp Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Ile Tyr Tyr Cys
                85                  90                  95

Ala Ser Leu Leu Asp Tyr Ser Met Asp Tyr Trp Gly Gln Gly Thr Ser
                100                 105                 110

Val Thr Val Ser Ser
            115

<210> SEQ ID NO 20
<211> LENGTH: 117
<212> TYPE: PRT
<213> ORGANISM: Mus musculus
<220> FEATURE:
<221> NAME/KEY: MOD_RES
<222> LOCATION: (1)..(1)
<223> OTHER INFORMATION: Gln or pyroglutamate -continued

<400> SEQUENCE: 20

Xaa Val Gln Leu Lys Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Pro Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser
        115

<210> SEQ ID NO 21
<211> LENGTH: 117
<212> TYPE: PRT
<213> ORGANISM: Mus musculus
<220> FEATURE:
<221> NAME/KEY: MOD_RES
<222> LOCATION: (1)..(1)
<223> OTHER INFORMATION: Glu or pyroglutamate

<400> SEQUENCE: 21

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser
        115

<210> SEQ ID NO 22
<211> LENGTH: 98
<212> TYPE: PRT
<213> ORGANISM: Homo sapiens

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Thr Gly Trp Val Arg Gln Met Pro Gly Lys Gly Leu Glu Trp Met
        35                  40                  45

```
Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 23
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 23

Xaa Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ala Phe Ser Ser Ser
                20                  25                  30

Trp Ile Asn Trp Val Arg Gln Met Pro Gly Lys Gly Leu Glu Trp Met
             35                  40                  45

Gly Arg Ile Tyr Pro Arg Asn Gly Asp Thr Asn Tyr Asn Gly Lys Phe
         50                  55                  60

Lys Asp Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Leu Asp Tyr Ser Met Asp Tyr Trp Gly Gln Gly Thr Leu
            100                 105                 110

Val Thr Val Ser Ser
        115

<210> SEQ ID NO 24
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 24

Xaa Val Gln Leu Val Gln Ser Gly Ala Glu Val Lys Lys Pro Gly Glu
 1               5                  10                  15

Ser Leu Lys Ile Ser Cys Lys Ala Ser Gly Tyr Ala Phe Ser Ser Ser
                20                  25                  30

Trp Ile Asn Trp Val Arg Gln Met Pro Gly Lys Gly Leu Glu Trp Met
             35                  40                  45

Gly Arg Ile Tyr Pro Arg Asn Gly Asp Thr Asn Tyr Asn Gly Lys Phe
         50                  55                  60
```

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser
        115

<210> SEQ ID NO 25
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 25

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Ala Gly Asp Thr Asn Tyr Ala Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Leu Asp Tyr Ser Met Asp Tyr Trp Gly Gln Gly Thr Leu
            100                 105                 110

Val Thr Val Ser Ser
        115

<210> SEQ ID NO 26
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 26

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

```
Gly Arg Ile Tyr Pro Arg Ser Gly Asp Thr Asn Tyr Ser Gly Lys Phe
         50                  55                  60

Lys Asp Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Leu Asp Tyr Ser Met Asp Tyr Trp Gly Gln Gly Thr Leu
             100                 105                 110

Val Thr Val Ser Ser
            115

<210> SEQ ID NO 27
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 27

Xaa Val Gln Leu Val Gln Ser Gly Ala Glu Val Lys Lys Pro Gly Glu
 1               5                  10                  15

Ser Leu Lys Ile Ser Cys Lys Ala Ser Gly Tyr Ala Phe Ser Ser Ser
                 20                  25                  30

Trp Ile Asn Trp Val Arg Gln Met Pro Gly Lys Gly Leu Glu Trp Met
             35                  40                  45

Gly Arg Ile Tyr Pro Arg Ala Gly Asp Thr Asn Tyr Ala Gly Lys Phe
         50                  55                  60

Lys Asp Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Ser Leu Leu Asp Tyr Ser Met Asp Tyr Trp Gly Gln Gly Thr Leu
             100                 105                 110

Val Thr Val Ser Ser
            115

<210> SEQ ID NO 28
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 28

Xaa Val Gln Leu Val Gln Ser Gly Ala Glu Val Lys Lys Pro Gly Glu
 1               5                  10                  15

Ser Leu Lys Ile Ser Cys Lys Ala Ser Gly Tyr Ala Phe Ser Ser Ser
                 20                  25                  30
```

```
Trp Ile Asn Trp Val Arg Gln Met Pro Gly Lys Gly Leu Glu Trp Met
        35                  40                  45

Gly Arg Ile Tyr Pro Arg Ser Gly Asp Thr Asn Tyr Ser Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
                100                 105                 110

Val Thr Val Ser Ser
        115

<210> SEQ ID NO 29
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 29

Xaa Val Lys Leu Val Glu Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Asn Gln Met Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
                100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 30

Xaa Val Lys Leu Val Glu Ser Gly Ala Glu Val Lys Lys Pro Gly Glu
1               5                   10                  15
```

```
Ser Leu Lys Ile Ser Cys Lys Ala Ser Gly Tyr Ala Phe Ser Ser Ser
            20                  25                  30

Trp Ile Asn Trp Val Asn Gln Met Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Gln Val Thr Leu Ser Ala Asp Arg Ser Ser Ser Thr Ala Tyr
 65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser
            115

<210> SEQ ID NO 31
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate
<220> FEATURE:
<221> NAME/KEY: MOD_RES
<222> LOCATION: (24)..(24)
<223> OTHER INFORMATION: Gly or Ala
<220> FEATURE:
<221> NAME/KEY: MOD_RES
<222> LOCATION: (55)..(55)
<223> OTHER INFORMATION: Asn, Ala or Ser
<220> FEATURE:
<221> NAME/KEY: MOD_RES
<222> LOCATION: (61)..(61)
<223> OTHER INFORMATION: Asn, Ala or Ser
<220> FEATURE:
<221> NAME/KEY: MOD_RES
<222> LOCATION: (98)..(98)
<223> OTHER INFORMATION: Arg or Ser

<400> SEQUENCE: 31

Xaa Val Gln Leu Val Gln Ser Gly Ala Glu Val Lys Lys Pro Gly Glu
  1               5                  10                  15

Ser Leu Lys Ile Ser Cys Lys Xaa Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Xaa Gly Asp Thr Asn Tyr Xaa Gly Lys Phe
    50                  55                  60

Lys Asp Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Xaa Leu Leu Asp Tyr Ser Met Asp Tyr Trp Gly Gln Gly Thr Leu
            100                 105                 110

Val Thr Val Ser Ser
            115
```

```
<210> SEQ ID NO 32
<211> LENGTH: 95
<212> TYPE: PRT
<213> ORGANISM: Mus musculus

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro
                85                  90                  95

<210> SEQ ID NO 33
<211> LENGTH: 107
<212> TYPE: PRT
<213> ORGANISM: Mus musculus

<400> SEQUENCE: 33

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 34
<211> LENGTH: 107
<212> TYPE: PRT
<213> ORGANISM: Mus musculus

<400> SEQUENCE: 34

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95
```

Thr Phe Gly Gly Gly Thr Lys Leu Glu Ile Lys
            100                 105

<210> SEQ ID NO 35
<211> LENGTH: 107
<212> TYPE: PRT
<213> ORGANISM: Mus musculus

<400> SEQUENCE: 35

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys
            100                 105

<210> SEQ ID NO 36
<211> LENGTH: 96
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

<210> SEQ ID NO 37
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys
                100                 105

<210> SEQ ID NO 38
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Ser
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
            50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys
                100                 105

<210> SEQ ID NO 39
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ile Gln Met Thr Gln Thr Pro Ser Ser Leu Ser Ala Ser Val Gly
1               5                   10                  15

Asp Arg Val Thr Ile Ser Cys Arg Ala Ser Gln Asp Ile Ser Ile Ser
                20                  25                  30

Leu Asn Trp Tyr Gln Gln Lys Pro Gly Lys Thr Pro Lys Leu Leu Ile
            35                  40                  45

Tyr Tyr Thr Ser Arg Leu His Ser Gly Val Pro Ser Arg Phe Ser Gly
            50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys
                100                 105

```
<210> SEQ ID NO 40
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Gln Met Thr Gln Thr Thr Ser Ser Leu Ser Ala Ser Val Gly
1               5                   10                  15

Asp Arg Val Thr Ile Ser Cys Arg Ala Ser Gln Asp Ile Ser Ile Ser
            20                  25                  30

Leu Asn Trp Tyr Gln Gln Lys Pro Gly Lys Thr Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Leu
                85                  90                  95

Thr Phe Gly Gln Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (31)..(31)
<223> OTHER INFORMATION: Asn or Ile
<220> FEATURE:
<221> NAME/KEY: MOD_RES
<222> LOCATION: (32)..(32)
<223> OTHER INFORMATION: Tyr or Ser
<220> FEATURE:
<221> NAME/KEY: MOD_RES
<222> LOCATION: (71)..(71)
<223> OTHER INFORMATION: Phe or Tyr

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Xaa Xaa
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Xaa Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys
            100                 105
```

```
<210> SEQ ID NO 42
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (31)..(32)
<223> OTHER INFORMATION: This region may encompass "Asn Tyr" or "Ile
      Ser"
<220> FEATURE:
<221> NAME/KEY: MOD_RES
<222> LOCATION: (71)..(71)
<223> OTHER INFORMATION: Phe or Tyr

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Xaa Xaa
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Xaa Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys
            100                 105

<210> SEQ ID NO 43
<211> LENGTH: 330
<212> TYPE: PRT
<213> ORGANISM: Mus musculus

<400> SEQUENCE: 43

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160
```

```
Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 44
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175
```

```
Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly
                325
```

<210> SEQ ID NO 45
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
                145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190
```

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 46
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Ala Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

```
Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly
                325

<210> SEQ ID NO 47
<211> LENGTH: 330
<212> TYPE: PRT
<213> ORGANISM: Homo sapiens

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 48
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 49
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 51
<211> LENGTH: 326
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 52
<211> LENGTH: 325
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325
```

<210> SEQ ID NO 53
<211> LENGTH: 326

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 54
<211> LENGTH: 325
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 55
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 55

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Ala
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 56
<211> LENGTH: 325
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Ala
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 57
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 58
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 59
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
50                  55                  60

```
Ile Trp Phe Thr Val Tyr Lys Gly Ala Glu Val Ala His Phe Met Asn
 65                  70                  75                  80

Ala Leu Arg Tyr Asp Ala Met Ala Leu Gly Asn His Glu Phe Asp Asn
                 85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Ala Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480
```

-continued

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
        515                 520                 525

Leu Glu His His His His His His His His Gly Gly Ser Gly
    530                 535                 540

Gly Leu Pro Glu Thr Gly Gly Asp Arg
545                 550

<210> SEQ ID NO 60
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Ile Arg Arg Ala
        35                  40                  45

Glu Pro Asn Val Leu Leu Leu Asp Ala Gly Asp Gln Tyr Gln Gly Thr
50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
            85                  90                  95

Gly Val Glu Gly Leu Ile Glu Pro Leu Leu Lys Glu Ala Lys Phe Pro
        100                 105                 110

Ile Leu Ser Ala Asn Ile Lys Ala Lys Gly Pro Leu Ala Ser Gln Ile
    115                 120                 125

Ser Gly Leu Tyr Leu Pro Ala Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
            165                 170                 175

Glu Val Asp Lys Leu Lys Thr Leu Asn Val Asn Lys Ile Ile Ala Leu
        180                 185                 190

Gly His Ser Gly Phe Glu Met Asp Lys Leu Ile Ala Gln Lys Val Arg
    195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
            245                 250                 255

Phe Gly Lys Tyr Leu Gly Tyr Leu Lys Ile Glu Phe Asp Glu Arg Gly
        260                 265                 270

```
Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
                340                 345                 350

Met Phe Trp Asn His Val Ser Met Cys Ile Leu Asn Gly Gly Gly Ile
            355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
            450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
                500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
            530                 535                 540

Gly Leu Pro Glu Thr Gly Gly Asp Arg
545                 550
```

<210> SEQ ID NO 61
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
50                  55                  60
```

```
Ile Trp Phe Thr Val Tyr Lys Gly Ala Glu Val Ala His Phe Met Asn
 65                  70                  75                  80

Ala Leu Arg Tyr Asp Ala Met Ala Leu Gly Asn His Glu Phe Asp Asn
                 85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Ala Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480
```

```
Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
        515                 520                 525

Leu Glu His His His His His His His His Gly Gly Ser Gly
        530                 535                 540

Gly Leu Pro Glu Thr Gly Gly Asp Arg
545                 550

<210> SEQ ID NO 62
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Ala Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270
```

```
Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Leu Arg His Thr Asp Glu
            340                 345                 350

Met Phe Trp Asn His Val Ser Met Cys Ile Leu Asn Gly Gly Gly Ile
            355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
                420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
            450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
            515                 520                 525

Leu Glu His His His His His His His His His Gly Gly Ser Gly
            530                 535                 540

Gly Leu Pro Glu Thr Gly Gly Asp Arg
545                 550

<210> SEQ ID NO 63
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 63

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
                20                  25                  30

Trp Ile Asn Trp Val Asn Gln Arg Pro Gly Lys Gly Leu Glu Trp Ile
            35                  40                  45
```

-continued

```
Gly Arg Ile Tyr Pro Arg Asn Gly Asp Thr Asn Tyr Asn Gly Lys Phe
         50                  55                  60

Lys Asp Arg Ala Thr Leu Thr Ala Asp Arg Ser Ser Ser Thr Ala Tyr
 65                  70                  75                  80

Leu Gln Leu Ser Ser Leu Thr Ser Glu Asp Ser Ala Val Tyr Phe Cys
                 85                  90                  95

Ala Ser Leu Leu Asp Tyr Ser Met Asp Tyr Trp Gly Gln Gly Thr Ser
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Ala Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445
```

<210> SEQ ID NO 64
<211> LENGTH: 446
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 64
```

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Ala Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

```
Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
                420                 425                 430

His Asn His His Thr Thr Lys Ser Phe Ser Arg Thr Pro Gly
            435                 440                 445

<210> SEQ ID NO 65
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Gln or pyroglutamate

<400> SEQUENCE: 65

Xaa Val Gln Leu Gln Gln Pro Gly Thr Val Leu Ala Arg Pro Gly Ala
1               5                   10                  15

Ser Val Lys Met Ser Cys Lys Thr Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Thr Ile Tyr Pro Arg Asn Ser Asp Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Ile Tyr Tyr Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 66
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Gln or pyroglutamate

<400> SEQUENCE: 66

Xaa Val Gln Leu Gln Gln Pro Gly Thr Val Leu Ala Arg Pro Gly Ala
1               5                   10                  15

Ser Val Lys Met Ser Cys Lys Thr Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Thr Ile Tyr Pro Arg Asn Ser Asp Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Ile Tyr Tyr Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 67
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Gln or pyroglutamate

<400> SEQUENCE: 67

Xaa Val Gln Leu Lys Gln Ser Gly Pro Glu Leu Val Lys Pro Gly Ala
1               5                   10                  15
```

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
            35                  40                  45

Gly Arg Ile Tyr Pro Arg Asn Gly Asp Thr Asn Tyr Asn Gly Lys Phe
50                      55                  60

Lys Asp Arg Ala Thr Leu Thr Ala Asp Arg Ser Ser Ser Thr Ala Tyr
65                      70                  75                  80

Leu Gln Leu Ser Ser Leu Thr Pro Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                     135                 140

Leu Val Lys Asp Tyr Phe Pro Glu Pro Val Thr Val Ser Trp Asn Ser
145                     150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                     215                 220

Thr Cys Pro Pro Cys Pro Ala Pro Glu Leu Leu Gly Gly Pro Ser Val
225                     230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
290                     295                 300

Val Leu Thr Val Leu His Gln Asp Trp Leu Asn Gly Lys Glu Tyr Lys
305                     310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                     375                 380

Gly Gln Pro Glu Asn Asn Tyr Lys Thr Thr Pro Pro Val Leu Asp Ser
385                     390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 68
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Gln or pyroglutamate

<400> SEQUENCE: 68

Xaa Val Gln Leu Lys Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Pro Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
        405                 410                 415

Trp Gln Gln Gly Asn Val Phe Ser Cys Ser Val Met His Glu Ala Leu
    420                 425                 430

His Asn His Tyr Thr Gln Lys Ser Leu Ser Leu Ser Pro Gly
            435                 440                 445

<210> SEQ ID NO 69
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 69

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Arg Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Ala Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 70
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 70

Xaa Val Lys Leu Val Glu Ser Gly Pro Glu Leu Val Lys Pro Gly Ala
1               5                   10                  15
Ser Val Lys Ile Ser Cys Lys Ala Ser Gly Tyr Ala Phe Ser Ser Ser
            20                  25                  30
Trp Ile Asn Trp Val Asn Gln Arg Pro Gly Lys Gly Leu Glu Trp Ile
        35                  40                  45
Gly Arg Ile Tyr Pro Arg Asn Gly Asp Thr Asn Tyr Asn Gly Lys Phe
50                  55                  60
Lys Asp Arg Ala Thr Leu Thr Ala Asp Arg Ser Ser Ser Thr Ala Tyr
65                  70                  75                  80
Leu Gln Leu Ser Ser Leu Thr Ser Glu Asp Ser Ala Val Tyr Phe Cys
                85                  90                  95
```

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 71
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 71

| | | | | | | | | | | | | | | |
|---|---|---|---|---|---|---|---|---|---|---|---|---|---|---|
| Xaa | Val | Lys | Leu | Val | Glu | Ser | Gly | Pro | Glu | Leu | Val | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Ala | Phe | Ser | Ser | Ser |
| | | | 20 | | | | | 25 | | | | | 30 | | |
| Trp | Ile | Asn | Trp | Val | Asn | Gln | Arg | Pro | Gly | Lys | Gly | Leu | Glu | Trp | Ile |
| | | | 35 | | | | 40 | | | | | 45 | | | |
| Gly | Arg | Ile | Tyr | Pro | Arg | Asn | Gly | Asp | Thr | Asn | Tyr | Asn | Gly | Lys | Phe |
| | 50 | | | | | 55 | | | | | 60 | | | | |
| Lys | Asp | Arg | Ala | Thr | Leu | Thr | Ala | Asp | Arg | Ser | Ser | Ser | Thr | Ala | Tyr |
| 65 | | | | | 70 | | | | | 75 | | | | | 80 |
| Leu | Gln | Leu | Ser | Ser | Leu | Thr | Ser | Glu | Asp | Ser | Ala | Val | Tyr | Phe | Cys |
| | | | | 85 | | | | | 90 | | | | | 95 | |
| Ala | Ser | Leu | Leu | Asp | Tyr | Ser | Met | Asp | Tyr | Trp | Gly | Gln | Gly | Thr | Ser |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | | 115 | | | | | 120 | | | | | 125 | | |
| Ala | Pro | Cys | Ser | Arg | Ser | Thr | Ser | Glu | Ser | Thr | Ala | Ala | Leu | Gly | Cys |
| | | 130 | | | | | 135 | | | | | 140 | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Asn |
| | | | 180 | | | | | 185 | | | | | 190 | | |
| Phe | Gly | Thr | Gln | Thr | Tyr | Thr | Cys | Asn | Val | Asp | His | Lys | Pro | Ser | Asn |
| | | | 195 | | | | | 200 | | | | | 205 | | |
| Thr | Lys | Val | Asp | Lys | Thr | Val | Glu | Arg | Lys | Cys | Cys | Val | Glu | Cys | Pro |
| | 210 | | | | | 215 | | | | | 220 | | | | |
| Pro | Cys | Pro | Ala | Pro | Pro | Val | Ala | Gly | Pro | Ser | Val | Phe | Leu | Phe | Pro |
| 225 | | | | | 230 | | | | | 235 | | | | | 240 |
| Pro | Lys | Pro | Lys | Asp | Thr | Leu | Met | Ile | Ser | Arg | Thr | Pro | Glu | Val | Thr |
| | | | | 245 | | | | | 250 | | | | | 255 | |
| Cys | Val | Val | Val | Asp | Val | Ser | His | Glu | Asp | Pro | Glu | Val | Gln | Phe | Asn |
| | | | 260 | | | | | 265 | | | | | 270 | | |
| Trp | Tyr | Val | Asp | Gly | Val | Glu | Val | His | Asn | Ala | Lys | Thr | Lys | Pro | Arg |
| | | 275 | | | | | 280 | | | | | 285 | | | |
| Glu | Glu | Gln | Phe | Asn | Ser | Thr | Phe | Arg | Val | Val | Ser | Val | Leu | Thr | Val |
| | 290 | | | | | 295 | | | | | 300 | | | | |
| Val | His | Gln | Asp | Trp | Leu | Asn | Gly | Lys | Glu | Tyr | Lys | Cys | Lys | Val | Ser |
| 305 | | | | | 310 | | | | | 315 | | | | | 320 |
| Asn | Lys | Gly | Leu | Pro | Ala | Pro | Ile | Glu | Lys | Thr | Ile | Ser | Lys | Thr | Lys |
| | | | | 325 | | | | | 330 | | | | | 335 | |
| Gly | Gln | Pro | Arg | Glu | Pro | Gln | Val | Tyr | Thr | Leu | Pro | Pro | Ser | Arg | Glu |
| | | | 340 | | | | | 345 | | | | | 350 | | |
| Glu | Met | Thr | Lys | Asn | Gln | Val | Ser | Leu | Thr | Cys | Leu | Val | Lys | Gly | Phe |
| | | | 355 | | | | | 360 | | | | | 365 | | |
| Tyr | Pro | Ser | Asp | Ile | Ala | Val | Glu | Trp | Glu | Ser | Asn | Gly | Gln | Pro | Glu |
| | | 370 | | | | | 375 | | | | | 380 | | | |
| Asn | Asn | Tyr | Lys | Thr | Thr | Pro | Pro | Met | Leu | Asp | Ser | Asp | Gly | Ser | Phe |
| 385 | | | | | 390 | | | | | 395 | | | | | 400 |

```
Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 72
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 72

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285
```

```
Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 73
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 73

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 74
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 74

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60
```

Lys Asp Arg Ala Thr Leu Thr Ala Asp Arg Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 75
<211> LENGTH: 443
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 75

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365
```

```
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 76
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 76

Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255
```

```
Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly
    435                 440

<210> SEQ ID NO 77
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 77

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Leu Leu Asp Tyr Ser Met Asp Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 78
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 78

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30
```

```
Trp Ile Asn Trp Val Arg Gln Met Pro Gly Lys Gly Leu Glu Trp Met
            35                  40                  45
Gly Arg Ile Tyr Pro Arg Asn Gly Asp Thr Asn Tyr Asn Gly Lys Phe
 50                  55                  60
Lys Asp Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Leu Leu Asp Tyr Ser Met Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Ala Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
            435                 440                 445
```

```
<210> SEQ ID NO 79
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 79

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

-continued

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 80
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 80

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

-continued

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
    435                 440                 445

<210> SEQ ID NO 81
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 81

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Ala Gly Asp Thr Asn Tyr Ala Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 82
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 82

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Ala Gly Asp Thr Asn Tyr Ala Gly Lys Phe
50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

-continued

```
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
        420                 425                 430
His Asn His Tyr Thr Gln Lys Ser Leu Ser Leu Ser Pro Gly
    435                 440                 445

<210> SEQ ID NO 83
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 83

Xaa Val Gln Leu Val Gln Ser Gly Ala Glu Val Lys Lys Pro Gly Glu
1               5                   10                  15
Ser Leu Lys Ile Ser Cys Lys Gly Ser Gly Tyr Ala Phe Ser Ser Ser
            20                  25                  30
Trp Ile Asn Trp Val Arg Gln Met Pro Gly Lys Gly Leu Glu Trp Met
        35                  40                  45
Gly Arg Ile Tyr Pro Arg Ser Gly Asp Thr Asn Tyr Ser Gly Lys Phe
    50                  55                  60
Lys Asp Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Leu Leu Asp Tyr Ser Met Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
```

```
Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 84
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 84

Xaa Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
                20                  25                  30

Trp Ile Asn Trp Val Arg Gln Met Pro Gly Lys Gly Leu Glu Trp Met
            35                  40                  45

Gly Arg Ile Tyr Pro Arg Ser Gly Asp Thr Asn Tyr Ser Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Leu Asp Tyr Ser Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 85
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 85

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Ala Gly Asp Thr Asn Tyr Ala Gly Lys Phe
    50                  55                  60

```
Lys Asp Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 86
<211> LENGTH: 446
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 86
```

| | | | | | | | | | | | | | | |
|---|---|---|---|---|---|---|---|---|---|---|---|---|---|---|
| Xaa | Val | Gln | Leu | Val | Gln | Ser | Gly | Ala | Glu | Val | Lys | Lys | Pro | Gly | Glu |
| 1 | | | | 5 | | | | | 10 | | | | | 15 |
| Ser | Leu | Lys | Ile | Ser | Cys | Lys | Ala | Ser | Gly | Tyr | Ala | Phe | Ser | Ser | Ser |
| | | | 20 | | | | | 25 | | | | | 30 | | |
| Trp | Ile | Asn | Trp | Val | Arg | Gln | Met | Pro | Gly | Lys | Gly | Leu | Glu | Trp | Met |
| | | 35 | | | | | 40 | | | | | 45 | | | |
| Gly | Arg | Ile | Tyr | Pro | Arg | Ala | Gly | Asp | Thr | Asn | Tyr | Ala | Gly | Lys | Phe |
| | 50 | | | | | 55 | | | | | 60 | | | | |
| Lys | Asp | Gln | Val | Thr | Ile | Ser | Ala | Asp | Lys | Ser | Ile | Ser | Thr | Ala | Tyr |
| 65 | | | | | 70 | | | | | 75 | | | | | 80 |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 | |
| Ala | Ser | Leu | Leu | Asp | Tyr | Ser | Met | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Arg | Val | Glu | Pro | Lys | Ser | Cys | Asp | Lys | Thr | His |
| 210 | | | | | 215 | | | | | 220 | | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Ala | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |

```
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly
                435                 440                 445

<210> SEQ ID NO 87
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 87

Xaa Val Gln Leu Val Gln Ser Gly Ala Glu Val Lys Lys Pro Gly Glu
1               5                   10                  15
Ser Leu Lys Ile Ser Cys Lys Ala Ser Gly Tyr Ala Phe Ser Ser Ser
                20                  25                  30
Trp Ile Asn Trp Val Arg Gln Met Pro Gly Lys Gly Leu Glu Trp Met
            35                  40                  45
Gly Arg Ile Tyr Pro Arg Ser Gly Asp Thr Asn Tyr Ser Gly Lys Phe
    50                  55                  60
Lys Asp Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Ser Leu Leu Asp Tyr Ser Met Asp Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
```

-continued

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 88
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 88

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Ser Gly Asp Thr Asn Tyr Ser Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 89
<211> LENGTH: 107
<212> TYPE: PRT
<213> ORGANISM: Mus musculus

<400> SEQUENCE: 89

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

```
Arg His Asn Ser Tyr Thr Cys Glu Ala Thr His Lys Thr Ser Thr Ser
            85                  90                  95

Pro Ile Val Lys Ser Phe Asn Arg Asn Glu Cys
            100                 105

<210> SEQ ID NO 90
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ile Lys Ala Lys Gly Pro Leu Ala Ser Gln Ile Ser Gly Leu Tyr Leu
1               5                   10                  15

Pro Tyr Lys Val Leu Pro Val Gly Asp Glu Val
            20                  25

<210> SEQ ID NO 91
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Asp Glu Ile Thr Ala Leu Gln Pro Glu Val Asp Lys Leu Lys Thr Leu
1               5                   10                  15

Asn Val Asn

<210> SEQ ID NO 92
<211> LENGTH: 214
<212> TYPE: PRT
<213> ORGANISM: Mus musculus

<400> SEQUENCE: 92

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160
```

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 93
<211> LENGTH: 107
<212> TYPE: PRT
<213> ORGANISM: Homo sapiens

<400> SEQUENCE: 93

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 94
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
            85                  90                  95

Thr Phe Gly Gly Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 95
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 96
<211> LENGTH: 214
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 96

```
Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 97
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Ser
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 99
<211> LENGTH: 574
<212> TYPE: PRT
<213> ORGANISM: Homo sapiens

<400> SEQUENCE: 99

```
Met Cys Pro Arg Ala Ala Arg Ala Pro Ala Thr Leu Leu Ala Leu
1               5                   10                  15

Gly Ala Val Leu Trp Pro Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380
```

```
Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
            405                 410                 415

Phe Gly Gly Thr Phe Asp Leu Val Gln Leu Lys Gly Ser Thr Leu Lys
        420                 425                 430

Lys Ala Phe Glu His Ser Val His Arg Tyr Gly Gln Ser Thr Gly Glu
    435                 440                 445

Phe Leu Gln Val Gly Gly Ile His Val Val Tyr Asp Leu Ser Arg Lys
450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
            485                 490                 495

Leu Pro Asn Phe Leu Ala Asn Gly Gly Asp Gly Phe Gln Met Ile Lys
        500                 505                 510

Asp Glu Leu Leu Arg His Asp Ser Gly Asp Gln Asp Ile Asn Val Val
    515                 520                 525

Ser Thr Tyr Ile Ser Lys Met Lys Val Ile Tyr Pro Ala Val Glu Gly
530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
            565                 570

<210> SEQ ID NO 100
<211> LENGTH: 524
<212> TYPE: PRT
<213> ORGANISM: Homo sapiens

<400> SEQUENCE: 100

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
            85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
            165                 170                 175
```

```
Thr Ser Lys Glu Thr Pro Phe Leu Ser Asn Pro Gly Thr Asn Leu Val
        180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
        210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                    245                 250                 255

Glu Val Pro Ala Gly Lys Tyr Pro Phe Ile Val Thr Ser Asp Asp Gly
        260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
        290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                    325                 330                 335

Gln Glu Leu Gly Lys Thr Ile Val Tyr Leu Asp Gly Ser Ser Gln Ser
        340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
        370                 375                 380

Ser Met Cys Ile Leu Asn Gly Gly Gly Ile Arg Ser Pro Ile Asp Glu
385                 390                 395                 400

Arg Asn Asn Gly Ile His Val Val Tyr Asp Leu Ser Arg Lys Pro Gly
                    405                 410                 415

Asp Arg Val Val Lys Leu Asp Val Leu Cys Thr Lys Cys Arg Val Pro
        420                 425                 430

Ser Tyr Asp Pro Leu Lys Met Asp Glu Val Tyr Lys Val Ile Leu Pro
        435                 440                 445

Asn Phe Leu Ala Asn Gly Gly Asp Gly Phe Gln Met Ile Lys Asp Glu
        450                 455                 460

Leu Leu Arg His Asp Ser Gly Asp Gln Asp Ile Asn Val Val Ser Thr
465                 470                 475                 480

Tyr Ile Ser Lys Met Lys Val Ile Tyr Pro Ala Val Glu Gly Arg Ile
                    485                 490                 495

Lys Phe Ser Thr Gly Ser His Cys His Gly Ser Phe Ser Leu Ile Phe
        500                 505                 510

Leu Ser Leu Trp Ala Val Ile Phe Val Leu Tyr Gln
        515                 520

<210> SEQ ID NO 101
<211> LENGTH: 574
<212> TYPE: PRT
<213> ORGANISM: Macaca mulatta

<400> SEQUENCE: 101

Met Cys Pro Arg Ala Ala Arg Ala Pro Ala Thr Leu Leu Leu Ala Val
1               5                   10                  15
```

```
Gly Ala Leu Leu Trp Ser Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
                115                 120                 125

Glu Pro Leu Leu Lys Glu Ala Lys Phe Pro Ile Leu Ser Ala Asn Ile
130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
                180                 185                 190

Phe Glu Asp Glu Ile Thr Ala Leu Gln Pro Glu Val Asp Lys Leu Lys
                195                 200                 205

Thr Leu Asn Val Asn Lys Ile Ile Ala Leu Gly His Ser Gly Phe Glu
210                 215                 220

Thr Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
                260                 265                 270

Arg Lys Val Pro Val Val Gln Ala Tyr Ala Phe Gly Lys Tyr Leu Gly
                275                 280                 285

Tyr Leu Lys Ile Glu Phe Asp Glu Arg Gly Asn Val Ile Ser Ser His
290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
                340                 345                 350

Cys Arg Phe Arg Glu Cys Asn Met Gly Asn Leu Ile Cys Asp Ala Met
                355                 360                 365

Ile Asn Asn Asn Leu Arg His Ala Asp Glu Met Phe Trp Asn His Val
                370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
                420                 425                 430
```

-continued

```
Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Ile Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Phe Cys Ala Val Ile Phe Val Leu Tyr Gln
                565                 570

<210> SEQ ID NO 102
<211> LENGTH: 576
<212> TYPE: PRT
<213> ORGANISM: Mus musculus

<400> SEQUENCE: 102

Met Arg Pro Ala Ala Lys Val Pro Lys Trp Leu Leu Ala Leu
1               5                   10                  15

Ser Ala Leu Leu Pro Gln Trp Pro Ala Ala Ser Ala Trp Glu Leu Thr
            20                  25                  30

Ile Leu His Thr Asn Asp Val His Ser Arg Leu Glu Gln Thr Ser Asp
        35                  40                  45

Asp Ser Thr Lys Cys Leu Asn Ala Ser Leu Cys Val Gly Gly Val Ala
    50                  55                  60

Arg Leu Phe Thr Lys Val Gln Gln Ile Arg Lys Glu Glu Pro Asn Val
65                  70                  75                  80

Leu Phe Leu Asp Ala Gly Asp Gln Tyr Gln Gly Thr Ile Trp Phe Thr
                85                  90                  95

Val Tyr Lys Gly Leu Glu Val Ala His Phe Met Asn Ile Leu Gly Tyr
            100                 105                 110

Asp Ala Met Ala Leu Gly Asn His Glu Phe Asp Asn Gly Val Glu Gly
        115                 120                 125

Leu Ile Asp Pro Leu Leu Arg Asn Val Lys Phe Pro Ile Leu Ser Ala
    130                 135                 140

Asn Ile Lys Ala Arg Gly Pro Leu Ala His Gln Ile Ser Gly Leu Phe
145                 150                 155                 160

Leu Pro Ser Lys Val Leu Ser Val Gly Gly Glu Val Val Gly Ile Val
                165                 170                 175

Gly Tyr Thr Ser Lys Glu Thr Pro Phe Leu Ser Asn Pro Gly Thr Asn
            180                 185                 190

Leu Val Phe Glu Asp Glu Ile Ser Ala Leu Gln Pro Glu Val Asp Lys
        195                 200                 205

Leu Lys Thr Leu Asn Val Asn Lys Ile Ile Ala Leu Gly His Ser Gly
    210                 215                 220

Phe Glu Met Asp Lys Leu Ile Ala Gln Lys Val Arg Gly Val Asp Ile
225                 230                 235                 240
```

```
Val Val Gly Gly His Ser Asn Thr Phe Leu Tyr Thr Gly Asn Pro Pro
                245                 250                 255

Ser Lys Glu Val Pro Ala Gly Lys Tyr Pro Phe Ile Val Thr Ala Asp
            260                 265                 270

Asp Gly Arg Gln Val Pro Val Gln Ala Tyr Ala Phe Gly Lys Tyr
        275                 280                 285

Leu Gly Tyr Leu Lys Val Glu Phe Asp Asp Lys Gly Asn Val Ile Thr
        290                 295                 300

Ser Tyr Gly Asn Pro Ile Leu Leu Asn Ser Ser Ile Pro Glu Asp Ala
305                 310                 315                 320

Thr Ile Lys Ala Asp Ile Asn Gln Trp Arg Ile Lys Leu Asp Asn Tyr
                325                 330                 335

Ser Thr Gln Glu Leu Gly Arg Thr Ile Val Tyr Leu Asp Gly Ser Thr
            340                 345                 350

Gln Thr Cys Arg Phe Arg Glu Cys Asn Met Gly Asn Leu Ile Cys Asp
        355                 360                 365

Ala Met Ile Asn Asn Asn Leu Arg His Pro Asp Glu Met Phe Trp Asn
        370                 375                 380

His Val Ser Met Cys Ile Val Asn Gly Gly Ile Arg Ser Pro Ile
385                 390                 395                 400

Asp Glu Lys Asn Asn Gly Thr Ile Thr Trp Glu Asn Leu Ala Ala Val
                405                 410                 415

Leu Pro Phe Gly Gly Thr Phe Asp Leu Val Gln Leu Lys Gly Ser Thr
            420                 425                 430

Leu Lys Lys Ala Phe Glu His Ser Val His Arg Tyr Gly Gln Ser Thr
        435                 440                 445

Gly Glu Phe Leu Gln Val Gly Gly Ile His Val Val Tyr Asp Ile Asn
450                 455                 460

Arg Lys Pro Trp Asn Arg Val Val Gln Leu Glu Val Leu Cys Thr Lys
465                 470                 475                 480

Cys Arg Val Pro Ile Tyr Glu Pro Leu Glu Met Asp Lys Val Tyr Lys
                485                 490                 495

Val Thr Leu Pro Ser Tyr Leu Ala Asn Gly Gly Asp Gly Phe Gln Met
            500                 505                 510

Ile Lys Asp Glu Leu Leu Lys His Asp Ser Gly Asp Gln Asp Ile Ser
        515                 520                 525

Val Val Ser Glu Tyr Ile Ser Lys Met Lys Val Val Tyr Pro Ala Val
        530                 535                 540

Glu Gly Arg Ile Lys Phe Ser Ala Ala Ser His Tyr Gln Gly Ser Phe
545                 550                 555                 560

Pro Leu Val Ile Leu Ser Phe Trp Ala Met Ile Leu Ile Leu Tyr Gln
                565                 570                 575

<210> SEQ ID NO 103
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Gly Gly Gly Ser Gly Gly Gly Ser Gly Gly Gly Ser Gly
1               5                   10                  15
```

Gly Gly Gly Ser Gly
            20

<210> SEQ ID NO 104
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Gly Gly Gly Ser Gly Gly Gly Gly Ser
1               5                   10

<210> SEQ ID NO 105
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Gly Gly Gly Ser Gly Gly Gly Ser Gly Gly Gly Gly Ser
1               5                   10                  15

<210> SEQ ID NO 106
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Gly Gly Ser Gly
1               5

<210> SEQ ID NO 107
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Ser Ala Gly Ser Ala Ala Gly Ser Gly Glu Phe
1               5                   10

<210> SEQ ID NO 108
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ala Glu Ala Ala Ala Lys Glu Ala Ala Ala Lys Ala
1               5                   10

<210> SEQ ID NO 109
<211> LENGTH: 161
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
                20                  25                  30

His Ile Asn Asn Asp Met Ile Val Thr Asp Asn Asn Gly Ala Val Lys
            35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp

<210> SEQ ID NO 110
<211> LENGTH: 169
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

```
Lys Lys Lys Pro Gly Glu Thr Phe Phe Met Cys Ser Cys Ser Ser Asp
    130                 135                 140
Glu Cys Asn Asp Asn Ile Ile Phe Ser Glu Glu Tyr Asn Thr Ser Asn
145                 150                 155                 160
Pro Asp Leu Leu Leu Val Ile Phe Gln
                165

<210> SEQ ID NO 111
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Ile Pro Pro His Val Gln Lys Ser Val Asn Asn Asp Met Ile Val Thr
1               5                   10                  15
Asp Asn Asn Gly Ala Val Lys Phe Pro Gln Leu Cys Lys Phe Cys Asp
            20                  25                  30
Val Arg Phe Ser Thr Cys Asp Asn Gln Lys Ser Cys Met Ser Asn Cys
        35                  40                  45
Ser Ile Thr Ser Ile Cys Glu Lys Pro Gln Glu Val Cys Val Ala Val
    50                  55                  60
Trp Arg Lys Asn Asp Glu Asn Ile Thr Leu Glu Thr Val Cys His Asp
65                  70                  75                  80
Pro Lys Leu Pro Tyr His Asp Phe Ile Leu Glu Asp Ala Ala Ser Pro
                85                  90                  95
Lys Cys Ile Met Lys Glu Lys Lys Pro Gly Glu Thr Phe Phe Met
            100                 105                 110
Cys Ser Cys Ser Ser Asp Glu Cys Asn Asp Asn Ile Ile Phe Ser Glu
        115                 120                 125
Glu Tyr Asn Thr Ser Asn Pro Asp
    130                 135

<210> SEQ ID NO 112
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Thr Ile Pro Pro His Val Gln Lys Ser Val Asn Asn Asp Met Ile Val
1               5                   10                  15
Thr Asp Asn Asn Gly Ala Val Lys Phe Pro Gln Leu Cys Lys Phe Cys
            20                  25                  30
Asp Val Arg Phe Ser Thr Cys Asp Asn Gln Lys Ser Cys Met Ser Asn
        35                  40                  45
Cys Ser Ile Thr Ser Ile Cys Glu Lys Pro Gln Glu Val Cys Val Ala
    50                  55                  60
Val Trp Arg Lys Asn Asp Glu Asn Ile Thr Leu Glu Thr Val Cys His
65                  70                  75                  80
Asp Pro Lys Leu Pro Tyr His Asp Phe Ile Leu Glu Asp Ala Ala Ser
                85                  90                  95
```

```
Pro Lys Cys Ile Met Lys Glu Lys Lys Pro Gly Glu Thr Phe Phe
                100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Leu Leu Leu Val Ile Phe Gln
130                 135                 140

<210> SEQ ID NO 113
<211> LENGTH: 597
<212> TYPE: PRT
<213> ORGANISM: Mus musculus
<220> FEATURE:
<221> NAME/KEY: MOD_RES
<222> LOCATION: (1)..(1)
<223> OTHER INFORMATION: Glu or pyroglutamate

<400> SEQUENCE: 113

Xaa Val Lys Leu Val Glu Ser Gly Pro Glu Leu Val Lys Pro Gly Ala
1               5                  10                  15

Ser Val Lys Ile Ser Cys Lys Ala Ser Gly Tyr Ala Phe Ser Ser Ser
                20                  25                  30

Trp Ile Asn Trp Val Asn Gln Arg Pro Gly Lys Gly Leu Glu Trp Ile
            35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
                100                 105                 110

Val Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
    195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
    275                 280                 285

Thr Gln Thr His Arg Glu Asp Tyr Ala Ser Thr Leu Arg Val Val Ser
    290                 295                 300
```

```
Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
        340                 345                 350

Pro Pro Glu Glu Glu Met Thr Lys Lys Gln Val Thr Leu Thr Cys Met
    355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
            405                 410                 415

Trp Val Glu Arg Asn Ser Tyr Ser Cys Ser Val Val His Glu Gly Leu
        420                 425                 430

His Asn His His Thr Thr Lys Ser Phe Ser Arg Thr Pro Gly Gly Gly
            435                 440                 445

Gly Gly Ser Gly Gly Gly Gly Ser Gly Gly Gly Gly Ser Ile Pro Pro
450                 455                 460

His Val Gln Lys Ser Val Asn Asn Asp Met Ile Val Thr Asp Asn Asn
465                 470                 475                 480

Gly Ala Val Lys Phe Pro Gln Leu Cys Lys Phe Cys Asp Val Arg Phe
            485                 490                 495

Ser Thr Cys Asp Asn Gln Lys Ser Cys Met Ser Asn Cys Ser Ile Thr
        500                 505                 510

Ser Ile Cys Glu Lys Pro Gln Glu Val Cys Val Ala Val Trp Arg Lys
    515                 520                 525

Asn Asp Glu Asn Ile Thr Leu Glu Thr Val Cys His Asp Pro Lys Leu
530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
            565                 570                 575

Ser Ser Asp Glu Cys Asn Asp Asn Ile Ile Phe Ser Glu Glu Tyr Asn
        580                 585                 590

Thr Ser Asn Pro Asp
        595

<210> SEQ ID NO 114
<211> LENGTH: 603
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 114

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30
```

-continued

Trp Ile Asn Trp Val Arg Gln Met Pro Gly Lys Gly Leu Glu Trp Met
             35                  40                  45
Gly Arg Ile Tyr Pro Arg Asn Gly Asp Thr Asn Tyr Asn Gly Lys Phe
 50                  55                  60
Lys Asp Gln Val Thr Ile Ser Ala Asp Lys Ser Ile Ser Thr Ala Tyr
65                   70                  75                  80
Leu Gln Trp Ser Ser Leu Lys Ala Ser Asp Thr Ala Met Tyr Tyr Cys
                 85                  90                  95
Ala Ser Leu Leu Asp Tyr Ser Met Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Ala Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
            435                 440                 445

-continued

```
Gly Gly Ser Gly Gly Gly Ser Gly Gly Gly Ser Gly Gly Gly
    450                 455                 460
Gly Ser Gly Ile Pro Pro His Val Gln Lys Ser Val Asn Asn Asp Met
465                 470                 475                 480
Ile Val Thr Asp Asn Asn Gly Ala Val Lys Phe Pro Gln Leu Cys Lys
                485                 490                 495
Phe Cys Asp Val Arg Phe Ser Thr Cys Asp Asn Gln Lys Ser Cys Met
            500                 505                 510
Ser Asn Cys Ser Ile Thr Ser Ile Cys Glu Lys Pro Gln Glu Val Cys
        515                 520                 525
Val Ala Val Trp Arg Lys Asn Asp Glu Asn Ile Thr Leu Glu Thr Val
530                 535                 540
Cys His Asp Pro Lys Leu Pro Tyr His Asp Phe Ile Leu Glu Asp Ala
545                 550                 555                 560
Ala Ser Pro Lys Cys Ile Met Lys Glu Lys Lys Pro Gly Glu Thr
                565                 570                 575
Phe Phe Met Cys Ser Cys Ser Ser Asp Glu Cys Asn Asp Asn Ile Ile
                580                 585                 590
Phe Ser Glu Glu Tyr Asn Thr Ser Asn Pro Asp
            595                 600
```

<210> SEQ ID NO 115
<211> LENGTH: 603
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 115

```
Xaa Val Gln Leu Val Gln Ser Gly Ala Glu Val Lys Lys Pro Gly Glu
1               5                   10                  15
Ser Leu Lys Ile Ser Cys Lys Ala Ser Gly Tyr Ala Phe Ser Ser Ser
                20                  25                  30
Trp Ile Asn Trp Val Arg Gln Met Pro Gly Lys Gly Leu Glu Trp Met
            35                  40                  45
Gly Arg Ile Tyr Pro Arg Ala Gly Asp Thr Asn Tyr Ala Gly Lys Phe
        50                  55                  60
Lys Asp Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Ser Leu Leu Asp Tyr Ser Met Asp Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Gly Gly Gly
    450                 455                 460

Gly Ser Gly Ile Pro Pro His Val Gln Lys Ser Val Asn Asn Asp Met
465                 470                 475                 480

Ile Val Thr Asp Asn Asn Gly Ala Val Lys Phe Pro Gln Leu Cys Lys
                485                 490                 495

Phe Cys Asp Val Arg Phe Ser Thr Cys Asp Asn Gln Lys Ser Cys Met
            500                 505                 510

Ser Asn Cys Ser Ile Thr Ser Ile Cys Glu Lys Pro Gln Glu Val Cys
        515                 520                 525

Val Ala Val Trp Arg Lys Asn Asp Glu Asn Ile Thr Leu Glu Thr Val
    530                 535                 540

Cys His Asp Pro Lys Leu Pro Tyr His Asp Phe Ile Leu Glu Asp Ala
545                 550                 555                 560

Ala Ser Pro Lys Cys Ile Met Lys Glu Lys Lys Pro Gly Glu Thr
                565                 570                 575

Phe Phe Met Cys Ser Cys Ser Ser Asp Glu Cys Asn Asp Asn Ile Ile
            580                 585                 590
```

```
Phe Ser Glu Glu Tyr Asn Thr Ser Asn Pro Asp
            595                 600
```

<210> SEQ ID NO 116
<211> LENGTH: 588
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 116

```
Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Ile Pro Pro His Val Gln Lys Ser Val Asn Asn Asp
    450                 455                 460

Met Ile Val Thr Asp Asn Asn Gly Ala Val Lys Phe Pro Gln Leu Cys
465                 470                 475                 480

Lys Phe Cys Asp Val Arg Phe Ser Thr Cys Asp Asn Gln Lys Ser Cys
                485                 490                 495

Met Ser Asn Cys Ser Ile Thr Ser Ile Cys Glu Lys Pro Gln Glu Val
            500                 505                 510

Cys Val Ala Val Trp Arg Lys Asn Asp Glu Asn Ile Thr Leu Glu Thr
        515                 520                 525

Val Cys His Asp Pro Lys Leu Pro Tyr His Asp Phe Ile Leu Glu Asp
    530                 535                 540

Ala Ala Ser Pro Lys Cys Ile Met Lys Glu Lys Lys Pro Gly Glu
545                 550                 555                 560

Thr Phe Phe Met Cys Ser Cys Ser Ser Asp Glu Cys Asn Asp Asn Ile
                565                 570                 575

Ile Phe Ser Glu Glu Tyr Asn Thr Ser Asn Pro Asp
            580                 585

<210> SEQ ID NO 117
<211> LENGTH: 588
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 117

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Ala Gly Asp Thr Asn Tyr Ala Gly Lys Phe
    50                  55                  60
```

```
Lys Asp Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Ile Pro Pro His Val Gln Lys Ser Val Asn Asn Asp
    450                 455                 460

Met Ile Val Thr Asp Asn Asn Gly Ala Val Lys Phe Pro Gln Leu Cys
465                 470                 475                 480
```

-continued

```
Lys Phe Cys Asp Val Arg Phe Ser Thr Cys Asp Asn Gln Lys Ser Cys
                485                 490                 495
Met Ser Asn Cys Ser Ile Thr Ser Ile Cys Glu Lys Pro Gln Glu Val
            500                 505                 510
Cys Val Ala Val Trp Arg Lys Asn Asp Glu Asn Ile Thr Leu Glu Thr
        515                 520                 525
Val Cys His Asp Pro Lys Leu Pro Tyr His Asp Phe Ile Leu Glu Asp
    530                 535                 540
Ala Ala Ser Pro Lys Cys Ile Met Lys Glu Lys Lys Pro Gly Glu
545                 550                 555                 560
Thr Phe Phe Met Cys Ser Cys Ser Ser Asp Glu Cys Asn Asp Asn Ile
                565                 570                 575
Ile Phe Ser Glu Glu Tyr Asn Thr Ser Asn Pro Asp
                580                 585

<210> SEQ ID NO 118
<211> LENGTH: 594
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 118

Xaa Val Gln Leu Val Gln Ser Gly Ala Glu Val Lys Lys Pro Gly Glu
1               5                   10                  15
Ser Leu Lys Ile Ser Cys Lys Ala Ser Gly Tyr Ala Phe Ser Ser Ser
            20                  25                  30
Trp Ile Asn Trp Val Arg Gln Met Pro Gly Lys Gly Leu Glu Trp Met
        35                  40                  45
Gly Arg Ile Tyr Pro Arg Asn Gly Asp Thr Asn Tyr Asn Gly Lys Phe
    50                  55                  60
Lys Asp Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Ser Leu Leu Asp Tyr Ser Met Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
    210                 215                 220
```

```
Thr Cys Pro Pro Cys Pro Ala Pro Glu Leu Leu Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Ala Glu
    435                 440                 445

Ala Ala Ala Lys Glu Ala Ala Ala Lys Ala Ile Pro Pro His Val Gln
450                 455                 460

Lys Ser Val Asn Asn Asp Met Ile Val Thr Asp Asn Asn Gly Ala Val
465                 470                 475                 480

Lys Phe Pro Gln Leu Cys Lys Phe Cys Asp Val Arg Phe Ser Thr Cys
            485                 490                 495

Asp Asn Gln Lys Ser Cys Met Ser Asn Cys Ser Ile Thr Ser Ile Cys
        500                 505                 510

Glu Lys Pro Gln Glu Val Cys Val Ala Val Trp Arg Lys Asn Asp Glu
    515                 520                 525

Asn Ile Thr Leu Glu Thr Val Cys His Asp Pro Lys Leu Pro Tyr His
530                 535                 540

Asp Phe Ile Leu Glu Asp Ala Ala Ser Pro Lys Cys Ile Met Lys Glu
545                 550                 555                 560

Lys Lys Lys Pro Gly Glu Thr Phe Phe Met Cys Ser Cys Ser Ser Asp
            565                 570                 575

Glu Cys Asn Asp Asn Ile Ile Phe Ser Glu Glu Tyr Asn Thr Ser Asn
        580                 585                 590

Pro Asp

<210> SEQ ID NO 119
<211> LENGTH: 594
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 119

Xaa Val Gln Leu Val Gln Ser Gly Ala Glu Val Lys Pro Gly Glu
1               5                   10                  15

Ser Leu Lys Ile Ser Cys Lys Ala Ser Gly Tyr Ala Phe Ser Ser
                20                  25                  30

Trp Ile Asn Trp Val Arg Gln Met Pro Gly Lys Gly Leu Glu Trp Met
                35                  40                  45

Gly Arg Ile Tyr Pro Arg Ala Gly Asp Thr Asn Tyr Ala Gly Lys Phe
        50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Ala Glu
        435                 440                 445

Ala Ala Ala Lys Glu Ala Ala Lys Ala Ile Pro Pro His Val Gln
450                 455                 460

Lys Ser Val Asn Asn Asp Met Ile Val Thr Asp Asn Asn Gly Ala Val
465                 470                 475                 480

Lys Phe Pro Gln Leu Cys Lys Phe Cys Asp Val Arg Phe Ser Thr Cys
                485                 490                 495

Asp Asn Gln Lys Ser Cys Met Ser Asn Cys Ser Ile Thr Ser Ile Cys
                500                 505                 510

Glu Lys Pro Gln Glu Val Cys Val Ala Val Trp Arg Lys Asn Asp Glu
                515                 520                 525

Asn Ile Thr Leu Glu Thr Val Cys His Asp Pro Lys Leu Pro Tyr His
530                 535                 540

Asp Phe Ile Leu Glu Asp Ala Ala Ser Pro Lys Cys Ile Met Lys Glu
545                 550                 555                 560

Lys Lys Lys Pro Gly Glu Thr Phe Phe Met Cys Ser Cys Ser Ser Asp
                565                 570                 575

Glu Cys Asn Asp Asn Ile Ile Phe Ser Glu Glu Tyr Asn Thr Ser Asn
                580                 585                 590

Pro Asp

<210> SEQ ID NO 120
<211> LENGTH: 594
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 120

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

-continued

```
Ala Ser Leu Leu Asp Tyr Ser Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Ser
        435                 440                 445

Ala Gly Ser Ala Ala Gly Ser Gly Glu Phe Ile Pro Pro His Val Gln
    450                 455                 460

Lys Ser Val Asn Asn Asp Met Ile Val Thr Asp Asn Asn Gly Ala Val
465                 470                 475                 480

Lys Phe Pro Gln Leu Cys Lys Phe Cys Asp Val Arg Phe Ser Thr Cys
                485                 490                 495

Asp Asn Gln Lys Ser Cys Met Ser Asn Cys Ser Ile Thr Ser Ile Cys
            500                 505                 510
```

-continued

Glu Lys Pro Gln Glu Val Cys Val Ala Val Trp Arg Lys Asn Asp Glu
            515                 520                 525

Asn Ile Thr Leu Glu Thr Val Cys His Asp Pro Lys Leu Pro Tyr His
        530                 535                 540

Asp Phe Ile Leu Glu Asp Ala Ala Ser Pro Lys Cys Ile Met Lys Glu
545                 550                 555                 560

Lys Lys Lys Pro Gly Glu Thr Phe Phe Met Cys Ser Cys Ser Ser Asp
                565                 570                 575

Glu Cys Asn Asp Asn Ile Ile Phe Ser Glu Glu Tyr Asn Thr Ser Asn
                580                 585                 590

Pro Asp

<210> SEQ ID NO 121
<211> LENGTH: 594
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 121

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
                20                  25                  30

Trp Ile Asn Trp Val Arg Gln Met Pro Gly Lys Gly Leu Glu Trp Met
            35                  40                  45

Gly Arg Ile Tyr Pro Arg Ala Gly Asp Thr Asn Tyr Ala Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

```
Phe Leu Phe Pro Pro Lys Pro Lys Asp Thr Leu Met Ile Ser Arg Thr
                245                 250                 255
Pro Glu Val Thr Cys Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Ala Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Ser
            435                 440                 445
Ala Gly Ser Ala Ala Gly Ser Gly Glu Phe Ile Pro Pro His Val Gln
    450                 455                 460
Lys Ser Val Asn Asn Asp Met Ile Val Thr Asp Asn Asn Gly Ala Val
465                 470                 475                 480
Lys Phe Pro Gln Leu Cys Lys Phe Cys Asp Val Arg Phe Ser Thr Cys
                485                 490                 495
Asp Asn Gln Lys Ser Cys Met Ser Asn Cys Ser Ile Thr Ser Ile Cys
            500                 505                 510
Glu Lys Pro Gln Glu Val Cys Val Ala Val Trp Arg Lys Asn Asp Glu
            515                 520                 525
Asn Ile Thr Leu Glu Thr Val Cys His Asp Pro Lys Leu Pro Tyr His
    530                 535                 540
Asp Phe Ile Leu Glu Asp Ala Ala Ser Pro Lys Cys Ile Met Lys Glu
545                 550                 555                 560
Lys Lys Lys Pro Gly Glu Thr Phe Phe Met Cys Ser Cys Ser Ser Asp
                565                 570                 575
Glu Cys Asn Asp Asn Ile Ile Phe Ser Glu Glu Tyr Asn Thr Ser Asn
            580                 585                 590
Pro Asp

<210> SEQ ID NO 122
<211> LENGTH: 100
<212> TYPE: PRT
<213> ORGANISM: Homo sapiens

<400> SEQUENCE: 122

Ser Asp Thr Gly Arg Pro Phe Val Glu Met Tyr Ser Glu Ile Pro Glu
1               5                   10                  15
```

```
Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr
            100
```

<210> SEQ ID NO 123
<211> LENGTH: 556
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 123

```
Xaa Val Lys Leu Val Glu Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile Asn Trp Val Asn Gln Arg Pro Gly Lys Gly Leu Glu Trp Ile
        35                  40                  45

Gly Arg Ile Tyr Pro Arg Asn Gly Asp Thr Asn Tyr Asn Gly Lys Phe
    50                  55                  60

Lys Asp Arg Ala Thr Leu Thr Ala Asp Arg Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Ser Leu Leu Asp Tyr Ser Met Asp Tyr Trp Gly Gln Gly Thr Ser
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240
```

```
Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Ala Ser Thr Leu Arg Val Val Ser
        290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Gly Gly
        435                 440                 445

Gly Gly Ser Gly Gly Gly Ser Ser Asp Thr Gly Arg Pro Phe Val
450                 455                 460

Glu Met Tyr Ser Glu Ile Pro Glu Ile Ile His Met Thr Glu Gly Arg
465                 470                 475                 480

Glu Leu Val Ile Pro Cys Arg Val Thr Ser Pro Asn Ile Thr Val Thr
                485                 490                 495

Leu Lys Lys Phe Pro Leu Asp Thr Leu Ile Pro Asp Gly Lys Arg Ile
            500                 505                 510

Ile Trp Asp Ser Arg Lys Gly Phe Ile Ile Ser Asn Ala Thr Tyr Lys
        515                 520                 525

Glu Ile Gly Leu Leu Thr Cys Glu Ala Thr Val Asn Gly His Leu Tyr
530                 535                 540

Lys Thr Asn Tyr Leu Thr His Arg Gln Thr Asn Thr
545                 550                 555

<210> SEQ ID NO 124
<211> LENGTH: 556
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 124

Xaa Val Gln Leu Val Gln Ser Gly Ala Glu Val Lys Lys Pro Gly Glu
1               5                   10                  15
```

```
Ser Leu Lys Ile Ser Cys Lys Ala Ser Gly Tyr Ala Phe Ser Ser
                20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Ala Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430
```

His Asn His His Thr Thr Lys Ser Phe Ser Arg Thr Pro Gly Gly
        435                 440                 445

Gly Gly Ser Gly Gly Gly Ser Ser Asp Thr Gly Arg Pro Phe Val
    450                 455                 460

Glu Met Tyr Ser Glu Ile Pro Glu Ile Ile His Met Thr Glu Gly Arg
465                 470                 475                 480

Glu Leu Val Ile Pro Cys Arg Val Thr Ser Pro Asn Ile Thr Val Thr
                485                 490                 495

Leu Lys Lys Phe Pro Leu Asp Thr Leu Ile Pro Asp Gly Lys Arg Ile
                500                 505                 510

Ile Trp Asp Ser Arg Lys Gly Phe Ile Ile Ser Asn Ala Thr Tyr Lys
                515                 520                 525

Glu Ile Gly Leu Leu Thr Cys Glu Ala Thr Val Asn Gly His Leu Tyr
                530                 535                 540

Lys Thr Asn Tyr Leu Thr His Arg Gln Thr Asn Thr
545                 550                 555

<210> SEQ ID NO 125
<211> LENGTH: 556
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 125

Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
                20                  25                  30

Trp Ile Asn Trp Val Arg Gln Met Pro Gly Lys Gly Leu Glu Trp Met
            35                  40                  45

Gly Arg Ile Tyr Pro Arg Ala Gly Asp Thr Asn Tyr Ala Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
                100                 105                 110

Val Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
                180                 185                 190

Pro Ser Gln Ser Ile Thr Cys Asn Val Ala His Pro Ala Ser Ser Thr
            195                 200                 205

-continued

```
Lys Val Asp Lys Lys Ile Glu Pro Arg Gly Pro Thr Ile Lys Pro Cys
    210                 215                 220
Pro Pro Cys Lys Cys Pro Ala Pro Asn Leu Leu Gly Gly Pro Ser Val
225                 230                 235                 240
Phe Ile Phe Pro Pro Lys Ile Lys Asp Val Leu Met Ile Ser Leu Ser
                245                 250                 255
Pro Ile Val Thr Cys Val Val Val Asp Val Ser Glu Asp Asp Pro Asp
                260                 265                 270
Val Gln Ile Ser Trp Phe Val Asn Asn Val Glu Val His Thr Ala Gln
                275                 280                 285
Thr Gln Thr His Arg Glu Asp Tyr Ala Ser Thr Leu Arg Val Val Ser
    290                 295                 300
Ala Leu Pro Ile Gln His Gln Asp Trp Met Ser Gly Lys Glu Phe Lys
305                 310                 315                 320
Cys Lys Val Asn Asn Lys Asp Leu Pro Ala Pro Ile Glu Arg Thr Ile
                325                 330                 335
Ser Lys Pro Lys Gly Ser Val Arg Ala Pro Gln Val Tyr Val Leu Pro
                340                 345                 350
Pro Pro Glu Glu Glu Met Thr Lys Lys Gln Val Thr Leu Thr Cys Met
                355                 360                 365
Val Thr Asp Phe Met Pro Glu Asp Ile Tyr Val Glu Trp Thr Asn Asn
370                 375                 380
Gly Lys Thr Glu Leu Asn Tyr Lys Asn Thr Glu Pro Val Leu Asp Ser
385                 390                 395                 400
Asp Gly Ser Tyr Phe Met Tyr Ser Lys Leu Arg Val Glu Lys Lys Asn
                405                 410                 415
Trp Val Glu Arg Asn Ser Tyr Ser Cys Ser Val Val His Glu Gly Leu
                420                 425                 430
His Asn His His Thr Thr Lys Ser Phe Ser Arg Thr Pro Gly Gly Gly
                435                 440                 445
Gly Gly Ser Gly Gly Gly Gly Ser Ser Asp Thr Gly Arg Pro Phe Val
    450                 455                 460
Glu Met Tyr Ser Glu Ile Pro Glu Ile Ile His Met Thr Glu Gly Arg
465                 470                 475                 480
Glu Leu Val Ile Pro Cys Arg Val Thr Ser Pro Asn Ile Thr Val Thr
                485                 490                 495
Leu Lys Lys Phe Pro Leu Asp Thr Leu Ile Pro Asp Gly Lys Arg Ile
                500                 505                 510
Ile Trp Asp Ser Arg Lys Gly Phe Ile Ile Ser Asn Ala Thr Tyr Lys
                515                 520                 525
Glu Ile Gly Leu Leu Thr Cys Glu Ala Thr Val Asn Gly His Leu Tyr
                530                 535                 540
Lys Thr Asn Tyr Leu Thr His Arg Gln Thr Asn Thr
545                 550                 555
```

<210> SEQ ID NO 126
<211> LENGTH: 556
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MOD_RES
<222> LOCATION: (1)..(1)

<223> OTHER INFORMATION: Glu or pyroglutamate

<400> SEQUENCE: 126

```
Xaa Val Gln Leu Val Gln Ser Gly Ala Glu Val Lys Lys Pro Gly Glu
1               5                   10                  15

Ser Leu Lys Ile Ser Cys Lys Ala Ser Gly Tyr Ala Phe Ser Ser Ser
            20                  25                  30

Trp Ile Asn Trp Val Arg Gln Met Pro Gly Lys Gly Leu Glu Trp Met
        35                  40                  45

Gly Arg Ile Tyr Pro Arg Asn Gly Asp Thr Asn Tyr Asn Gly Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Leu Leu Asp Tyr Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
        435                 440                 445
Gly Gly Ser Gly Gly Gly Ser Ser Asp Thr Gly Arg Pro Phe Val
    450                 455                 460
Glu Met Tyr Ser Glu Ile Pro Glu Ile Ile His Met Thr Glu Gly Arg
465                 470                 475                 480
Glu Leu Val Ile Pro Cys Arg Val Thr Ser Pro Asn Ile Thr Val Thr
                485                 490                 495
Leu Lys Lys Phe Pro Leu Asp Thr Leu Ile Pro Asp Gly Lys Arg Ile
                500                 505                 510
Ile Trp Asp Ser Arg Lys Gly Phe Ile Ile Ser Asn Ala Thr Tyr Lys
            515                 520                 525
Glu Ile Gly Leu Leu Thr Cys Glu Ala Thr Val Asn Gly His Leu Tyr
        530                 535                 540
Lys Thr Asn Tyr Leu Thr His Arg Gln Thr Asn Thr
545                 550                 555

<210> SEQ ID NO 127
<211> LENGTH: 556
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Glu or pyroglutamate

<400> SEQUENCE: 127

Xaa Val Gln Leu Val Gln Ser Gly Ala Glu Val Lys Lys Pro Gly Glu
1               5                   10                  15
Ser Leu Lys Ile Ser Cys Lys Ala Ser Gly Tyr Ala Phe Ser Ser Ser
            20                  25                  30
Trp Ile Asn Trp Val Arg Gln Met Pro Gly Lys Gly Leu Glu Trp Met
        35                  40                  45
Gly Arg Ile Tyr Pro Arg Ala Gly Asp Thr Asn Tyr Ala Gly Lys Phe
    50                  55                  60
Lys Asp Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Ser Leu Leu Asp Tyr Ser Met Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Ser Asp Thr Gly Arg Pro Phe Val
    450                 455                 460

Glu Met Tyr Ser Glu Ile Pro Glu Ile Ile His Met Thr Glu Gly Arg
465                 470                 475                 480

Glu Leu Val Ile Pro Cys Arg Val Thr Ser Pro Asn Ile Thr Val Thr
                485                 490                 495

Leu Lys Lys Phe Pro Leu Asp Thr Leu Ile Pro Asp Gly Lys Arg Ile
            500                 505                 510

Ile Trp Asp Ser Arg Lys Gly Phe Ile Ile Ser Asn Ala Thr Tyr Lys
        515                 520                 525

Glu Ile Gly Leu Leu Thr Cys Glu Ala Thr Val Asn Gly His Leu Tyr
    530                 535                 540

Lys Thr Asn Tyr Leu Thr His Arg Gln Thr Asn Thr
545                 550                 555

<210> SEQ ID NO 128
<211> LENGTH: 214
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 129
<211> LENGTH: 574
<212> TYPE: PRT
<213> ORGANISM: Homo sapiens

<400> SEQUENCE: 129

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

```
Glu Pro Leu Leu Lys Glu Ala Lys Phe Pro Ile Leu Ser Ala Asn Ile
130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Ala Asp Glu Thr Phe Trp Asn His Val
370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
530                 535                 540
```

```
Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570
```

<210> SEQ ID NO 130
<211> LENGTH: 524
<212> TYPE: PRT
<213> ORGANISM: Homo sapiens

<400> SEQUENCE: 130

```
Met Cys Pro Arg Ala Ala Arg Ala Pro Ala Thr Leu Leu Ala Leu
1               5                   10                  15

Gly Ala Val Leu Trp Pro Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
                115                 120                 125

Glu Pro Leu Leu Lys Glu Ala Lys Phe Pro Ile Leu Ser Ala Asn Ile
                130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
                180                 185                 190

Phe Glu Asp Glu Ile Thr Ala Leu Gln Pro Glu Val Asp Lys Leu Lys
                195                 200                 205

Thr Leu Asn Val Asn Lys Ile Ile Ala Leu Gly His Ser Gly Phe Glu
                210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
                260                 265                 270

Arg Lys Val Pro Val Val Gln Ala Tyr Ala Phe Gly Lys Tyr Leu Gly
                275                 280                 285

Tyr Leu Lys Ile Glu Phe Asp Glu Arg Gly Asn Val Ile Ser Ser His
                290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335
```

```
Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
            355                 360                 365

Ile Asn Asn Leu Arg His Ala Asp Glu Met Phe Trp Asn His Val
            370                 375                 380

Ser Met Cys Ile Leu Asn Gly Gly Ile Arg Ser Pro Ile Asp Glu
385                 390                 395                 400

Arg Asn Asn Gly Ile His Val Val Tyr Asp Leu Ser Arg Lys Pro Gly
            405                 410                 415

Asp Arg Val Val Lys Leu Asp Val Leu Cys Thr Lys Cys Arg Val Pro
            420                 425                 430

Ser Tyr Asp Pro Leu Lys Met Asp Glu Val Tyr Lys Val Ile Leu Pro
            435                 440                 445

Asn Phe Leu Ala Asn Gly Gly Asp Gly Phe Gln Met Ile Lys Asp Glu
            450                 455                 460

Leu Leu Arg His Asp Ser Gly Asp Gln Asp Ile Asn Val Val Ser Thr
465                 470                 475                 480

Tyr Ile Ser Lys Met Lys Val Ile Tyr Pro Ala Val Glu Gly Arg Ile
            485                 490                 495

Lys Phe Ser Thr Gly Ser His Cys His Gly Ser Phe Ser Leu Ile Phe
            500                 505                 510

Leu Ser Leu Trp Ala Val Ile Phe Val Leu Tyr Gln
            515                 520

<210> SEQ ID NO 131
<211> LENGTH: 574
<212> TYPE: PRT
<213> ORGANISM: Macaca fascicularis

<400> SEQUENCE: 131

Met Cys Pro Arg Ala Ala Arg Ala Pro Ala Lys Leu Leu Leu Ala Val
1               5                   10                  15

Gly Ala Leu Leu Trp Ser Ala Ala Gly Ala Trp Glu Leu Thr Ile Leu
            20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
            85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
            130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
            165                 170                 175
```

```
Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
        210                 215                 220

Thr Asp Lys Leu Ile Ala Gln Lys Val Arg Gly Val Asp Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
        290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Ala Asp Glu Met Phe Trp Asn His Val
        370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
        450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Ile Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
        530                 535                 540

Arg Ile Lys Phe Ser Thr Gly Ser His Cys His Gly Ser Phe Ser Leu
545                 550                 555                 560

Ile Phe Leu Ser Phe Cys Ala Val Ile Phe Val Leu Tyr Gln
                565                 570

<210> SEQ ID NO 132
<211> LENGTH: 553
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 132

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ala Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365
```

```
Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
        515                 520                 525

Leu Glu His His His His His His His His His Gly Gly Ser Gly
530                 535                 540

Gly Leu Pro Glu Thr Gly Gly Asp Arg
545                 550

<210> SEQ ID NO 133
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Ala Leu Pro Ala Lys Val Leu Ala Val Gly Ala Glu Val
    130                 135                 140

Val Gly Ile Val Gly Tyr Thr Ser Lys Glu Thr Pro Phe Leu Ser Asn
145                 150                 155                 160
```

```
Pro Gly Thr Asn Leu Val Phe Glu Asp Glu Ile Thr Ala Leu Gln Pro
            165                 170                 175

Glu Val Asp Lys Leu Lys Thr Leu Asn Val Asn Lys Ile Ile Ala Leu
        180                 185                 190

Gly His Ser Gly Phe Glu Met Asp Lys Leu Ile Ala Gln Lys Val Arg
    195                 200                 205

Gly Val Asp Val Val Gly Gly His Ser Asn Thr Phe Leu Tyr Thr
210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Gln Ala Tyr Ala
            245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
        290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Leu Arg His Thr Asp Glu
            340                 345                 350

Met Phe Trp Asn His Val Ser Met Cys Ile Leu Asn Gly Gly Gly Ile
            355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
            405                 410                 415

Gly Gln Ser Thr Gly Glu Phe Leu Gln Val Gly Gly Ile His Val Val
        420                 425                 430

Tyr Asp Leu Ser Arg Lys Pro Gly Asp Arg Val Val Lys Leu Asp Val
    435                 440                 445

Leu Cys Thr Lys Cys Arg Val Pro Ser Tyr Asp Pro Leu Lys Met Asp
        450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
530                 535                 540

Gly Leu Pro Glu Thr Gly Gly Asp Arg
545                 550

<210> SEQ ID NO 134
<211> LENGTH: 553
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Asp Ala Gly Asp Gln Tyr Gln Gly Thr
 50                  55                  60

Ile Trp Phe Thr Val Tyr Lys Gly Ala Glu Val Ala His Phe Met Asn
 65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Phe Leu Pro Ser Lys Val Leu Ser Val Gly Gly Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380
```

```
Leu Ala Ala Val Leu Pro Phe Gly Gly Thr Phe Asp Leu Val Gln Leu
385                 390                 395                 400

Lys Gly Ser Thr Leu Lys Ala Phe Glu His Ser Val His Arg Tyr
            405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
                435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
                500                 505                 510

Tyr Pro Ala Val Glu Gly Arg Ile Lys Glu Asn Leu Tyr Phe Gln Gly
            515                 520                 525

Leu Glu His His His His His His His His His Gly Gly Ser Gly
            530                 535                 540

Gly Leu Pro Glu Thr Gly Gly Asp Arg
545                 550

<210> SEQ ID NO 135
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala His Gln Ile
        115                 120                 125

Ser Gly Leu Phe Leu Pro Ser Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175
```

```
Glu Val Asp Lys Leu Lys Thr Leu Asn Val Asn Lys Ile Ile Ala Leu
                180                 185                 190
Gly His Ser Gly Phe Glu Met Asp Lys Leu Ile Ala Gln Lys Val Arg
            195                 200                 205
Gly Val Asp Val Val Gly Gly His Ser Asn Thr Phe Leu Tyr Thr
        210                 215                 220
Gly Asn Pro Pro Ser Lys Glu Val Pro Ala Gly Lys Tyr Pro Phe Ile
225                 230                 235                 240
Val Thr Ser Asp Asp Gly Arg Lys Val Pro Val Gln Ala Tyr Ala
                245                 250                 255
Phe Gly Lys Tyr Leu Gly Tyr Leu Lys Ile Glu Phe Asp Glu Arg Gly
            260                 265                 270
Asn Val Ile Ser Ser His Gly Asn Pro Ile Leu Leu Asn Ser Ser Ile
                275                 280                 285
Pro Glu Asp Pro Ser Ile Lys Ala Asp Ile Asn Lys Trp Arg Ile Lys
            290                 295                 300
Leu Asp Asn Tyr Ser Thr Gln Glu Leu Gly Lys Thr Ile Val Tyr Leu
305                 310                 315                 320
Asp Gly Ser Ser Gln Ser Cys Arg Phe Arg Glu Cys Asn Met Gly Asn
                325                 330                 335
Leu Ile Cys Asp Ala Met Ile Asn Asn Asn Leu Arg His Thr Asp Glu
                340                 345                 350
Met Phe Trp Asn His Val Ser Met Cys Ile Leu Asn Gly Gly Ile
            355                 360                 365
Arg Ser Pro Ile Asp Glu Arg Asn Asn Gly Thr Ile Thr Trp Glu Asn
370                 375                 380
Leu Ala Ala Val Leu Pro Phe Gly Gly Thr Phe Asp Leu Val Gln Leu
385                 390                 395                 400
Lys Gly Ser Thr Leu Lys Lys Ala Phe Glu His Ser Val His Arg Tyr
            405                 410                 415
Gly Gln Ser Thr Gly Glu Phe Leu Gln Val Gly Gly Ile His Val Val
                420                 425                 430
Tyr Asp Leu Ser Arg Lys Pro Gly Asp Arg Val Val Lys Leu Asp Val
            435                 440                 445
Leu Cys Thr Lys Cys Arg Val Pro Ser Tyr Asp Pro Leu Lys Met Asp
            450                 455                 460
Glu Val Tyr Lys Val Ile Leu Pro Asn Phe Leu Ala Asn Gly Gly Asp
465                 470                 475                 480
Gly Phe Gln Met Ile Lys Asp Glu Leu Leu Arg His Asp Ser Gly Asp
                485                 490                 495
Gln Asp Ile Asn Val Val Ser Thr Tyr Ile Ser Lys Met Lys Val Ile
                500                 505                 510
Tyr Pro Ala Val Glu Gly Arg Ile Lys Glu Asn Leu Tyr Phe Gln Gly
            515                 520                 525
Leu Glu His His His His His His His His Gly Gly Ser Gly
            530                 535                 540
Gly Leu Pro Glu Thr Gly Gly Asp Arg
545                 550

<210> SEQ ID NO 136
<211> LENGTH: 553
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 136

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Ser Val Gly Gly Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400
```

-continued

```
Lys Gly Ser Thr Leu Lys Lys Ala Phe Glu His Ser Val His Arg Tyr
            405                 410                 415

Gly Gln Ser Thr Gly Glu Phe Leu Gln Val Gly Ile His Val Val
            420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
            450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
            485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
            530                 535                 540

Gly Leu Pro Glu Thr Gly Gly Asp Arg
545                 550
```

```
<210> SEQ ID NO 137
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Trp Glu Leu Thr Ile Leu His Thr Asn Asp Val His Ser Arg Leu Glu
1               5                   10                  15

Gln Thr Ser Asp Asp Ser Thr Lys Cys Leu Asn Ala Ser Leu Cys Val
            20                  25                  30

Gly Gly Val Ala Arg Leu Phe Thr Lys Val Gln Gln Ile Arg Lys Glu
            35                  40                  45

Glu Pro Asn Val Leu Phe Leu Asp Ala Gly Asp Gln Tyr Gln Gly Thr
            50                  55                  60

Ile Trp Phe Thr Val Tyr Lys Gly Leu Glu Val Ala His Phe Met Asn
65                  70                  75                  80

Ala Leu Arg Tyr Asp Ala Met Ala Leu Gly Asn His Glu Phe Asp Asn
            85                  90                  95

Gly Val Glu Gly Leu Ile Asp Pro Leu Leu Arg Asn Val Lys Phe Pro
            100                 105                 110

Ile Leu Ser Ala Asn Ile Lys Ala Arg Gly Pro Leu Ala Ser Gln Ile
            115                 120                 125

Ser Gly Leu Tyr Leu Pro Tyr Lys Val Leu Pro Val Gly Asp Glu Val
            130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
            165                 170                 175

Glu Val Asp Lys Leu Lys Thr Leu Asn Val Asn Lys Ile Ile Ala Leu
            180                 185                 190
```

```
Gly His Ser Gly Phe Glu Met Asp Lys Leu Ile Ala Gln Lys Val Arg
            195                 200                 205

Gly Val Asp Ile Val Val Gly Gly His Ser Asn Thr Phe Leu Tyr Thr
            210                 215                 220

Gly Asn Pro Pro Ser Lys Glu Val Pro Ala Gly Lys Tyr Pro Phe Ile
225                 230                 235                 240

Val Thr Ala Asp Asp Gly Arg Gln Val Pro Val Gln Ala Tyr Ala
                245                 250                 255

Phe Gly Lys Tyr Leu Gly Tyr Leu Lys Val Glu Phe Asp Glu Arg Gly
            260                 265                 270

Asn Val Ile Thr Ser Tyr Gly Asn Pro Ile Leu Leu Asn Ser Ser Ile
            275                 280                 285

Pro Glu Asp Ala Thr Ile Lys Ala Asp Ile Asn Gln Trp Arg Ile Lys
            290                 295                 300

Leu Asp Asn Tyr Ser Thr Gln Glu Leu Gly Arg Thr Ile Val Tyr Leu
305                 310                 315                 320

Asp Gly Ser Thr Gln Thr Cys Arg Phe Arg Glu Cys Asn Met Gly Asn
                325                 330                 335

Leu Ile Cys Asp Ala Met Ile Asn Asn Asn Leu Arg His Pro Asp Glu
            340                 345                 350

Met Phe Trp Asn His Val Ser Met Cys Ile Val Asn Gly Gly Gly Ile
            355                 360                 365

Arg Ser Pro Ile Asp Glu Lys Asn Asn Gly Thr Ile Thr Trp Glu Asn
            370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Ile His Val Val
            420                 425                 430

Tyr Asp Ile Asn Arg Lys Pro Trp Asn Arg Val Val Gln Leu Glu Val
            435                 440                 445

Leu Cys Thr Lys Cys Arg Val Pro Ile Tyr Glu Pro Leu Glu Met Asp
450                 455                 460

Lys Val Tyr Lys Val Thr Leu Pro Ser Tyr Leu Ala Asn Gly Gly Asp
465                 470                 475                 480

Gly Phe Gln Met Ile Lys Asp Glu Leu Leu Lys His Asp Ser Gly Asp
                485                 490                 495

Gln Asp Ile Ser Val Val Ser Tyr Ile Ser Lys Met Lys Val Val
            500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
            530                 535                 540

Gly Leu Pro Glu Thr Gly Gly Asp Arg
545                 550

<210> SEQ ID NO 138
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 138

Trp Glu Leu Thr Ile Leu His Thr Asn Asp Val His Ser Arg Leu Glu
1               5                   10                  15

Gln Thr Ser Asp Asp Ser Thr Lys Cys Leu Asn Ala Ser Leu Cys Val
            20                  25                  30

Gly Gly Val Ala Arg Leu Phe Thr Lys Val Gln Gln Ile Arg Lys Glu
        35                  40                  45

Glu Pro Asn Val Leu Phe Leu Asp Ala Gly Asp Gln Tyr Gln Gly Thr
    50                  55                  60

Ile Trp Phe Thr Val Tyr Lys Gly Leu Glu Val Ala His Phe Met Asn
65                  70                  75                  80

Ile Leu Gly Tyr Asp Ala Met Ala Leu Gly Asn His Glu Phe Asp Asn
                85                  90                  95

Gly Val Glu Gly Leu Ile Asp Pro Leu Leu Arg Asn Val Lys Phe Pro
            100                 105                 110

Ile Leu Ser Ala Asn Ile Lys Ala Arg Gly Pro Leu Ala His Gln Ile
        115                 120                 125

Ser Gly Leu Phe Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Ser Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Ile Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ala Asp Asp Gly Arg Gln Val Pro Val Val Gln Ala Tyr Ala
                245                 250                 255

Phe Gly Lys Tyr Leu Gly Tyr Leu Lys Val Glu Phe Asp Asp Lys Gly
            260                 265                 270

Asn Val Ile Thr Ser Tyr Gly Asn Pro Ile Leu Leu Asn Ser Ser Ile
        275                 280                 285

Pro Glu Asp Ala Thr Ile Lys Ala Asp Ile Asn Gln Trp Arg Ile Lys
    290                 295                 300

Leu Asp Asn Tyr Ser Thr Gln Glu Leu Gly Arg Thr Ile Val Tyr Leu
305                 310                 315                 320

Asp Gly Ser Thr Gln Thr Cys Arg Phe Arg Glu Cys Asn Met Gly Asn
                325                 330                 335

Leu Ile Cys Asp Ala Met Ile Asn Asn Asn Leu Arg His Pro Asp Glu
            340                 345                 350

Met Phe Trp Asn His Val Ser Met Cys Ile Val Asn Gly Gly Gly Ile
        355                 360                 365

Arg Ser Pro Ile Asp Glu Lys Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415
```

```
Gly Gln Ser Thr Gly Glu Phe Leu Gln Val Gly Ile His Val Val
                420                 425                 430

Tyr Asp Ile Asn Arg Lys Pro Trp Asn Arg Val Val Gln Leu Glu Val
                435                 440                 445

Leu Cys Thr Lys Cys Arg Val Pro Ile Tyr Glu Pro Leu Glu Met Asp
            450                 455                 460

Lys Val Tyr Lys Val Thr Leu Pro Ser Tyr Leu Ala Asn Gly Gly Asp
465                 470                 475                 480

Gly Phe Gln Met Ile Lys Asp Glu Leu Leu Lys His Asp Ser Gly Asp
                485                 490                 495

Gln Asp Ile Ser Val Val Ser Glu Tyr Ile Ser Lys Met Lys Val Val
                500                 505                 510

Tyr Pro Ala Val Glu Gly Arg Ile Lys Glu Asn Leu Tyr Phe Gln Gly
            515                 520                 525

Leu Glu His His His His His His His His His Gly Gly Ser Gly
            530                 535                 540

Gly Leu Pro Glu Thr Gly Gly Asp Arg
545                 550

<210> SEQ ID NO 139
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
                20                  25                  30

Gly Gly Val Ala Arg Leu Phe Thr Lys Val Gln Gln Ile Arg Arg Ala
            35                  40                  45

Glu Pro Asn Val Leu Leu Leu Asp Ala Gly Asp Gln Tyr Gln Gly Thr
        50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Ala Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205
```

Gly Val Asp Val Val Gly Gly His Ser Asn Thr Phe Leu Tyr Thr
210             215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
            485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
530                 535                 540

Gly Leu Pro Glu Thr Gly Gly Asp Arg
545                 550

<210> SEQ ID NO 140
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 140

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Ala Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400
```

```
Lys Gly Ser Thr Leu Lys Lys Ala Phe Glu His Ser Val His Arg Tyr
            405                 410                 415

Gly Gln Ser Thr Gly Glu Phe Leu Gln Val Gly Ile His Val Val
            420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
            450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
                500                 505                 510

Tyr Pro Ala Val Glu Gly Arg Ile Lys Glu Asn Leu Tyr Phe Gln Gly
                515                 520                 525

Leu Glu His His His His His His His His Gly Gly Ser Gly
            530                 535                 540

Gly Leu Pro Glu Thr Gly Gly Asp Arg
545                 550
```

<210> SEQ ID NO 141
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190
```

```
Gly His Ser Gly Phe Glu Met Asp Lys Leu Ile Ala Gln Lys Val Arg
        195                 200                 205

Gly Val Asp Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
        290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
        370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
        530                 535                 540

Gly Leu Pro Glu Thr Gly Gly Asp Arg
545                 550
```

<210> SEQ ID NO 142
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

```
<400> SEQUENCE: 142

Trp Glu Leu Thr Ile Leu His Thr Asn Asp Val His Ser Arg Leu Glu
1               5                   10                  15

Gln Thr Ser Asp Asp Ser Thr Lys Cys Leu Asn Ala Ser Leu Cys Val
            20                  25                  30

Gly Gly Val Ala Arg Leu Phe Thr Lys Val Gln Gln Ile Arg Lys Glu
        35                  40                  45

Glu Pro Asn Val Leu Phe Leu Asp Ala Gly Asp Gln Tyr Gln Gly Thr
    50                  55                  60

Ile Trp Phe Thr Val Tyr Lys Gly Leu Glu Val Ala His Phe Met Asn
65                  70                  75                  80

Ile Leu Gly Tyr Asp Ala Met Ala Leu Gly Asn His Glu Phe Asp Asn
                85                  90                  95

Gly Val Glu Gly Leu Ile Asp Pro Leu Leu Arg Asn Val Lys Phe Pro
            100                 105                 110

Ile Leu Ser Ala Asn Ile Lys Ala Arg Gly Pro Leu Ala His Gln Ile
        115                 120                 125

Ser Gly Leu Phe Leu Pro Ser Lys Val Leu Ser Val Gly Gly Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Ser Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Ile Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ala Asp Asp Gly Arg Gln Val Pro Val Val Gln Ala Tyr Ala
                245                 250                 255

Phe Gly Lys Tyr Leu Gly Tyr Leu Lys Val Glu Phe Asp Asp Lys Gly
            260                 265                 270

Asn Val Ile Thr Ser Tyr Gly Asn Pro Ile Leu Leu Asn Ser Ser Ile
        275                 280                 285

Pro Glu Asp Ala Thr Ile Lys Ala Asp Ile Asn Gln Trp Arg Ile Lys
    290                 295                 300

Leu Asp Asn Tyr Ser Thr Gln Glu Leu Gly Arg Thr Ile Val Tyr Leu
305                 310                 315                 320

Asp Gly Ser Thr Gln Thr Cys Arg Phe Arg Glu Cys Asn Met Gly Asn
                325                 330                 335

Leu Ile Cys Asp Ala Met Ile Asn Asn Asn Leu Arg His Pro Asp Glu
            340                 345                 350

Met Phe Trp Asn His Val Ser Met Cys Ile Val Asn Gly Gly Gly Ile
        355                 360                 365

Arg Ser Pro Ile Asp Glu Lys Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415
```

-continued

```
Gly Gln Ser Thr Gly Glu Phe Leu Gln Val Gly Ile His Val Val
            420                 425                 430

Tyr Asp Ile Asn Arg Lys Pro Trp Asn Arg Val Val Gln Leu Glu Val
                435                 440                 445

Leu Cys Thr Lys Cys Arg Val Pro Ile Tyr Glu Pro Leu Glu Met Asp
    450                 455                 460

Lys Val Tyr Lys Val Thr Leu Pro Ser Tyr Leu Ala Asn Gly Asp
465                 470                 475                 480

Gly Phe Gln Met Ile Lys Asp Glu Leu Leu Lys His Asp Ser Gly Asp
                485                 490                 495

Gln Asp Ile Ser Val Val Ser Glu Tyr Ile Ser Lys Met Lys Val Val
                500                 505                 510

Tyr Pro Ala Val Glu Gly Arg Ile Lys Glu Asn Leu Tyr Phe Gln Gly
            515                 520                 525

Leu Glu His His His His His His His His Gly Gly Ser Gly
    530                 535                 540

Gly Leu Pro Glu Thr Gly Gly Asp Arg
545                 550

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gly Tyr Ala Phe Ser Ser Ser Trp
1               5

<210> SEQ ID NO 144
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Ile Tyr Pro Arg Ala Gly Asp Thr
1               5

<210> SEQ ID NO 145
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ala Ser Leu Leu Asp Tyr Ser Met Asp Tyr
1               5                   10

<210> SEQ ID NO 146
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 146

Gln Asp Ile Ser Asn Tyr
1               5

<210> SEQ ID NO 147
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Tyr Thr Ser
1

<210> SEQ ID NO 148
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gly Tyr Ala Phe Ser Ser Ser
1               5

<210> SEQ ID NO 149
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Tyr Pro Arg Ala Gly Asp
1               5

<210> SEQ ID NO 150
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ala Ser Gly Tyr Ala Phe Ser Ser Ser Trp
1               5                   10

<210> SEQ ID NO 151
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 151

Ile Tyr Pro Arg Ala Gly Asp Thr Asn Tyr Ala Gly Lys Phe Lys Asp
1               5                   10                  15

Gln

<210> SEQ ID NO 152
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Leu Leu Asp Tyr Ser Met Asp
1               5

<210> SEQ ID NO 153
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Ala Ser Gln Asp Ile Ser Asn Tyr
1               5

<210> SEQ ID NO 154
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Tyr Thr Ser Arg Leu His Ser Gly Val Pro Ser Arg
1               5                   10

<210> SEQ ID NO 155
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Gly Asn Thr Leu Pro Leu
1               5

<210> SEQ ID NO 156
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 156

Ile Tyr Pro Arg Asn Gly Asp Thr
1               5

<210> SEQ ID NO 157
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Tyr Pro Arg Asn Gly Asp
1               5

<210> SEQ ID NO 158
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ile Tyr Pro Arg Asn Gly Asp Thr Asn Tyr Asn Gly Lys Phe Lys Asp
1               5                   10                  15

Gln
```

ANTI-CD73 ANTIBODIES AND METHODS OF USE THEREOF

RELATED APPLICATIONS

This application claims priority to U.S. Provisional Patent Application Ser. No. 62/640,850, filed Mar. 9, 2018, the entire disclosure of which is hereby incorporated herein by reference.

REFERENCE TO SEQUENCE LISTING SUBMITTED ELECTRONICALLY

The content of the following submission on ASCII text file is incorporated herein by reference in its entirety: a computer readable form (CRF) of the Sequence Listing (file name: 616082011800SEQLIST.TXT, date recorded: Jul. 24, 2019, size: 382 KB).

1. FIELD

The instant disclosure relates to antibodies that specifically bind to CD73 (e.g., human CD73) and methods of using the same.

2. BACKGROUND

CD73, also known as ecto-5'-nucleotidase, ecto-5'-NT, 5'-NT, and NT5E, is a glycosylphosphatidylinisotol (GPI)-linked cell surface enzyme. The enzymatic activity of CD73 catalyzes hydrolysis of extracellular adenosine monophosphate (AMP) into adenosine. This activity, along with the activity of CD39 to catalyze hydrolysis of extracellular adenosine triphosphate (ATP) into AMP, constitutes a major adenosine-generating system in the extracellular space. Adenosine is a ligand of a number of G protein-coupled receptors (GPCRs), and is implicated in immune escape, angiogenesis, and tumor motility. CD73 is broadly expressed in many tissues, and has been found to be upregulated in late-stage primary and metastatic tumors. Studies in animal models have shown that blockade of CD73 activity using an anti-CD73 antibody suppresses tumor growth and prolongs survival by promoting anti-tumor adaptive immunity (Forte et al. (2012) *J Immunol.* 189(5):2226-33).

Transforming growth factor-β (TGFβ) is a pleiotropic cytokine that is expressed at elevated levels in late-stage primary and metastatic tumors, and is associated with proliferation, invasion, metastasis, and angiogenesis of tumor cells. TGFβ has also been shown to promote the expansion of immunosuppressive immune populations, such as regulatory T cells (Tregs) and myeloid-derived suppressor cells (MDSCs). See Wang et al. (2017) *Front Immunol.* 8: 1934.

Given the apparent role of human CD73 and TGFβ in modulating immune responses to tumors, therapeutic agents designed to antagonize CD73 activity, or both CD73 activity and TGFβ signaling, hold great promise for cancer treatment.

3. SUMMARY

The instant disclosure provides antibodies that specifically bind to CD73 (e.g., human CD73) and antagonize CD73 function, e.g., the enzymatic activity to promote AMP conversion to adenosine. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for boosting immune responses to a tumor antigen, and hence, are useful for treating cancer in a subject.

Accordingly, in one aspect, the instant disclosure provides an isolated antibody that specifically binds to human CD73, the antibody comprising a heavy chain variable region comprising complementarity determining regions (CDRs) CDRH1, CDRH2, and CDRH3, and a light chain variable region comprising complementarity determining regions CDRL1, CDRL2, and CDRL3, wherein:

(a) CDRH1 comprises the amino acid sequence of $X_1X_2WX_3X_4$ (SEQ ID NO: 13), wherein
  $X_1$ is S or N;
  $X_2$ is S or Y;
  $X_3$ is I or M; and
  $X_4$ is N or H;
(b) CDRH2 comprises the amino acid sequence of $X_1IYPRX_2X_3DTNYX_4X_5KFKX_6$ (SEQ ID NO: 14), wherein
  $X_1$ is R or T;
  $X_2$ is N, A, or S;
  $X_3$ is G or S;
  $X_4$ is N, A, or S;
  $X_5$ is G or Q; and
  $X_6$ is D or G;
(c) CDRH3 comprises the amino acid sequence of LLDYSMDY (SEQ ID NO: 7);
(d) CDRL1 comprises the amino acid sequence of $RASQDISX_1X_2LN$ (SEQ ID NO: 16), wherein
  $X_1$ is N or I; and
  $X_2$ is Y or S;
(e) CDRL2 comprises the amino acid sequence of YTSRLHS (SEQ ID NO: 10); and/or
(f) CDRL3 comprises the amino acid sequence of QQGNTLPXT (SEQ ID NO: 17), wherein:
  X is L or W.

In certain embodiments, CDRH1 comprises an amino acid sequence selected from the group consisting of SEQ ID NOs: 1 and 2. In certain embodiments, CDRH2 comprises an amino acid sequence selected from the group consisting of SEQ ID NOs: 3-6. In certain embodiments, CDRL1 comprises an amino acid sequence selected from the group consisting of SEQ ID NOs: 8 and 9. In certain embodiments, CDRL3 comprises an amino acid sequence selected from the group consisting of SEQ ID NOs: 11 and 12.

In certain embodiments,
(a) CDRH1 comprises the amino acid sequence of SSWIN (SEQ ID NO: 2);
(b) CDRH2 comprises the amino acid sequence of $RIYPRX_1GDTNYX_2GKFKD$ (SEQ ID NO: 15), wherein
  $X_1$ is N, A, or S; and
  $X_2$ is N, A, or S;
(c) CDRL1 comprises the amino acid sequence of $RASQDISX_1X_2LN$ (SEQ ID NO: 16), wherein
  $X_1$ is N or I; and
  $X_2$ is Y or S; and/or
(d) CDRL3 comprises the amino acid sequence of QQGNTLPLT (SEQ ID NO: 12).

In certain embodiments, CDRH2 comprises an amino acid sequence selected from the group consisting of SEQ ID NOs: 4-6. In certain embodiments, CDRL1 comprises an amino acid sequence selected from the group consisting of SEQ ID NOs: 8 and 9.

In certain embodiments, CDRH1, CDRH2, and CDRH3 comprise the CDRH1, CDRH2, and CDRH3 amino acid sequences, respectively, set forth in SEQ ID NOs: 2, 4, and 7; 2, 5, and 7; 1, 3, and 7; or 2, 6, and 7. In certain embodiments, CDRL1, CDRL2, and CDRL3 comprise the CDRL1, CDRL2, and CDRL3 amino acid sequences, respectively, set forth in SEQ ID NOs: 8, 10, and 12; 9, 10, and 12; or 8, 10, and 11. In certain embodiments, CDRH1, CDRH2, CDRH3, CDRL1, CDRL2, and CDRL3 comprise the CDRH1, CDRH2, CDRH3, CDRL1, CDRL2, and CDRL3 amino acid sequences, respectively, set forth in SEQ ID NOs: 2, 4, 7, 8, 10, and 12; 2, 5, 7, 8, 10, and 12; 1, 3, 7, 8, 10, and 11; 2, 4, 7, 8, 10, and 11; 2, 4, 7, 9, 10, and 12; 2, 6, 7, 8, 10, and 12; 2, 5, 7, 9, 10, and 12; or 2, 6, 7, 9, 10, and 12. In certain embodiments, CDRH1, CDRH2, CDRH3, CDRL1, CDRL2, and CDRL3 comprise the CDRH1, CDRH2, CDRH3, CDRL1, CDRL2, and CDRL3 amino acid sequences, respectively, set forth in SEQ ID NOs: 2, 4, 7, 8, 10, and 12; or 2, 5, 7, 8, 10, and 12.

In another aspect, the instant disclosure provides an isolated antibody that specifically binds to human CD73, the antibody comprising a heavy chain variable region comprising CDRs CDRH1, CDRH2, and CDRH3, and a light chain variable region comprising complementarity determining regions CDRL1, CDRL2, and CDRL3, wherein CDRH3 comprises the amino acid sequence of LLDYSMDY (SEQ ID NO: 7); and/or CDRL3 comprises the amino acid sequence of QQGNTLPLT (SEQ ID NO: 12) or QQGNTLPWT (SEQ ID NO: 11).

In certain embodiments, the antibody comprises a heavy chain variable region comprising the amino acid sequence of SEQ ID NO: 31. In certain embodiments, the antibody comprises a heavy chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 19-21 and 23-30. In certain embodiments, the heavy chain variable region comprises an amino acid sequence selected from the group consisting of SEQ ID NOs: 19-21 and 23-30. In certain embodiments, the antibody comprises a heavy chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 23-30. In certain embodiments, the heavy chain variable region comprises an amino acid sequence selected from the group consisting of SEQ ID NOs: 23-30. In certain embodiments, the heavy chain variable region comprises the amino acid sequence of SEQ ID NO: 24 or 27. In certain embodiments, the antibody comprises a heavy chain variable region comprising an amino acid sequence derived from a human germline sequence as set forth in SEQ ID NO: 22.

In certain embodiments, the antibody comprises a light chain variable region comprising an amino acid sequence of SEQ ID NO: 41 or 42. In certain embodiments, the antibody comprises a light chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 33-35 and 37-40. In certain embodiments, the light chain variable region comprises an amino acid sequence selected from the group consisting of SEQ ID NOs: 33-35 and 37-40. In certain embodiments, the antibody comprises a light chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 37-40. In certain embodiments, the light chain variable region comprises an amino acid sequence selected from the group consisting of SEQ ID NOs: 37-40. In certain embodiments, the light chain variable region comprises the amino acid sequence of SEQ ID NO: 37. In certain embodiments, the antibody comprises a light chain variable region comprising an amino acid sequence derived from a human germline sequence as set forth in SEQ ID NO: 36.

In certain embodiments, the heavy chain variable region and the light chain variable region, respectively, comprise the amino acid sequences set forth in SEQ ID NOs: 24 and 37; 27 and 37; 19 and 33; 20 and 34; 21 and 35; 23 and 37; 23 and 38; 24 and 38; 25 and 37; 26 and 37; 28 and 37; 25 and 38; 26 and 38; 27 and 38; 28 and 38; 29 and 37; 30 and 37; 23 and 39; or 23 and 40. In certain embodiments, the heavy chain variable region and the light chain variable region, respectively, comprise the amino acid sequences set forth in SEQ ID NOs: 24 and 37; or 27 and 37.

In certain embodiments, the antibody comprises a heavy chain variable region comprising an amino acid sequence at least 75%, 80%, 85%, 90%, 91%, 92%, 93%, 94%, 95%, 96%, 97%, 98%, 99%, or 100% identical to SEQ ID NOs: 27, and/or a light chain variable region comprising an amino acid sequence at least 75%, 80%, 85%, 90%, 91%, 92%, 93%, 94%, 95%, 96%, 97%, 98%, 99%, or 100% identical to SEQ ID NOs: 37

In certain embodiments, the antibody comprises a heavy chain comprising an amino acid sequence at least 75%, 80%, 85%, 90%, 91%, 92%, 93%, 94%, 95%, 96%, 97%, 98%, 99%, or 100% identical to SEQ ID NOs: 85, and/or a light chain comprising an amino acid sequence at least 75%, 80%, 85%, 90%, 91%, 92%, 93%, 94%, 95%, 96%, 97%, 98%, 99%, or 100% identical to SEQ ID NOs: 97.

In certain embodiments, the antibody comprises a heavy chain comprising an amino acid sequence at least 75%, 80%, 85%, 90%, 91%, 92%, 93%, 94%, 95%, 96%, 97%, 98%, 99%, or 100% identical to SEQ ID NOs: 115, and/or a light chain comprising an amino acid sequence at least 75%, 80%, 85%, 90%, 91%, 92%, 93%, 94%, 95%, 96%, 97%, 98%, 99%, or 100% identical to SEQ ID NOs: 97.

In certain embodiments, the antibody comprises a heavy chain constant region selected from the group consisting of human IgG$_1$, IgG$_2$, IgG$_3$, IgG$_4$, IgA$_1$, and IgA$_2$. In certain embodiments, the heavy chain constant region is IgG$_1$. In certain embodiments, the amino acid sequence of IgG$_1$ comprises a N297A mutation, numbered according to the EU numbering system. In certain embodiments, the heavy chain constant region comprises the amino acid sequence of SEQ ID NO: 50, 49, 46, 45, 55, or 56. In certain embodiments, the antibody comprises a heavy chain comprising an amino acid sequence selected from the group consisting of SEQ ID NOs: 63-88.

In certain embodiments, the antibody comprises a light chain constant region selected from the group consisting of human Igκ and Igλ. In certain embodiments, the light chain constant region is Igκ. In certain embodiments, the light chain constant region comprises the amino acid sequence of SEQ ID NO: 93 or 89. In certain embodiments, the antibody comprises a light chain comprising the amino acid sequence selected from the group consisting of SEQ ID NO: 92 and 94-98.

In certain embodiments, the antibody comprises a heavy chain and a light chain comprising the amino acid sequences set forth in any row of Table 4, preferably the amino acid sequence selected from the group consisting of SEQ ID NOs: 79 and 97; 85 and 97; 77 and 97; 80 and 97; 86 and 97; 64 and 92; 70 and 96; or 78 and 97, respectively.

In certain embodiments reciting any one of SEQ ID NOs: 19, 20, and 65-68, the X in any one of SEQ ID NOs: 19, 20, and 65-68 is glutamine. In certain embodiments reciting any one of SEQ ID NOs: 21, 23-30, 63, 64, 69-88, the X in any one of SEQ ID NOs: 21, 23-30, 63, 64, 69-88 is glutamate. In certain embodiments reciting any one of SEQ ID NOs: 19-21, 23-30, and 63-88, the X in any one of SEQ ID NOs: 19-21, 23-30, and 63-88 is pyroglutamate.

In another aspect, the instant disclosure provides an isolated antibody that binds to the same epitope of human CD73 as the antibody of any one of the preceding claims.

In certain embodiments of any one of the foregoing aspects, the antibody is a humanized antibody. In certain embodiments, the antibody is antagonistic to human CD73. In certain embodiments, the antibody deactivates, reduces, or inhibits an activity of human CD73. In certain embodiments, the antibody attenuates the ability of human CD73 to convert adenosine monophosphate to adenosine. In certain embodiments, the antibody is internalized upon binding to cells expressing human CD73.

In certain embodiments, the isolated antibody further comprises a TGFβ-binding moiety. In certain embodiments, the TGFβ-binding moiety is linked to the heavy chain variable region. In certain embodiments, the TGFβ-binding moiety is linked to the heavy chain variable region via a peptide linker. In certain embodiments, the isolated antibody further comprises a TGFβ-binding moiety linked to the heavy chain constant region. In certain embodiments, the TGFβ-binding moiety is linked to the C-terminal residue of the heavy chain constant region. In certain embodiments, the N-terminal residue of the TGFβ-binding moiety is linked to the C-terminal residue of the heavy chain constant region via a peptide linker. In certain embodiments, the peptide linker comprises an amino acid sequence selected from the group consisting of SEQ ID NOs: 103-108.

In certain embodiments, the TGFβ-binding moiety specifically binds to human TGFβ. In certain embodiments, the TGFβ-binding moiety comprises an extracellular domain of a human TGFβ receptor. In certain embodiments, the human TGFβ receptor is selected from the group consisting of human TGFβR1, TGFβR2, and TGFβR3. In certain embodiments, the human TGFβ receptor is human TGFβR2. In certain embodiments, the TGFβ-binding moiety comprises an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112. In certain embodiments, the TGFβ-binding moiety consists of an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112. In certain embodiments, the TGFβ-binding moiety comprises an amino acid sequence selected from the group consisting of SEQ ID NOs: 109-112, preferably SEQ ID NO: 111. In certain embodiments, the TGFβ-binding moiety consists of an amino acid sequence selected from the group consisting of SEQ ID NOs: 109-112, preferably SEQ ID NO: 111.

In certain embodiments, the isolated antibody comprises a polypeptide comprising an amino acid sequence selected from the group consisting of SEQ ID NOs: 113-121, preferably SEQ ID NO: 114 or 115. In certain embodiments, the isolated antibody comprises a polypeptide comprising an amino acid sequence selected from the group consisting of SEQ ID NOs: 113-121 and a polypeptide comprising the amino acid sequence of SEQ ID NO: 92 or 97. In certain embodiments, the isolated antibody comprises two polypeptides each comprising an amino acid sequence selected from the group consisting of SEQ ID NOs: 113-121 and two polypeptides each comprising the amino acid sequence of SEQ ID NO: 92 or 97. In certain embodiments, the isolated antibody comprises two polypeptides each comprising the amino acid sequence of SEQ ID NO: 115 and two polypeptides each comprising the amino acid sequence of SEQ ID NO: 97.

In another aspect, the instant disclosure provides an isolated antibody that specifically binds to human CD73, the antibody comprising a TGFβ-binding moiety. In certain embodiments, the antibody is antagonistic to human CD73. In certain embodiments, the antibody deactivates, reduces, or inhibits an activity of human CD73. In certain embodiments, the antibody attenuates the ability of human CD73 to convert adenosine monophosphate to adenosine. In certain embodiments, the antibody, when bound to TGFβ, is antagonistic to human CD73.

In certain embodiments, the TGFβ-binding moiety specifically binds to human TGFβ. In certain embodiments, the TGFβ-binding moiety comprises an extracellular domain of a human TGFβ receptor. In certain embodiments, the human TGFβ receptor is selected from the group consisting of human TGFβR1, TGFβR2, and TGFβR3. In certain embodiments, the human TGFβ receptor is human TGFβR2. In certain embodiments, the TGFβ-binding moiety comprises an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112. In certain embodiments, the TGFβ-binding moiety consists of an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112. In certain embodiments, the TGFβ-binding moiety comprises an amino acid sequence selected from the group consisting of SEQ ID NOs: 109-112, preferably SEQ ID NO: 111. In certain embodiments, the TGFβ-binding moiety consists of an amino acid sequence selected from the group consisting of SEQ ID NOs: 109-112, preferably SEQ ID NO: 111.

In certain embodiments, the isolated antibody further comprises a VEGF-binding moiety. In certain embodiments, the VEGF-binding moiety is linked to the heavy chain variable region. In certain embodiments, the VEGF-binding moiety is linked to the heavy chain variable region via a peptide linker. In certain embodiments, the isolated antibody further comprises a VEGF-binding moiety linked to the heavy chain constant region. In certain embodiments, the VEGF-binding moiety is linked to the C-terminal residue of the heavy chain constant region. In certain embodiments, the N-terminal residue of the VEGF-binding moiety is linked to the C-terminal residue of the heavy chain constant region via a peptide linker. In certain embodiments, the peptide linker comprises an amino acid sequence selected from the group consisting of SEQ ID NOs: 103-108.

In certain embodiments, the VEGF-binding moiety specifically binds to human VEGF. In certain embodiments, the VEGF-binding moiety comprises an extracellular domain of a human VEGF receptor. In certain embodiments, the human VEGF receptor is selected from the group consisting of human VEGFR1, VEGFR2, and VEGFR3. In certain embodiments, the human VEGF receptor is human VEGFR1. In certain embodiments, the VEGF-binding moiety comprises an amino acid sequence at least 75%, 80%, 85%, 90%, 91%, 92%, 93%, 94%, 95%, 96%, 97%, 98%, or 99% identical to the sequence set forth in SEQ ID NO: 122. In certain embodiments, the VEGF-binding moiety consists of an amino acid sequence at least 75%, 80%, 85%, 90%, 91%, 92%, 93%, 94%, 95%, 96%, 97%, 98%, or 99% identical to the sequence set forth in SEQ ID NO: 122. In certain embodiments, the VEGF-binding moiety comprises the sequence set forth in SEQ ID NO: 122. In certain embodiments, the VEGF-binding moiety consists of the sequence set forth in SEQ ID NO: 122.

In certain embodiments, the isolated antibody comprises a polypeptide comprising an amino acid sequence selected from the group consisting of SEQ ID NOs: 123-127. In certain embodiments, the antibody comprises a polypeptide comprising an amino acid sequence selected from the group consisting of SEQ ID NOs: 123-127 and a polypeptide comprising an amino acid sequence selected from the group consisting of SEQ ID NOs: 92, 128, and 97. In certain embodiments, the antibody comprises two polypeptides comprising an amino acid sequence selected from the group consisting of SEQ ID NOs: 123-127 and two polypeptides comprising an amino acid sequence selected from the group consisting of SEQ ID NOs: 92, 128, and 97.

In another aspect, the instant disclosure provides an isolated antibody that specifically binds to human CD73, the antibody comprising a VEGF-binding moiety. In certain embodiments, the antibody is antagonistic to human CD73. In certain embodiments, the antibody deactivates, reduces, or inhibits an activity of human CD73. In certain embodiments, the antibody attenuates the ability of human CD73 to convert adenosine monophosphate to adenosine. In certain embodiments, the antibody, when bound to VEGF, is antagonistic to human CD73.

In certain embodiments, the VEGF-binding moiety specifically binds to human VEGF. In certain embodiments, the VEGF-binding moiety comprises an extracellular domain of a human VEGF receptor. In certain embodiments, the human VEGF receptor is selected from the group consisting of human VEGFR1, VEGFR2, and VEGFR3. In certain embodiments, the human VEGF receptor is human VEGFR1. In certain embodiments, the VEGF-binding moiety comprises an amino acid sequence at least 75%, 80%, 85%, 90%, 91%, 92%, 93%, 94%, 95%, 96%, 97%, 98%, or 99% identical to the sequence set forth in SEQ ID NO: 122. In certain embodiments, the VEGF-binding moiety consists of an amino acid sequence at least 75%, 80%, 85%, 90%, 91%, 92%, 93%, 94%, 95%, 96%, 97%, 98%, or 99% identical to the sequence set forth in SEQ ID NO: 122. In certain embodiments, the VEGF-binding moiety comprises the amino acid sequence as set forth in SEQ ID NO: 122. In certain embodiments, the VEGF-binding moiety consists of the amino acid sequence as set forth in SEQ ID NO: 122.

In certain embodiments of any one of the foregoing aspects, the antibody further comprises a conjugated cytotoxic agent, cytostatic agent, toxin, radionuclide, or detectable label.

In certain embodiments of any one of the foregoing aspects, the antibody binds to an epitope located within a region of human CD73, the amino acid sequence of the region consisting of the amino acid sequence of SEQ ID NOs: 90 and/or 91.

In certain embodiments, the antibody binds to at least one residue in the amino acid sequence of SEQ ID NOs: 90 and/or 91.

In certain embodiments, the antibody binds to one or more amino acid residues of human CD73 selected from the group consisting of Y158, Y161, P165, or D168, numbered according to the amino acid sequence of SEQ ID NO: 99.

In certain embodiments, the binding affinity of the antibody for a protein comprising the amino acid sequence of SEQ ID NO: 133 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the maximal binding of the antibody for a protein comprising the amino acid sequence of SEQ ID NO: 133 is substantially reduced (e.g., reduced by at least 30%, 40%, 50%, 60%, 70%, 80% or 90%) relative to the maximal binding of the antibody for a protein comprising the amino acid sequence of SEQ ID NO: 141.

In certain embodiments, the binding affinity of the antibody for a protein comprising the amino acid sequence of SEQ ID NO: 134 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the maximal binding of the antibody for a protein comprising the amino acid sequence of SEQ ID NO: 134 is substantially reduced (e.g., reduced by at least 30%, 40%, 50%, 60%, 70%, 80% or 90%) relative to the maximal binding of the antibody for a protein comprising the amino acid sequence of SEQ ID NO: 141.

In certain embodiments, the antibody binds to amino acid residue Y158 of human CD73, numbered according to the amino acid sequence of SEQ ID NO: 99.

In certain embodiments, the binding affinity of the antibody for a protein comprising the amino acid sequence of SEQ ID NO: 59 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the antibody binds to amino acid residue Y161 of human CD73, numbered according to the amino acid sequence of SEQ ID NO: 99.

In certain embodiments, the binding affinity of the antibody for a protein comprising the amino acid sequence of SEQ ID NO: 60 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the maximal binding of the antibody for a protein comprising the amino acid sequence of SEQ ID NO: 60 is substantially reduced (e.g., reduced by at least 30%, 40%, 50%, 60%, 70%, 80% or 90%) relative to the maximal binding of the antibody for a protein comprising the amino acid sequence of SEQ ID NO: 141.

In certain embodiments, the antibody binds to amino acid residue P165 of human CD73, numbered according to the amino acid sequence of SEQ ID NO: 99.

In certain embodiments, the binding affinity of the antibody for a protein comprising the amino acid sequence of SEQ ID NO: 139 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the antibody binds to amino acid residue D168 of human CD73, numbered according to the amino acid sequence of SEQ ID NO: 99.

In certain embodiments, the binding affinity of the antibody for a protein comprising the amino acid sequence of SEQ ID NO: 140 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the binding affinity of the antibody for a protein comprising the amino acid sequence of SEQ ID NO: 135 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the binding affinity of the antibody for a protein comprising the amino acid sequence of SEQ ID NO: 136 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In certain embodiments, the binding affinity of the antibody for a protein comprising the amino acid sequence of SEQ ID NO: 142 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141, and wherein the binding affinity of the antibody for a protein comprising the amino acid sequence of SEQ ID NO: 137 is not substantially reduced (e.g., not reduced by more than 4 times, 5 times, 6 times, 7 times, 8 times, 9 times, or 10 times) relative to the binding affinity of the antibody for a protein comprising the amino acid sequence of SEQ ID NO: 141.

In certain embodiments, the maximal binding of the antibody for a protein comprising the amino acid sequence of SEQ ID NO: 142 is substantially reduced (e.g., reduced by at least 30%, 40%, 50%, 60%, 70%, 80% or 90%) relative to the maximal binding of the antibody for a protein comprising the amino acid sequence of SEQ ID NO: 141, and wherein the maximal binding of the antibody for a protein comprising the amino acid sequence of SEQ ID NO: 137 is not substantially reduced (e.g., not reduced by more than 30%, 40%, 50%, 60%, 70%, 80% or 90%) relative to the maximal binding of the antibody for a protein comprising the amino acid sequence of SEQ ID NO: 141.

In certain embodiments, the binding affinity of the antibody to a protein comprising the amino acid sequence of SEQ ID NO: 142 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141, and wherein the binding affinity of the antibody for a protein comprising the amino acid sequence of SEQ ID NO: 138 is not substantially reduced (e.g., not reduced by more than 4 times, 5 times, 6 times, 7 times, 8 times, 9 times, or 10 times) relative to the binding affinity of the antibody for a protein comprising the amino acid sequence of SEQ ID NO: 141.

In certain embodiments, the maximal binding of the antibody for a protein comprising the amino acid sequence of SEQ ID NO: 142 is substantially reduced (e.g., reduced by at least 30%, 40%, 50%, 60%, 70%, 80% or 90%) relative to the maximal binding of the antibody for a protein comprising the amino acid sequence of SEQ ID NO: 141, and wherein the maximal binding of the antibody for a protein comprising the amino acid sequence of SEQ ID NO: 138 is not substantially reduced (e.g., not reduced by more than 30%, 40%, 50%, 60%, 70%, 80% or 90%) relative to the maximal binding of the antibody for a protein comprising the amino acid sequence of SEQ ID NO: 141.

In another aspect, the instant disclosure provides an isolated antibody that specifically binds to human CD73, wherein the antibody binds to an epitope located within a region of human CD73, the amino acid sequence of the region consisting of the amino acid sequence of SEQ ID NOs: 90 and/or 91.

In another aspect, the instant disclosure provides an isolated antibody that specifically binds to human CD73, wherein the antibody binds to at least one residue in the amino acid sequence of SEQ ID NOs: 90 and/or 91.

In another aspect, the instant disclosure provides an isolated antibody that specifically binds to human CD73, wherein the antibody binds to one or more amino acid residues of human CD73 selected from the group consisting of Y158, Y161, P165, or D168, numbered according to the amino acid sequence of SEQ ID NO: 99.

In another aspect, the instant disclosure provides an isolated antibody that specifically binds to human CD73, wherein the binding affinity of the antibody for a protein comprising the amino acid sequence of SEQ ID NO: 133 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the maximal binding of the antibody for a protein comprising the amino acid sequence of SEQ ID NO: 133 is substantially reduced (e.g., reduced by at least 30%, 40%, 50%, 60%, 70%, 80% or 90%) relative to the maximal binding of the antibody for a protein comprising the amino acid sequence of SEQ ID NO: 141.

In another aspect, the instant disclosure provides an isolated antibody that specifically binds to human CD73, wherein the binding affinity of the antibody for a protein comprising the amino acid sequence of SEQ ID NO: 134 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the maximal binding of the antibody for a protein comprising the amino acid sequence of SEQ ID NO: 134 is substantially reduced (e.g., reduced by at least 30%, 40%, 50%, 60%, 70%, 80% or 90%) relative to the maximal binding of the antibody for a protein comprising the amino acid sequence of SEQ ID NO: 141.

In another aspect, the instant disclosure provides an isolated antibody that specifically binds to human CD73, wherein the antibody binds to amino acid residue Y158 of human CD73, numbered according to the amino acid sequence of SEQ ID NO: 99.

In another aspect, the instant disclosure provides an isolated antibody that specifically binds to human CD73, wherein the binding affinity of the antibody for a protein comprising the amino acid sequence of SEQ ID NO: 59 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the antibody binds to amino acid residue Y161 of human CD73, numbered according to the amino acid sequence of SEQ ID NO: 99.

In another aspect, the instant disclosure provides an isolated antibody that specifically binds to human CD73, wherein the binding affinity of the antibody for a protein comprising the amino acid sequence of SEQ ID NO: 60 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the maximal binding of the antibody for a protein comprising the amino acid sequence of SEQ ID NO: 60 is substantially reduced (e.g., reduced by at least 30%, 40%, 50%, 60%, 70%, 80% or 90%) relative to the maximal binding of the antibody for a protein comprising the amino acid sequence of SEQ ID NO: 141.

In another aspect, the instant disclosure provides an isolated antibody that specifically binds to human CD73, wherein the antibody binds to amino acid residue P165 of human CD73, numbered according to the amino acid sequence of SEQ ID NO: 99.

In another aspect, the instant disclosure provides an isolated antibody that specifically binds to human CD73, wherein the binding affinity of the antibody for a protein comprising the amino acid sequence of SEQ ID NO: 139 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the antibody binds to amino acid residue D168 of human CD73, numbered according to the amino acid sequence of SEQ ID NO: 99.

In another aspect, the instant disclosure provides an isolated antibody that specifically binds to human CD73, wherein the binding affinity of the antibody for a protein comprising the amino acid sequence of SEQ ID NO: 140 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the binding affinity of the antibody for a protein comprising the amino acid sequence of SEQ ID NO: 135 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the binding affinity of the antibody for a protein comprising the amino acid sequence of SEQ ID NO: 136 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the binding affinity of the antibody for a protein comprising the amino acid sequence of SEQ ID NO: 142 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141, and wherein the binding affinity of the antibody for a protein comprising the amino acid sequence of SEQ ID NO: 137 is not substantially reduced (e.g., not reduced by more than 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the maximal binding of the antibody for a protein comprising the amino acid sequence of SEQ ID NO: 142 is substantially reduced (e.g., reduced by at least 30%, 40%, 50%, 60%, 70%, 80% or 90%) relative to the maximal binding of the antibody for a protein comprising the amino acid sequence of SEQ ID NO: 141, and wherein the maximal binding of the antibody for a protein comprising the amino acid sequence of SEQ ID NO: 137 is not substantially reduced (e.g., not reduced by more than 30%, 40%, 50%, 60%, 70%, 80% or 90%) relative to the maximal binding of the antibody for a protein comprising the amino acid sequence of SEQ ID NO: 141.

In another aspect, the instant disclosure provides an isolated antibody that specifically binds to human CD73, wherein the binding affinity of the antibody to a protein comprising the amino acid sequence of SEQ ID NO: 142 is substantially reduced (e.g., reduced by at least 4 times, 5 times, 6 times, 7 times, 8 times, 9 times, or 10 times) relative to the binding affinity of the antibody for a protein comprising the amino acid sequence of SEQ ID NO: 141, and wherein the binding affinity of the antibody for a protein comprising the amino acid sequence of SEQ ID NO: 138 is not substantially reduced (e.g., not reduced by more than 4 times, 5 times, 6 times, 7 times, 8 times, 9 times, or 10 times) relative to the binding affinity of the antibody for a protein comprising the amino acid sequence of SEQ ID NO: 141.

In another aspect, the instant disclosure provides an isolated antibody that specifically binds to human CD73, wherein the maximal binding of the antibody for a protein comprising the amino acid sequence of SEQ ID NO: 142 is substantially reduced (e.g., reduced by at least 30%, 40%, 50%, 60%, 70%, 80% or 90%) relative to the maximal binding of the antibody for a protein comprising the amino acid sequence of SEQ ID NO: 141, and wherein the maximal binding of the antibody for a protein comprising the amino acid sequence of SEQ ID NO: 138 is not substantially reduced (e.g., not reduced by more than 30%, 40%, 50%, 60%, 70%, 80% or 90%) relative to the maximal binding of the antibody for a protein comprising the amino acid sequence of SEQ ID NO: 141.

In another aspect, the instant disclosure provides a compound or molecule comprising a CD73-binding moiety and a TGFβ-binding moiety.

In another aspect, the instant disclosure provides a pharmaceutical composition comprising the antibody disclosed herein and a pharmaceutically acceptable carrier or excipient.

In another aspect, the instant disclosure provides an isolated polynucleotide encoding a polypeptide of the antibody disclosed herein. In certain embodiments, the polynucleotide comprises cDNA or mRNA. In another aspect, the instant disclosure provides a vector comprising the polynucleotide. In certain embodiments, the vector is a plasmid vector or a viral vector. In another aspect, the instant disclosure provides a recombinant host cell comprising the polynucleotide or the vector. In another aspect, the instant disclosure provides a lipid nanoparticle comprising the polynucleotide or the vector. In another aspect, the instant disclosure provides a method of producing an antibody, the method comprising culturing the host cell under suitable conditions so that the polynucleotide is expressed and the antibody is produced. In another aspect, the instant disclosure provides a pharmaceutical composition comprising the antibody, polynucleotide, vector, or lipid nanoparticle and a pharmaceutically acceptable carrier or excipient.

In another aspect, the instant disclosure provides a method of treating cancer in a subject, the method comprising administering to the subject an effective amount of the antibody, polynucleotide, vector, lipid nanoparticle, or pharmaceutical composition disclosed herein. In another aspect, the instant disclosure provides a method of inhibiting cancer metastasis in a subject, the method comprising administering to the subject an effective amount of the antibody, polynucleotide, vector, lipid nanoparticle, or pharmaceutical composition disclosed herein. In certain embodiments, the antibody, polynucleotide, vector, lipid nanoparticle, or pharmaceutical composition is administered intravenously intravenously, intratumorally, subcutaneously, intradermally, intramuscularly, intravesically, intracranially, intracavitary or intraventricularly. In certain embodiments, the antibody, polynucleotide, vector, lipid nanoparticle, or pharmaceutical composition is administered intratumorally.

In certain embodiments, the method further comprises administering one or more additional therapeutic agent to the subject. In certain embodiments, the antibody, polynucleotide, vector, lipid nanoparticle, or pharmaceutical composition, and the one or more additional therapeutic agents are co-administered according to the same schedule (e.g., co-administered at the same time intervals). In certain embodiments, the antibody, polynucleotide, vector, lipid nanoparticle, or pharmaceutical composition, and the one or more additional therapeutic agents are co-administered according to different schedules (e.g., co-administered at different time intervals). In certain embodiments, the antibody, polynucleotide, vector, lipid nanoparticle, or pharmaceutical composition is co-administered with one or more additional therapeutic agents comprising an activator or agonist of a fms related tyrosine kinase 3 (FLT3; CD135) receptor, a toll-like receptor (TLR) or a stimulator of interferon genes (STING) receptor. In certain embodiments, the TLR agonist or activator is selected from the group consisting of a TLR2 agonist, a TLR3 agonist, a TLR7 agonist, a TLR8 agonist and a TLR9 agonist. In certain embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In certain embodiments, the antibody, polynucleotide, vector, lipid nanoparticle, or pharmaceutical composition is co-administered with one or more additional therapeutic agents comprising an inhibitor or antagonist of: protein tyrosine phosphatase, non-receptor type 11 (PTPN11 or SHP2); myeloid cell leukemia sequence 1 (MCL1) apoptosis regulator; mitogen-activated protein kinase kinase kinase kinase 1 (MAP4K1) (also called Hematopoietic Progenitor Kinase 1 (HPK1)); diacylglycerol kinase alpha (DGKA, DAGK, DAGK1 or DGK-alpha); 5'-nucleotidase ecto (NT5E or CD73); transforming growth factor beta 1 (TGFB1 or TGFβ); heme oxygenase 1 (HMOX1, HO-1 or HO1); vascular endothelial growth factor A (VEGFA or VEGF); erb-b2 receptor tyrosine kinase 2 (ERBB2 HER2, HER2/neu or CD340); epidermal growth factor receptor (EGFR, ERBB, ERBB1 or HER1); ALK receptor tyrosine kinase (ALK, CD246); poly(ADP-ribose) polymerase 1 (PARP1 or PARP); cyclin dependent kinase 4 (CDK4); cyclin dependent kinase 6 (CDK6); C-C motif chemokine receptor 8 (CCR8, CDw198); CD274 molecule (CD274, PDL1 or PD-L1); programmed cell death 1 (PDCD1, PD1 or PD-1); and/or cytotoxic T-lymphocyte associated protein 4 (CTLA4, CTLA-4, CD152). In certain embodiments, the inhibitor comprises an antigen binding molecule, an antibody or an antigen-binding fragment thereof. In certain embodiments, the inhibitor comprises a small organic molecule. In certain embodiments, the inhibitor of MCL1 is selected from the group consisting of AMG-176, AMG-397, S-64315, AZD-5991, 483-LM, A 1210477, UMI-77 and JKY-5-037. In certain embodiments, the inhibitor of PTPN11 or SHP2 is selected from the group consisting of TNO155 (SHP-099), RMC-4550, JAB-3068 and RMC-4630.

In certain embodiments, the one or more additional therapeutic agent is a chemotherapeutic, an anti-neoplastic, a radiotherapeutic, or a checkpoint targeting agent. In certain embodiments, the one or more anti-neoplastic or chemotherapeutic agents are selected from the group consisting of a nucleoside analog (e.g., 5-fluorouracil, gemcitabine, cytarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), and mixtures thereof.

In certain embodiments, the additional therapeutic agent is a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD137 antibody, and an agonist anti-OX40 antibody. In certain embodiments, the additional therapeutic agent is an anti-PD-1 antibody, optionally wherein the anti-PD-1 antibody is pembrolizumab or nivolumab. In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the inhibitor is epacadostat. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 and is complexed with a tumor-associated antigenic peptide, wherein the HSPPC is derived from a tumor obtained from a subject. In certain embodiments, the additional therapeutic agent is etoposide or doxorubicin.

In another aspect, the antibody, polynucleotide, vector, lipid nanoparticle, or pharmaceutical composition is co-administered with a FOLFOX regimen, a FOLFOXIRI regimen or a FOLFIRINOX regimen. In another aspect, the antibody, polynucleotide, vector, lipid nanoparticle, or pharmaceutical composition is co-administered with an immunotherapy, an immunostimulatory therapy, a cellular therapy or a gene therapy.

In another aspect, the instant disclosure provides an isolated antibody, polynucleotide, vector, lipid nanoparticle, or pharmaceutical composition disclosed herein for use in the treatment of cancer.

In another aspect, the instant disclosure provides use of an isolated antibody, polynucleotide, vector, lipid nanoparticle, or pharmaceutical composition disclosed herein for the preparation of a medicament for treating cancer.

In certain embodiments of any one of the aspects of method of treating cancer in a subject, the instant disclosure provides an isolated antibody, polynucleotide, vector, lipid nanoparticle, or pharmaceutical composition for use in the treatment of cancer, or use of an isolated antibody, polynucleotide, vector, lipid nanoparticle, or pharmaceutical composition disclosed herein for the preparation of a medicament for treating cancer, the cancer is selected from the group consisting of a solid tumor, a hematological cancer, and a metastatic lesion. In certain embodiments, the cancer is a solid tumor. In certain embodiments, the solid tumor is selected from the group consisting of a sarcoma, a fibroblastic sarcoma, a carcinoma, and an adenocarcinoma. In certain embodiments, the cancer is a hematological cancer. In certain embodiments, the hematological cancer is selected from the group consisting of a leukemia, a lymphoma, and a myeloma. In certain embodiments, the cancer is selected from the group consisting of a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, and an extranodal marginal zone lymphoma. In certain embodiments, the cancer is a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma, mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g. carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma, hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma, lobular carcinoma, including without limitation, pleomorphic carcinoma, signet ring cell carcinoma, peritoneum (e.g., mesothelioma, primary peritoneal cancer)); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC) adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma, Epstein-Barr virus (EBV)-associated lymphoproliferative diseases, including B cell lymphomas and T cell lymphomas (e.g., Burkitt lymphoma, large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, sub ependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, pituitary adenomas, cranial and paraspinal nerve tumors, stellar region tumors), neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma. In certain embodiments, the cancer is selected from the group consisting of a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, and an endometrial cancer.

In another aspect, the instant disclosure provides the use of an isolated antibody, polynucleotide, vector, lipid nanoparticle, or pharmaceutical composition as disclosed herein in any of the foregoing methods for the treatment of cancer.

In another aspect, the instant disclosure provides an isolated antibody, polynucleotide, vector, lipid nanoparticle, or pharmaceutical composition as disclosed herein, for use in any one of the foregoing methods for the treatment of cancer.

Additional or alternative embodiments of the invention disclosed herein are set forth below.

Embodiment 1. An antibody that binds to human CD73, the antibody comprising a heavy chain variable region comprising complementarity determining regions (CDRs) CDRH1, CDRH2, and CDRH3, and a light chain variable region comprising complementarity determining regions CDRL1, CDRL2, and CDRL3, wherein:

(a) CDRH1 comprises the amino acid sequence of $X_1X_2WX_3X_4$ (SEQ ID NO: 13), wherein
  $X_1$ is S or N;
  $X_2$ is S or Y;
  $X_3$ is I or M; and
  $X_4$ is N or H;
(b) CDRH2 comprises the amino acid sequence of $X_1$IYPRX$_2$X$_3$DTNYX$_4$X$_5$KFKX$_6$ (SEQ ID NO: 14), wherein
  $X_1$ is R or T;
  $X_2$ is N, A, or S;
  $X_3$ is G or S;
  $X_4$ is N, A, or S;
  $X_5$ is G or Q; and
  $X_6$ is D or G;
(c) CDRH3 comprises the amino acid sequence of LLDYSMDY (SEQ ID NO: 7);
(d) CDRL1 comprises the amino acid sequence of RASQDISX$_1$X$_2$LN (SEQ ID NO: 16), wherein
  $X_1$ is N or I; and
  $X_2$ is Y or S;
(e) CDRL2 comprises the amino acid sequence of YTSRLHS (SEQ ID NO: 10); and/or
(f) CDRL3 comprises the amino acid sequence of QQGNTLPXT (SEQ ID NO: 17), wherein: X is L or W.

Embodiment 2. The antibody of embodiment 1, wherein CDRH1 comprises an amino acid sequence selected from the group consisting of SEQ ID NOs: 1 and 2.

Embodiment 3. The antibody of embodiment 1 or 2, wherein CDRH2 comprises an amino acid sequence selected from the group consisting of SEQ ID NOs: 3-6.

Embodiment 4. The antibody of any one of the preceding embodiments, wherein CDRL1 comprises an amino acid sequence selected from the group consisting of SEQ ID NOs: 8 and 9.

Embodiment 5. The antibody of any one of the preceding embodiments, wherein CDRL3 comprises an amino acid sequence selected from the group consisting of SEQ ID NOs: 11 and 12.

Embodiment 6. The antibody of any one of the preceding embodiments, wherein:
(a) CDRH1 comprises the amino acid sequence of SSWIN (SEQ ID NO: 2);
(b) CDRH2 comprises the amino acid sequence of RIYPRX$_1$GDTNYX$_2$GKFKD (SEQ ID NO: 15), wherein
  $X_1$ is N, A, or S; and
  $X_2$ is N, A, or S;
(c) CDRL1 comprises the amino acid sequence of RASQDISX$_1$X$_2$LN (SEQ ID NO: 16), wherein
  $X_1$ is N or I; and
  $X_2$ is Y or S; and/or
(d) CDRL3 comprises the amino acid sequence of QQGNTLPLT (SEQ ID NO: 12).

Embodiment 7. The antibody of embodiment 6, wherein CDRH2 comprises an amino acid sequence selected from the group consisting of SEQ ID NOs: 4-6.

Embodiment 8. The antibody of embodiment 6 or 7, wherein CDRL1 comprises an amino acid sequence selected from the group consisting of SEQ ID NOs: 8 and 9.

Embodiment 9. The antibody of any one of the preceding embodiments, wherein CDRH1, CDRH2, and CDRH3 comprise the CDRH1, CDRH2, and CDRH3 amino acid sequences, respectively, set forth in SEQ ID NOs: 2, 4, and 7; 2, 5, and 7; 1, 3, and 7; or 2, 6, and 7.

Embodiment 10. The antibody of any one of the preceding embodiments, wherein CDRL1, CDRL2, and CDRL3 comprise the CDRL1, CDRL2, and CDRL3 amino acid sequences, respectively, set forth in SEQ ID NOs: 8, 10, and 12; 9, 10, and 12; or 8, 10, and 11.

Embodiment 11. The antibody of any one of the preceding embodiments, wherein CDRH1, CDRH2, CDRH3, CDRL1, CDRL2, and CDRL3 comprise the CDRH1, CDRH2, CDRH3, CDRL1, CDRL2, and CDRL3 amino acid sequences, respectively, set forth in SEQ ID NOs: 2, 4, 7, 8, 10, and 12; 2, 5, 7, 8, 10, and 12; 1, 3, 7, 8, 10, and 11; 2, 4, 7, 8, 10, and 11; 2, 4, 7, 9, 10, and 12; 2, 6, 7, 8, 10, and 12; 2, 5, 7, 9, 10, and 12; or 2, 6, 7, 9, 10, and 12.

Embodiment 12. The antibody of embodiment 11, wherein CDRH1, CDRH2, CDRH3, CDRL1, CDRL2, and CDRL3 comprise the CDRH1, CDRH2, CDRH3, CDRL1, CDRL2, and CDRL3 amino acid sequences, respectively, set forth in SEQ ID NOs: 2, 4, 7, 8, 10, and 12; or 2, 5, 7, 8, 10, and 12.

Embodiment 13. An antibody that binds to human CD73, the antibody comprising a heavy chain variable region comprising CDRs CDRH1, CDRH2, and CDRH3, and a light chain variable region comprising complementarity determining regions CDRL1, CDRL2, and CDRL3, wherein CDRH3 comprises the amino acid sequence of LLDYSMDY (SEQ ID NO: 7); and/or CDRL3 comprises the amino acid sequence of QQGNTLPLT (SEQ ID NO: 12) or QQGNTLPWT (SEQ ID NO: 11).

Embodiment 14. The antibody of any one of the preceding embodiments, wherein the antibody comprises a heavy chain variable region comprising the amino acid sequence of SEQ ID NO: 31.

Embodiment 15. The antibody of any one of the preceding embodiments, wherein the antibody comprises a heavy chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 19-21 and 23-30.

Embodiment 16. The antibody of embodiment 15, wherein the heavy chain variable region comprises an amino acid sequence selected from the group consisting of SEQ ID NOs: 19-21 and 23-30.

Embodiment 17. The antibody of any one of the preceding embodiments, wherein the antibody comprises a heavy chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 23-30.

Embodiment 18. The antibody of embodiment 17, wherein the heavy chain variable region comprises an amino acid sequence selected from the group consisting of SEQ ID NOs: 23-30.

Embodiment 19. The antibody of embodiment 18, wherein the heavy chain variable region comprises the amino acid sequence of SEQ ID NO: 24 or 27.

Embodiment 20. The antibody of any one of the preceding embodiments, wherein the antibody comprises a heavy chain variable region comprising an amino acid sequence derived from a human germline sequence as set forth in SEQ ID NO: 22.

Embodiment 21. The antibody of any one of the preceding embodiments, wherein the antibody comprises a light chain variable region comprising an amino acid sequence of SEQ ID NO: 41 or 42.

Embodiment 22. The antibody of any one of the preceding embodiments, wherein the antibody comprises a light chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 33-35 and 37-40.

Embodiment 23. The antibody of embodiment 22, wherein the light chain variable region comprises an amino acid sequence selected from the group consisting of SEQ ID NOs: 33-35 and 37-40.

Embodiment 24. The antibody of any one of the preceding embodiments, wherein the antibody comprises a light chain variable region comprising an amino acid sequence at least 75%, 80%, 85%, 90%, 91%, 92%, 93%, 94%, 95%, 96%, 97%, 98%, 99%, or 100% identical to an amino acid sequence selected from the group consisting of SEQ ID NOs: 37-40.

Embodiment 25. The antibody of embodiment 24, wherein the light chain variable region comprises an amino acid sequence selected from the group consisting of SEQ ID NOs: 37-40.

Embodiment 26. The antibody of embodiment 25, wherein the light chain variable region comprises the amino acid sequence of SEQ ID NO: 37.

Embodiment 27. The antibody of any one of the preceding embodiments, wherein the antibody comprises a light chain variable region comprising an amino acid sequence derived from a human germline sequence as set forth in SEQ ID NO: 36.

Embodiment 28. The antibody of any one of the preceding embodiments, wherein the heavy chain variable region and the light chain variable region, respectively, comprise the amino acid sequences set forth in SEQ ID NOs: 24 and 37; 27 and 37; 19 and 33; 20 and 34; 21 and 35; 23 and 37; 23 and 38; 24 and 38; 25 and 37; 26 and 37; 28 and 37; 25 and 38; 26 and 38; 27 and 38; 28 and 38; 29 and 37; 30 and 37; 23 and 39; or 23 and 40.

Embodiment 29. The antibody of embodiment 28, wherein the heavy chain variable region and the light chain variable region, respectively, comprise the amino acid sequences set forth in SEQ ID NOs: 24 and 37; or 27 and 37.

Embodiment 30. The antibody of any one of the preceding embodiments, wherein the antibody comprises a heavy chain constant region selected from the group consisting of human IgG$_1$, IgG$_2$, IgG$_3$, IgG$_4$, IgA$_1$, and IgA$_2$.

Embodiment 31. The antibody of embodiment 30, wherein the heavy chain constant region is IgG$_1$.

Embodiment 32. The antibody of embodiment 31, wherein the amino acid sequence of IgG$_1$ comprises a N297A mutation, numbered according to the EU numbering system.

Embodiment 33. The antibody of embodiment 32, wherein the heavy chain constant region comprises the amino acid sequence of SEQ ID NO: 50, 49, 46, 45, 55, or 56.

Embodiment 34. The antibody of any one of the preceding embodiments, wherein the antibody comprises a heavy chain comprising an amino acid sequence selected from the group consisting of SEQ ID NOs: 63-88.

Embodiment 35. The antibody of any one of the preceding embodiments, wherein the antibody comprises a light chain constant region selected from the group consisting of human Igκ and Igλ.

Embodiment 36. The antibody of embodiment 35, wherein the light chain constant region is Igκ.

Embodiment 37. The antibody of embodiment 36, wherein the light chain constant region comprises the amino acid sequence of SEQ ID NO: 93 or 89.

Embodiment 38. The antibody of any one of the preceding embodiments, wherein the antibody comprises a light chain comprising the amino acid sequence selected from the group consisting of SEQ ID NO: 92 and 94-98.

Embodiment 39. The antibody of any one of the preceding embodiments, wherein the antibody comprises a heavy chain and a light chain comprising the amino acid sequences set forth in any row of Table 4, preferably the amino acid sequence selected from the group consisting of SEQ ID NOs: 79 and 97; 85 and 97; 77 and 97; 80 and 97; 86 and 97; 64 and 92; 70 and 96; or 78 and 97, respectively.

Embodiment 40. The antibody of any one of embodiments 15-39, wherein the X in any one of SEQ ID NOs: 19, 20, and 65-68 is glutamine.

Embodiment 41. The antibody of any one of embodiments 15-39, wherein the X in any one of SEQ ID NOs: 21, 23-30, 63, 64, 69-88 is glutamate.

Embodiment 42. The antibody of any one of embodiments 15-39, wherein the X in any one of SEQ ID NOs: 19-21, 23-30, and 63-88 is pyroglutamate.

Embodiment 43. An antibody that binds to the same epitope of human CD73 as the antibody of any one of the preceding embodiments.

Embodiment 44. The antibody of any one of the preceding embodiments, wherein the antibody is a humanized antibody.

Embodiment 45. The antibody of any one of the preceding embodiments, wherein the antibody is antagonistic to human CD73.

Embodiment 46. The antibody of embodiment 45, wherein the antibody deactivates, reduces, or inhibits an activity of human CD73.

Embodiment 47. The antibody of embodiment 45 or 46, wherein the antibody attenuates the ability of human CD73 to convert adenosine monophosphate to adenosine.

Embodiment 48. The antibody of any one of the preceding embodiments, wherein the antibody is internalized upon binding to cells expressing human CD73.

Embodiment 49. The antibody of any one of embodiments 1-48, further comprising a TGFβ-binding moiety.

Embodiment 50. The antibody of embodiment 49, wherein the TGFβ-binding moiety is linked to the heavy chain variable region.

Embodiment 51. The antibody of embodiment 50, wherein the TGFβ-binding moiety is linked to the heavy chain variable region via a peptide linker.

Embodiment 52. The antibody of any one of embodiments 30-48, further comprising a TGFβ-binding moiety linked to the heavy chain constant region.

Embodiment 53. The antibody of embodiment 52, wherein the TGFβ-binding moiety is linked to the C-terminal residue of the heavy chain constant region.

Embodiment 54. The antibody of embodiment 52 or 53, wherein the N-terminal residue of the TGFβ-binding moiety is linked to the C-terminal residue of the heavy chain constant region via a peptide linker.

Embodiment 55. The antibody of embodiment 51 or 54, wherein the peptide linker comprises an amino acid sequence selected from the group consisting of SEQ ID NOs: 103-108.

Embodiment 56. The antibody of any one of embodiments 49-55, wherein the TGFβ-binding moiety binds to human TGFβ.

Embodiment 57. The antibody of any one of embodiments 49-56, wherein the TGFβ-binding moiety comprises an extracellular domain of a human TGFβ receptor.

Embodiment 58. The antibody of embodiment 57, wherein the human TGFβ receptor is selected from the group consisting of human TGFβR1, TGFβR2, and TGFβR3.

Embodiment 59. The antibody of embodiment 57 or 58, wherein the human TGFβ receptor is human TGFβR2.

Embodiment 60. The antibody of any one of embodiments 49-59, wherein the TGFβ-binding moiety comprises an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112.

Embodiment 61. The antibody of any one of embodiments 49-60, wherein the TGFβ-binding moiety consists of an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112.

Embodiment 62. The antibody of any one of embodiments 49-61, wherein the TGFβ-binding moiety comprises an amino acid sequence selected from the group consisting of SEQ ID NOs: 109-112, preferably SEQ ID NO: 111.

Embodiment 63. The antibody of any one of embodiments 49-62, wherein the TGFβ-binding moiety consists of an amino acid sequence selected from the group consisting of SEQ ID NOs: 109-112, preferably SEQ ID NO: 111.

Embodiment 64. The antibody of any one of embodiments 49-63, the antibody comprising a polypeptide comprising an amino acid sequence selected from the group consisting of SEQ ID NOs: 113-121, preferably SEQ ID NO: 114 or 115.

Embodiment 65. The antibody of any one of embodiments 49-64, wherein the antibody comprises a polypeptide comprising an amino acid sequence selected from the group consisting of SEQ ID NOs: 113-121 and a polypeptide comprising the amino acid sequence of SEQ ID NO: 92 or 97.

Embodiment 66. The antibody of any one of embodiments 49-65, wherein the antibody comprises two polypeptides each comprising an amino acid sequence selected from the group consisting of SEQ ID NOs: 113-121 and two polypeptides each comprising the amino acid sequence of SEQ ID NO: 92 or 97.

Embodiment 67. The antibody of any one of embodiments 49-66, wherein the antibody comprises two polypeptides each comprising the amino acid sequence of SEQ ID NO: 115 and two polypeptides each comprising the amino acid sequence of SEQ ID NO: 97.

Embodiment 68. An antibody that binds to human CD73, the antibody comprising a TGFβ-binding moiety.

Embodiment 69. The antibody of embodiment 68, wherein the antibody is antagonistic to human CD73.

Embodiment 70. The antibody of embodiment 69, wherein the antibody deactivates, reduces, or inhibits an activity of human CD73.

Embodiment 71. The antibody of embodiment 69 or 70, wherein the antibody attenuates the ability of human CD73 to convert adenosine monophosphate to adenosine.

Embodiment 72. The antibody of any one of embodiments 68-71, wherein the antibody, when bound to TGFβ, is antagonistic to human CD73.

Embodiment 73. The antibody of any one of embodiments 68-72, wherein the TGFβ-binding moiety binds to human TGFβ.

Embodiment 74. The antibody of any one of embodiments 68-73, wherein the TGFβ-binding moiety comprises an extracellular domain of a human TGFβ receptor.

Embodiment 75. The antibody of any one of embodiments 68-74, wherein the human TGFβ receptor is selected from the group consisting of human TGFβR1, TGFβR2, and TGFβR3.

Embodiment 76. The antibody of embodiment 74 or 75, wherein the human TGFβ receptor is human TGFβR2.

Embodiment 77. The antibody of any one of embodiments 68-76, wherein the TGFβ-binding moiety comprises an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112.

Embodiment 78. The antibody of any one of embodiments 68-77, wherein the TGFβ-binding moiety consists of an amino acid sequence at least 75%, 80%, 85%, 90%, 91%, 92%, 93%, 94%, 95%, 96%, 97%, 98%, or 99% identical to a sequence selected from the group consisting of SEQ ID NOs: 109-112.

Embodiment 79. The antibody of any one of embodiments 68-78, wherein the TGFβ-binding moiety comprises an amino acid sequence selected from the group consisting of SEQ ID NOs: 109-112, preferably SEQ ID NO: 111.

Embodiment 80. The antibody of any one of embodiments 68-79, wherein the TGFβ-binding moiety consists of an amino acid sequence selected from the group consisting of SEQ ID NOs: 109-112, preferably SEQ ID NO: 111.

Embodiment 81. The antibody of any one of embodiments 1-48, further comprising a VEGF-binding moiety.

Embodiment 82. The antibody of embodiment 81, wherein the VEGF-binding moiety is linked to the heavy chain variable region.

Embodiment 83. The antibody of embodiment 82, wherein the VEGF-binding moiety is linked to the heavy chain variable region via a peptide linker.

Embodiment 84. The antibody of any one of embodiments 30-48, further comprising a VEGF-binding moiety linked to the heavy chain constant region.

Embodiment 85. The antibody of embodiment 84, wherein the VEGF-binding moiety is linked to the C-terminal residue of the heavy chain constant region.

Embodiment 86. The antibody of embodiment 84 or 85, wherein the N-terminal residue of the VEGF-binding moiety is linked to the C-terminal residue of the heavy chain constant region via a peptide linker.

Embodiment 87. The antibody of embodiment 83 or 86, wherein the peptide linker comprises an amino acid sequence selected from the group consisting of SEQ ID NOs: 103-108.

Embodiment 88. The antibody of any one of embodiments 81-87, wherein the VEGF-binding moiety binds to human VEGF.

Embodiment 89. The antibody of any one of embodiments 81-88, wherein the VEGF-binding moiety comprises an extracellular domain of a human VEGF receptor.

Embodiment 90. The antibody of any one of embodiments 81-89, wherein the human VEGF receptor is selected from the group consisting of human VEGFR1, VEGFR2, and VEGFR3.

Embodiment 91. The antibody of embodiment 89 or 90, wherein the human VEGF receptor is human VEGFR1.

Embodiment 92. The antibody of any one of embodiments 81-91, wherein the VEGF-binding moiety comprises an amino acid sequence at least 75%, 80%, 85%, 90%, 91%, 92%, 93%, 94%, 95%, 96%, 97%, 98%, or 99% identical to the sequence set forth in SEQ ID NO: 122.

Embodiment 93. The antibody of any one of embodiments 81-92, wherein the VEGF-binding moiety consists of an amino acid sequence at least 75%, 80%, 85%, 90%, 91%, 92%, 93%, 94%, 95%, 96%, 97%, 98%, or 99% identical to the sequence set forth in SEQ ID NO: 122.

Embodiment 94. The antibody of any one of embodiments 81-93, wherein the VEGF-binding moiety comprises the sequence set forth in SEQ ID NO: 122.

Embodiment 95. The antibody of any one of embodiments 81-94, wherein the VEGF-binding moiety consists of the sequence set forth in SEQ ID NO: 122.

Embodiment 96. The antibody of any one of embodiments 81-92, the antibody comprising a polypeptide comprising an amino acid sequence selected from the group consisting of SEQ ID NOs: 123-127.

Embodiment 97. The antibody of any one of embodiments 81-96, wherein the antibody comprises a polypeptide comprising an amino acid sequence selected from the group consisting of SEQ ID NOs: 123-127 and a polypeptide comprising an amino acid sequence selected from the group consisting of SEQ ID NOs: 92, 128, and 97.

Embodiment 98. The antibody of any one of embodiments 81-97, wherein the antibody comprises two polypeptides comprising an amino acid sequence selected from the group consisting of SEQ ID NOs: 123-127 and two polypeptides comprising an amino acid sequence selected from the group consisting of SEQ ID NOs: 92, 128, and 97.

Embodiment 99. An antibody that binds to human CD73, the antibody comprising a VEGF-binding moiety.

Embodiment 100. The antibody of embodiment 99, wherein the antibody is antagonistic to human CD73.

Embodiment 101. The antibody of embodiment 100, wherein the antibody deactivates, reduces, or inhibits an activity of human CD73.

Embodiment 102. The antibody of embodiment 100, wherein the antibody attenuates the ability of human CD73 to convert adenosine monophosphate to adenosine.

Embodiment 103. The antibody of any one of embodiments 99-102, wherein the antibody, when bound to VEGF, is antagonistic to human CD73.

Embodiment 104. The antibody of embodiment any one of embodiments 99-103, wherein the VEGF-binding moiety binds to human VEGF.

Embodiment 105. The antibody of any one of embodiments 99-104, wherein the VEGF-binding moiety comprises an extracellular domain of a human VEGF receptor.

Embodiment 106. The antibody of any one of embodiments 99-105, wherein the human VEGF receptor is selected from the group consisting of human VEGFR1, VEGFR2, and VEGFR3.

Embodiment 107. The antibody of embodiment 105 or 106, wherein the human VEGF receptor is human VEGFR1.

Embodiment 108. The antibody of any one of embodiments 99-107, wherein the VEGF-binding moiety comprises an amino acid sequence at least 75%, 80%, 85%, 90%, 91%, 92%, 93%, 94%, 95%, 96%, 97%, 98%, or 99% identical to the sequence set forth in SEQ ID NO: 122.

Embodiment 109. The antibody of any one of embodiments 99-108, wherein the VEGF-binding moiety consists of an amino acid sequence at least 75%, 80%, 85%, 90%, 91%, 92%, 93%, 94%, 95%, 96%, 97%, 98%, or 99% identical to the sequence set forth in SEQ ID NO: 122.

Embodiment 110. The antibody of any one of embodiments 99-109, wherein the VEGF-binding moiety comprises the amino acid sequence as set forth in SEQ ID NO: 122.

Embodiment 111. The antibody of any one of embodiments 99-110, wherein the VEGF-binding moiety consists of the amino acid sequence as set forth in SEQ ID NO: 122.

Embodiment 112. The antibody of any one of the preceding embodiments, further comprising a conjugated cytotoxic agent, cytostatic agent, toxin, radionuclide, or detectable label.

Embodiment 113. The antibody of any one of the preceding embodiments, wherein the antibody binds to an epitope located within a region of human CD73, the amino acid sequence of the region consisting of the amino acid sequence of SEQ ID NOs: 90 and/or 91.

Embodiment 114. The antibody of any one of the preceding embodiments, wherein the antibody binds to at least one residue in the amino acid sequence of SEQ ID NOs: 90 and/or 91.

Embodiment 115. The antibody of any one of the preceding embodiments, wherein the antibody binds to one or more amino acid residues of human CD73 selected from the group consisting of Y158, Y161, P165, or D168, numbered according to the amino acid sequence of SEQ ID NO: 99.

Embodiment 116. The antibody of any one of the preceding embodiments, wherein the binding affinity of the antibody for a protein comprising the amino acid sequence of SEQ ID NO: 133 is substantially reduced relative to the binding affinity of the antibody for a protein comprising the amino acid sequence of SEQ ID NO: 141.

Embodiment 117. The antibody of any one of the preceding embodiments, wherein the binding affinity of the antibody for a protein comprising the amino acid sequence of SEQ ID NO: 134 is substantially reduced relative to the binding affinity of the antibody for a protein comprising the amino acid sequence of SEQ ID NO: 141.

Embodiment 118. The antibody of any one of the preceding embodiments, wherein the antibody binds to amino acid residue Y158 of human CD73, numbered according to the amino acid sequence of SEQ ID NO: 99.

Embodiment 119. The antibody of any one of the preceding embodiments, wherein the binding affinity of the antibody for a protein comprising the amino acid sequence of SEQ ID NO: 59 is substantially reduced relative to the binding affinity of the antibody for a protein comprising the amino acid sequence of SEQ ID NO: 141.

Embodiment 120. The antibody of any one of the preceding embodiments, wherein the antibody binds to amino acid residue Y161 of human CD73, numbered according to the amino acid sequence of SEQ ID NO: 99.

Embodiment 121. The antibody of any one of the preceding embodiments, wherein the binding affinity of the antibody for a protein comprising the amino acid sequence of SEQ ID NO: 60 is substantially reduced relative to the binding affinity of the antibody for a protein comprising the amino acid sequence of SEQ ID NO: 141.

Embodiment 122. The antibody of any one of the preceding embodiments, wherein the antibody binds to amino acid residue P165 of human CD73, numbered according to the amino acid sequence of SEQ ID NO: 99.

Embodiment 123. The antibody of any one of the preceding embodiments, wherein the binding affinity of the antibody for a protein comprising the amino acid sequence of SEQ ID NO: 139 is substantially reduced relative to the binding affinity of the antibody for a protein comprising the amino acid sequence of SEQ ID NO: 141.

Embodiment 124. The antibody of any one of the preceding embodiments, wherein the antibody binds to amino acid residue D168 of human CD73, numbered according to the amino acid sequence of SEQ ID NO: 99.

Embodiment 125. The antibody of any one of the preceding embodiments, wherein the binding affinity of the antibody for a protein comprising the amino acid sequence of SEQ ID NO: 140 is substantially reduced relative to the binding affinity of the antibody for a protein comprising the amino acid sequence of SEQ ID NO: 141.

Embodiment 126. The antibody of any one of the preceding embodiments, wherein the binding affinity of the antibody for a protein comprising the amino acid sequence of SEQ ID NO: 135 is substantially reduced relative to the binding affinity of the antibody for a protein comprising the amino acid sequence of SEQ ID NO: 141.

Embodiment 127. The antibody of any one of the preceding embodiments, wherein the binding affinity of the antibody for a protein comprising the amino acid sequence of SEQ ID NO: 136 is substantially reduced relative to the binding affinity of the antibody for a protein comprising the amino acid sequence of SEQ ID NO: 141.

Embodiment 128. The antibody of any one of the preceding embodiments, wherein the binding affinity of the antibody for a protein comprising the amino acid sequence of SEQ ID NO: 142 is substantially reduced relative to the binding affinity of the antibody for a protein comprising the amino acid sequence of SEQ ID NO: 141, and wherein the binding affinity of the antibody for a protein comprising the amino acid sequence of SEQ ID NO: 137 is not substantially reduced relative to the binding affinity of the antibody for a protein comprising the amino acid sequence of SEQ ID NO: 141.

Embodiment 129. The antibody of any one of the preceding embodiments, wherein the binding affinity of the antibody to a protein comprising the amino acid sequence of SEQ ID NO: 142 is substantially reduced relative to the binding affinity of the antibody for a protein comprising the amino acid sequence of SEQ ID NO: 141, and wherein the binding affinity of the antibody for a protein comprising the amino acid sequence of SEQ ID NO: 138 is not substantially reduced relative to the binding affinity of the antibody for a protein comprising the amino acid sequence of SEQ ID NO: 141.

Embodiment 130. An antibody that binds to human CD73, wherein the antibody binds to an epitope located within a region of human CD73, the amino acid sequence of the region consisting of the amino acid sequence of SEQ ID NOs: 90 and/or 91.

Embodiment 131. An antibody that binds to human CD73, wherein the antibody binds to at least one residue in the amino acid sequence of SEQ ID NOs: 90 and/or 91.

Embodiment 132. An antibody that binds to human CD73, wherein the antibody binds to one or more amino acid residues of human CD73 selected from the group consisting of Y158, Y161, P165, or D168, numbered according to the amino acid sequence of SEQ ID NO: 99.

Embodiment 133. An antibody that binds to human CD73, wherein the binding affinity of the antibody for a protein comprising the amino acid sequence of SEQ ID NO: 133 is substantially reduced relative to the binding affinity of the antibody for a protein comprising the amino acid sequence of SEQ ID NO: 141.

Embodiment 134. An antibody that binds to human CD73, wherein the binding affinity of the antibody for a protein comprising the amino acid sequence of SEQ ID NO: 134 is substantially reduced relative to the binding affinity of the antibody for a protein comprising the amino acid sequence of SEQ ID NO: 141.

Embodiment 135. An antibody that binds to human CD73, wherein the antibody binds to amino acid residue Y158 of human CD73, numbered according to the amino acid sequence of SEQ ID NO: 99.

Embodiment 136. An antibody that binds to human CD73, wherein the binding affinity of the antibody for a protein comprising the amino acid sequence of SEQ ID NO: 59 is substantially reduced relative to the binding affinity of the antibody for a protein comprising the amino acid sequence of SEQ ID NO: 141.

Embodiment 137. An antibody that binds to human CD73, wherein the antibody binds to amino acid residue Y161 of human CD73, numbered according to the amino acid sequence of SEQ ID NO: 99.

Embodiment 138. An antibody that binds to human CD73, wherein the binding affinity of the antibody for a protein comprising the amino acid sequence of SEQ ID NO: 60 is substantially reduced relative to the binding affinity of the antibody for a protein comprising the amino acid sequence of SEQ ID NO: 141.

Embodiment 139. An antibody that binds to human CD73, wherein the antibody binds to amino acid residue P165 of human CD73, numbered according to the amino acid sequence of SEQ ID NO: 99.

Embodiment 140. An antibody that binds to human CD73, wherein the binding affinity of the antibody for a protein comprising the amino acid sequence of SEQ ID NO: 139 is substantially reduced relative to the binding affinity of the antibody for a protein comprising the amino acid sequence of SEQ ID NO: 141.

Embodiment 141. An antibody that binds to human CD73, wherein the antibody binds to amino acid residue D168 of human CD73, numbered according to the amino acid sequence of SEQ ID NO: 99.

Embodiment 142. An antibody that binds to human CD73, wherein the binding affinity of the antibody for a protein comprising the amino acid sequence of SEQ ID NO: 140 is substantially reduced relative to the binding affinity of the antibody for a protein comprising the amino acid sequence of SEQ ID NO: 141.

Embodiment 143. An antibody that binds to human CD73, wherein the binding affinity of the antibody for a protein comprising the amino acid sequence of SEQ ID NO: 135 is substantially reduced relative to the binding affinity of the antibody for a protein comprising the amino acid sequence of SEQ ID NO: 141.

Embodiment 144. An antibody that binds to human CD73, wherein the binding affinity of the antibody for a protein comprising the amino acid sequence of SEQ ID NO: 136 is substantially reduced relative to the binding affinity of the antibody for a protein comprising the amino acid sequence of SEQ ID NO: 141.

Embodiment 145. An antibody that binds to human CD73, wherein the binding affinity of the antibody for a protein comprising the amino acid sequence of SEQ ID NO: 142 is substantially reduced relative to the binding affinity of the antibody for a protein comprising the amino acid sequence of SEQ ID NO: 141, and wherein the binding affinity of the antibody for a protein comprising the amino acid sequence of SEQ ID NO: 137 is not substantially reduced relative to the binding affinity of the antibody for a protein comprising the amino acid sequence of SEQ ID NO: 141.

Embodiment 146. An antibody that binds to human CD73, wherein the binding affinity of the antibody to a protein comprising the amino acid sequence of SEQ ID NO: 142 is substantially reduced relative to the binding affinity of the antibody for a protein comprising the amino acid sequence of SEQ ID NO: 141, and wherein the binding affinity of the antibody for a protein comprising the amino acid sequence of SEQ ID NO: 138 is not substantially reduced relative to the binding affinity of the antibody for a protein comprising the amino acid sequence of SEQ ID NO: 141.

Embodiment 147. A compound or molecule comprising a CD73-binding moiety and a TGFβ-binding moiety.

Embodiment 148. A polynucleotide encoding a polypeptide of the antibody of any one of embodiments 1-146.

Embodiment 149. The polynucleotide of embodiment 148, wherein the polynucleotide comprises cDNA or mRNA.

Embodiment 150. A vector comprising the polynucleotide of embodiment 148 or 149.

Embodiment 151. The vector of embodiment 150, wherein the vector is a plasmid vector or a viral vector.

Embodiment 152. A recombinant host cell comprising the polynucleotide of embodiment 148 or 149, or the vector of embodiment 150 or 151.

Embodiment 153. A lipid nanoparticle comprising the polynucleotide of embodiment 148 or 149, or the vector of embodiment 150 or 151.

Embodiment 154. A pharmaceutical composition comprising the antibody, polynucleotide, vector, or lipid nanoparticle of any one of embodiments 1-146 or 148-153 and a pharmaceutically acceptable carrier or excipient.

Embodiment 155. A method of producing an antibody, the method comprising culturing the host cell of embodiment 152 under suitable conditions so that the polynucleotide is expressed and the antibody is produced.

Embodiment 156. A method of treating cancer in a subject, the method comprising administering to the subject an effective amount of the antibody, polynucleotide, vector, lipid nanoparticle, or pharmaceutical composition of any one of embodiments 1-146, 148-151, 153, or 154.

Embodiment 157. A method of inhibiting cancer metastasis in a subject, the method comprising administering to the subject an effective amount of the antibody, polynucleotide, vector, lipid nanoparticle, or pharmaceutical composition of any one of embodiments 1-146, 148-151, 153, or 154.

Embodiment 158. The method of embodiment 156 or 157, wherein the antibody, polynucleotide, vector, lipid nanoparticle, or pharmaceutical composition is administered intravenously, intratumorally, subcutaneously, intradermally, intramuscularly, intravesically, intracranially, intracavitary or intraventricularly.

Embodiment 159. The method of embodiment 156 or 157, wherein the antibody, polynucleotide, vector, lipid nanoparticle, or pharmaceutical composition is administered intratumorally.

Embodiment 160. The method of any one of embodiments 156-159, further comprising administering one or more additional therapeutic agents to the subject.

Embodiment 161. The method of any one of embodiments 156-160, wherein the antibody, polynucleotide, vector, lipid nanoparticle, or pharmaceutical composition, and the one or more additional therapeutic agents are co-administered according to the same schedule (e.g., co-administered at the same time intervals).

Embodiment 162. The method of any one of embodiments 156-160, wherein the antibody, polynucleotide, vector, lipid nanoparticle, or pharmaceutical composition, and the one or more additional therapeutic agents are co-administered according to different schedules (e.g., co-administered at different time intervals).

Embodiment 163. The method of any one of embodiments 156-162, wherein the antibody, polynucleotide, vector, lipid nanoparticle, or pharmaceutical composition is co-administered with one or more additional therapeutic agents comprising an activator or agonist of a fms related tyrosine kinase 3 (FLT3; CD135) receptor, a toll-like receptor (TLR) or a stimulator of interferon genes (STING) receptor.

Embodiment 164. The method of embodiment 163, wherein the TLR agonist or activator is selected from the group consisting of a TLR2 agonist, a TLR3 agonist, a TLR7 agonist, a TLR8 agonist and a TLR9 agonist.

Embodiment 165. The method of embodiment 163, wherein the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

Embodiment 166. The method of any one of embodiments 156-165, wherein the antibody, polynucleotide, vector, lipid nanoparticle, or pharmaceutical composition is co-administered with one or more additional therapeutic agents comprising an inhibitor or antagonist of: protein tyrosine phosphatase, non-receptor type 11 (PTPN11 or SHP2), myeloid cell leukemia sequence 1 (MCL1) apoptosis regulator; mitogen-activated protein kinase kinase kinase kinase 1 (MAP4K1) (also called Hematopoietic Progenitor Kinase 1 (HPK1)); diacylglycerol kinase alpha (DGKA, DAGK, DAGK1 or DGK-alpha); 5'-nucleotidase ecto (NT5E or CD73); transforming growth factor beta 1 (TGFB1 or TGFβ); heme oxygenase 1 (HMOX1, HO-1 or HO1); vascular endothelial growth factor A (VEGFA or VEGF); erb-b2 receptor tyrosine kinase 2 (ERBB2 HER2, HER2/neu or CD340); epidermal growth factor receptor (EGFR, ERBB, ERBB1 or HER1); ALK receptor tyrosine kinase (ALK, CD246); poly(ADP-ribose) polymerase 1 (PARP1 or PARP); cyclin dependent kinase 4 (CDK4); cyclin dependent kinase 6 (CDK6); C-C motif chemokine receptor 8 (CCR8, CDw198); CD274 molecule (CD274, PDL1 or PD-L1); programmed cell death 1 (PDCD1, PD1 or PD-1); and/or cytotoxic T-lymphocyte associated protein 4 (CTLA4, CTLA-4, CD152).

Embodiment 167. The method of embodiment 166, wherein the inhibitor comprises an antigen binding molecule, an antibody or an antigen-binding fragment thereof.

Embodiment 168. The method of embodiment 166, wherein the inhibitor comprises a small organic molecule.

Embodiment 169. The method of embodiment 166, wherein the inhibitor of MCL1 is selected from the group consisting of AMG-176, AMG-397, S-64315, AZD-5991, 483-LM, A 1210477, UMI-77, and JKY-5-037.

Embodiment 170. The method of embodiment 166, wherein the inhibitor of PTPN11 or SHP2 is selected from the group consisting of TNO155 (SHP-099), RMC-4550, JAB-3068 and RMC-4630.

Embodiment 171. The method of embodiment 160, wherein the additional therapeutic agent is a chemotherapeutic, an anti-neoplastic, a radiotherapeutic, or a checkpoint targeting agent.

Embodiment 172. The method of embodiment 160, wherein the one or more anti-neoplastic or chemotherapeutic agents are selected from the group consisting of a nucleoside analog (e.g., 5-fluorouracil, gemcitabine, cytarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), and mixtures thereof.

Embodiment 173. The method of embodiment 160, wherein the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD137 antibody, and an agonist anti-OX40 antibody.

Embodiment 174. The method of embodiment 173, wherein the additional therapeutic agent is an anti-PD-1 antibody, optionally wherein the anti-PD-1 antibody is pembrolizumab or nivolumab.

Embodiment 175. The method of embodiment 160, wherein the additional therapeutic agent is an inhibitor of indoleamine-2,3-dioxygenase (IDO).

Embodiment 176. The method of embodiment 175, wherein the inhibitor is selected from the group consisting of epacadostat, F001287, indoximod, and NLG919.

Embodiment 177. The method of embodiment 176, wherein the inhibitor is epacadostat.

Embodiment 178. The method of embodiment 160, wherein the additional therapeutic agent is a vaccine.

Embodiment 179. The method of embodiment 178, wherein the vaccine comprises a heat shock protein peptide complex (HSPPC) comprising a heat shock protein complexed with an antigenic peptide.

Embodiment 180. The method of embodiment 179, wherein the heat shock protein is hsc70 and is complexed with a tumor-associated antigenic peptide.

Embodiment 181. The method of embodiment 179, wherein the heat shock protein is gp96 and is complexed with a tumor-associated antigenic peptide, wherein the HSPPC is derived from a tumor obtained from a subject.

Embodiment 182. The method of embodiment 160, wherein the additional therapeutic agent is etoposide or doxorubicin.

Embodiment 183. The method of any one of embodiments 156-182, wherein the antibody, polynucleotide, vector, lipid nanoparticle, or pharmaceutical composition is co-administered with a FOLFOX regimen, a FOLFOXIRI regimen or a FOLFIRINOX regimen.

Embodiment 184. The method of any one of embodiments 156-183, wherein the antibody, polynucleotide, vector, lipid nanoparticle, or pharmaceutical composition is co-administered with an immunotherapy, an immunostimulatory therapy, a cellular therapy or a gene therapy.

Embodiment 185. The method of any one of embodiments 156-184, wherein the cancer is selected from the group consisting of a solid tumor, a hematological cancer, and a metastatic lesion.

Embodiment 186. The method of embodiment 185, wherein the solid tumor is selected from the group consisting of a sarcoma, a fibroblastic sarcoma, a carcinoma, and an adenocarcinoma.

Embodiment 187. The method of embodiment 185, wherein the hematological cancer is selected from the group consisting of a leukemia, a lymphoma, and a myeloma.

Embodiment 188. The method of any one of embodiments 156-184, wherein the cancer is selected from the group consisting of a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, and an extranodal marginal zone lymphoma.

Embodiment 189. The method of any one of embodiments 156 to 184, wherein the cancer is selected from the group consisting of an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), and a lymphoma.

Embodiment 190. The method of any one of embodiments 156 to 184, wherein the cancer is a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma, mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g. carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma, hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma, lobular carcinoma, including without limitation, pleomorphic carcinoma, signet ring cell carcinoma, peritoneum (e.g., mesothelioma, primary peritoneal cancer)); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma, Epstein-Barr virus (EBV)-associated lymphoproliferative diseases, including B cell lymphomas and T cell lymphomas (e.g., Burkitt lymphoma, large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, pituitary adenomas, cranial and paraspinal nerve tumors, stellar region tumors), neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, a Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma.

Embodiment 191. The method of any one of embodiments 156-184, wherein the cancer is selected from the group consisting of a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, and an endometrial cancer.

Embodiment 192. The antibody, polynucleotide, vector, lipid nanoparticle, or pharmaceutical composition of any one of embodiments 1-146, 148-151, 153, or 154 for use in the treatment of cancer.

Embodiment 193. The antibody, polynucleotide, vector, lipid nanoparticle, or pharmaceutical composition for use of embodiment 192, wherein the cancer is selected from the group consisting of a solid tumor, a hematological cancer, and a metastatic lesion.

Embodiment 194. The antibody, polynucleotide, vector, lipid nanoparticle, or pharmaceutical composition for use of embodiment 192, wherein the solid tumor is selected from the group consisting of a sarcoma, a fibroblastic sarcoma, a carcinoma, and an adenocarcinoma.

Embodiment 195. The antibody, polynucleotide, vector, lipid nanoparticle, or pharmaceutical composition for use of embodiment 192, wherein the hematological cancer is selected from the group consisting of a leukemia, a lymphoma, and a myeloma.

Embodiment 196. The antibody, polynucleotide, vector, lipid nanoparticle, or pharmaceutical composition for use of any one of embodiments 192-195, wherein the cancer is selected from the group consisting of a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, and an extranodal marginal zone lymphoma.

Embodiment 197. The antibody, polynucleotide, vector, lipid nanoparticle, or pharmaceutical composition of any one of embodiments 192-195, wherein the cancer is selected from the group consisting of a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, and an endometrial cancer.

Embodiment 198. Use of the antibody, polynucleotide, vector, lipid nanoparticle, or pharmaceutical composition of any one of embodiments 1-146, 148-151, 153, or 154 for the preparation of a medicament for treating cancer.

Embodiment 199. The use of embodiment 198, wherein the cancer is selected from the group consisting of a solid tumor, a hematological cancer, and a metastatic lesion.

Embodiment 200. The use of embodiment 199, wherein the solid tumor is selected from the group consisting of a sarcoma, a fibroblastic sarcoma, a carcinoma, and an adenocarcinoma.

Embodiment 201. The use of embodiment 199, wherein the hematological cancer is selected from the group consisting of a leukemia, a lymphoma, and a myeloma.

Embodiment 202. The use of any one of embodiments 198-201, wherein the cancer is selected from the group consisting of a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, and an extranodal marginal zone lymphoma.

Embodiment 203. The use of any one of embodiments 198-201, wherein the cancer is selected from the group consisting of a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, and an endometrial cancer.

Embodiment 204. The antibody, polynucleotide, vector, lipid nanoparticle, or pharmaceutical composition of any one of embodiments 1-146, 148-151, 153, or 154, for use in the method of any one of embodiments 156-191.

Embodiment 205. Use of the antibody, polynucleotide, vector, lipid nanoparticle, or pharmaceutical composition of any one of embodiments 1-146, 148-151, 153, or 154 in the method of any one of embodiments 156-191.

4. BRIEF DESCRIPTION OF THE DRAWINGS

FIG. 1 is a set of graphs showing the binding of anti-CD73 antibodies (BA013, BA014, BA015, or a reference antibody ("RA001")), or an isotype control antibody, to Chinese hamster ovarian (CHO) cells ectopically expressing mouse, cynomolgus, or human CD73 (left to right in the figure), as measured by flow cytometry. The median fluorescence intensity (MFI) values are plotted against antibody concentrations.

FIGS. 2A-2B are a set of graphs showing the extent of inhibition of CD73 enzymatic activity by anti-CD73 antibodies (BA013, BA014, BA015, or RA001) or an isotype control (FIG. 2A), or by anti-CD73 antibody BA015 or the isotype control (FIG. 2B). The percent activity of CD73 ectopically expressed on the surface of Jurkat cells (FIG. 2A) or CHO cells (FIG. 2B) is plotted as luminescence levels (measured in Relative Light Unit (RLU)) relative to the levels observed in the absence of antibody.

FIGS. 3A-3C are a set of graphs and images showing internalization of anti-CD73 antibodies and antibody-mediated internalization of CD73. FIG. 3A shows results of a cytotoxicity assay measuring antibody internalization by incubating CD73-expressing cells with test antibodies (BA015, RA001, or a second reference antibody ("RA002")), isotype control, or no antibody, and a secondary antibody conjugated with cytotoxic monomethyl auristatin E (MMAE). The levels of antibody internalization are plotted as the viability of CD73-expressing cells (normalized to the viability of control cells that were not treated with any primary or secondary antibodies ("NT")) against antibody concentration. FIG. 3B shows a series of representative images from a CD73 internalization assay, wherein cells expressing a HaloTag®-CD73 fusion protein are detected by confocal fluorescence microscopy after incubation of the cells with a HaloTag® Alexa Fluor™ 488 ligand that stains the fusion protein and treatment with anti-CD73 or control antibodies. FIG. 3C is a graph showing quantification of intracellular HaloTag®-CD73 from four images acquired in the FITC channel (to detect HaloTag® Alexa Fluor™ 488) every hour for each condition over a course of 6 hours.

FIGS. 4A-4P are a set of graphs showing binding of an isotope control, RA001, RA002, BA015, and humanized anti-CD73 antibodies BA019-BA030 to CHO cells ectopically expressing cynomolgus CD73, as measured by flow cytometry. The MFI values are plotted against antibody concentrations to show binding curves.

FIGS. 5A-5P are a set of graphs showing binding of an isotope control, RA001, RA002, BA015, and humanized anti-CD73 antibodies BA019-BA030 to CHO cells ectopically expressing human CD73, as measured by flow cytometry. A negative control without any antibody, designated "no antibody," was used for comparison in FIG. 5A. The MFI values are plotted against antibody concentrations to show binding curves.

FIGS. 6A-6P are a set of graphs showing the extent of inhibition of CD73 enzymatic activity by an isotope control, RA001, RA002, BA015, and humanized anti-CD73 antibodies BA019-BA030. The percent activity of CD73 ectopically expressed on the surface of Jurkat cells is plotted as luminescence levels (measured in RLU) relative to the levels in the absence of antibody.

FIGS. 7A-7P are a set of graphs showing the extent of inhibition of CD73 enzymatic activity by an isotope control, RA001, RA002, BA015, and humanized anti-CD73 antibodies BA019-BA030. The percent activity of immobilized, recombinant CD73 is plotted as luminescence levels (measured in RLU) relative to the levels in the absence of antibody.

FIGS. 8A-8M are a set of graphs showing the results of a cytotoxicity assay that measures antibody internalization by incubating CD73-expressing cells with no antibody, isotope control, BA015, or a humanized anti-CD73 antibody, and a secondary antibody conjugated with MMAE. The levels of antibody internalization are plotted as the viability of the CD73-expressing cells (normalized to the viability of control cells that were not treated with any primary or secondary antibodies ("NT")) against antibody concentrations.

Figure 9B:
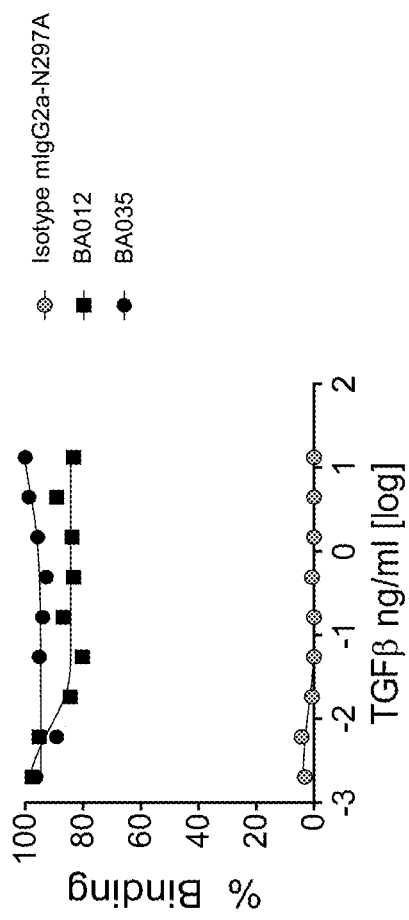
Figure 9A:
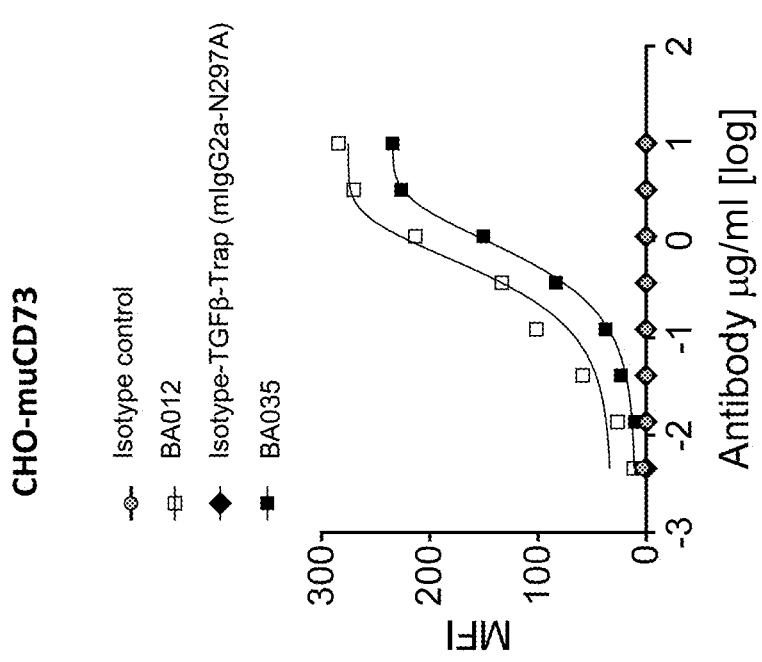
Figure 9C:
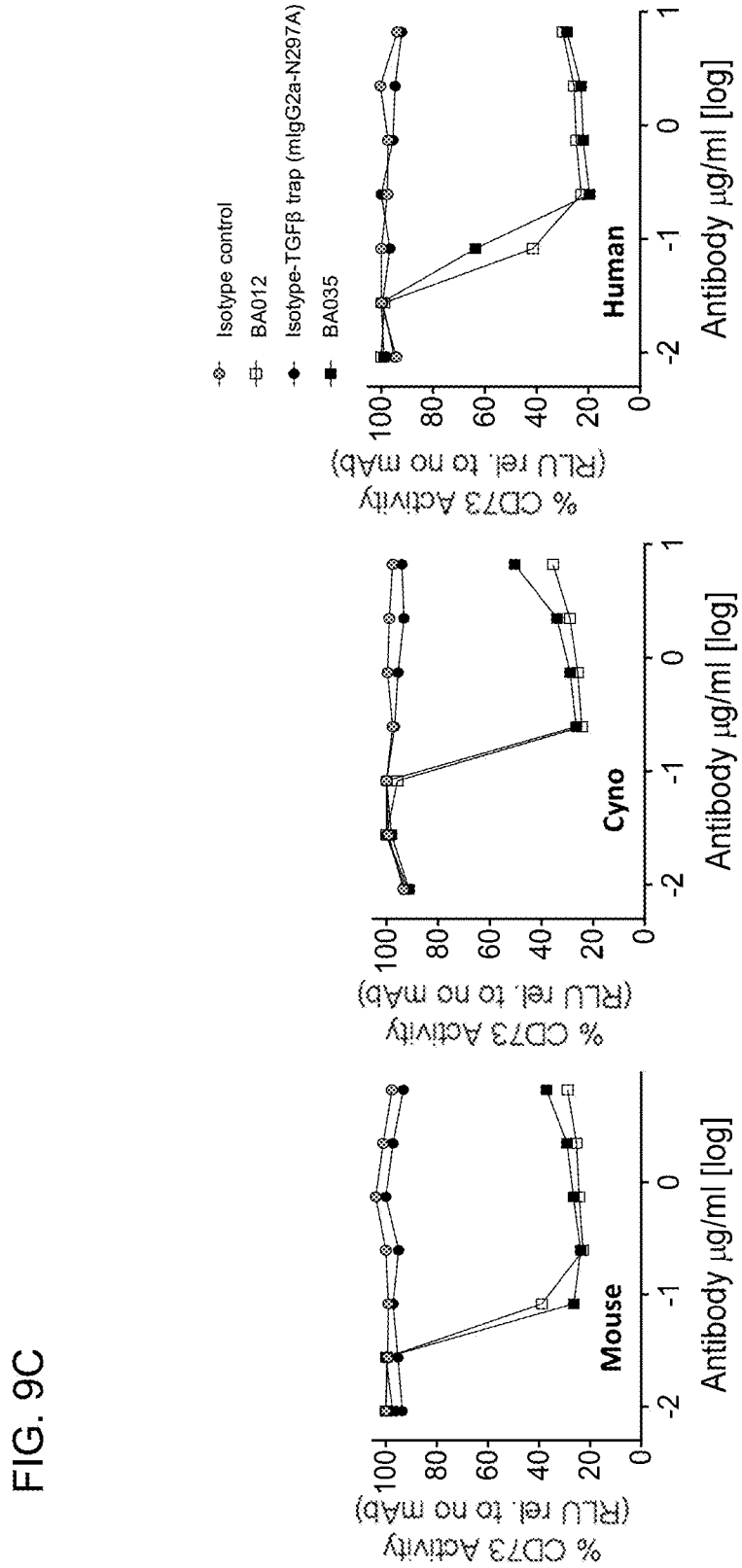
Figure 9D:
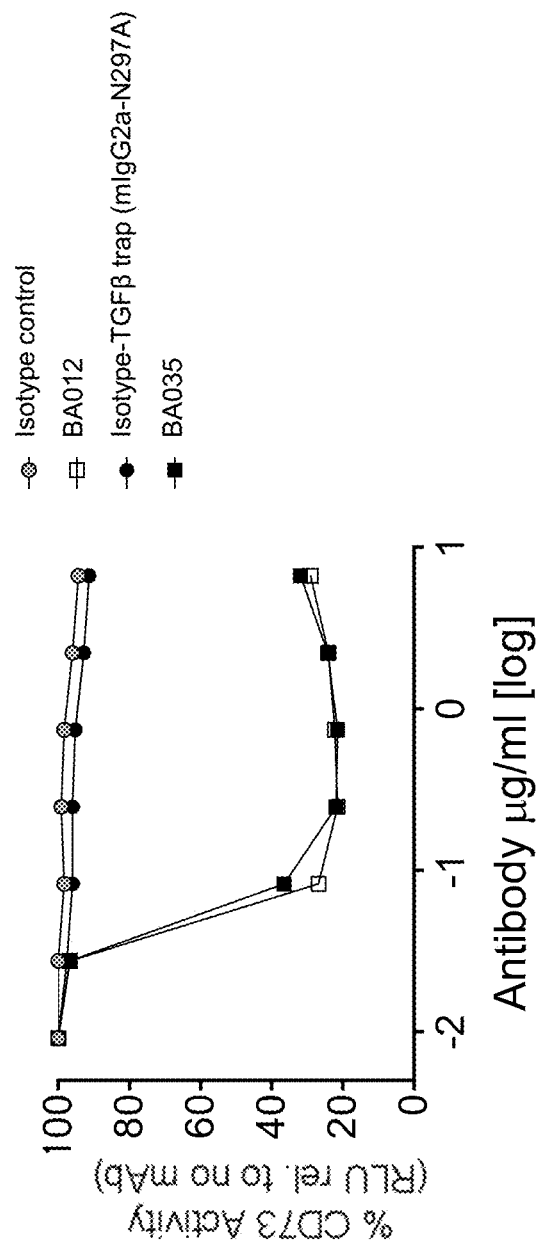
Figure 9E:
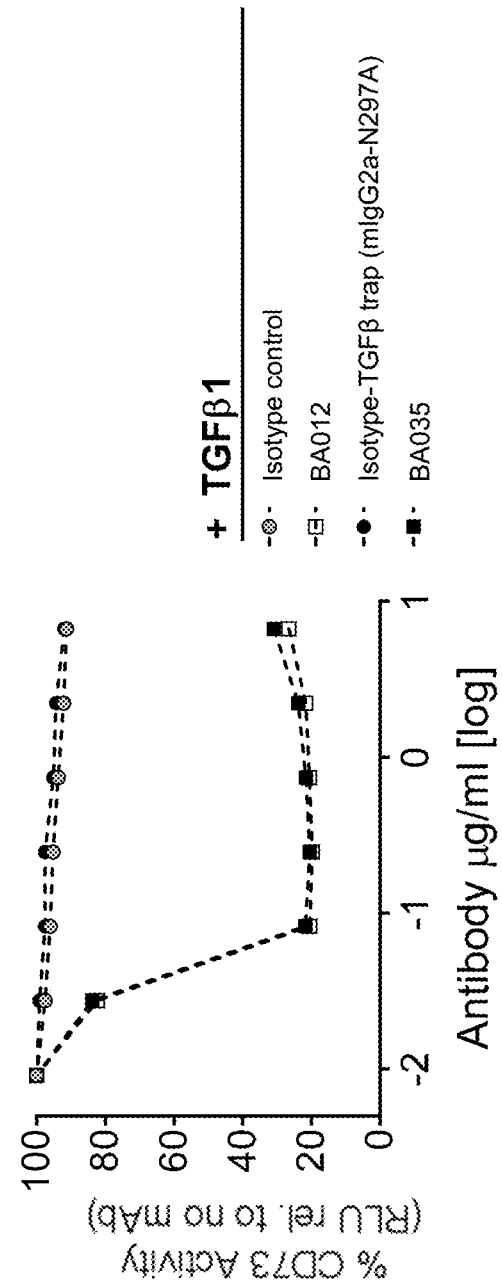

FIGS. 9A-9E are a set of graphs showing the abilities of an anti-CD73 antibody (BA012) or an anti-CD73-TGFβ trap fusion protein (BA035), but not isotype controls (an isotype antibody control and a fusion protein control comprising such isotype antibody and the TGFβ trap), to bind CD73 and inhibit CD73 enzymatic activity. FIGS. 9A and 9B show binding of BA012 or BA035, but not isotype controls, to CHO cells ectopically expressing mouse CD73 in the absence (FIG. 9A) or presence (FIG. 9B) of TGFβ1. The levels of binding, as measured by flow cytometry, are plotted as absolute MFI values (FIG. 9A) or as percentage MFI values relative to the MFI value of each test condition in the absence of TGFβ1 (FIG. 9B). FIGS. 9C-9E show inhibition of CD73 enzymatic activity by BA012 or BA035, but not the isotype control, in the absence (FIGS. 9C and 9D) or presence (FIG. 9E) of TGFβ1. The percent activity of CD73 ectopically expressed on the surface of CHO cells is plotted as luminescence levels (measured in RLU) relative to the levels in the absence of antibody.

Figure 10A:
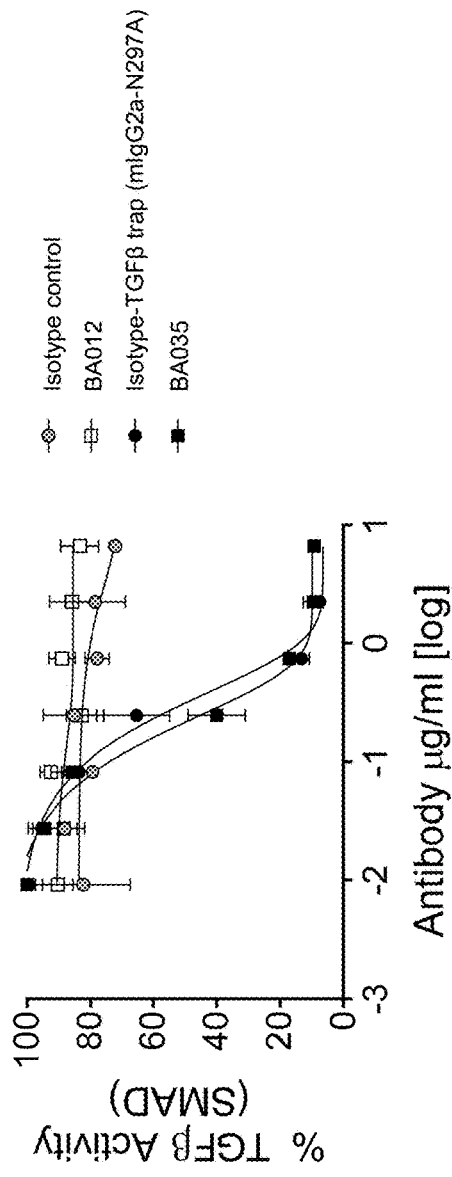
Figure 10B:
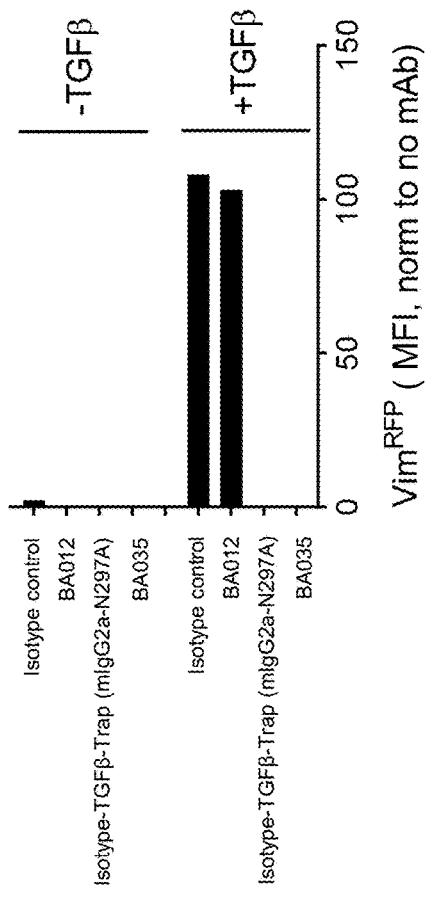

FIGS. 10A and 10B are a set of graphs showing antagonism of TGFβ-induced signaling by BA012 or BA035, but not isotype controls. In FIG. 10A, relative luminescence levels, which correlate with TGFβ1-induced expression of luciferase in HEK293-SMAD reporter cells, are plotted as percentage values relative to the luminescence levels in the absence of antibody. In FIG. 10B, the expression levels of red fluorescent protein (RFP), which correlate with TGFβ1-induced expression of Vimentin in A549-Vimentin-RFP cells, are plotted as absolute fluorescence values minus the background fluorescence levels in the absence of antibody or TGFβ1.

Figure 11A:
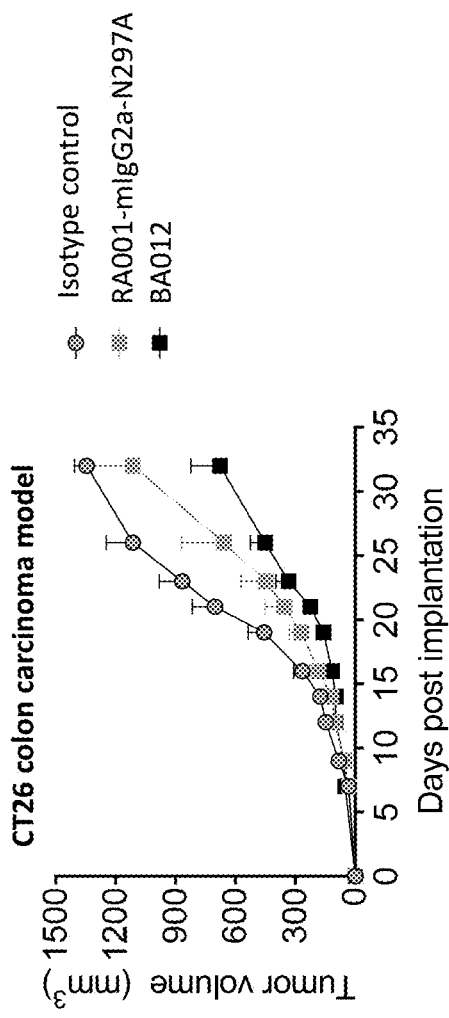
Figure 11B:
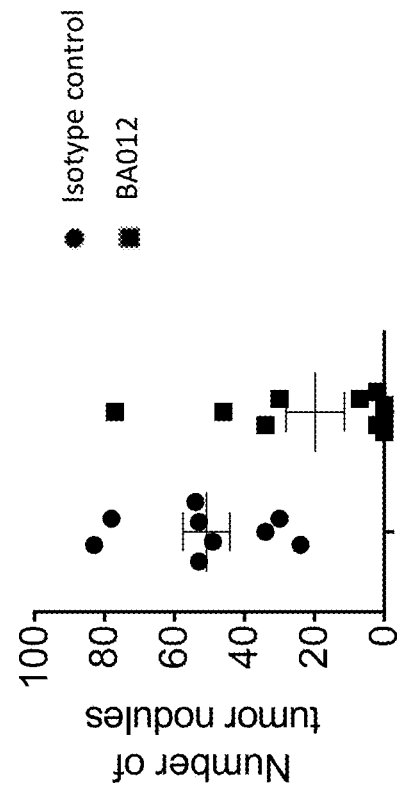

FIGS. 11A and 11B are a set of graphs showing the inhibition of tumor growth and metastasis by anti-CD73 antibodies (an isotope control, BA012, and a reference antibody comprising the variable domain of RA001 and a murine IgG2a-N297A constant domain, designated RA001-IgG2a-N297A). FIG. 11A shows mean calculated tumor volumes of 8-10 mice/group implanted subcutaneously with CT26 tumor cells and treated with the indicated antibodies. FIG. 11B shows the numbers of tumor nodules in the lungs of each mouse implanted intravenously with EMT6 tumor cells and treated with BA012 or isotype control antibody.

Figure 12A:
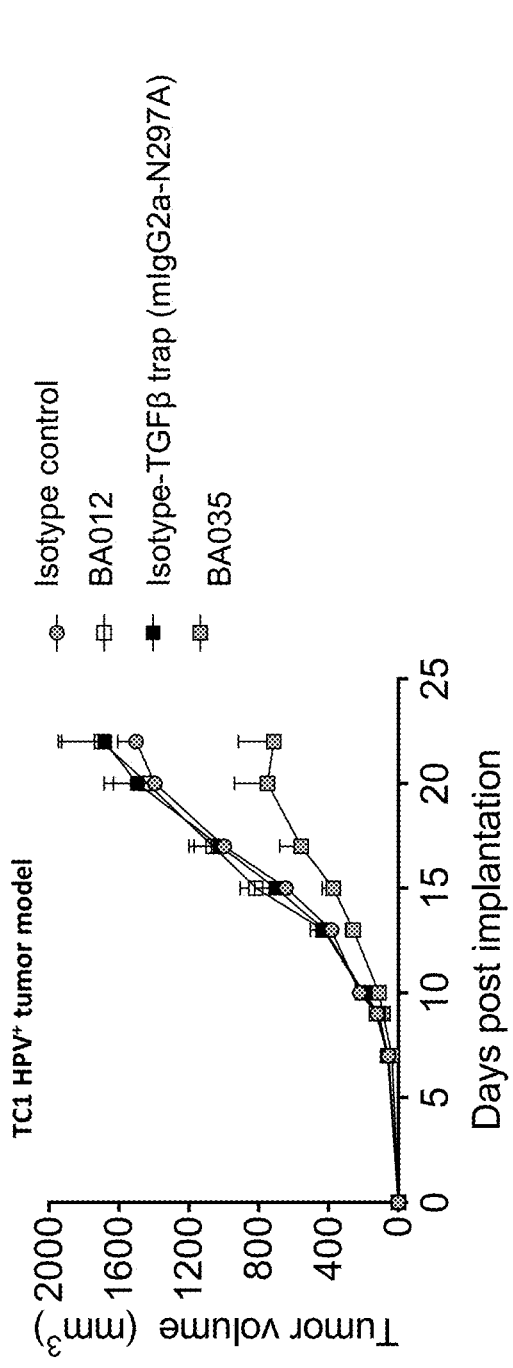
Figure 12B:
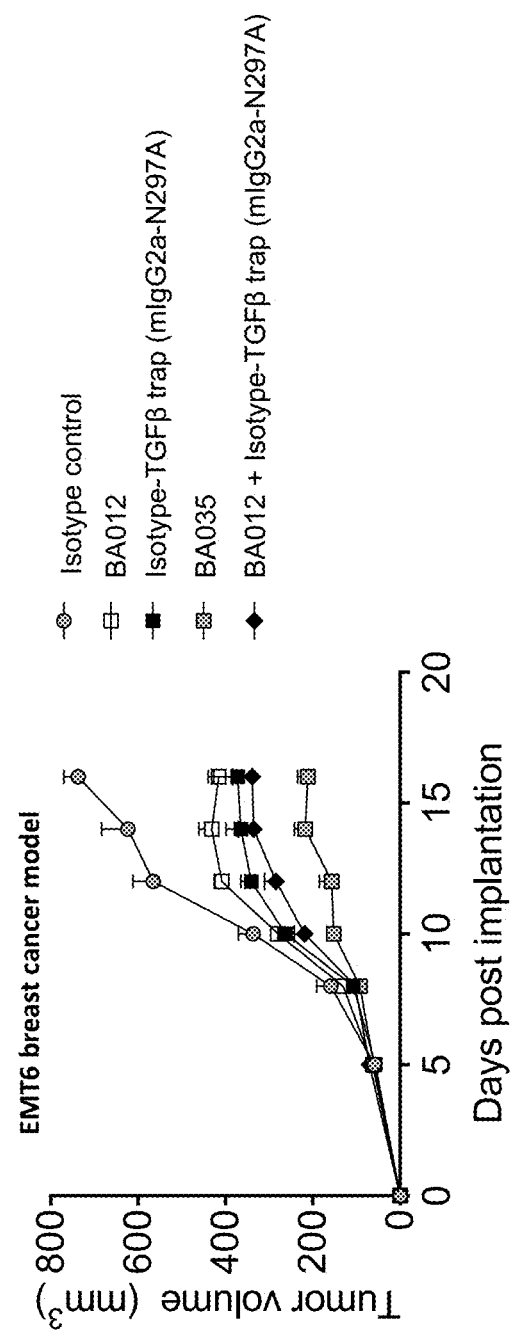
Figures 14C, 14D:
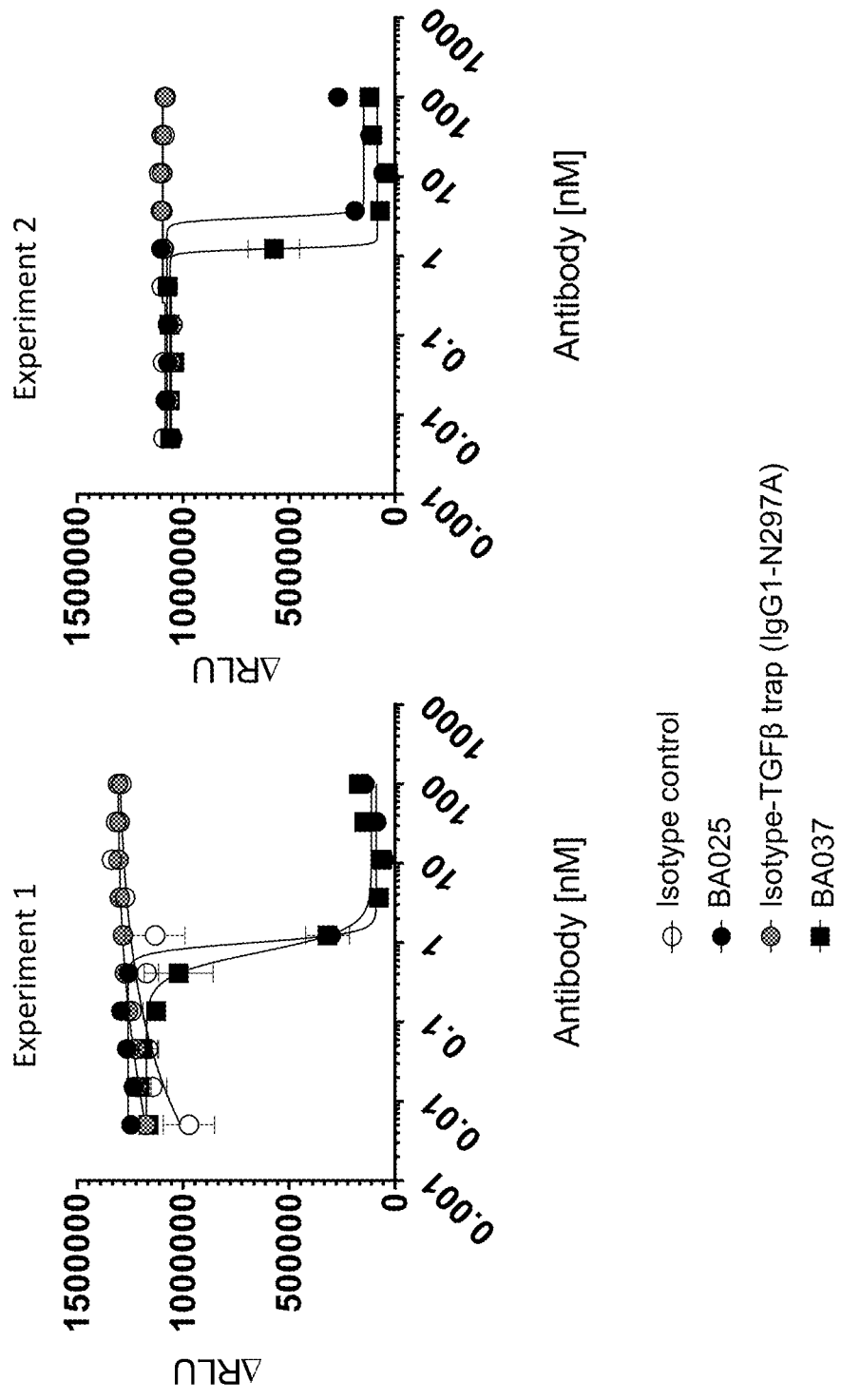
Figures 15A, 15B:
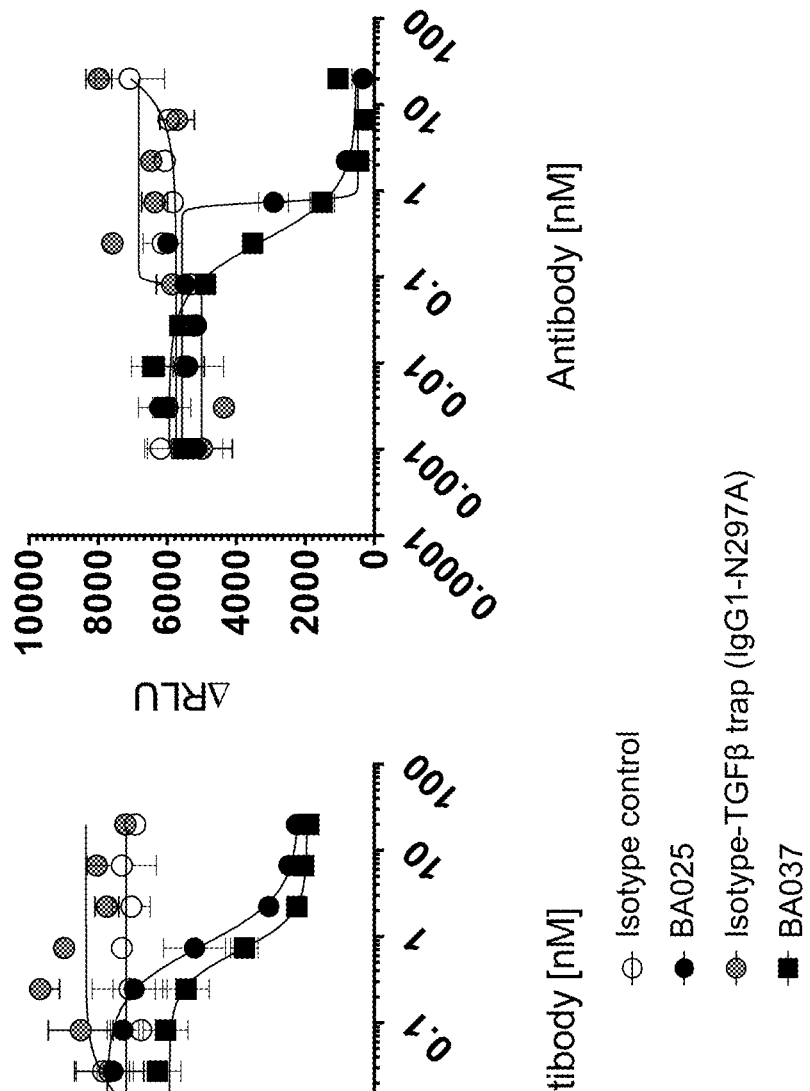

FIGS. 12A and 12B are a set of graphs showing inhibition of tumor growth by BA012, BA035, or isotype controls. FIG. 12A shows mean calculated tumor volumes of 5-7 mice/group implanted with TC1 tumor cells subcutaneously and treated with the indicated antibodies. FIG. 12B shows calculated tumor volumes of 8-10 mice/group implanted with EMT6 tumor cells subcutaneously and treated with the indicated antibodies.

FIGS. 13A and 13B are a set of graphs showing the binding of an anti-CD73 antibody (BA025), an anti-CD73-TGFβ trap fusion protein (BA037), an isotype control antibody, or an isotype-TGFβ trap to CD8+ T cells isolated from PBMCs of either human (FIG. 13A) or cynomolgus monkey (FIG. 13B), as measured by flow cytometry. The median MFI values are plotted against antibody concentrations.

FIGS. 14A-14D are a set of graphs showing the extent of inhibition of recombinant human CD73 enzymatic activity in a biochemical assay by an anti-CD73 antibody (BA025), an anti-CD73-TGFβ trap fusion protein (BA037), an isotype control antibody, or an isotype-TGFβ trap. The results of two experiments are shown. The activity of immobilized plate-bound CD73 (FIGS. 14A and 14B) or soluble CD73 (FIGS. 14C and 14D) is plotted as luminescence levels (measured in RLU) relative to the levels in the absence of antibody.

FIGS. 15A-15D are a set of graphs showing the extent of inhibition of recombinant cynomolgus monkey CD73 enzymatic activity in a biochemical assay by an anti-CD73 antibody (BA025), an anti-CD73-TGFβ trap fusion protein (BA037), an isotype control antibody, or an isotype-TGFβ trap. The results of two experiments are shown. The activity of immobilized plate-bound CD73 (FIGS. 15A and 15B) or soluble CD73 (FIGS. 15C and 15D) is plotted as luminescence levels (measured in RLU) relative to the levels in the absence of antibody.

FIGS. 16A and 16B are a set of graphs showing the extent of inhibition of CD73 enzymatic activity by an anti-CD73 antibody (BA025), an anti-CD73-TGFβ trap fusion protein (BA037), an isotype control antibody, or an isotype-TGFβ trap. The percent activity of CD73 ectopically expressed on the surface of Jurkat cells in two experiments (FIG. 16A and FIG. 16B) is plotted as luminescence levels (measured in RLU) relative to the levels in the absence of antibody.

Figures 17A, 17B, 17C:
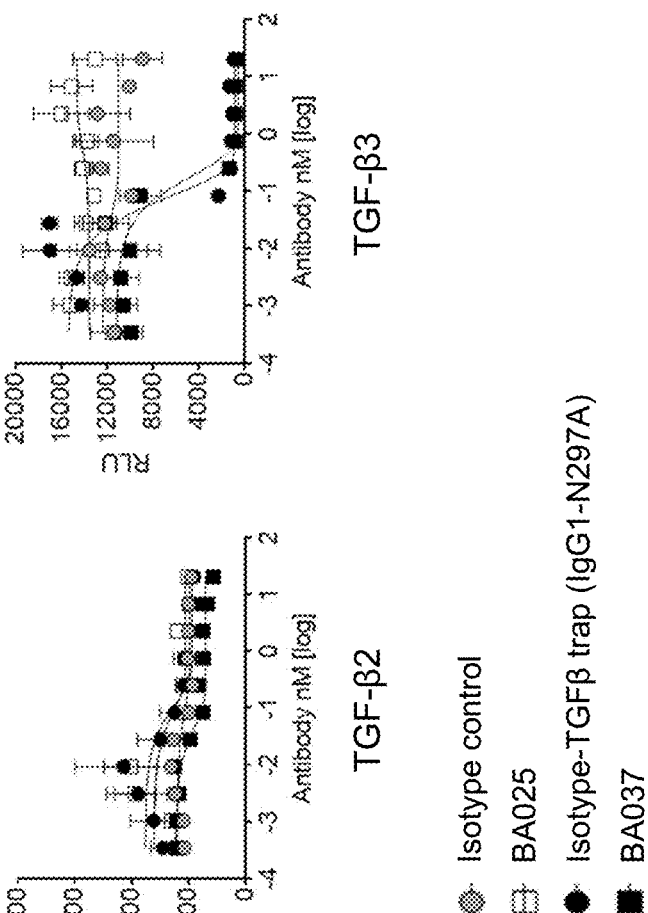

FIGS. 17A-17C are a set of graphs showing antagonism of TGFβ-induced signaling in an HEK293 SMAD-luciferase reporter assay by an anti-CD73 antibody (BA025), an anti-CD73-TGFβ trap fusion protein (BA037), an isotype control antibody, or an isotype-TGFβ trap. Each TGFβ isoform was tested separately. The TGFβ-induced SMAD signaling activity (which correlates with luciferase activity in the HEK293-SMAD-luciferase cells) is plotted as luminescence levels (measured in RLU) relative to the levels in the absence of antibody.

FIGS. 18A-18I are a set of graphs showing antagonism of TGFβ-induced signaling in an A549-Vimentin-RFP reporter cell assay by an anti-CD73 antibody (BA025), an anti-CD73-TGFβ trap fusion protein (BA037), an isotype control antibody, or an isotype-TGFβ trap. Each TGFβ isoform was tested separately. The results of three experiments are shown. Two experiments (FIGS. 18A-18C and 18D-18F) were conducted at room temperature. One experiment (FIGS. 18G-18I) was conducted at 37° C. The TGFβ-induced signaling activity (which correlate with RFP expression in the A549-Vimentin-RFP cells) is plotted as MFI of RFP relative to the levels in the absence of antibody.

FIGS. 19A-19D are a set of graphs showing internalization of anti-CD73 antibodies and antibody-mediated internalization of CD73. The graphs show results of a cytotoxicity assay measuring antibody internalization by incubating CD73-expressing cells with an anti-CD73 antibody (BA025), an anti-CD73-TGFβ trap fusion protein (BA037), an isotype control antibody, or no antibody, in each case together with a secondary antibody conjugated with the cytotoxic agent DM1. The levels of antibody internalization are measured by cell death which is indicated by a loss of fluorescence intensity (measured in RLU). The data are plotted as the RLU of CD73-expressing cells against antibody concentration. Data from two experiments are shown.

FIGS. 20A and 20B are a set of graphs showing ability of an anti-CD73 antibody (BA025), an anti-CD73-TGFβ trap fusion protein (BA037), an isotype control antibody, an isotype-TGFβ trap, and an Fc-competent anti-CD73 to activate FcγR receptors on Jurkat cells containing an NFAT-luciferase reporter construct and expressing either FcγRIIA (H131) (FIG. 20A) or Jurkat FcγRIIIA (V158) (FIG. 20B), in each case in the presence of CHO cells expressing CD73. FcγR receptor activation is plotted as luminescence levels (measured in RLU) relative to the levels in the absence of antibody.

Figure 21:
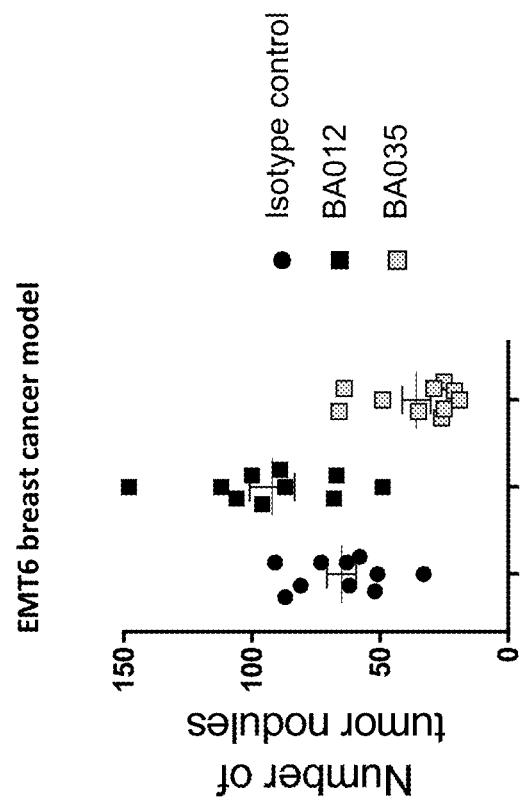

FIG. 21 is a graph showing the inhibition of metastasis by BA035. The graph shows the numbers of tumor nodules in the lungs of each mouse implanted intravenously with EMT6 tumor cells and treated with BA012, BA035 or isotype control antibody.

Figure 22:
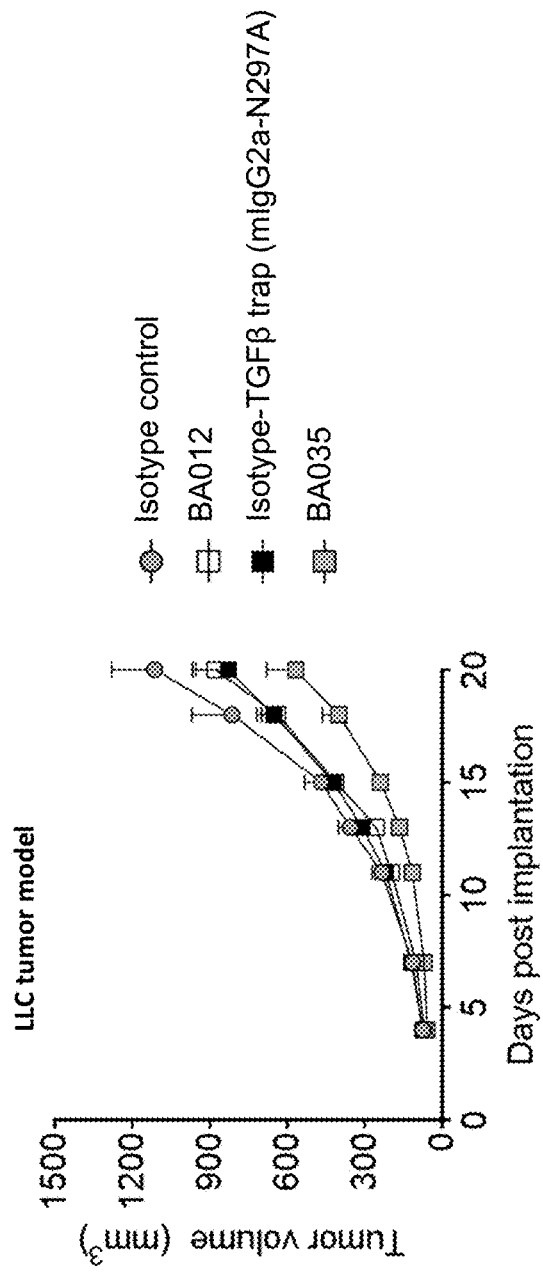

FIG. 22 is a graph showing inhibition of tumor growth by BA012, BA035, or isotype controls. The graph shows mean calculated tumor volumes from 5-7 mice/group implanted with LLC tumor cells and treated with the indicated antibodies.

Figure 23:
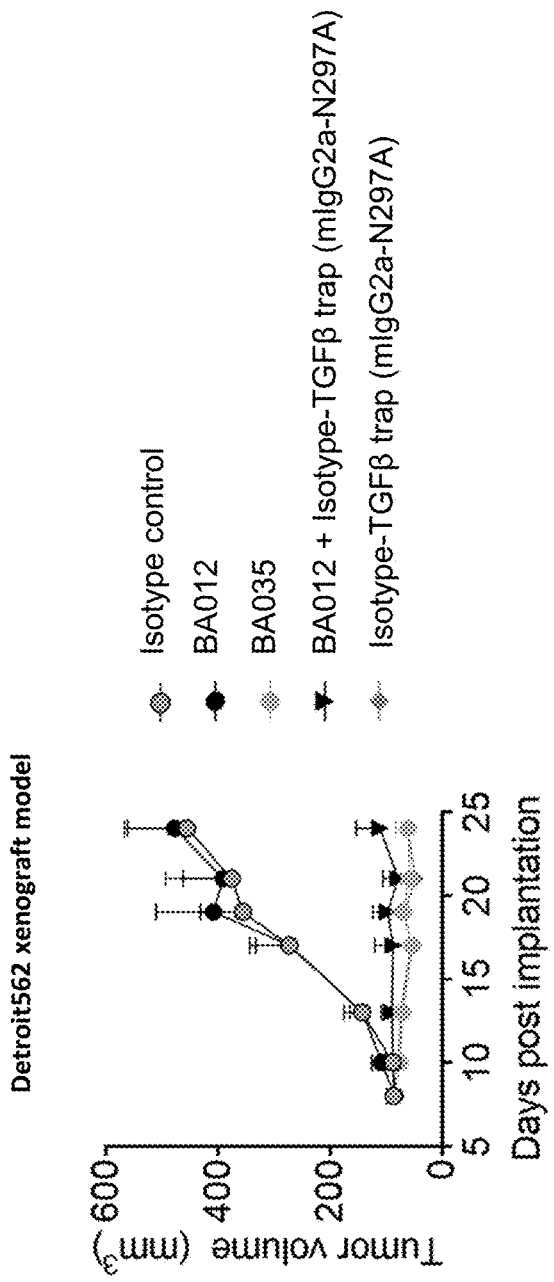

FIG. 23 is a graph showing inhibition of tumor growth by BA012, BA035, or isotype controls. The graph shows mean calculated tumor volumes of 8-10 mice/group implanted with Detroit562 tumor cells subcutaneously and treated with the indicated antibodies.

Figure 24A:
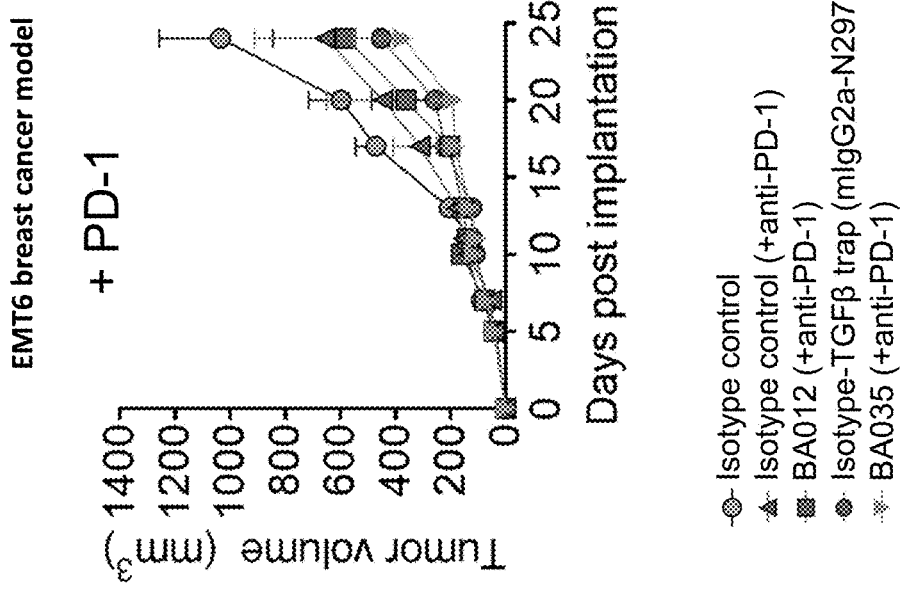
Figure 24B:
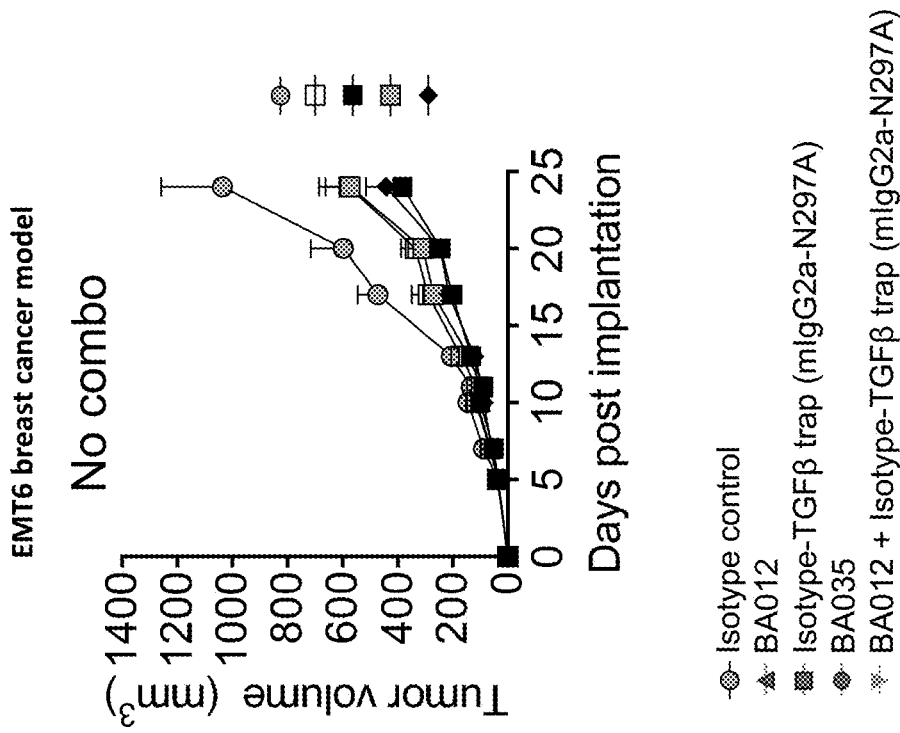
Figure 24C:
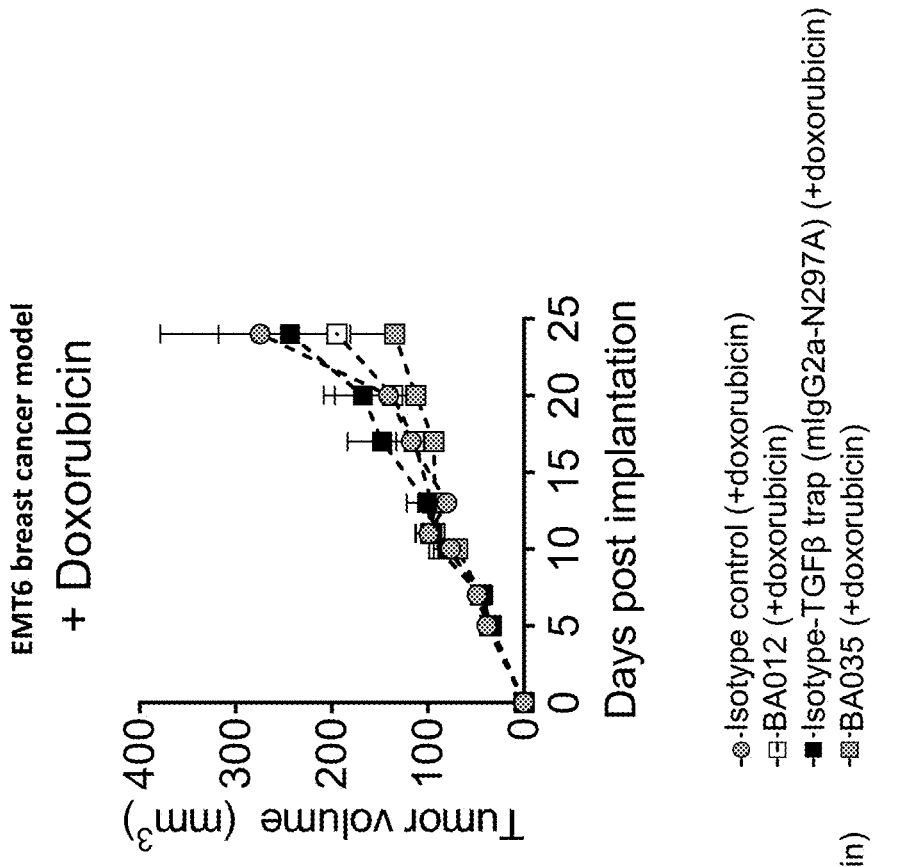
Figure 24D:
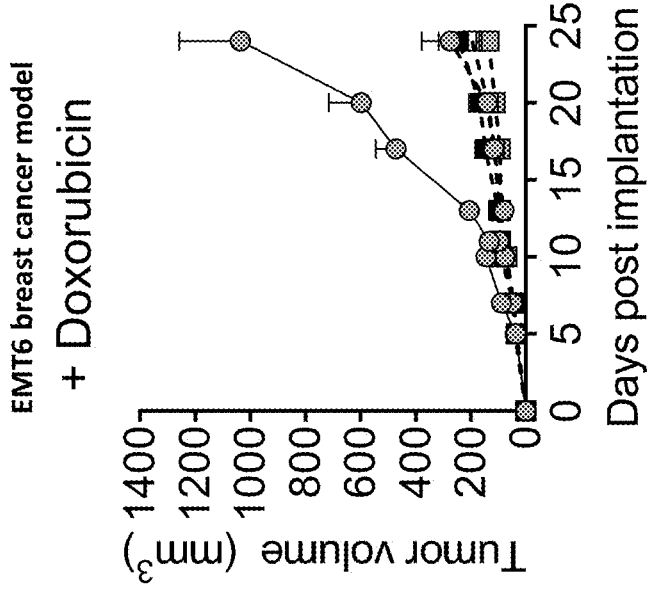

FIGS. 24A-24D are a set of graphs showing inhibition of tumor growth by BA012, BA035, or isotype controls, administered alone or in combination with either an anti-PD-1 antibody or doxorubicin. The graphs show calculated tumor volumes of 6-9 mice/group implanted subcutaneously with EMT6 tumor cells and treated with the indicated antibodies. FIG. 24A shows data from mice that did not receive a combination treatment. FIG. 24B shows data from mice that received anti-PD-1 in addition to the indicated antibodies. FIGS. 24C and 24D show data from mice that received doxorubicin in addition to the indicated antibodies. The graph in FIG. 24D shows the same data as the graph in FIG. 24C, except that the isotype control data has been removed and the x-axis has been replotted to better separate data from the different treatment groups.

Figure 25:
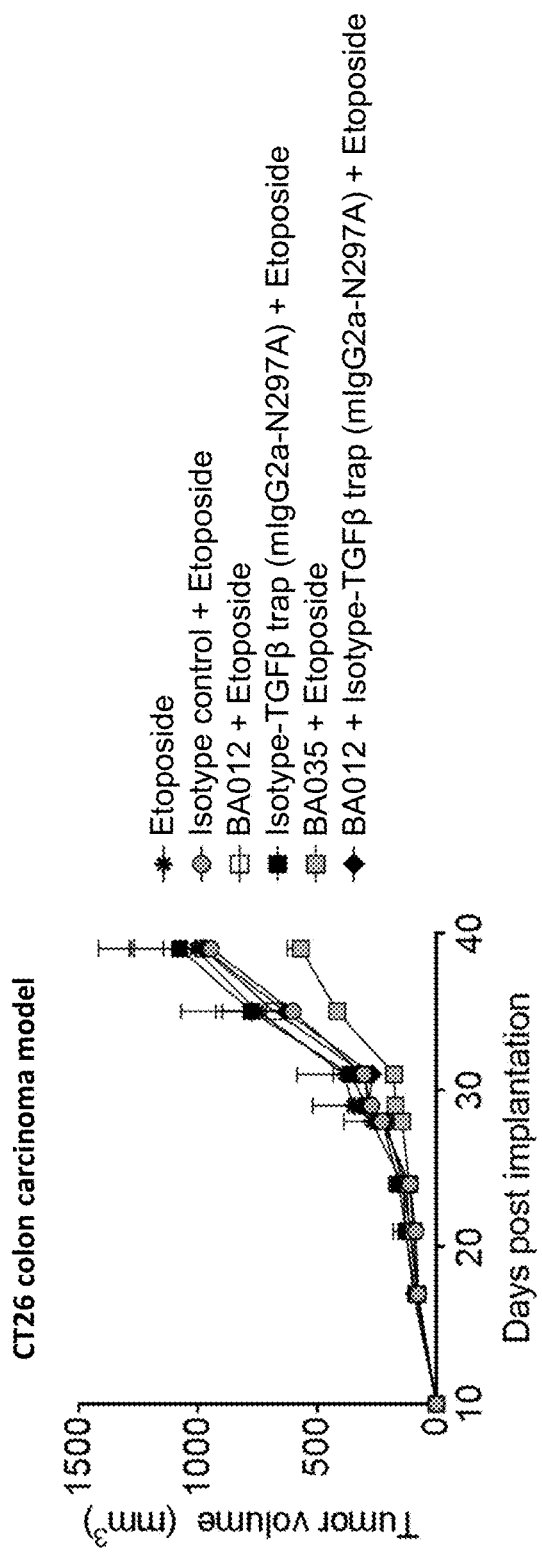

FIG. 25 is a graph showing the inhibition of tumor growth by BA012, BA035, or isotype controls in combination with etoposide, or by etoposide alone. The graph shows mean calculated tumor volumes of 5-8 mice/group implanted subcutaneously with CT26 tumor cells and treated with the indicated antibodies.

5. DETAILED DESCRIPTION

The instant disclosure provides antibodies that specifically bind to CD73 (e.g., human CD73, cynomolgus CD73, or mouse CD73) and antagonize CD73 function, e.g., the enzymatic activity to promote AMP conversion to adenosine. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for boosting immune responses to a tumor antigen, and hence, are useful for treating cancer in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "CD73" (also known as ecto-5'-nucleotidase, ecto-5'-NT, 5'-NT, and NT5E) refers to a protein that in humans is encoded by the NT5E gene. As used herein, the term "human CD73" refers to a CD73 protein encoded by a human NT5E gene (e.g., a wild-type human NT5E gene) or an extracellular domain of such a protein. Exemplary wild-type human CD73 proteins are provided by GenBank™ accession numbers NP_002517.1, NP_001191742.1, AAH65937, and EAW48635. For this definition and the definitions of other proteins herein, the skilled worker will appreciate that a protein encoded by a gene can be in its mature form, e.g., with its signal peptide removed. Exemplary amino acid sequences of an immature human CD73 protein are provided as SEQ ID NOs: 99, 100, 129, and 130. Exemplary amino acid sequence of a mature human CD73 protein are provided as amino acid residues Trp27-Gln574 of SEQ ID NO: 99 and amino acid residues Trp27-Gln524 of SEQ ID NO: 100. Exemplary amino acid sequences of an extracellular domain of a mature human CD73 protein are provided as amino acid residues Trp27-Lys547 of SEQ ID NO: 99 and Trp27-Lys497 of SEQ ID NO: 100.

As used herein, the terms "transforming growth factor beta" and "TGFβ" refer to any of the TGFβ family proteins that in human are encoded by the TGFB1, TGFB2, and TGFB3 genes. As used herein, the term "human TGFβ1" refers to a TGFβ1 protein encoded by a human TGFB1 gene (e.g., a wild-type human TGFB1 gene). An exemplary wild-type human TGFβ1 protein is provided by GenBank™ accession number NP_000651.3. As used herein, the term "human TGFβ2" refers to a TGFβ2 protein encoded by a human TGFB2 gene (e.g., a wild-type human TGFB2 gene). Exemplary wild-type human TGFβ2 proteins are provided by GenBank™ accession numbers NP_001129071.1 and NP_003229.1. As used herein, the term "human TGFβ3" refers to a TGFβ3 protein encoded by a human TGFB3 gene (e.g., a wild-type human TGFB3 gene). Exemplary wild-type human TGFβ3 proteins are provided by GenBank™ accession numbers NP_003230.1, NP_001316868.1, and NP_001316867.1.

As used herein, the terms "transforming growth factor beta receptor" and "TGFβ receptor" refer to any of the TGFβ receptor family proteins that in human are encoded by the TGFBR1, TGFBR2, and TGFBR3 genes. As used herein, the term "human TGFβR1" refers to a TGFβR1 protein encoded by a human TGFBR1 gene (e.g., a wild-type human TGFBR1 gene). Exemplary wild-type human TGFβR1 proteins are provided by GenBank™ accession numbers NP_004603.1, NP_001124388.1, and NP_001293139.1. As used herein, the term "human TGFβ2" refers to a TGFβ2 protein encoded by a human TGFB2 gene (e.g., a wild-type human TGFB2 gene). Exemplary wild-type human TGFβ2 proteins are provided by GenBank™ accession numbers NP_001129071.1 and NP_003229.1. As used herein, the term "human TGFβ3" refers to a TGFβ3 protein encoded by a human TGFB3 gene (e.g., a wild-type human TGFB3 gene). Exemplary wild-type human TGFβ3 proteins are provided by GenBank™ accession numbers NP_003230.1, NP_001316868.1, and NP_001316867.1.

As used herein, the terms "vascular endothelial growth factor" and "VEGF" refer to any of the VEGF family proteins that in human are encoded by the VEGFA, VEGFB, VEGFC, and VEGFD genes. As used herein, the term "human VEGF-A" refers to a VEGF-A protein encoded by a human VEGFA gene (e.g., a wild-type human VEGFA gene). Exemplary wild-type human VEGF-A proteins are provided by GenBank™ accession numbers NP_001020537.2, NP_001020538.2, NP_001020539.2, NP_001020540.2, NP_001020541.2, NP_001028928.1, NP_001165093.1, NP_001165094.1, NP_001165095.1, NP_001165096.1, NP_001165097.1, NP_001165098.1, NP_001165099.1, NP_001165100.1, NP_001165101.1, NP_001191313.1, NP_001191314.1, NP_001273973.1, NP_001303939.1, and NP_003367.4. As used herein, the term "human VEGF-B" refers to a VEGF-B protein encoded by a human VEGFB gene (e.g., a wild-type human VEGFB gene). Exemplary wild-type human VEGF-B proteins are provided by GenBank™ accession numbers NP_001230662.1 and NP_003368.1. As used herein, the term "human VEGF-C" refers to a VEGF-C protein encoded by a human VEGFC gene (e.g., a wild-type human VEGFC gene). Exemplary wild-type human VEGF-C proteins are provided by GenBank™ accession number NP_005420.1. As used herein, the term "human VEGF-D" refers to a VEGF-D protein encoded by a human VEGFD gene (e.g., a wild-type human VEGFD gene). Exemplary wild-type human VEGF-D proteins are provided by GenBank™ accession number NP_004460.1.

As used herein, the terms "vascular endothelial growth factor receptor" and "VEGFR" refer to any of the VEGF receptor family proteins that in human are encoded by the FLT1 (also known as VEGFR1, KDR (also known as VEGFR2), and FLT4 (also known as VEGFR3) genes. As used herein, the term "human VEGFR1" refers to a VEGFR1 protein encoded by a human FLT1 gene (e.g., a wild-type FLT1 gene). Exemplary wild-type human VEGFR1 proteins are provided by GenBank™ accession numbers NP_002010.2, NP_001153392.1, NP_001153502.1, and NP_001153503.1. As used herein, the term "human VEGFR2" refers to a VEGFR2 protein encoded by a human KDR gene (e.g., a wild-type human KDR gene). An exemplary wild-type human VEGFR2 protein is provided by GenBank™ accession number NP_002244.1. As used herein, the term "human VEGFR3" refers to a VEGFR3 protein encoded by a human FLT4 gene (e.g., a wild-type human FLT4 gene). Exemplary wild-type human VEGFR3 proteins are provided by GenBank™ accession numbers NP_891555.2, NP_002011.2, and NP_001341918.1.

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above, and conjugates or fusion proteins comprising any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_2$a or IgG$_2$b) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody. In certain embodiments, an antibody, as described herein, comprises a full-length antibody (e.g., a full-length antibody that specifically binds to CD73), or an antigen-binding fragment thereof, linked to a ligand binding moiety that specifically binds to a molecule other than CD73 (e.g., a ligand binding moiety that specifically binds to TGFβ or VEGF, e.g., a ligand binding moiety comprising one or more ectodomains of a TGFβ receptor or VEGF receptor).

As used herein, the terms "VH region" and "VL region" refer, respectively, to single antibody heavy and light chain variable regions, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dithel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus CD73). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an antibody variable region. The term "framework region" or "FR region" as used herein, includes the amino acid residues that are part of the variable region, but are not part of the CDRs (e.g., using the Kabat or MacCallum definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., IgG$_1$, IgG$_2$, IgG$_3$, and IgG$_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

As used herein, the term "binding moiety" refers to a moiety that has the ability to specifically bind to a target molecule or complex. The binding moiety can comprise a small molecule, peptide, modified peptide (e.g., peptides having non-natural amino acid residues, and/or stapled peptides), polypeptide, protein, antibody, antibody fragment, scFv, Fc-containing polypeptide, fusion antibody, ligand, aptamer, nucleic acid, variants thereof, or any combination thereof. In certain embodiments, the binding moiety comprises a domain of a natural protein or a variant thereof, wherein the natural protein binds to the target molecule or complex via the domain. For example, the term "TGFβ-binding moiety" refers to a moiety that specifically binds to one or more proteins of the TGFβ family (e.g., TGFβ1, TGFβ2, or TGFβ3), and in certain embodiments can comprise an extracellular domain of a TGFβ receptor (e.g., TGFβR1, TGFβR2, or TGFβR3). The term "VEGF-binding moiety" refers to a moiety that specifically binds to one or more proteins of the VEGF family (e.g., VEGF-A, VEGF-B, VEGF-C, or VEGF-D), and in certain embodiments can comprise an extracellular domain of a VEGF receptor (e.g., VEGFR1, VEGFR2, or VEGFR3).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA. As used herein, a "lower affinity" refers to a larger $K_D$.

As used herein, the term "maximal binding" refers to the maximal signal (expressed in resonance units (RU)) observed for the binding of an antigen (e.g., a CD73 protein) at a given concentration to an antibody (e.g., an anti-CD73 antibody) in a surface plasmon resonance binding assay (e.g., a surface plasmon resonance binding assay described in section 6.5.2 herein).

As used herein in the context of binding affinity, the binding affinity of a test antibody for a first antigen is "substantially reduced" relative to the binding affinity of the test antibody for a second antigen if the binding affinity of the test antibody for the first antigen is reduced by at least 30%, 40%, 50%, 60%, 70%, 80% or 90% relative to the binding affinity of the test antibody for the second antigen, e.g., in a given experiment, or using mean values from multiple experiments, as assessed by, e.g., a binding affinity assay disclosed herein. As used herein in the context of maximal binding, the binding between a test antibody and a first antigen is "substantially reduced" relative to the maximal binding between the test antibody and a second antigen if the maximal binding between the test antibody and the first antigen is reduced by at least 30%, 40%, 50%, 60%, 70%, 80% or 90% relative to the maximal binding between the test antibody and the second antigen, e.g., in a given experiment, or using mean values from multiple experiments, as assessed by, e.g., a binding assay disclosed herein.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs (e.g., factors of 10), 2.5 logs, 3 logs, 4 logs or greater than the $K_A$ when the molecules bind non-specifically to another antigen. The skilled worker will appreciate that an antibody, as described herein, can specifically bind to more than one antigen (e.g., via different regions of the antibody molecule). For example, an antibody, as described herein, can specifically bind to CD73 and TGFβ or specifically bind to CD73 and VEGF.

As used herein, the term "immunoglobulin chain" refers to a polypeptide of an antibody that comprises an antibody VH or VL, or an antigen-binding fragment thereof. An immunoglobulin chain can comprise, for example, a VH, a VL, a full-length antibody heavy chain, a full-length antibody light chain, or an antigen binding fragment of any of the foregoing.

As used herein, the term "linked to" refers to covalent or noncovalent binding between two molecules or moieties. The skilled worker will appreciate that when a first molecule or moiety is linked to a second molecule or moiety, the linkage need not be direct, but instead, can be via an intervening molecule or moiety. For example, when a heavy chain variable region of a full-length antibody is linked to a ligand-binding moiety, the ligand-binding moiety can bind a constant region (e.g., a heavy chain constant region) of the full-length antibody (e.g., via a peptide bond), rather than bind directly to the heavy chain variable region.

In another specific embodiment, molecules that specifically bind to an antigen do not cross react with other proteins under similar binding conditions. In another specific embodiment, molecules that specifically bind to CD73 do not cross react with other non-CD73 proteins. In a specific embodiment, provided herein is an antibody that binds to CD73 (e.g., human CD73) with higher affinity than to another unrelated antigen. In certain embodiments, provided herein is an antibody that binds to CD73 (e.g., human CD73) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-CD73 antibody described herein to an unrelated, non-CD73 protein is less than 10%, 15%, or 20% of the binding of the antibody to CD73 protein as measured by, e.g., a radioimmunoassay.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics. In a specific embodiment, the epitope of an antibody is determined by protein mutagenesis, e.g., by generating switch mutants of an antigen with portions of its ortholog from another species and then testing the switch mutants for loss of antibody binding (e.g., by a FACS-based cell binding assay, as described herein).

As used herein, the term "an epitope located within" a region of human CD73 refers to an epitope comprising one or more of the amino acid residues of the specified region. In certain embodiments, the epitope comprises each one of the amino acid residues located within the specified region. In certain embodiments, the epitope consists of each one of the amino acid residues located within the specified region. In certain embodiments, one or more additional amino acid residues of human CD73 outside the specified region bind to an antibody together with an epitope located within the specified region.

As used herein, the terms "T cell receptor" and "TCR" are used interchangeably and refer to full-length heterodimeric $\alpha\beta$ or $\gamma\delta$ TCRs, antigen-binding fragments of full-length TCRs, and molecules comprising TCR CDRs or variable regions. Examples of TCRs include, but are not limited to, full-length TCRs, antigen-binding fragments of full-length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multi-specific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "lipid nanoparticle" refers to one or more spherical nanoparticles with an average diameter of between about 10 to about 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety.

5.2 Anti-CD73 Antibodies

In one aspect, the instant disclosure provides antibodies that specifically bind to CD73 (e.g., human CD73, cynomolgus CD73, or mouse CD73) and antagonize CD73 function. The amino acid sequences of exemplary antibodies are set forth in Table 1, herein.

TABLE 1

Amino acid sequences of exemplary anti-CD73 antibodies.

| Description | Amino Acid Sequence | SEQ ID NO |
|---|---|---|
| BA010 CDRH1 (Kabat) | NYWMH | 1 |
| BA011 CDRH1 (Kabat) | SSWIN | 2 |
| BA010 CDRH2 (Kabat) | TIYPRNSDTNYNQKFKG | 3 |
| BA011 CDRH2 (Kabat) | RIYPRNGDTNYNGKFKD | 4 |
| BA023 CDRH2 (Kabat) | RIYPRAGDTNYAGKFKD | 5 |
| BA024 CDRH2 (Kabat) | RIYPRSGDTNYSGKFKD | 6 |
| BA010 CDRH3 (Kabat) | LLDYSMDY | 7 |
| BA010 CDRL1 (Kabat) | RASQDISNYLN | 8 |
| BA021 CDRL1 (Kabat) | RASQDISISLN | 9 |
| BA010 CDRL2 (Kabat) | YTSRLHS | 10 |
| BA010 CDRL3 (Kabat) | QQGNTLPWT | 11 |
| BA012 CDRL3 (Kabat) | QQGNTLPLT | 12 |
| BA025 CDRH1 (IMGT unique) | GYAFSSSW | 143 |
| BA025 CDRH2 (IMGT unique) | IYPRAGDT | 144 |

TABLE 1-continued

Amino acid sequences of exemplary anti-CD73 antibodies.

| Description | Amino Acid Sequence | SEQ ID NO |
|---|---|---|
| BA025 CDRH3 (IMGT unique) | ASLLDYSMDY | 145 |
| BA025 CDRL1 (IMGT unique) | QDISNY | 146 |
| BA025 CDRL2 (IMGT unique) | YTS | 147 |
| BA025 CDRL3 (IMGT unique) | QQGNTLPLT | 12 |
| BA025 CDRH1 (Chothia) | GYAFSSS | 148 |
| BA025 CDRH2 (Chothia) | YPRAGD | 149 |
| BA025 CDRH3 (Chothia) | LLDYSMDY | 7 |
| BA025 CDRL1 (Chothia) | RASQDISNYLN | 8 |
| BA025 CDRL2 (Chothia) | YTSRLHS | 10 |
| BA025 CDRL3 (Chothia) | QQGNTLPLT | 12 |
| BA025 CDRH1 (AHo) | ASGYAFSSSW | 150 |
| BA025 CDRH2 (AHo) | IYPRAGDTNYAGKFKDQ | 151 |
| BA025 CDRH3 (AHo) | LLDYSMD | 152 |
| BA025 CDRL1 (AHo) | ASQDISNY | 153 |
| BA025 CDRL2 (AHo) | YTSRLHSGVPSR | 154 |
| BA025 CDRL3 (AHo) | GNTLPL | 155 |
| BA020 CDRH1 (IMGT unique) | GYAFSSSW | 143 |
| BA020 CDRH2 (IMGT unique) | IYPRNGDT | 156 |
| BA020 CDRH3 (IMGT unique) | ASLLDYSMDY | 145 |
| BA020 CDRL1 (IMGT unique) | QDISNY | 146 |
| BA020 CDRL2 (IMGT unique) | YTS | 147 |
| BA020 CDRL3 (IMGT unique) | QQGNTLPLT | 12 |
| BA020 CDRH1 (Chothia) | GYAFSSS | 148 |
| BA020 CDRH2 (Chothia) | YPRNGD | 157 |
| BA020 CDRH3 (Chothia) | LLDYSMDY | 7 |

TABLE 1-continued

Amino acid sequences of exemplary anti-CD73 antibodies.

| Description | Amino Acid Sequence | SEQ ID NO |
|---|---|---|
| BA020 CDRL1 (Chothia) | RASQDISNYLN | 8 |
| BA020 CDRL2 (Chothia) | YTSRLHS | 10 |
| BA020 CDRL3 (Chothia) | QQGNTLPLT | 12 |
| BA020 CDRH1 (AHo) | ASGYAFSSSW | 150 |
| BA020 CDRH2 (AHo) | IYPRNGDTNYNGKFKDQ | 158 |
| BA020 CDRH3 (AHo) | LLDYSMD | 152 |
| BA020 CDRL1 (AHo) | ASQDISNY | 153 |
| BA020 CDRL2 (AHo) | YTSRLHSGVPSR | 154 |
| BA020 CDRL3 (AHo) | GNTLPL | 155 |
| CDRH1 consensus sequence | $X_1X_2WX_3X_4$, wherein: $X_1$ is S or N; $X_2$ is S or Y; $X_3$ is I or M; and $X_4$ is N or H | 13 |
| CDRH2 consensus sequence 1 | $X_1IYPRX_2X_3DTNYX_4X_5KFKX_6$, wherein: $X_1$ is R or T; $X_2$ is N, A, or S; $X_3$ is G or S; $X_4$ is N, A, or S; $X_5$ is G or Q; and $X_6$ is D or G | 14 |
| CDRH2 consensus sequence 2 | RIYPRX$_1$GDTNYX$_2$GKFKD, wherein: $X_1$ is N, A, or S; and $X_2$ is N, A, or S | 15 |
| CDRL1 consensus sequence | RASQDISX$_1$X$_2$LN, wherein: $X_1$ is N or I; and $X_2$ is Y or S | 16 |
| CDRL3 consensus sequence | QQGNTLPXT, wherein: X is L or W | 17 |
| Murine $V_H$ germline sequence muIgHV1S12 | QVQLQQSGPELVKPGASVKISCKASGYTFTSYYIHWVK QRPGQGLEWIGYIYPRDGSTNYNEKFKGKATLTADTSS STAYMQLSSLTSEDSAVYFCAR | 18 |
| BA010 $V_H$ (murine) | XVQLQQPGTVLARPGASVKMSCKTSGYTFTNYWMEIW VKQRPGQGLEWIGTIYPRNSDTNYNQKFKGKAKLTAV TSASTAYMELSSLTNEDSAIYYCASLLDYSMDYWGQG TSVTVSS, wherein X is Q or pyroglutamate | 19 |
| BA011 $V_H$ (murine) | XVQLKQSGPELVKPGASVKISCKASGYAFSSSWINWVN QRPGKGLEWIGRIYPRNGDTNYNGKFKDRATLTADRSS STAYLQLSSLTPEDSAVYFCASLLDYSMDYWGQGTSVT VSS, wherein X is Q or pyroglutamate | 20 |
| BA012 $V_H$ (murine) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSS, wherein X is E or pyroglutamate | 21 |
| Human $V_H$ germline sequence huIgHV5-51*02 | EVQLVQSGAEVKKPGESLKISCKGSGYSFTSYWTGWV RQMPGKGLEWMGIIYPGDSDTRYSPSFQGQVTISADKSI STAYLQWSSLKASDTAMYYCAR | 22 |

TABLE 1-continued

Amino acid sequences of exemplary anti-CD73 antibodies.

| Description | Amino Acid Sequence | SEQ ID NO |
|---|---|---|
| BA019 V$_H$ (humanized) | XVQLVQSGAEVKKPGESLKISCKGSGYAFSSSWINWVR QMPGKGLEWMGRIYPRNGDTNYNGKFKDQVTISADKS ISTAYLQWSSLKASDTAMYYCARLLDYSMDYWGQGT LVTVSS, wherein X is E or pyroglutamate | 23 |
| BA020 V$_H$ (humanized) | XVQLVQSGAEVKKPGESLKISCKASGYAFSSSWINWVR QMPGKGLEWMGRIYPRNGDTNYNGKFKDQVTISADKS ISTAYLQWSSLKASDTAMYYCASLLDYSMDYWGQGTL VTVSS, wherein X is E or pyroglutamate | 24 |
| BA023 V$_H$ (humanized) | XVQLVQSGAEVKKPGESLKISCKGSGYAFSSSWINWVR QMPGKGLEWMGRIYPRAGDTNYAGKFKDQVTISADKS ISTAYLQWSSLKASDTAMYYCARLLDYSMDYWGQGT LVTVSS, wherein X is E or pyroglutamate | 25 |
| BA024 V$_H$ (humanized) | XVQLVQSGAEVKKPGESLKISCKGSGYAFSSSWINWVR QMPGKGLEWMGRIYPRSGDTNYSGKFKDQVTISADKSI STAYLQWSSLKASDTAMYYCARLLDYSMDYWGQGTL VTVSS, wherein X is E or pyroglutamate | 26 |
| BA025 V$_H$ (humanized) | XVQLVQSGAEVKKPGESLKISCKASGYAFSSSWINWVR QMPGKGLEWMGRIYPRAGDTNYAGKFKDQVTISADKS ISTAYLQWSSLKASDTAMYYCASLLDYSMDYWGQGTL VTVSS, wherein X is E or pyroglutamate | 27 |
| BA026 V$_H$ (humanized) | XVQLVQSGAEVKKPGESLKISCKASGYAFSSSWINWVR QMPGKGLEWMGRIYPRSGDTNYSGKFKDQVTISADKSI STAYLQWSSLKASDTAMYYCASLLDYSMDYWGQGTL VTVSS, wherein X is E or pyroglutamate | 28 |
| BA031 V$_H$ (humanized) | XVKLVESGAEVKKPGESLKISCKASGYAFSSSWINWVN QMPGKGLEWIGRIYPRNGDTNYNGKFKDQVTISADKSI STAYLQWSSLKASDTAMYYCASLLDYSMDYWGQGTL VTVSS, wherein X is E or pyroglutamate | 29 |
| BA032 V$_H$ (humanized) | XVKLVESGAEVKKPGESLKISCKASGYAFSSSWINWVN QMPGKGLEWIGRIYPRNGDTNYNGKFKDQVTLSADRS SSTAYLQWSSLKASDTAMYYCASLLDYSMDYWGQGT LVTVSS, wherein X is E or pyroglutamate | 30 |
| Humanized V$_H$ consensus sequence | X$_1$VQLVQSGAEVKKPGESLKISCKX$_2$SGYAFSSSWINWV RQMPGKGLEWMGRIYPRX$_3$GDTNYX$_4$GKFKDQVTISAD KSISTAYLQWSSLKASDTAMYYCAX$_5$LLDYSMDYWGQ GTLVTVSS, wherein:<br>X$_1$ is E or pyroglutamate;<br>X$_2$ is G or A;<br>X$_3$ is N, A, or S;<br>X$_4$ is N, A, or S; and<br>X$_5$ is R or S | 31 |
| Murine V$_L$ germline sequence muIgKV10-96 | DIQMTQTTSSLSASLGDRVTISCRASQDISNYLNWYQQ KPDGTVKLLIYYTSRLHSGVPSRFSGSGSGTDYSLTISNL EQEDIATYFCQQGNTLP | 32 |
| BA010 V$_L$ (murine) | DIQMTQSTSSLSASLGDRVTISCRASQDISNYLNWYQQK PDGTVKLLIYYTSRLHSGVPSRFSGSGSGTDYSLTISNLE QEDIATYFCQQGNTLPWTFGGGTKLEIK | 33 |
| BA011 V$_L$ (murine) | DIQMTQTTSSLSASLGDRVTISCRASQDISNYLNWYQQ KPDGTVKLLIYYTSRLHSGVPSRFSGSGSGTDYSLTISNL EQEDIATYFCQQGNTLPWTFGGGTKLEIK | 34 |
| BA012 V$_L$ (murine) | DIQMTQSTSSLSASLGDRVTISCRASQDISNYLNWYQQK PDGTVKLLIYYTSRLHSGVPSRFSGSGSGTDYSLTISNLE QEDIATYFCQQGNTLPLTFGAGTKLELK | 35 |
| Human V$_L$ germline sequence huIgKV1-33*01 | DIQMTQSPSSLSASVGDRVTITCQASQDISNYLNWYQQ KPGKAPKLLIYDASNLETGVPSRFSGSGSGTDFTFTISSL QPEDIATYYCQQYDNLPP | 36 |
| BA019 V$_L$ (humanized) | DIQMTQSPSSLSASVGDRVTITCRASQDISNYLNWYQQ KPGKAPKLLIYYTSRLHSGVPSRFSGSGSGTDFTFTISSL QPEDIATYYCQQGNTLPLTFGQGTKVEIK | 37 |

TABLE 1-continued

Amino acid sequences of exemplary anti-CD73 antibodies.

| Description | Amino Acid Sequence | SEQ ID NO |
|---|---|---|
| BA021 V$_L$ (humanized) | DIQMTQSPSSLSASVGDRVTITCRASQDISISLNWYQQK PGKAPKLLIYYTSRLHSGVPSRFSGSGSGTDYTFTISSLQ PEDIATYYCQQGNTLPLTFGQGTKVEIK | 38 |
| BA033 V$_L$ (humanized) | DIQMTQTPSSLSASVGDRVTISCRASQDISISLNWYQQK PGKTPKLLIYYTSRLHSGVPSRFSGSGSGTDYTFTISSLQ PEDIATYYCQQGNTLPLTFGQGTKVEIK | 39 |
| BA034 V$_L$ (humanized) | DIQMTQTTSSLSASVGDRVTISCRASQDISISLNWYQQK PGKTPKLLIYYTSRLHSGVPSRFSGSGSGTDYTLTISSLQ PEDIATYFCQQGNTLPLTFGQGTKVEIK | 40 |
| Humanized V$_L$ consensus sequence 1 | DIQMTQSPSSLSASVGDRVTITCRASQDISX$_1$X$_2$LNWYQ QKPGKAPKLLIYYTSRLHSGVPSRFSGSGSGTDX$_3$TFTIS SLQPEDIATYYCQQGNTLPLTFGQGTKVEIK, wherein: X$_1$ is N or I; X$_2$ is Y or S; and X$_3$ is F or Y | 41 |
| Humanized V$_L$ consensus sequence 2 | DIQMTQSPSSLSASVGDRVTITCRASQDISX$_1$X$_2$LNWYQ QKPGKAPKLLIYYTSRLHSGVPSRFSGSGSGTDX$_3$TFTIS SLQPEDIATYYCQQGNTLPLTFGQGTKVEIK, wherein: X$_1$X$_2$ is NY or IS; and X$_3$ is F or Y | 42 |
| Mouse IgG2a heavy chain constant region | AKTTAPSVYPLAPVCGDTTGSSVTLGCLVKGYFPEPVT LTWNSGSLSSGVHTFPAVLQSDLYTLSSSVTVTSSTWPS QSITCNVAHPASSTKVDKKIEPRGPTIKPCPPCKCPAPNL LGGPSVFIFPPKIKDVLMISLSPIVTCVVVDVSEDDPDVQ ISWFVNNVEVHTAQTQTHREDYNSTLRVVSALPIQHQD WMSGKEFKCKVNNKDLPAPIERTISKPKGSVRAPQVYV LPPPEEEMTKKQVTLTCMVTDFMPEDIYVEWTNNGKT ELNYKNTEPVLDSDGSYFMYSKLRVEKKNWVERNSYS CSVVHEGLHNHEITTKSFSRTPGK | 43 |
| Mouse IgG2a heavy chain constant region (without C-terminal lysine) | AKTTAPSVYPLAPVCGDTTGSSVTLGCLVKGYFPEPVT LTWNSGSLSSGVHTFPAVLQSDLYTLSSSVTVTSSTWPS QSITCNVAHPASSTKVDKKIEPRGPTIKPCPPCKCPAPNL LGGPSVFIFPPKIKDVLMISLSPIVTCVVVDVSEDDPDVQ ISWFVNNVEVHTAQTQTHREDYNSTLRVVSALPIQHQD WMSGKEFKCKVNNKDLPAPIERTISKPKGSVRAPQVYV LPPPEEEMTKKQVTLTCMVTDFMPEDIYVEWTNNGKT ELNYKNTEPVLDSDGSYFMYSKLRVEKKNWVERNSYS CSVVHEGLHNHHTTKSFSRTPG | 44 |
| Mouse IgG2a heavy chain constant region with N297A mutation | AKTTAPSVYPLAPVCGDTTGSSVTLGCLVKGYFPEPVT LTWNSGSLSSGVHTFPAVLQSDLYTLSSSVTVTSSTWPS QSITCNVAHPASSTKVDKKIEPRGPTIKPCPPCKCPAPNL LGGPSVFIFPPKIKDVLMISLSPIVTCVVVDVSEDDPDVQ ISWFVNNVEVHTAQTQTHREDYASTLRVVSALPIQHQD WMSGKEFKCKVNNKDLPAPIERTISKPKGSVRAPQVYV LPPPEEEMTKKQVTLTCMVTDFMPEDIYVEWTNNGKT ELNYKNTEPVLDSDGSYFMYSKLRVEKKNWVERNSYS CSVVHEGLHNHHTTKSFSRTPGK | 45 |
| Mouse IgG2a heavy chain constant region with N297A mutation (without C-terminal lysine) | AKTTAPSVYPLAPVCGDTTGSSVTLGCLVKGYFPEPVT LTWNSGSLSSGVHTFPAVLQSDLYTLSSSVTVTSSTWPS QSITCNVAHPASSTKVDKKIEPRGPTIKPCPPCKCPAPNL LGGPSVFIFPPKIKDVLMISLSPIVTCVVVDVSEDDPDVQ ISWFVNNVEVHTAQTQTHREDYASTLRVVSALPIQHQD WMSGKEFKCKVNNKDLPAPIERTISKPKGSVRAPQVYV LPPPEEEMTKKQVTLTCMVTDFMPEDIYVEWTNNGKT ELNYKNTEPVLDSDGSYFMYSKLRVEKKNWVERNSYS CSVVHEGLHNHHTTKSFSRTPG | 46 |
| Human IgG$_1$ heavy chain constant region | ASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPAPIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPGK | 47 |

TABLE 1-continued

Amino acid sequences of exemplary anti-CD73 antibodies.

| Description | Amino Acid Sequence | SEQ ID NO |
|---|---|---|
| Human IgG1 heavy chain constant region (without C-terminal lysine) | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPAPIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPG | 48 |
| Human IgG1 heavy chain constant region with N297A mutation | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYASTYRVVSVLTV LHQDWLNGKEYKCKVSNKALPAPIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPGK | 49 |
| Human IgG1 heavy chain constant region with N297A mutation (without C-terminal lysine) | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYASTYRVVSVLTV LHQDWLNGKEYKCKVSNKALPAPIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPG | 50 |
| Human IgG2 heavy chain constant region | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKCCVECPPCPAPPVA GPSVFLFPPKPKDTLMISRTPEVTCVVVDVSHEDPEVQF NWYVDGVEVHNAKTKPREEQFNSTFRVVSVLTVVHQD WLNGKEYKCKVSNKGLPAPIEKTISKTKGQPREPQVYT LPPSREEMTKNQVSLTCLVKGFYPSDIAVEWESNGQPE NNYKTTPPMLDSDGSFFLYSKLTVDKSRWQQGNVFSCS VMHEALHNHYTQKSLSLSPGK | 51 |
| Human IgG2 heavy chain constant region (without C-terminal lysine) | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKCCVECPPCPAPPVA GPSVFLFPPKPKDTLMISRTPEVTCVVVDVSHEDPEVQF NWYVDGVEVHNAKTKPREEQFNSTFRVVSVLTVVHQD WLNGKEYKCKVSNKGLPAPIEKTISKTKGQPREPQVYT LPPSREEMTKNQVSLTCLVKGFYPSDIAVEWESNGQPE NNYKTTPPMLDSDGSFFLYSKLTVDKSRWQQGNVFSCS VMHEALHNHYTQKSLSLSPG | 52 |
| Human IgG1 A330S-P331S/G2 hybrid heavy chain constant region | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKSCVECPPCPAPPVAG PSVFLFPPKPKDTLMISRTPEVTCVVVDVSHEDPEVKFN WYVDGVEVHNAKTKPREEQYNSTYRVVSVLTVLHQD WLNGKEYKCKVSNKALPSSIEKTISKAKGQPREPQVYT LPPSREEMTKNQVSLTCLVKGFYPSDIAVEWESNGQPE NNYKTTPPVLDSDGSFFLYSKLTVDKSRWQQGNVFSCS VMHEALHNHYTQKSLSLSPGK | 53 |
| Human IgG1 A330S-P331S/G2 hybrid heavy chain constant region (without C-terminal lysine) | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKSCVECPPCPAPPVAG PSVFLFPPKPKDTLMISRTPEVTCVVVDVSHEDPEVKFN WYVDGVEVHNAKTKPREEQYNSTYRVVSVLTVLHQD WLNGKEYKCKVSNKALPSSIEKTISKAKGQPREPQVYT LPPSREEMTKNQVSLTCLVKGFYPSDIAVEWESNGQPE NNYKTTPPVLDSDGSFFLYSKLTVDKSRWQQGNVFSCS VMHEALHNHYTQKSLSLSPG | 54 |
| Human IgG1 N297A/G2 hybrid heavy chain constant region | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKSCVECPPCPAPPVAG PSVFLFPPKPKDTLMISRTPEVTCVVVDVSHEDPEVKFN | 55 |

TABLE 1-continued

Amino acid sequences of exemplary anti-CD73 antibodies.

| Description | Amino Acid Sequence | SEQ ID NO |
|---|---|---|
| | WYVDGVEVHNAKTKPREEQYASTYRVVSVLTVLHQD WLNGKEYKCKVSNKALPAPIEKTISKAKGQPREPQVYT LPPSREEMTKNQVSLTCLVKGFYPSDIAVEWESNGQPE NNYKTTPPVLDSDGSFFLYSKLTVDKSRWQQGNVFSCS VMHEALHNHYTQKSLSLSPGK | |
| Human IgG$_1$ N297A/G$_2$ hybrid heavy chain constant region (without C-terminal lysine) | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKSCVECPPCPAPPVAG PSVFLFPPKPKDTLMISRTPEVTCVVVDVSHEDPEVKFN WYVDGVEVHNAKTKPREEQYASTYRVVSVLTVLHQD WLNGKEYKCKVSNKALPAPIEKTISKAKGQPREPQVYT LPPSREEMTKNQVSLTCLVKGFYPSDIAVEWESNGQPE NNYKTTPPVLDSDGSFFLYSKLTVDKSRWQQGNVFSCS VMHEALHNHYTQKSLSLSPG | 56 |
| Human IgG$_4$ heavy chain constant region with S228P mutation | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLG GPSVFLFPPKPKDTLMISRTPEVTCVVVDVSQEDPEVQF NWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQP ENNYKTTPPVLDSDGSFFLYSRLTVDKSRWQEGNVFSC SVMHEALHNHYTQKSLSLSLGK | 57 |
| Human IgG$_4$ heavy chain constant region with S228P mutation (without C-terminal lysine) | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLG GPSVFLFPPKPKDTLMISRTPEVTCVVVDVSQEDPEVQF NWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQP ENNYKTTPPVLDSDGSFFLYSRLTVDKSRWQEGNVFSC SVMHEALHNHYTQKSLSLSLG | 58 |
| B A012 full-length murine heavy chain (murine IgG2a backbone with N297A mutation) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSAKTTAPSVYPLAPVCGDTTGSSVTLGCLVKGYFPEP VTLTWNSGSLSSGVHTFPAVLQSDLYTLSSSVTVTSST WPSQSITCNVAHPASSTKVDKKIEPRGPTIKPCPPCKCPA PNLLGGPSVFIFPPKIKDVLMISLSPIVTCVVVDVSEDDP DVQISWFVNNVEVHTAQTQTHREDYASTLRVVSALPIQ HQDWMSGKEFKCKVNNKDLPAPIERTISKPKGSVRAPQ VYVLPPPEEEMTKKQVTLTCMVTDFMPEDIYVEWTNN GKTELNYKNTEPVLDSDGSYFMYSKLRVEKKNWVERN SYSCSVVHEGLHNHHTTKSFSRTPGK, wherein X is E or pyroglutamate | 63 |
| BA012 full-length murine heavy chain (murine IgG2a backbone with N297A mutation and without C-terminal lysine) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSAKTTAPSVYPLAPVCGDTTGSSVTLGCLVKGYFPEP VTLTWNSGSLSSGVHTFPAVLQSDLYTLSSSVTVTSST WPSQSITCNVAHPASSTKVDKKIEPRGPTIKPCPPCKCPA PNLLGGPSVFIFPPKIKDVLMISLSPIVTCVVVDVSEDDP DVQISWFVNNVEVHTAQTQTHREDYASTLRVVSALPIQ HQDWMSGKEFKCKVNNKDLPAPIERTISKPKGSVRAPQ VYVLPPPEEEMTKKQVTLTCMVTDFMPEDIYVEWTNN GKTELNYKNTEPVLDSDGSYFMYSKLRVEKKNWVERN SYSCSVVHEGLHNHHTTKSFSRTPG, wherein X is E or pyroglutamate | 64 |
| BA013 full-length chimeric heavy chain (murine variable domain + human IgG1 constant domain with N297A mutation) | XVQLQQPGTVLARPGASVKMSCKTSGYTFTNYWMHW VKQRPGQGLEWIGTIYPRNSDTNYNQKFKGKAKLTAV TSASTAYMELSSLTNEDSAIYYCASLLDYSMDYWGQG TSVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTC PPCPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKAK GQPREPQVYTLPPSREEMTKNQVSLTCLVKGFYPSDIA VEWESNGQPENNYKTTPPVLDSDGSFFLYSKLTVDKSR | 65 |

TABLE 1-continued

Amino acid sequences of exemplary anti-CD73 antibodies.

| Description | Amino Acid Sequence | SEQ ID NO |
|---|---|---|
| | WQQGNVFSCSVMHEALHNHYTQKSLSLSPGK, wherein X is Q or pyroglutamate | |
| BA013 full-length chimeric heavy chain (murine variable domain + human IgG1 constant domain with N297A mutation and without C-terminal lysine) | XVQLQQPGTVLARPGASVKMSCKTSGYTFTNYWMHW VKQRPGQGLEWIGTIYPRNSDTNYNQKFKGKAKLTAV TSASTAYMELSSLTNEDSAIYYCASLLDYSMDYWGQG TSVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTC PPCPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKAK GQPREPQVYTLPPSREEMTKNQVSLTCLVKGFYPSDIA VEWESNGQPENNYKTTPPVLDSDGSFFLYSKLTVDKSR WQQGNVFSCSVMHEALHNHYTQKSLSLSPG, wherein X is Q or pyroglutamate | 66 |
| BA014 full-length chimeric heavy chain (murine variable domain + human IgG1 constant domain with N297A mutation) | XVQLKQSGPELVKPGASVKISCKASGYAFSSSWINWVN QRPGKGLEWIGRIYPRNGDTNYNGKFKDRATLTADRSS STAYLQLSSLTPEDSAVYFCASLLDYSMDYWGQGTSVT VSSASTKGPSVFPLAPSSKSTSGGTAALGCLVKDYFPEP VTVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSHE DPEVKFNWYVDGVEVHNAKTKPREEQYASTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPGK, wherein X is Q or pyroglutamate | 67 |
| BA014 full-length chimeric heavy chain (murine variable domain + human IgG1 constant domain with N297A mutation and without C-terminal lysine) | XVQLKQSGPELVKPGASVKISCKASGYAFSSSWINWVN QRPGKGLEWIGRIYPRNGDTNYNGKFKDRATLTADRSS STAYLQLSSLTPEDSAVYFCASLLDYSMDYWGQGTSVT VSSASTKGPSVFPLAPSSKSTSGGTAALGCLVKDYFPEP VTVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSHE DPEVKFNWYVDGVEVHNAKTKPREEQYASTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG, wherein X is Q or pyroglutamate | 68 |
| BA015 full-length chimeric heavy chain (murine variable domain + human IgG1 constant domain with N297A mutation) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPSSKSTSGGTAALGCLVKDYFPEP VTVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSHE DPEVKFNWYVDGVEVHNAKTKPREEQYASTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPGK, wherein X is E or pyroglutamate | 69 |
| BA015 full-length chimeric heavy chain (murine variable domain + human IgG1 constant domain with N297A mutation and without C-terminal lysine) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPSSKSTSGGTAALGCLVKDYFPEP VTVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSHE DPEVKFNWYVDGVEVHNAKTKPREEQYASTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG, wherein X is E or pyroglutamate | 70 |
| BA016 full-length chimeric heavy chain | XVKLVESGPELVKPGASVKISCKASGYAFSSSWINWVN QRPGKGLEWIGRIYPRNGDTNYNGKFKDRATLTADRSS | 71 |

TABLE 1-continued

Amino acid sequences of exemplary anti-CD73 antibodies.

| Description | Amino Acid Sequence | SEQ ID NO |
|---|---|---|
| (murine variable region + human IgG$_2$ constant region) | STAYLQLSSLTSEDSAVYFCASLLDYSMDYWGQGTSVT VSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKCCVECPPCPAP PVAGPSVFLFPPKPKDTLMISRTPEVTCVVVDVSHEDPE VQFNWYVDGVEVHNAKTKPREEQFNSTFRVVSVLTVV HQDWLNGKEYKCKVSNKGLPAPIEKTISKTKGQPREPQ VYTLPPSREEMTKNQVSLTCLVKGFYPSDIAVEWESNG QPENNYKTTPPMLDSDGSFFLYSKLTVDKSRWQQGNV FSCSVMHEALHNHYTQKSLSLSPGK, wherein X is E or pyroglutamate | |
| BA016 full-length chimeric heavy chain (murine variable region + human IgG$_2$ constant region and without C-terminal lysine) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKCCVECPPCPAP PVAGPSVFLFPPKPKDTLMISRTPEVTCVVVDVSHEDPE VQFNWYVDGVEVHNAKTKPREEQFNSTFRVVSVLTVV HQDWLNGKEYKCKVSNKGLPAPIEKTISKTKGQPREPQ VYTLPPSREEMTKNQVSLTCLVKGFYPSDIAVEWESNG QPENNYKTTPPMLDSDGSFFLYSKLTVDKSRWQQGNV FSCSVMHEALHNHYTQKSLSLSPG, wherein X is E or pyroglutamate | 72 |
| BA017 full-length chimeric heavy chain (murine variable region + human IgG$_1$-A330S-P331S/IgG$_2$ hybrid constant region) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKSCVECPPCPAP PVAGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPSSIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPGK, wherein X is E or pyroglutamate | 73 |
| BA017 full-length chimeric heavy chain (murine variable region + human IgG$_1$-A330S-P331S/IgG$_2$ hybrid constant region and without C-terminal lysine) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKSCVECPPCPAP PVAGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPSSIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPG, wherein X is E or pyroglutamate | 74 |
| BA018 full-length chimeric heavy chain (murine variable region + human IgG$_1$-N297A/IgG$_2$ hybrid constant region) | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKSCVECPPCPAP PVAGPSVFLFPPKPKDTLMISRTPEVTCVVVDVSHEDPE VKFNWYVDGVEVHNAKTKPREEQYASTYRVVSVLTV LHQDWLNGKEYKCKVSNKALPAPIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPGK, wherein X is E or pyroglutamate | 75 |
| BA018 full-length chimeric heavy chain (murine variable region + human IgG$_1$-N297A/IgG$_2$ hybrid constant region and | XVKLVESGPELVKPGASVKISCKASGYAFSSSWINWVN QRPGKGLEWIGRIYPRNGDTNYNGKFKDRATLTADRSS STAYLQLSSLTSEDSAVYFCASLLDYSMDYWGQGTSVT VSSASTKGPSVFPLAPCSRSTSESTAALGCLVKDYFPEP VTVSWNSGALTSGVHTFPAVLQSSGLYSLSSVVTVPSS NFGTQTYTCNVDHKPSNTKVDKTVERKSCVECPPCPAP | 76 |

TABLE 1-continued

Amino acid sequences of exemplary anti-CD73 antibodies.

| Description | Amino Acid Sequence | SEQ ID NO |
|---|---|---|
| without C-terminal lysine) | PVAGPSVFLFPPKPKDTLMISRTPEVTCVVVDVSHEDPE VKFNWYVDGVEVHNAKTKPREEQYASTYRVVSVLTV LHQDWLNGKEYKCKVSNKALPAPIEKTISKAKGQPREP QVYTLPPSREEMTKNQVSLTCLVKGFYPSDIAVEWESN GQPENNYKTTPPVLDSDGSFFLYSKLTVDKSRWQQGN VFSCSVMHEALHNHYTQKSLSLSPG, wherein X is E or pyroglutamate | |
| BA019 full-length humanized heavy chain (human IgG₁ backbone with N297A mutation) | XVQLVQSGAEVKKPGESLKISCKGSGYAFSSSWINWVR QMPGKGLEWMGRIYPRNGDTNYNGKFKDQVTISADKS ISTAYLQWSSLKASDTAMYYCARLLDYSMDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCP PCPAPELLGGPSVFLFPPKPKDTLMISRTPEVTCVVVDV SHEDPEVKFNWYVDGVEVHNAKTKPREEQYASTYRVV SVLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK, wherein X is E or pyroglutamate | 77 |
| BA019 full-length humanized heavy chain (human IgG₁ backbone with N297A mutation and without C-terminal lysine) | XVQLVQSGAEVKKPGESLKISCKGSGYAFSSSWINWVR QMPGKGLEWMGRIYPRNGDTNYNGKFKDQVTISADKS ISTAYLQWSSLKASDTAMYYCARLLDYSMDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCP PCPAPELLGGPSVFLFPPKPKDTLMISRTPEVTCVVVDV SHEDPEVKFNWYVDGVEVHNAKTKPREEQYASTYRVV SVLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG, wherein X is E or pyroglutamate | 78 |
| BA020 full-length humanized heavy chain (human IgG₁ backbone with N297A mutation) | XVQLVQSGAEVKKPGESLKISCKASGYAFSSSWINWVR QMPGKGLEWMGRIYPRNGDTNYNGKFKDQVTISADKS ISTAYLQWSSLKASDTAMYYCASLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK, wherein X is E or pyroglutamate | 79 |
| BA020 full-length humanized heavy chain (human IgG₁ backbone with N297A mutation and without C-terminal lysine) | XVQLVQSGAEVKKPGESLKISCKASGYAFSSSWINWVR QMPGKGLEWMGRIYPRNGDTNYNGKFKDQVTISADKS ISTAYLQWSSLKASDTAMYYCASLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG, wherein X is E or pyroglutamate | 80 |
| BA023 full-length humanized heavy chain (human IgG1 backbone with N297A mutation) | XVQLVQSGAEVKKPGESLKISCKGSGYAFSSSWINWVR QMPGKGLEWMGRIYPRAGDTNYAGKFKDQVTISADKS ISTAYLQWSSLKASDTAMYYCARLLDYSMDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCP PCPAPELLGGPSVFLFPPKPKDTLMISRTPEVTCVVVDV SHEDPEVKFNWYVDGVEVHNAKTKPREEQYASTYRVV SVLTVLHQDWLNGKEYKCKVSNKALPAPIEKTISKAKG | 81 |

TABLE 1-continued

Amino acid sequences of exemplary anti-CD73 antibodies.

| Description | Amino Acid Sequence | SEQ ID NO |
|---|---|---|
| | QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK, wherein X is E or pyroglutamate | |
| BA023 full-length humanized heavy chain (human IgG$_1$ backbone with N297A mutation and without C-terminal lysine) | XVQLVQSGAEVKKPGESLKISCKGSGYAFSSSWINWVR QMPGKGLEWMGRIYPRAGDTNYAGKFKDQVTISADKS ISTAYLQWSSLKASDTAMYYCARLLDYSMDWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCP PCPAPELLGGPSVFLFPPKPKDTLMISRTPEVTCVVVDV SHEDPEVKFNWYVDGVEVHNAKTKPREEQYASTYRVV SVLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG, wherein X is E or pyroglutamate | 82 |
| BA024 full-length humanized heavy chain (human IgG$_1$ backbone with N297A mutation) | XVQLVQSGAEVKKPGESLKISCKGSGYAFSSSWINWVR QMPGKGLEWMGRIYPRSGDTNYSGKFKDQVTISADKSI STAYLQWSSLKASDTAMYYCARLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK, wherein X is E or pyroglutamate | 83 |
| BA024 full-length humanized heavy chain (human IgG$_1$ backbone with N297A mutation and without C-terminal lysine) | XVQLVQSGAEVKKPGESLKISCKGSGYAFSSSWINWVR QMPGKGLEWMGRIYPRSGDTNYSGKFKDQVTISADKSI STAYLQWSSLKASDTAMYYCARLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG, wherein X is E or pyroglutamate | 84 |
| BA025 full-length humanized heavy chain (human IgG$_1$ backbone with N297A mutation) | XVQLVQSGAEVKKPGESLKISCKASGYAFSSSWINWVR QMPGKGLEWMGRIYPRAGDTNYAGKFKDQVTISADKS ISTAYLQWSSLKASDTAMYYCASLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK, wherein X is E or pyroglutamate | 85 |
| BA025 full-length humanized heavy chain (human IgG$_1$ backbone with N297A mutation and without C-terminal lysine) | XVQLVQSGAEVKKPGESLKISCKASGYAFSSSWINWVR QMPGKGLEWMGRIYPRAGDTNYAGKFKDQVTISADKS ISTAYLQWSSLKASDTAMYYCASLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG, wherein X is E or pyroglutamate | 86 |

TABLE 1-continued

Amino acid sequences of exemplary anti-CD73 antibodies.

| Description | Amino Acid Sequence | SEQ ID NO |
|---|---|---|
| BA026 full-length humanized heavy chain (human IgG₁ backbone with N297A mutation) | XVQLVQSGAEVKKPGESLKISCKASGYAFSSSWINWVR QMPGKGLEWMGRIYPRSGDTNYSGKFKDQVTISADKSI STAYLQWSSLKASDTAMYYCASLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGK, wherein X is E or pyroglutamate | 87 |
| BA026 full-length humanized heavy chain (human IgG₁ backbone with N297A mutation and without C-terminal lysine) | XVQLVQSGAEVKKPGESLKISCKASGYAFSSSWINWVR QMPGKGLEWMGRIYPRSGDTNYSGKFKDQVTISADKSI STAYLQWSSLKASDTAMYYCASLLDYSMDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYASTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPG, wherein X is E or pyroglutamate | 88 |
| Murine Igκ light chain constant region | RADAAPTVSIFPPSSEQLTSGGASVVCFLNNFYPKDINV KWKIDGSERQNGVLNSWTDQDSKDSTYSMSSTLTLTK DEYERHNSYTCEATHKTSTSPIVKSFNRNEC | 89 |
| BA012 full-length light chain (murine) | DIQMTQSTSSLSASLGDRVTISCRASQDISNYLNWYQQK PDGTVKLLIYYTSRLHSGVPSRFSGSGSGTDYSLTISNLE QEDIATYFCQQGNTLPLTFGAGTKLELKRADAAPTVSIF PPS SEQLTSGGASVVCFLNNFYPKDINVKWKIDGSERQ NGVLNSWTDQDSKDSTYSMSSTLTLTKDEYERHNSYT CEATHKTSTSPIVKSFNRNEC | 92 |
| Human Igκ light chain constant region | RTVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 93 |
| BA013 full-length light chain (chimeric; murine variable + human Igκ constant region) | DIQMTQSTSSLSASLGDRVTISCRASQDISNYLNWYQQK PDGTVKLLIYYTSRLHSGVPSRFSGSGSGTDYSLTISNLE QEDIATYFCQQGNTLPWTFGGGTKLEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | 94 |
| BA014 full-length light chain (chimeric; murine variable + human Igκ constant region) | DIQMTQTTSSLSASLGDRVTISCRASQDISNYLNWYQQ KPDGTVKLLIYYTSRLHSGVPSRFSGSGSGTDYSLTISNL EQEDIATYFCQQGNTLPWTFGGGTKLEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 95 |
| BA015 full-length light chain (chimeric; murine variable + human Igκ constant region) | DIQMTQSTSSLSASLGDRVTISCRASQDISNYLNWYQQK PDGTVKLLIYYTSRLHSGVPSRFSGSGSGTDYSLTISNLE QEDIATYFCQQGNTLPLTFGAGTKLELKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | 96 |
| BA019 full-length light chain (humanized) | DIQMTQSPSSLSASVGDRVTITCRASQDISNYLNWYQQ KPGKAPKLLIYYTSRLHSGVPSRFSGSGSGTDFTFTISSL QPEDIATYYCQQGNTLPLTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 97 |
| BA021 full-length light chain (humanized) | DIQMTQSPSSLSASVGDRVTITCRASQDISISLNWYQQK PGKAPKLLIYYTSRLHSGVPSRFSGSGSGTDYTFTISSLQ PEDIATYYCQQGNTLPLTFGQGTKVEIKRTVAAPSVFIF | 98 |

TABLE 1-continued

Amino acid sequences of exemplary anti-CD73 antibodies.

| Description | Amino Acid Sequence | SEQ ID NO |
|---|---|---|
| | PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | |

TABLE 2

Heavy chain CDR sequences of exemplary anti-CD73 antibodies

| Antibody | CDRH1 (SEQ ID NO) | CDRH2 (SEQ ID NO) | CDRH3 (SEQ ID NO) |
|---|---|---|---|
| BA010 | NYWMH (1) | TIYPRNSDTNYNQKFKG (3) | LLDYSMDY (7) |
| BA011 | SSWIN (2) | RIYPRNGDTNYNGKFKD (4) | LLDYSMDY (7) |
| BA012 | SSWIN (2) | RIYPRNGDTNYNGKFKD (4) | LLDYSMDY (7) |
| BA013 | NYWMH (1) | TIYPRNSDTNYNQKFKG (3) | LLDYSMDY (7) |
| BA014 | SSWIN (2) | RIYPRNGDTNYNGKFKD (4) | LLDYSMDY (7) |
| BA015 | SSWIN (2) | RIYPRNGDTNYNGKFKD (4) | LLDYSMDY (7) |
| BA016 | SSWIN (2) | RIYPRNGDTNYNGKFKD (4) | LLDYSMDY (7) |
| BA017 | SSWIN (2) | RIYPRNGDTNYNGKFKD (4) | LLDYSMDY (7) |
| BA018 | SSWIN (2) | RIYPRNGDTNYNGKFKD (4) | LLDYSMDY (7) |
| BA019 | SSWIN (2) | RIYPRNGDTNYNGKFKD (4) | LLDYSMDY (7) |
| BA020 | SSWIN (2) | RIYPRNGDTNYNGKFKD (4) | LLDYSMDY (7) |
| BA021 | SSWIN (2) | RIYPRNGDTNYNGKFKD (4) | LLDYSMDY (7) |
| BA022 | SSWIN (2) | RIYPRNGDTNYNGKFKD (4) | LLDYSMDY (7) |
| BA023 | SSWIN (2) | RIYPRAGDTNYAGKFKD (5) | LLDYSMDY (7) |
| BA024 | SSWIN (2) | RIYPRSGDTNYSGKFKD (6) | LLDYSMDY (7) |
| BA025 | SSWIN (2) | RIYPRAGDTNYAGKFKD (5) | LLDYSMDY (7) |
| BA026 | SSWIN (2) | RIYPRSGDTNYSGKFKD (6) | LLDYSMDY (7) |
| BA027 | SSWIN (2) | RIYPRAGDTNYAGKFKD (5) | LLDYSMDY (7) |
| BA028 | SSWIN (2) | RIYPRSGDTNYSGKFKD (6) | LLDYSMDY (7) |
| BA029 | SSWIN (2) | RIYPRAGDTNYAGKFKD (5) | LLDYSMDY (7) |
| BA030 | SSWIN (2) | RIYPRSGDTNYSGKFKD (6) | LLDYSMDY (7) |
| BA031 | SSWIN (2) | RIYPRNGDTNYNGKFKD (4) | LLDYSMDY (7) |
| BA032 | SSWIN (2) | RIYPRNGDTNYNGKFKD (4) | LLDYSMDY (7) |
| BA033 | SSWIN (2) | RIYPRNGDTNYNGKFKD (4) | LLDYSMDY (7) |
| BA034 | SSWIN (2) | RIYPRNGDTNYNGKFKD (4) | LLDYSMDY (7) |
| BA035 | SSWIN (2) | RIYPRNGDTNYNGKFKD (4) | LLDYSMDY (7) |
| BA036 | SSWIN (2) | RIYPRNGDTNYNGKFKD (4) | LLDYSMDY (7) |
| BA037 | SSWIN (2) | RIYPRAGDTNYAGKFKD (5) | LLDYSMDY (7) |
| BA038 | SSWIN (2) | RIYPRNGDTNYNGKFKD (4) | LLDYSMDY (7) |
| BA039 | SSWIN (2) | RIYPRNGDTNYNGKFKD (4) | LLDYSMDY (7) |
| BA040 | SSWIN (2) | RIYPRAGDTNYAGKFKD (5) | LLDYSMDY (7) |
| BA041 | SSWIN (2) | RIYPRNGDTNYNGKFKD (4) | LLDYSMDY (7) |
| BA042 | SSWIN (2) | RIYPRAGDTNYAGKFKD (5) | LLDYSMDY (7) |
| BA043 | SSWIN (2) | RIYPRNGDTNYNGKFKD (4) | LLDYSMDY (7) |
| BA044 | SSWIN (2) | RIYPRAGDTNYAGKFKD (5) | LLDYSMDY (7) |
| BA045 | SSWIN (2) | RIYPRNGDTNYNGKFKD (4) | LLDYSMDY (7) |
| BA046 | SSWIN (2) | RIYPRAGDTNYAGKFKD (5) | LLDYSMDY (7) |
| BA047 | SSWIN (2) | RIYPRNGDTNYNGKFKD (4) | LLDYSMDY (7) |
| BA048 | SSWIN (2) | RIYPRAGDTNYAGKFKD (5) | LLDYSMDY (7) |

The $V_H$ CDRs in Table 2 are determined according to Kabat.

TABLE 3

Light chain CDR sequences of exemplary anti-CD73 antibodies

| Antibody | CDRL1 (SEQ ID NO) | CDRL2 (SEQ ID NO) | CDRL3 (SEQ ID NO) |
|---|---|---|---|
| BA010 | RASQDISNYLN (8) | YTSRLHS (10) | QQGNTLPWT (11) |
| BA011 | RASQDISNYLN (8) | YTSRLHS (10) | QQGNTLPWT (11) |
| BA012 | RASQDISNYLN (8) | YTSRLHS (10) | QQGNTLPLT (12) |
| BA013 | RASQDISNYLN (8) | YTSRLHS (10) | QQGNTLPWT (11) |
| BA014 | RASQDISNYLN (8) | YTSRLHS (10) | QQGNTLPWT (11) |
| BA015 | RASQDISNYLN (8) | YTSRLHS (10) | QQGNTLPLT (12) |
| BA016 | RASQDISNYLN (8) | YTSRLHS (10) | QQGNTLPLT (12) |
| BA017 | RASQDISNYLN (8) | YTSRLHS (10) | QQGNTLPLT (12) |
| BA018 | RASQDISNYLN (8) | YTSRLHS (10) | QQGNTLPLT (12) |
| BA019 | RASQDISNYLN (8) | YTSRLHS (10) | QQGNTLPLT (12) |
| BA020 | RASQDISNYLN (8) | YTSRLHS (10) | QQGNTLPLT (12) |
| BA021 | RASQDISISLN (9) | YTSRLHS (10) | QQGNTLPLT (12) |
| BA022 | RASQDISISLN (9) | YTSRLHS (10) | QQGNTLPLT (12) |
| BA023 | RASQDISNYLN (8) | YTSRLHS (10) | QQGNTLPLT (12) |
| BA024 | RASQDISNYLN (8) | YTSRLHS (10) | QQGNTLPLT (12) |

TABLE 3-continued

Light chain CDR sequences of exemplary anti-CD73 antibodies

| Antibody | CDRL1 (SEQ ID NO) | CDRL2 (SEQ ID NO) | CDRL3 (SEQ ID NO) |
|---|---|---|---|
| BA025 | RASQDISNYLN (8) | YTSRLHS (10) | QQGNTLPLT (12) |
| BA026 | RASQDISNYLN (8) | YTSRLHS (10) | QQGNTLPLT (12) |
| BA027 | RASQDISISLN (9) | YTSRLHS (10) | QQGNTLPLT (12) |
| BA028 | RASQDISISLN (9) | YTSRLHS (10) | QQGNTLPLT (12) |
| BA029 | RASQDISISLN (9) | YTSRLHS (10) | QQGNTLPLT (12) |
| BA030 | RASQDISISLN (9) | YTSRLHS (10) | QQGNTLPLT (12) |
| BA031 | RASQDISISLN (9) | YTSRLHS (10) | QQGNTLPLT (12) |
| BA032 | RASQDISISLN (9) | YTSRLHS (10) | QQGNTLPLT (12) |
| BA033 | RASQDISISLN (9) | YTSRLHS (10) | QQGNTLPLT (12) |
| BA034 | RASQDISISLN (9) | YTSRLHS (10) | QQGNTLPLT (12) |
| BA035 | RASQDISNYLN (8) | YTSRLHS (10) | QQGNTLPLT (12) |
| BA036 | RASQDISNYLN (8) | YTSRLHS (10) | QQGNTLPLT (12) |
| BA037 | RASQDISNYLN (8) | YTSRLHS (10) | QQGNTLPLT (12) |
| BA038 | RASQDISNYLN (8) | YTSRLHS (10) | QQGNTLPLT (12) |
| BA039 | RASQDISNYLN (8) | YTSRLHS (10) | QQGNTLPLT (12) |
| BA040 | RASQDISNYLN (8) | YTSRLHS (10) | QQGNTLPLT (12) |
| BA041 | RASQDISNYLN (8) | YTSRLHS (10) | QQGNTLPLT (12) |
| BA042 | RASQDISNYLN (8) | YTSRLHS (10) | QQGNTLPLT (12) |
| BA043 | RASQDISNYLN (8) | YTSRLHS (10) | QQGNTLPLT (12) |
| BA044 | RASQDISNYLN (8) | YTSRLHS (10) | QQGNTLPLT (12) |
| BA045 | RASQDISNYLN (8) | YTSRLHS (10) | QQGNTLPLT (12) |
| BA046 | RASQDISNYLN (8) | YTSRLHS (10) | QQGNTLPLT (12) |
| BA047 | RASQDISNYLN (8) | YTSRLHS (10) | QQGNTLPLT (12) |
| BA048 | RASQDISNYLN (8) | YTSRLHS (10) | QQGNTLPLT (12) |

The $V_L$ CDRs in Table 3 are determined according to Kabat.

TABLE 4

VH, VL, full-length heavy chain, and full-length light chain sequences of exemplary anti-CD73 antibodies*

| Antibody | $V_H$ SEQ ID NO. | Full-length heavy chain SEQ ID NO. | $V_L$ SEQ ID NO. | Full-length light chain SEQ ID NO. |
|---|---|---|---|---|
| BA010 | 19 | N/A | 33 | N/A |
| BA011 | 20 | N/A | 34 | N/A |
| BA012 | 21 | 64 | 35 | 92 |
| BA013 | 19 | 65 | 33 | 94 |
| BA014 | 20 | 67 | 34 | 95 |
| BA015 | 21 | 70 | 35 | 96 |
| BA016 | 21 | 71 | 35 | 96 |
| BA017 | 21 | 73 | 35 | 96 |
| BA018 | 21 | 75 | 35 | 96 |
| BA019 | 23 | 77 | 37 | 97 |
| BA020 | 24 | 79 | 37 | 97 |
| BA021 | 23 | 77 | 38 | 98 |
| BA022 | 24 | 79 | 38 | 98 |
| BA023 | 25 | 81 | 37 | 97 |
| BA024 | 26 | 83 | 37 | 97 |
| BA025 | 27 | 85 | 37 | 97 |
| BA026 | 28 | 87 | 37 | 97 |
| BA027 | 25 | 81 | 38 | 98 |
| BA028 | 26 | 83 | 38 | 98 |
| BA029 | 27 | 85 | 38 | 98 |
| BA030 | 28 | 87 | 38 | 98 |
| BA031 | 29 | N/A | 37 | N/A |
| BA032 | 30 | N/A | 37 | N/A |
| BA033 | 23 | N/A | 39 | N/A |
| BA034 | 23 | N/A | 40 | N/A |
| BA035 | 21 | 113 | 35 | 92 |
| BA036 | 24 | 114 | 37 | 97 |
| BA037 | 27 | 115 | 37 | 97 |
| BA038 | 21 | 123 | 35 | 92 |
| BA039 | 24 | 124 | 37 | 128 |
| BA040 | 27 | 125 | 37 | 128 |
| BA041 | 24 | 126 | 37 | 97 |
| BA042 | 27 | 127 | 37 | 97 |
| BA043 | 24 | 116 | 37 | 97 |
| BA044 | 27 | 117 | 37 | 97 |
| BA045 | 24 | 118 | 37 | 97 |
| BA046 | 27 | 119 | 37 | 97 |
| BA047 | 24 | 120 | 37 | 97 |
| BA048 | 27 | 121 | 37 | 97 |

*In this table, a polypeptide of an anti-CD73 antibody comprising a ligand binding moiety is referred to as a full-length heavy chain if it comprises a full-length heavy chain.

TABLE 5

Exemplary sequences of CD73 and family members.

| Description | Amino Acid Sequence | SEQ ID NO |
|---|---|---|
| Human CD73 isoform 1 (NCBI Reference Sequence: NP_002517.1) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVDK LKTLNVNKIIALGHSGFEMDKLIAQKVRGVDVVGGHSNTF LYTGNPPSKEVPAGKYPFIVTSDDGRKVPVVQAYAFGKYLG YLKIEFDERGNVISSHGNPILLNSSIPEDPSIKADINKWRIKLD NYSTQELGKTIVYLDGSSQSCRFRECNMGNLICDAMINNNLR HTDEMFWNHVSMCILNGGGIRSPIDERNNGTITWENLAAVLP FGGTFDLVQLKGSTLKKAFEHSVHRYGQSTGEFLQVGGIHV VYDLSRKPGDRVVKLDVLCTKCRVPSYDPLKMDEVYKVILP NFLANGGDGFQMIKDELLRHDSGDQDINVVSTYISKMKVIYP AVEGRIKFSTGSHCHGSFSLIFLSLWAVIFVLYQ | 99 |

TABLE 5-continued

Exemplary sequences of CD73 and family members.

| Description | Amino Acid Sequence | SEQ ID NO |
|---|---|---|
| Human CD73 isoform 2 (NCBI Reference Sequence: NP_001191742.1) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVDK LKTLNVNKIIALGHSGFEMDKLIAQKVRGVDVVVGGHSNTF LYTGNPPSKEVPAGKYPFIVTSDDGRKVPVVQAYAFGKYLG YLKIEFDERGNVISSHGNPILLNSSIPEDPSIKADINKWRIKLD NYSTQELGKTIVYLDGSSQSCRFRECNMGNLICDAMINNNLR HTDEMFWNHVSMCILNGGGIRSPIDERNNGIHVVYDLSRKPG DRVVKLDVLCTKCRVPSYDPLKMDEVYKVILPNFLANGGDG FQMIKDELLRHDSGDQDINVVSTYISKMKVIYPAVEGRIKFST GSHCHGSFSLIFLSLWAVIFVLYQ | 100 |
| Human CD73 isoform 3 (NCBI Reference Sequence: AAH65937) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVDK LKTLNVNKIIALGHSGFEMDKLIAQKVRGVDVVVGGHSNTF LYTGNPPSKEVPAGKYPFIVTSDDGRKVPVVQAYAFGKYLG YLKIEFDERGNVISSHGNPILLNSSIPEDPSIKADINKWRIKLD NYSTQELGKTIVYLDGSSQSCRFRECNMGNLICDAMINNNLR HADETFWNHVSMCILNGGGIRSPIDERNNGTITWENLAAVLP FGGTFDLVQLKGSTLKKAFEHSVHRYGQSTGEFLQVGGIHV VYDLSRKPGDRVVKLDVLCTKCRVPSYDPLKMDEVYKVILP NFLANGGDGFQMIKDELLRHDSGDQDINVVSTYISKMKVIYP AVEGRIKFSTGSHCHGSFSLIFLSLWAVIFVLYQ | 129 |
| Human CD73 isoform 4 (NCBI Reference Sequence: EAW48635.1) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVDK LKTLNVNKIIALGHSGFEMDKLIAQKVRGVDVVVGGHSNTF LYTGNPPSKEVPAGKYPFIVTSDDGRKVPVVQAYAFGKYLG YLKIEFDERGNVISSHGNPILLNSSIPEDPSIKADINKWRIKLD NYSTQELGKTIVYLDGSSQSCRFRECNMGNLICDAMINNNLR HADEMFWNHVSMCILNGGGIRSPIDERNNGIHVVYDLSRKP GDRVVKLDVLCTKCRVPSYDPLKMDEVYKVILPNFLANGGD GFQMIKDELLRHDSGDQDINVVSTYISKMKVIYPAVEGRIKF STGSHCHGSFSLIFLSLWAVIFVLYQ | 130 |
| Cynomolgus CD73 variant 1 (NCBI Reference Sequence: XP_001086989.1) | MCPRAARAPATLLLAVGALLWSAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVDK LKTLNVNKIIALGHSGFETDKLIAQKVRGVDVVVGGHSNTFL YTGNPPSKEVPAGKYPFIVTSDDGRKVPVVQAYAFGKYLGY LKIEFDERGNVISSHGNPILLNSSIPEDPSIKADINKWRIKLDN YSTQELGKTIVYLDGSSQSCRFRECNMGNLICDAMINNNLRH ADEMFWNHVSMCILNGGGIRSPIDERNNGTITWENLAAVLPF GGTFDLVQLKGSTLKKAFEHSVHRYGQSTGEFLQVGGIHVV YDLSRKPGDRVVKLDVLCTKCRVPSYDPLKMDEIYKVILPNF LANGGDGFQMIKDELLRHDSGDQDINVVSTYISKMKVIYPA VEGRIKFSTGSHCHGSFSLIFLSLFCAVIFVLYQ | 101 |
| Cynomolgus CD73 variant 2 (NCBI Reference Sequence: EHH53214.1) | MCPRAARAPAKLLLAVGALLWSAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVDK LKTLNVNKIIALGHSGFETDKLIAQKVRGVDVVVGGHSNTFL YTGNPPSKEVPAGKYPFIVTSDDGRKVPVVQAYAFGKYLGY LKIEFDERGNVISSHGNPILLNSSIPEDPSIKADINKWRIKLDN YSTQELGKTIVYLDGSSQSCRFRECNMGNLICDAMINNNLRH ADEMFWNHVSMCILNGGGIRSPIDERNNGTITWENLAAVLPF GGTFDLVQLKGSTLKKAFEHSVHRYGQSTGEFLQVGGIHVV YDLSRKPGDRVVKLDVLCTKCRVPSYDPLKMDEIYKVILPNF LANGGDGFQMIKDELLRHDSGDQDINVVSTYISKMKVIYPA VEGRIKFSTGSHCHGSFSLIFLSLFCAVIFVLYQ | 131 |

TABLE 5-continued

Exemplary sequences of CD73 and family members.

| Description | Amino Acid Sequence | SEQ ID NO |
|---|---|---|
| Mouse CD73 (NCBI Reference Sequence: NP_035981.1) | MRPAAAKVPKWLLLALSALLPQWPAASAWELTILHTNDVH SRLEQTSDDSTKCLNASLCVGGVARLFTKVQQIRKEEPNVLF LDAGDQYQGTIWFTVYKGLEVAHFMNILGYDAMALGNHEF DNGVEGLIDPLLRNVKFPILSANIKARGPLAHQISGLFLPSKV LSVGGEVVGIVGYTSKETPFLSNPGTNLVFEDEISALQPEVDK LKTLNVNKIIALGHSGFEMDKLIAQKVRGVDIVVGGHSNTFL YTGNPPSKEVPAGKYPFIVTADDGRQVPVVQAYAFGKYLGY LKVEFDDKGNVITSYGNPILLNSSIPEDATIKADINQWRIKLD NYSTQELGRTIVYLDGSTQTCRFRECNIVIGNLICDAMINNNLR HPDEMFWNHVSMCIVNGGGIRSPIDEKNNGTITWENLAAVL PFGGTFDLVQLKGSTLKKAFEHSVHRYGQSTGEFLQVGGIHV VYDINRKPWNRVVQLEVLCTKCRVPIYEPLEMDKVYKVTLP SYLANGGDGFQMIKDELLKHDSGDQDISVVSEYISKMKVVY PAVEGRIKFSAASHYQGSFPLVILSFWAMILILYQ | 102 |
| Human CD73 isoform 1 with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGDEVVGIVGYTSKETPFLSNPGTNLV FEDEITALQPEVDKLKTLNVNKIIALGHSGFEMDKLIAQKVR GVDVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNMG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHG GSGGLPETGGDR | 141 |
| Mouse CD73 with His-tag | WELTILHTNDVHSRLEQTSDDSTKCLNASLCVGGVARLFTK VQQIRKEEPNVLFLDAGDQYQGTIWFTVYKGLEVAHFMNIL GYDAMALGNHEFDNGVEGLIDPLLRNVKFPILSANIKARGPL AHQISGLFLPSKVLSVGGEVVGIVGYTSKETPFLSNPGTNLVF EDEISALQPEVDKLKTLNVNKIIALGHSGFEMDKLIAQKVRG VDIVVGGHSNTFLYTGNPPSKEVPAGKYPFIVTADDGRQVPV VQAYAFGKYLGYLKVEFDDKGNVITSYGNPILLNSSIPEDATI KADINQWRIKLDNYSTQELGRTIVYLDGSTQTCRFRECNMG NLICDAMINNNLRHPDEMFWNHVSMCIVNGGGIRSPIDEKN NGTITWENLAAVLPFGGTFDLVQLKGSTLKKAFEHSVHRYG QSTGEFLQVGGIHVVYDINRKPWNRVVQLEVLCTKCRVPIYE PLEMDKVYKVTLPSYLANGGDGFQMIKDELLKHDSGDQDIS VVSEYISKMKVVYPAVEGRIKENLYFQGLEHHHHHHHH GGSGGLPETGGDR | 142 |
| Human CD73 Y158A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLALPYKVLPVGDEVVGIVGYTSKETPFLSNPGTNLV FEDEITALQPEVDKLKTLNVNKIIALGHSGFEMDKLIAQKVR GVDVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNNIG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHG GSGGLPETGGDR | 59 |
| Human CD73 Y161A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPAKVLPVGDEVVGIVGYTSKETPFLSNPGTNLV FEDEITALQPEVDKLKTLNVNKIIALGHSGFEMDKLIAQKVR GVDVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNNIG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHG GSGGLPETGGDR | 60 |

TABLE 5-continued

Exemplary sequences of CD73 and family members.

| Description | Amino Acid Sequence | SEQ ID NO |
|---|---|---|
| Human CD73 P165A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLAVGDEVVGIVGYTSKETPFLSNPGTNL VFEDEITALQPEVDKLKTLNVNKIIALGHSGFEMDKLIAQKV RGVDVVVGGHSNTFLYTGNPPSKEVPAGKYPFIVTSDDGRK VPVVQAYAFGKYLGYLKIEFDERGNVISSHGNPILLNSSIPED PSIKADINKWRIKLDNYSTQELGKTIVYLDGSSQSCRFRECN MGNLICDAMINNNLRHTDEMFWNHVSMCILNGGGIRSPIDE RNNGTITWENLAAVLPFGGTFDLVQLKGSTLKKAFEHSVHR YGQSTGEFLQVGGIHVVYDLSRKPGDRVVKLDVLCTKCRVP SYDPLKMDEVYKVILPNFLANGGDGFQMIKDELLRHDSGDQ DINVVSTYISKMKVIYPAVEGRIKENLYFQGLEHHHHHHHH HGGSGGLPETGGDR | 139 |
| Human CD73 D168A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGAEVVGIVGYTSKETPFLSNPGTNLV FEDEITALQPEVDKLKTLNVNKIIALGHSGFEMDKLIAQKVR GVDVVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNNIG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHHG GSGGLPETGGDR | 140 |
| Human CD73 T198A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGDEVVGIVGYTSKETPFLSNPGTNLV FEDEIAALQPEVDKLKTLNVNKIIALGHSGFEMDKLIAQKVR GVDVVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNNIG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHHG GSGGLPETGGDR | 61 |
| Human CD73 K274A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGDEVVGIVGYTSKETPFLSNPGTNLV FEDEITALQPEVDKLKTLNVNKIIALGHSGFEMDKLIAQKVR GVDVVVGGHSNTFLYTGNPPSKEVPAGKYPFIVTSDDGRAV PVVQAYAFGKYLGYLKIEFDERGNVISSHGNPILLNSSIPEDPS IKADINKWRIKLDNYSTQELGKTIVYLDGSSQSCRFRECNNIG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHHG GSGGLPETGGDR | 62 |
| Human CD73 S269A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGDEVVGIVGYTSKETPFLSNPGTNLV FEDEITALQPEVDKLKTLNVNKIIALGHSGFEMDKLIAQKVR GVDVVVGGHSNTFLYTGNPPSKEVPAGKYPFIVTADDGRKV PVVQAYAFGKYLGYLKIEFDERGNVISSHGNPILLNSSIPEDPS IKADINKWRIKLDNYSTQELGKTIVYLDGSSQSCRFRECNMG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHHG GSGGLPETGGDR | 132 |

TABLE 5-continued

Exemplary sequences of CD73 and family members.

| Description | Amino Acid Sequence | SEQ ID NO |
|---|---|---|
| Human CD73 I158A, Y161A, P165A D168A mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLALPAKVLAVGAEVVGIVGYTSKETPFLSNPGTNL VFEDEITALQPEVDKLKTLNVNKIIALGHSGFEMDKLIAQKV RGVDVVVGGHSNTFLYTGNPPSKEVPAGKYPFIVTSDDGRK VPVVQAYAFGKYLGYLKIEFDERGNVISSHGNPILLNSSIPED PSIKADINKWRIKLDNYSTQELGKTIVYLDGSSQSCRFRECN MGNLICDAMINNNLRHTDEMFWNHVSMCILNGGGIRSPIDE RNNGTITWENLAAVLPFGGTFDLVQLKGSTLKKAFEHSVHR YGQSTGEFLQVGGIHVVYDLSRKPGDRVVKLDVLCTKCRVP SYDPLKMDEVYKVILPNFLANGGDGFQMIKDELLRHDSGDQ DINVVSTYISKMKVIYPAVEGRIKENLYFQGLEHHHHHHHH HGGSGGLPETGGDR | 133 |
| Human CD73 Y158F, Y161S, P165S, D168G mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLFLPSKVLSVGGEVVGIVGYTSKETPFLSNPGTNLV FEDEITALQPEVDKLKTLNVNKIIALGHSGFEMDKLIAQKVR GVDVVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNMG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHHG GSGGLPETGGDR | 134 |
| Human CD73 S152H, Y158F, Y161S mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LAHQISGLFLPSKVLPVGDEVVGIVGYTSKETPFLSNPGTNLV FEDEITALQPEVDKLKTLNVNKIIALGHSGFEMDKLIAQKVR GVDVVVGGHSNTFLYTGNPPSKEVPAGKYPFIVTSDDGRKV PVVQAYAFGKYLGYLKIEFDERGNVISSHGNPILLNSSIPEDPS IKADINKWRIKLDNYSTQELGKTIVYLDGSSQSCRFRECNMG NLICDAMINNNLRHTDEMFWNHVSMCILNGGGIRSPIDERNN GTITWENLAAVLPFGGTFDLVQLKGSTLKKAFEHSVHRYGQ STGEFLQVGGIHVVYDLSRKPGDRVVKLDVLCTKCRVPSYD PLKMDEVYKVILPNFLANGGDGFQMIKDELLRHDSGDQDIN VVSTYISKMKVIYPAVEGRIKENLYFQGLEHHHHHHHHHHG GSGGLPETGGDR | 135 |
| Human CD73 P165S, D168G mutant with His-tag | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLSVGGEVVGIVGYTSKETPFLSNPGTNL VFEDEITALQPEVDKLKTLNVNKIIALGHSGFEMDKLIAQKV RGVDVVVGGHSNTFLYTGNPPSKEVPAGKYPFIVTSDDGRK VPVVQAYAFGKYLGYLKIEFDERGNVISSHGNPILLNSSIPED PSIKADINKWRIKLDNYSTQELGKTIVYLDGSSQSCRFRECN MGNLICDAMINNNLRHTDEMFWNHVSMCILNGGGIRSPIDE RNNGTITWENLAAVLPFGGTFDLVQLKGSTLKKAFEHSVHR YGQSTGEFLQVGGIHVVYDLSRKPGDRVVKLDVLCTKCRVP SYDPLKMDEVYKVILPNFLANGGDGFQMIKDELLRHDSGDQ DINVVSTYISKMKVIYPAVEGRIKENLYFQGLEHHHHHHHH HGGSGGLPETGGDR | 136 |
| Mouse CD73 I109A, G111R, H154S, F160Y, S163Y, S167P, G170D, S200T, D298E, K299R mutant with His-tag | WELTILHTNDVHSRLEQTSDDSTKCLNASLCVGGVARLFTK VQQIRKEEPNVLFLDAGDQYQGTIWFTVYKGLEVAHFMNAL RRYDAMALGNHEFDNGVEGLIDPLLRNVKFPILSANIKARGPL ASQISGLYLPYKVLPVGDEVVGIVGYTSKETPFLSNPGTNLVF EDEITALQPEVDKLKTLNVNKIIALGHSGFEMDKLIAQKVRG VDIVVGGHSNTFLYTGNPPSKEVPAGKYPFIVTADDGRQVPV VQAYAFGKYLGYLKVEFDERGNVITSYGNPILLNSSIPEDATI KADINQWRIKLDNYSTQELGRTIVYLDGSTQTCRFRECNMG NLICDAMINNNLRHPDEMFWNHVSMCIVNGGGIRSPIDEKN NGTITWENLAAVLPFGGTFDLVQLKGSTLKKAFEHSVHRYG QSTGEFLQVGGIHVVYDINRKPWNRVVQLEVLCTKCRVPIYE PLEMDKVYKVTLPSYLANGGDGFQMIKDELLKHDSGDQDIS VVSEYISKMKVVYPAVEGRIKENLYFQGLEHHHHHHHHHH GGSGGLPETGGDR | 137 |

TABLE 5-continued

Exemplary sequences of CD73 and family members.

| Description | Amino Acid Sequence | SEQ ID NO |
|---|---|---|
| Mouse CD73 S163Y, S167P, G170D mutant with His-tag | WELTILHTNDVHSRLEQTSDDSTKCLNASLCVGGVARLFTK VQQIRKEEPNVLFLDAGDQYQGTIWFTVYKGLEVAHFMNIL GYDAMALGNHEFDNGVEGLIDPLLRNVKFPILSANIKARGPL AHQISGLFLPYKVLPVGDEVVGIVGYTSKETPFLSNPGTNLVF EDEISALQPEVDKLKTLNVNKIIALGHSGFEMDKLIAQKVRG VDIVVGGHSNTFLYTGNPPSKEVPAGKYPFIVTADDGRQVPV VQAYAFGKYLGYLKVEFDDKGNVITSYGNPILLNSSIPEDATI KADINQWRIKLDNYSTQELGRTIVYLDGSTQTCRFRECNMG NLICDAMINNNLRHPDEMEWNHVSMCIVNGGGIRSPIDEKN NGTITWENLAAVLPFGGTFDLVQLKGSTLKKAFEHSVHRYG QSTGEFLQVGGIHVVYDINRKPWNRVVQLEVLCTKCRVPIYE PLEMDKVYKVTLPSYLANGGDGFQMIKDELLKHDSGDQDIS VVSEYISKMKVVYPAVEGRIKENLYFQGLEHHHHHHHHHH GGSGGLPETGGDR | 138 |

TABLE 6

Exemplary sequences of linkers, ligand binding moieties, and anti-CD73 antibodies comprising ligand binding moieties*

| Description | Amino Acid Sequence | SEQ ID NO |
|---|---|---|
| Peptide linker 1 | GGGGSGGGGSGGGGSGGGGSG | 103 |
| Peptide linker 2 | GGGGSGGGGS | 104 |
| Peptide linker 3 | GGGGSGGGGSGGGGS | 105 |
| Peptide linker 4 | GGGGSG | 106 |
| Peptide linker 5 | GSAGSAAGSGEF | 107 |
| Peptide linker 6 | AEAAAKEAAAKA | 108 |
| TGFβR2 extracellular domain variant 1 from TGFβR2 isoform A | IPPHVQKSDVEMEAQKDEIICPSCNRTAHPLRHINNDMIVTD NNGAVKFPQLCKFCDVRFSTCDNQKSCMSNCSITSICEKPQE VCVAVWRKNDENITLETVCHDPKLPYHDFILEDAASPKCIM KEKKKPGETFFMCSCSSDECNDNIIFSEEYNTSNPD | 109 |
| TGFβR2 extracellular domain variant 2 from TGFβR2 isoform A | TIPPHVQKSDVEMEAQKDEIICPSCNRTAHPLRHINNDMIVT DNNGAVKFPQLCKFCDVRFSTCDNQKSCMSNCSITSICEKP QEVCVAVWRKNDENITLETVCHDPKLPYHDFILEDAASPKC IMKEKKKPGETFFMCSCSSDECNDNIIFSEEYNTSNPDLLLVI FQ | 110 |
| TGFβR2 extracellular domain variant 3 from TGFβR2 isoform B | IPPHVQKSVNNDMIVTDNNGAVKFPQLCKFCDVRFSTCDNQ KSCMSNCSITSICEKPQEVCVAVWRKNDENITLETVCHDPKL PYHDFILEDAASPKCIMKEKKKPGETFFMCSCSSDECNDNIIF SEEYNTSNPD | 111 |
| TGFβR2 extracellular domain variant 4 from TGFβR2 isoform B | TIPPHVQKSVNNDMIVTDNNGAVKFPQLCKFCDVRFSTCDN QKSCMSNCSITSICEKPQEVCVAVWRKNDENITLETVCHDP KLPYHDFILEDAASPKCIMKEKKKPGETFFMCSCSSDECND NIIFSEEYNTSNPDLLLVIFQ | 112 |
| BA035 full-length murine heavy chain | XVKLVESGPELVKPGASVKISCKASGYAFSSSWINWVQRP GKGLEWIGRIYPRNGDTNYNGKFKDRATLTADRSSSTAYLQ LSSLTSEDSAVYFCASLLDYSMDYWGQGTSVTVSSAKTTAP SVYPLAPVCGDTTGSSVTLGCLVKGYFPEPVTLTWNSGSLS SGVHTFPAVLQSDLYTLSSSVTVTSSTWPSQSITCNVAHPAS STKVDKKIEPRGPTIKPCPPCKCPAPNLLGGPSVFIFPPKIKDV LMISLSPIVTCVVVDVSEDDPDVQISWFVNNVEVHTAQTQT HREDYASTLRVVSALPIQHQDWMSGKEFKCKVNNKDLPAPI ERTISKPKGSVRAPQVYVLPPPEEEMTKKQVTLTCMVTDFM PEDIYVEWTNNGKTELNYKNTEPVLDSDGSYFMYSKLRVE KKNWVERNSYSCSVVHEGLHNHHTTKSFSRTPGGGGSGG | 113 |

TABLE 6-continued

Exemplary sequences of linkers, ligand binding moieties, and anti-CD73 antibodies comprising ligand binding moieties*

| Description | Amino Acid Sequence | SEQ ID NO |
|---|---|---|
| | GGSGGGGSIPPHVQKSVNNDMIVTDNNGAVKFPQLCKFCD<br>VRFSTCDNQKSCMSNCSITSICEKPQEVCVAVWRKNDENITL<br>ETVCHDPKLPYHDFILEDAASPKCIMKEKKKPGETFFMCSCS<br>SDECNDNIIFSEEYNTSNPD, wherein X is E or pyroglutamate | |
| BA036 full-length humanized heavy chain | XVQLVQSGAEVKKPGESLKISCKASGYAFSSSWINWVRQM<br>PGKGLEWMGRIYPRNGDTNYNGKFKDQVTISADKSISTAYL<br>QWSSLKASDTAMYYCASLLDYSMDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTHTCPPCPAPELLGGPSVFLFPP<br>KPKDTLMISRTPEVTCVVVDVSHEDPEVKFNWYVDGVEVH<br>NAKTKPREEQYASTYRVVSVLTVLHQDWLNGKEYKCKVS<br>NKALPAPIEKTISKAKGQPREPQVYTLPPSREEMTKNQVSLT<br>CLVKGFYPSDIAVEWESNGQPENNYKTTPPVLDSDGSFFLY<br>SKLTVDKSRWQQGNVFSCSVMHEALHNHYTQKSLSLSPGG<br>GGGSGGGGSGGGGSGGGGSIPPHVQKSVNNDMIVTDNNG<br>AVKFPQLCKFCDVRFSTCDNQKSCMSNCSITSICEKPQEVCV<br>AVWRKNDENITLETVCHDPKLPYHDFILEDAASPKCIMKEK<br>KKPGETFFMCSCSSDECNDNIIFSEEYNTSNPD, wherein X is E<br>or pyroglutamate | 114 |
| BA037 full-length humanized heavy chain | XVQLVQSGAEVKKPGESLKISCKASGYAFSSSWINWVRQM<br>PGKGLEWMGRIYPRAGDTNYAGKFKDQVTISADKSISTAYL<br>QWSSLKASDTAMYYCASLLDYSMDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTHTCPPCPAPELLGGPSVFLFPP<br>KPKDTLMISRTPEVTCVVVDVSHEDPEVKFNWYVDGVEVH<br>NAKTKPREEQYASTYRVVSVLTVLHQDWLNGKEYKCKVS<br>NKALPAPIEKTISKAKGQPREPQVYTLPPSREEMTKNQVSLT<br>CLVKGFYPSDIAVEWESNGQPENNYKTTPPVLDSDGSFFLY<br>SKLTVDKSRWQQGNVFSCSVMHEALHNHYTQKSLSLSPGG<br>GGGSGGGGSGGGGSGGGGSIPPHVQKSVNNDMIVTDNNG<br>AVKFPQLCKFCDVRFSTCDNQKSCMSNCSITSICEKPQEVCV<br>AVWRKNDENITLETVCHDPKLPYHDFILEDAASPKCIMKEK<br>KKPGETFFMCSCSSDECNDNIIFSEEYNTSNPD, wherein X is E<br>or pyroglutamate | 115 |
| BA043 full-length humanized heavy chain | XVQLVQSGAEVKKPGESLKISCKASGYAFSSSWINWVRQM<br>PGKGLEWMGRIYPRNGDTNYNGKFKDQVTISADKSISTAYL<br>QWSSLKASDTAMYYCASLLDYSMDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTHTCPPCPAPELLGGPSVFLFPP<br>KPKDTLMISRTPEVTCVVVDVSHEDPEVKFNWYVDGVEVH<br>NAKTKPREEQYASTYRVVSVLTVLHQDWLNGKEYKCKVS<br>NKALPAPIEKTISKAKGQPREPQVYTLPPSREEMTKNQVSLT<br>CLVKGFYPSDIAVEWESNGQPENNYKTTPPVLDSDGSFFLY<br>SKLTVDKSRWQQGNVFSCSVMHEALHNHYTQKSLSLSPGG<br>GGGSIPPHVQKSVNNDMIVTDNNGAVKFPQLCKFCDVRFS<br>TCDNQKSCMSNCSITSICEKPQEVCVAVWRKNDENITLETV<br>CHDPKLPYHDFILEDAASPKCIMKEKKKPGETFFMCSCSSDE<br>CNDNIIFSEEYNTSNPD, wherein X is E or pyroglutamate | 116 |
| BA044 full-length humanized heavy chain | XVQLVQSGAEVKKPGESLKISCKASGYAFSSSWINWVRQM<br>PGKGLEWMGRIYPRAGDTNYAGKFKDQVTISADKSISTAYL<br>QWSSLKASDTAMYYCASLLDYSMDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTHTCPPCPAPELLGGPSVFLFPP<br>KPKDTLMISRTPEVTCVVVDVSHEDPEVKFNWYVDGVEVH<br>NAKTKPREEQYASTYRVVSVLTVLHQDWLNGKEYKCKVS<br>NKALPAPIEKTISKAKGQPREPQVYTLPPSREEMTKNQVSLT<br>CLVKGFYPSDIAVEWESNGQPENNYKTTPPVLDSDGSFFLY<br>SKLTVDKSRWQQGNVFSCSVMHEALHNHYTQKSLSLSPGG<br>GGGSIPPHVQKSVNNDMIVTDNNGAVKFPQLCKFCDVRFS<br>TCDNQKSCMSNCSITSICEKPQEVCVAVWRKNDENITLETV<br>CHDPKLPYHDFILEDAASPKCIMKEKKKPGETFFMCSCSSDE<br>CNDNIIFSEEYNTSNPD, wherein X is E or pyroglutamate | 117 |

TABLE 6-continued

Exemplary sequences of linkers, ligand binding moieties, and anti-CD73 antibodies comprising ligand binding moieties*

| Description | Amino Acid Sequence | SEQ ID NO |
|---|---|---|
| BA045 full-length humanized heavy chain | XVQLVQSGAEVKKPGESLKISCKASGYAFSSSWINWVRQM PGKGLEWMGRIYPRNGDTNYNGKFKDQVTISADKSISTAYL QWSSLKASDTAMYYCASLLDYSMDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYASTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGA EAAAKEAAAKAIPPHVQKSVNNDMIVTDNNGAVKFPQLCK FCDVRFSTCDNQKSCMSNCSITSICEKPQEVCVAVWRKNDE NITLETVCHDPKLPYHDFILEDAASPKCIMKEKKKPGETFFM CSCSSDECNDNIIFSEEYNTSNPD, wherein X is E or pyroglutamate | 118 |
| BA046 full-length humanized heavy chain | XVQLVQSGAEVKKPGESLKISCKASGYAFSSSWINWVRQM PGKGLEWMGRIYPRAGDTNYAGKFKDQVTISADKSISTAYL QWSSLKASDTAMYYCASLLDYSMDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYASTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGA EAAAKEAAAKAIPPHVQKSVNNDMIVTDNNGAVKFPQLCK FCDVRFSTCDNQKSCMSNCSITSICEKPQEVCVAVWRKNDE NITLETVCHDPKLPYHDFILEDAASPKCIMKEKKKPGETFFM CSCSSDECNDNIIFSEEYNTSNPD, wherein X is E or pyroglutamate | 119 |
| BA047 full-length humanized heavy chain | XVQLVQSGAEVKKPGESLKISCKASGYAFSSSWINWVRQM PGKGLEWMGRIYPRNGDTNYNGKFKDQVTISADKSISTAYL QWSSLKASDTAMYYCASLLDYSMDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYASTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGG SAGSAAGSGEFIPPHVQKSVNNDMIVTDNNGAVKFPQLCKF CDVRFSTCDNQKSCMSNCSITSICEKPQEVCVAVWRKNDEN ITLETVCHDPKLPYHDFILEDAASPKCIMKEKKKPGETFFMC SCSSDECNDNIIFSEEYNTSNPD, wherein X is E or pyroglutamate | 120 |
| BA048 full-length humanized heavy chain | XVQLVQSGAEVKKPGESLKISCKASGYAFSSSWINWVRQM PGKGLEWMGRIYPRAGDTNYAGKFKDQVTISADKSISTAYL QWSSLKASDTAMYYCASLLDYSMDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYASTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGG SAGSAAGSGEFIPPHVQKSVNNDMIVTDNNGAVKFPQLCKF CDVRFSTCDNQKSCMSNCSITSICEKPQEVCVAVWRKNDEN ITLETVCHDPKLPYHDFILEDAASPKCIMKEKKKPGETFFMC SCSSDECNDNIIFSEEYNTSNPD, wherein X is E or pyroglutamate | 121 |
| Human VEGFR1 extracellular domain | SDTGRPFVEMYSEIPEIIHMTEGRELVIPCRVTSPNITVTLKKF PLDTLIPDGKRIIWDSRKGFIISNATYKEIGLLTCEATVNGHL YKTNYLTHRQTNT | 122 |

TABLE 6-continued

Exemplary sequences of linkers, ligand binding moieties, and anti-CD73 antibodies comprising ligand binding moieties*

| Description | Amino Acid Sequence | SEQ ID NO |
|---|---|---|
| BA038 full-length heavy chain (murine antibody heavy chain + human VEGFR1 extracellular domain) | XVKLVESGPELVKPGASVKISCKASGYAFSSSWINWVNQRP GKGLEWIGRIYPRNGDTNYNGKFKDRATLTADRSSSTAYLQ LSSLTSEDSAVYFCASLLDYSMDYWGQGTSVTVSSAKTTAP SVYPLAPVCGDTTGSSVTLGCLVKGYFPEPVTLTWNSGSLS SGVHTFPAVLQSDLYTLSSSVTVTSSTWPSQSITCNVAHPAS STKVDKKIEPRGPTIKPCPPCKCPAPNLLGGPSVFIFPPKIKDV LMISLSPIVTCVVVDVSEDDPDVQISWFVNNVEVHTAQTQT HREDYASTLRVVSALPIQHQDWMSGKEFKCKVNNKDLPAPI ERTISKPKGSVRAPQVYVLPPPEEEMTKKQVTLTCMVTDFM PEDIYVEWTNNGKTELNYKNTEPVLDSDGSYFMYSKLRVE KKNWVERNSYSCSVVHEGLHNHHTTKSFSRTPGGGGSGG GGSSDTGRPFVEMYSEIPEIIHMTEGRELVIPCRVTSPNITVTL KKFPLDTLIPDGKRIIWDSRKGFIISNATYKEIGLLTCEATVN GHLYKTNYLTHRQTNT, wherein X is E or pyroglutamate | 123 |
| BA039 full-length heavy chain 1 (humanized variable + murine constant + human VEGFR1 extracellular domain) | XVQLVQSGAEVKKPGESLKISCKASGYAFSSSWINWVRQM PGKGLEWMGRIYPRNGDTNYNGKFKDQVTISADKSISTAYL QWSSLKASDTAMYYCASLLDYSMDYWGQGTLVTVSSAKT TAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNLLGGPSVFIFPPKI KDVLMISLSPIVTCVVVDVSEDDPDVQISWFVNNVEVHTAQ TQTHREDYASTLRVVSALPIQHQDWMSGKEFKCKVNNKDL PAPIERTISKPKGSVRAPQVYVLPPPEEEMTKKQVTLTCMVT DFMPEDIYVEWTNNGKTELNYKNTEPVLDSDGSYFMYSKL RVEKKNWVERNSYSCSVVHEGLHNHHTTKSFSRTPGGGGG SGGGGSSDTGRPFVEMYSEIPEIIRMTEGRELVIPCRVTSPNIT VTLKKFPLDTLIPDGKRIIWDSRKGFIISNATYKEIGLLTCEAT VNGHLYKTNYLTHRQTNT, wherein X is E or pyroglutamate | 124 |
| BA040 full-length heavy chain 2 (humanized variable + murine constant + human VEGFR1 extracellular domain) | XVQLVQSGAEVKKPGESLKISCKASGYAFSSSWINWVRQM PGKGLEWMGRIYPRAGDTNYAGKFKDQVTISADKSISTAYL QWSSLKASDTAMYYCASLLDYSMDYWGQGTLVTVSSAKT TAPSVYPLAPVCGDTTGSSVTLGCLVKGYFPEPVTLTWNSG SLSSGVHTFPAVLQSDLYTLSSSVTVTSSTWPSQSITCNVAH PASSTKVDKKIEPRGPTIKPCPPCKCPAPNLLGGPSVFIFPPKI KDVLMISLSPIVTCVVVDVSEDDPDVQISWFVNNVEVHTAQ TQTHREDYASTLRVVSALPIQHQDWMSGKEFKCKVNNKDL PAPIERTISKPKGSVRAPQVYVLPPPEEEMTKKQVTLTCMVT DFMPEDIYVEWTNNGKTELNYKNTEPVLDSDGSYFMYSKL RVEKKNWVERNSYSCSVVHEGLHNHHTTKSFSRTPGGGGG SGGGGSSDTGRPFVEMYSEIPEIIRMTEGRELVIPCRVTSPNIT VTLKKFPLDTLIPDGKRIIWDSRKGFIISNATYKEIGLLTCEAT VNGHLYKTNYLTHRQTNT, wherein X is E or pyroglutamate | 125 |
| BA041 full-length heavy chain (humanized) | XVQLVQSGAEVKKPGESLKISCKASGYAFSSSWINWVRQM PGKGLEWMGRIYPRNGDTNYNGKFKDQVTISADKSISTAYL QWSSLKASDTAMYYCASLLDYSMDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYASTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGG GGGSGGGSSDTGRPFVEMYSEIPEIIHMTEGRELVIPCRVTS PNITVTLKKFPLDTLIPDGKRIIWDSRKGFIISNATYKEIGLLT CEATVNGHLYKTNYLTHRQTNT, wherein X is E or pyroglutamate | 126 |
| BA042 full-length heavy chain (humanized) | XVQLVQSGAEVKKPGESLKISCKASGYAFSSSWINWVRQM PGKGLEWMGRIYPRAGDTNYAGKFKDQVTISADKSISTAYL QWSSLKASDTAMYYCASLLDYSMDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYASTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGG | 127 |

TABLE 6-continued

Exemplary sequences of linkers, ligand binding moieties, and anti-CD73 antibodies comprising ligand binding moieties*

| Description | Amino Acid Sequence | SEQ ID NO |
|---|---|---|
| | GGGSGGGGSSDTGRPFVEMYSEIPEIIHMTEGRELVIPCRVTS PNITVTLKKFPLDTLIPDGKRIIWDSRKGFIISNATYKEIGLLT CEATVNGHLYKTNYLTHRQTNT, wherein X is E or pyroglutamate | |
| BA039 full-length light chain (chimeric; humanized variable + murine constant) | DIQMTQSPSSLSASVGDRVTITCRASQDISNYLNWYQQKPG KAPKLLIYYTSRLHSGVPSRFSGSGSGTDFTFTISSLQPEDIAT YYCQQGNTLPLTFGQGTKVEIKRADAAPTVSIFPPSSEQLTS GGASVVCFLNNFYPKDINVKWKIDGSERQNGVLNSWTDQD SKDSTYSMSSTLTLTKDEYERHNSYTCEATHKTSTSPIVKSF NRNEC | 128 |

*In this table, a polypeptide of an anti-CD73 antibody comprising a ligand binding moiety is referred to as a full-length heavy chain if it comprises a full-length heavy chain.

In certain embodiments, the instant disclosure provides an isolated antibody that specifically binds to CD73 (e.g., human, mouse, or cynomolgus CD73), the antibody comprising a VH domain comprising one, two, or all three of the CDRs of a VH domain set forth in Table 1 herein. In certain embodiments, the antibody comprises the CDRH1 of a VH domain set forth in Table 1. In certain embodiments, the antibody comprises the CDRH2 of a VH domain set forth in Table 1. In certain embodiments, the antibody comprises the CDRH3 of a VH domain set forth in Table 1.

In certain embodiments, the instant disclosure provides an isolated antibody that specifically binds to CD73 (e.g., human, mouse, or cynomolgus CD73), the antibody comprising a VL domain comprising one, two, or all three of the CDRs of a VL domain disclosed in Table 1 herein. In certain embodiments, the antibody comprises the CDRL1 of a VL domain set forth in Table 1. In certain embodiments, the antibody comprises the CDRL2 of a VL domain set forth in Table 1. In certain embodiments, the antibody comprises the CDRL3 of a VL domain set forth in Table 1.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety. In certain embodiments, the light chain CDRs of an antibody are determined according to Kabat and the heavy chain CDRs of an antibody are determined according to MacCallum (supra). In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus CD73).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the instant disclosure provides an isolated antibody that specifically binds to CD73 (e.g., human, mouse, or cynomolgus CD73), the antibody comprising the Chothia VH CDRs of a VH disclosed in Table 1 herein. In certain embodiments, the instant disclosure provides an isolated antibody that specifically binds to CD73 (e.g., human, mouse, or cynomolgus CD73), the antibody comprising the Chothia VL CDRs of a VL disclosed in Table 1 herein. In certain embodiments, the instant disclosure provides an isolated antibody that specifically binds to CD73 (e.g., human, mouse, or cynomolgus CD73), the antibody comprising the Chothia VH CDRs and Chothia VL CDRs of an antibody disclosed in Table 1 herein. In certain embodiments, antibodies that specifically bind to CD73 (e.g., human, mouse, or cynomolgus CD73) comprise one or more CDRs, in which the Chothia and Kabat CDRs have the same amino acid sequence. In certain embodiments, the instant disclosure provides an isolated antibody that specifically binds to CD73 (e.g., human, mouse, or cynomolgus CD73) and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97. IMGT unique numbering may also be defined as in Lefranc M-P et al., (2009) Nucleic Acids Res 37: D1006-D1012 and the IMGT database.

In certain embodiments, the instant disclosure provides antibodies that specifically bind to CD73 (e.g., human, mouse, or cynomolgus CD73) and comprise CDRs of an antibody disclosed in Table 1 herein, as determined by the IMGT numbering system, for example, as described in Lefranc M-P (1999) supra and Lefranc M-P et al., (1999) supra or Lefranc M-P et al., (2009) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to CD73 (e.g., human, mouse, or cynomolgus CD73) and comprise CDRs of an antibody disclosed in Table 1 herein as determined by the AbM numbering scheme.

In certain embodiments, the CDRs of an antibody can be determined according to the AHo numbering system (as described in Honegger and Plückthun, A., J. Mol. Biol. 309:657-670 (2001), herein incorporated by reference in its entirety). In certain embodiments, the instant disclosure provides antibodies that specifically bind to CD73 (e.g., human, mouse, or cynomolgus CD73) and comprise CDRs of an antibody disclosed in Table 1 herein as determined by the AHo numbering scheme.

In certain embodiments, the instant disclosure provides an isolated antibody that specifically binds to CD73 (e.g., human, mouse, or cynomolgus CD73), wherein the antibody comprises a heavy chain variable region comprising the CDRH1, CDRH2, and CDRH3 region amino acid sequences of a VH domain set forth in SEQ ID NO: 19, 20, 21, 23, 24, 25, 26, 27, 28, 29, or 30, and a light chain variable region comprising the CDRL1, CDRL2, and CDRL3 region amino acid sequences of a VL domain set forth in SEQ ID NO: 33, 34, 35, 37, 38, 39, or 40, wherein each CDR is defined in accordance with the MacCallum definition, the Kabat definition, the Chothia definition, the IMGT numbering system, the AbM definition of CDR, structural analysis, or a combination thereof, wherein the structural analysis identifies residues in the variable region(s) predicted to make contact with an epitope region of CD73 (e.g., human, mouse, or cynomolgus CD73). In certain embodiments, the instant disclosure provides an isolated antibody that specifically binds to CD73 (e.g., human, mouse, or cynomolgus CD73), wherein the antibody comprises a heavy chain variable region comprising the CDRH1, CDRH2, and CDRH3 region amino acid sequences of a VH domain, and a light chain variable region comprising the CDRL1, CDRL2, and CDRL3 region amino acid sequences of a VL domain, wherein the VH domain and the VL domain comprise the amino acid sequences set forth in SEQ ID NOs: 19 and 33; 20 and 34; 21 and 35; 23 and 37; 24 and 37; 25 and 37; 26 and 37; 27 and 37; 28 and 37; 29 and 37; 30 and 37; 23 and 38; 24 and 38; 25 and 38; 26 and 38; 27 and 38; 28 and 38; 23 and 39; or, 23 and 40, respectively, and wherein each CDR is defined in accordance with the MacCallum definition, the Kabat definition, the Chothia definition, the IMGT numbering system, the AbM definition of CDR, structural analysis, or a combination thereof, wherein the structural analysis identifies residues in the variable region(s) predicted to make contact with an epitope region of CD73 (e.g., human, mouse, or cynomolgus CD73). In certain embodiments, the instant disclosure provides an isolated antibody that specifically binds to CD73 (e.g., human, mouse, or cynomolgus CD73) and comprises a combination of CDRs defined by the Kabat definition and CDRs defined by structural analysis of the antibody, wherein the structural analysis identifies residues in the variable region(s) predicted to make contact with an epitope region of CD73 (e.g., human, mouse, or cynomolgus CD73).

In certain embodiments, the instant disclosure provides an isolated antibody that specifically binds to CD73 (e.g., human, mouse, or cynomolgus CD73), the antibody comprising the six CDRs present in the BA025 antibody disclosed herein, as defined by one or more of the Kabat, IMGT (e.g., IMGT unique), AHo or Chothia antibody numbering schemes. In certain embodiments, the antibody comprises at least one, at least two, at least three, at least four, or at least five of the CDRs present in the BA025 antibody. The Kabat, IMGT unique, Aho, and Chothia CDRs of the BA025 antibody are provided in Table 1 herein.

In certain embodiments, the instant disclosure provides an isolated antibody that specifically binds to CD73 (e.g., human, mouse, or cynomolgus CD73), the antibody comprising the six CDRs present in the BA020 antibody disclosed herein, as defined by one or more of the Kabat, IMGT (e.g., IMGT unique), AHo or Chothia antibody numbering schemes. In certain embodiments, the antibody comprises at least one, at least two, at least three, at least four, or at least five of the CDRs present in the BA020 antibody. The Kabat, IMGT unique, Aho, and Chothia CDRs of the BA020 antibody are provided in Table 1 herein.

In certain embodiments, the instant disclosure provides an isolated antibody that specifically binds to CD73 (e.g., human, mouse, or cynomolgus CD73), the antibody comprising:
(a) CDRH1 comprises the amino acid sequence of $X_1X_2WX_3X_4$ (SEQ ID NO: 13), wherein
  $X_1$ is S or N;
  $X_2$ is S or Y;
  $X_3$ is I or M; and
  $X_4$ is N or H;
(b) CDRH2 comprises the amino acid sequence of $X_1IYPRX_2X_3DTNYX_4X_5KFKX_6$ (SEQ ID NO: 14), wherein
  $X_1$ is R or T;
  $X_2$ is N, A, or S;
  $X_3$ is G or S;
  $X_4$ is N, A, or S;
  $X_5$ is G or Q; and
  $X_6$ is D or G;
(c) CDRH3 comprises the amino acid sequence of LLDYSMDY (SEQ ID NO: 7);
(d) CDRL1 comprises the amino acid sequence of $RASQDISX_1X_2LN$ (SEQ ID NO: 16), wherein
  $X_1$ is N or I; and
  $X_2$ is Y or S;
(e) CDRL2 comprises the amino acid sequence of YTSRLHS (SEQ ID NO: 10); and/or
(f) CDRL3 comprises the amino acid sequence of QQGNTLPXT (SEQ ID NO: 17), wherein
  X is L or W.

In certain embodiments, the instant disclosure provides an isolated antibody that specifically binds to CD73 (e.g., human, mouse, or cynomolgus CD73), the antibody comprising:

(a) CDRH1 comprises the amino acid sequence of SSWIN (SEQ ID NO: 2);
(b) CDRH2 comprises the amino acid sequence of RIYPRX$_1$GDTNYX$_2$GKFKD (SEQ ID NO: 15), wherein
X$_1$ is N, A, or S; and
X$_2$ is N, A, or S;
(c) CDRH3 comprises the amino acid sequence of LLDYSMDY (SEQ ID NO: 7);
(d) CDRL1 comprises the amino acid sequence of RASQDISX1X2LN (SEQ ID NO: 16), wherein
X$_1$ is N or I; and
X$_2$ is Y or S;
(e) CDRL2 comprises the amino acid sequence of YTSRLHS (SEQ ID NO: 10); and/or
(f) CDRL3 comprises the amino acid sequence of QQGNTLPLT (SEQ ID NO: 12)

In certain embodiments, the instant disclosure provides an isolated antibody that specifically binds to CD73 (e.g., human, mouse, or cynomolgus CD73), wherein the antibody comprises a VH domain comprising the CDRH1, CDRH2 and CDRH3 amino acid sequences set forth in SEQ ID NOs: 1, 3, and 7, respectively. In certain embodiments, the instant disclosure provides an isolated antibody that specifically binds to CD73 (e.g., human, mouse, or cynomolgus CD73), wherein the antibody comprises a VH domain comprising the CDRH1, CDRH2 and CDRH3 amino acid sequences set forth in SEQ ID NOs: 2, 4, and 7, respectively. In certain embodiments, the instant disclosure provides an isolated antibody that specifically binds to CD73 (e.g., human, mouse, or cynomolgus CD73), wherein the antibody comprises a VH domain comprising the CDRH1, CDRH2 and CDRH3 amino acid sequences set forth in SEQ ID NOs: 2, 5, and 7, respectively. In certain embodiments, the instant disclosure provides an isolated antibody that specifically binds to CD73 (e.g., human, mouse, or cynomolgus CD73), wherein the antibody comprises a VH domain comprising the CDRH1, CDRH2 and CDRH3 amino acid sequences set forth in SEQ ID NOs: 2, 6, and 7, respectively. In certain embodiments, the instant disclosure provides an isolated antibody that specifically binds to CD73 (e.g., human, mouse, or cynomolgus CD73), wherein the antibody comprises a VL domain comprising the CDRL1, CDRL2 and CDRL3 amino acid sequences set forth in SEQ ID NOs: 8, 10, and 11, respectively. In certain embodiments, the instant disclosure provides an isolated antibody that specifically binds to CD73 (e.g., human, mouse, or cynomolgus CD73), wherein the antibody comprises a VL domain comprising the CDRL1, CDRL2 and CDRL3 amino acid sequences set forth in SEQ ID NOs: 9, 10, and 12, respectively. In certain embodiments, the instant disclosure provides an isolated antibody that specifically binds to CD73 (e.g., human, mouse, or cynomolgus CD73), wherein the antibody comprises a VL domain comprising the CDRL1, CDRL2 and CDRL3 amino acid sequences set forth in SEQ ID NOs: 8, 10, and 12, respectively.

In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 3, 7, 8, 10, and 11, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 4, 7, 8, 10, and 11, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 4, 7, 8, 10, and 12, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 4, 7, 9, 10, and 12, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 5, 7, 8, 10, and 12, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 6, 7, 8, 10, and 12, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 5, 7, 9, 10, and 12, respectively. In certain embodiments, the instant disclosure provides an isolated antibody that specifically binds to CD73 (e.g., human, mouse, or cynomolgus CD73), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 6, 7, 9, 10, and 12, respectively.

In certain embodiments, the instant disclosure provides an isolated antibody that specifically binds to CD73 (e.g., human, mouse, or cynomolgus CD73), comprising a heavy chain variable region comprising the amino acid sequence of SEQ ID NO: 31. In certain embodiments, the instant disclosure provides an isolated antibody that specifically binds to CD73 (e.g., human, mouse, or cynomolgus CD73), comprising a heavy chain variable region comprising an amino acid sequence selected from the group consisting of SEQ ID NOs: 19-21 and 23-30. In certain embodiments, the instant disclosure provides an isolated antibody that specifically binds to CD73 (e.g., human, mouse, or cynomolgus CD73), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 19-21 and 23-30.

In certain embodiments, the instant disclosure provides an isolated antibody that specifically binds to CD73 (e.g., human, mouse, or cynomolgus CD73), comprising a light chain variable region comprising the amino acid sequence of SEQ ID NO: 41 or 42. In certain embodiments, the instant disclosure provides an isolated antibody that specifically binds to CD73 (e.g., human, mouse, or cynomolgus CD73), comprising a light chain variable region comprising an amino acid sequence selected from the group consisting of SEQ ID NOs: 33-35 and 37-40. In certain embodiments, the instant disclosure provides an isolated antibody that specifically binds to CD73 (e.g., human, mouse, or cynomolgus CD73), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 33-35 and 37-40.

In certain embodiments, the instant disclosure provides an isolated antibody that specifically binds to CD73 (e.g., human, mouse, or cynomolgus CD73), comprising a heavy chain variable region comprising the amino acid sequence of SEQ ID NO: 31 and a light chain variable region comprising the amino acid sequence of SEQ ID NO: 41 or 42. In certain embodiments, the instant disclosure provides an isolated antibody that specifically binds to CD73 (e.g., human, mouse, or cynomolgus CD73), comprising a heavy chain variable region comprising an amino acid sequence selected from the group consisting of SEQ ID NOs: 19-21 and 23-30, and a light chain variable region comprising an amino acid sequence selected from the group consisting of SEQ ID NOs: 33-35 and 37-40. In certain embodiments, the instant disclosure provides an isolated antibody that specifically binds to CD73 (e.g., human, mouse, or cynomolgus CD73), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 19-21 and 23-30, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 33-35 and 37-40.

In certain embodiments, the instant disclosure provides an isolated antibody that specifically binds to CD73 (e.g., human, mouse, or cynomolgus CD73), comprising a heavy chain variable region and a light chain variable region comprising the amino acid sequences set forth in SEQ ID NOs: 19 and 33; 20 and 34; 21 and 35; 23 and 37; 24 and 37; 25 and 37; 26 and 37; 27 and 37; 28 and 37; 29 and 37; 30 and 37; 23 and 38; 24 and 38; 25 and 38; 26 and 38; 27 and 38; 28 and 38; 23 and 39; or, 23 and 40, respectively. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 19, and a light chain variable region comprising an amino acid sequence of SEQ ID NO: 33. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 20, and a light chain variable region comprising an amino acid sequence of SEQ ID NO: 34. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 21, and a light chain variable region comprising an amino acid sequence of SEQ ID NO: 35. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 23, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 24, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 23, and a light chain variable region comprising an amino acid sequence of SEQ ID NO: 38. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 24, and a light chain variable region comprising an amino acid sequence of SEQ ID NO: 38. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 25, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 26, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 27, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 28, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 25, and a light chain variable region comprising an amino acid sequence of SEQ ID NO: 38. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 26, and a light chain variable region comprising an amino acid sequence of SEQ ID NO: 38. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 27, and a light chain variable region comprising an amino acid sequence of SEQ ID NO: 38. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 28, and a light chain variable region comprising an amino acid sequence of SEQ ID NO: 38. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 29, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 30, and a light chain variable region comprising an amino acid sequence of SEQ ID NO: 37. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 23, and a light chain variable region comprising an amino acid sequence of SEQ ID NO: 39. In certain embodiments, the instant disclosure provides an isolated antibody that specifically binds to CD73 (e.g., human, mouse, or cynomolgus CD73), comprising a heavy chain variable region comprising an amino acid sequence of SEQ ID NO: 23, and a light chain variable region comprising an amino acid sequence of SEQ ID NO: 40.

In certain embodiments, the instant disclosure provides an isolated antibody that specifically binds to CD73 (e.g., human, mouse, or cynomolgus CD73), comprising a heavy chain variable region comprising an amino acid sequence derived from a murine IgHV1S12 germline sequence. In certain embodiments, the murine IgHV1S12 germline sequence is set forth in SEQ ID NO: 18. One or more regions selected from framework 1, framework 2, framework 3, CDRH1, and CDRH2 (e.g., two, three, four or five of these regions) can be derived from a murine IgHV1S12 germline sequence. In one embodiment, framework 1, framework 2, framework 3, CDRH1, and CDRH2 are all derived from a murine IgHV1S12 germline sequence. In certain embodiments, the heavy chain variable region comprises a CDRH3 comprising the amino acid sequence set forth in SEQ ID NO: 7.

In certain embodiments, the instant disclosure provides an isolated antibody that specifically binds to CD73 (e.g., human, mouse, or cynomolgus CD73), comprising a light chain variable region comprising an amino acid sequence derived from a murine IgKV10-96 germline sequence. In certain embodiments, the murine IgKV10-96 germline sequence is set forth in SEQ ID NO: 32. One or more regions selected from framework 1, framework 2, framework 3, CDRL1, and CDRL2 (e.g., two, three, four or five of these regions) can be derived from a murine germline sequence of IgKV10-96. In one embodiment, framework 1, framework 2, framework 3, CDRL1, and CDRL2 are all derived from a murine germline sequence of IgKV10-96. In certain embodiments, the light chain variable region comprises a CDRL3 comprising the amino acid sequence set forth in SEQ ID NO: 11 or 12.

In certain embodiments, the instant disclosure provides an isolated antibody that specifically binds to CD73 (e.g., human, mouse, or cynomolgus CD73), comprising a heavy chain variable region comprising an amino acid sequence derived from a murine IgHV1S12 germline sequence (e.g., SEQ ID NO: 18); and a light chain variable region comprising an amino acid sequence derived from a murine germline sequence derived from a murine IgKV10-96 germline sequence (e.g., SEQ ID NO: 32). In certain embodiments, the heavy chain variable region comprises a CDRH3 comprising the amino acid sequence set forth in SEQ ID NO: 7, and the light chain variable region comprises a CDRL3 comprising the amino acid sequence set forth in SEQ ID NO: 11 or 12.

In certain embodiments, the instant disclosure provides an isolated antibody that specifically binds to CD73 (e.g., human, mouse, or cynomolgus CD73), comprising a heavy chain variable region comprising an amino acid sequence derived from a human IgHV5-51 germline sequence. In certain embodiments, the human IgHV5-51 germline sequence is a human IgHV5-51*02 germline sequence (e.g., comprising the amino acid sequence of SEQ ID NO: 22). One or more regions selected from framework 1, framework 2, framework 3, CDRH1, and CDRH2 (e.g., two, three, four or five of these regions) can be derived from a human IgHV5-51 germline sequence. In one embodiment, framework 1, framework 2, framework 3, CDRH1, and CDRH2 are all derived from a human IgHV5-51 germline sequence. In certain embodiments, the heavy chain variable region comprises a CDRH3 comprising the amino acid sequence set forth in SEQ ID NO: 7.

In certain embodiments, the instant disclosure provides an isolated antibody that specifically binds to CD73 (e.g., human, mouse, or cynomolgus CD73), comprising a light chain variable region comprising an amino acid sequence derived from a human IGKV1-33 germline sequence (e.g., IGKV1-33*01, e.g., comprising the amino acid sequence of SEQ ID NO: 36). One or more regions selected from framework 1, framework 2, framework 3, CDRL1, and CDRL2 (e.g., two, three, four or five of these regions) can be derived from a human germline sequence selected from the group consisting of IGKV1-33 (e.g., IGKV1-33*01, e.g., comprising the amino acid sequence of SEQ ID NO: 36). In one embodiment, framework 1, framework 2, framework 3, CDRL1, and CDRL2 are all derived from a human IGKV1-33 germline sequence (e.g., IGKV1-33*01, e.g., comprising the amino acid sequence of SEQ ID NO: 36). In certain embodiments, the light chain variable region comprises a CDRL3 comprising the amino acid sequence set forth in SEQ ID NO: 12.

In certain embodiments, the instant disclosure provides an isolated antibody that specifically binds to CD73 (e.g., human, mouse, or cynomolgus CD73), comprising a heavy chain variable region comprising an amino acid sequence derived from a human IgHV5-51 germline sequence (e.g., a human IgHV5-51*02 germline sequence, e.g., comprising the amino acid sequence of SEQ ID NO: 22); and a light chain variable region comprising an amino acid sequence derived from a human IGKV1-33 germline sequence (e.g., IGKV1-33*01, e.g., comprising the amino acid sequence of SEQ ID NO: 36). In certain embodiments, the heavy chain variable region comprises a CDRH3 comprising the amino acid sequence set forth in SEQ ID NO: 7, and the light chain variable region comprises a CDRL3 comprising the amino acid sequence set forth in SEQ ID NO: 12.

In certain embodiments, the instant disclosure provides an isolated antibody that cross-competes for binding to CD73 (e.g., human, mouse, or cynomolgus CD73) with any of the anti-CD73 antibodies disclosed herein, including an antibody comprising the heavy chain variable region and light chain variable region amino acid sequences set forth in SEQ ID NOs: 19 and 33; 20 and 34; 21 and 35; 23 and 37; 24 and 37; 25 and 37; 26 and 37; 27 and 37; 28 and 37; 29 and 37; 30 and 37; 23 and 38; 24 and 38; 25 and 38; 26 and 38; 27 and 38; 28 and 38; 23 and 39; or, 23 and 40, respectively. In certain embodiments, the instant disclosure provides an isolated antibody that cross-competes for binding to CD73 (e.g., human, mouse, or cynomolgus CD73) with an antibody comprising the heavy and light chain variable region amino acid sequences set forth in SEQ ID NOs: 24 and 37, respectively. In certain embodiments, the instant disclosure provides an isolated antibody that cross-competes for binding to CD73 (e.g., human, mouse, or cynomolgus CD73) with an antibody comprising the heavy and light chain variable region amino acid sequences set forth in SEQ ID NOs: 27 and 37, respectively.

In certain embodiments, the instant disclosure provides an isolated antibody that binds to the same or an overlapping epitope of CD73 (e.g., an epitope of human, mouse, or cynomolgus CD73) as an antibody described herein, e.g., an antibody comprising the heavy and light chain variable region amino acid sequences set forth in SEQ ID NOs: 19 and 33; 20 and 34; 21 and 35; 23 and 37; 24 and 37; 25 and 37; 26 and 37; 27 and 37; 28 and 37; 29 and 37; 30 and 37; 23 and 38; 24 and 38; 25 and 38; 26 and 38; 27 and 38; 28 and 38; 23 and 39; or, 23 and 40, respectively. In certain embodiments, the instant disclosure provides an isolated antibody that binds to the same or an overlapping epitope of CD73 (e.g., an epitope of human, mouse, or an epitope of cynomolgus CD73) as an antibody described herein, e.g., an antibody comprising the heavy and light chain variable region amino acid sequences set forth in SEQ ID NOs: 24 and 37, respectively. In certain embodiments, the instant disclosure provides an isolated antibody that binds to the same or an overlapping epitope of CD73 (e.g., an epitope of human, mouse, or an epitope of cynomolgus CD73) as an antibody described herein, e.g., an antibody comprising the heavy and light chain variable region amino acid sequences set forth in SEQ ID NOs: 27 and 37, respectively. In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of CD73 (e.g., human, mouse, or cynomolgus CD73) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as CD73 (e.g., human, mouse, or cynomolgus CD73). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label MA using I-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., CD73, such as human, mouse, or cynomolgus CD73) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

Any immunoglobulin (Ig) constant region can be used in the antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In certain embodiments, the instant disclosure provides an isolated antibody that specifically binds to CD73 (e.g., human, mouse, or cynomolgus CD73), the antibody comprising a heavy chain constant region comprising the amino acid sequence of SEQ ID NO: 43, 44, 45, 46, 47, 48, 49, 50, 51, 52, 53, 54, 55, 56, 57, or 58. In certain embodiments, the instant disclosure provides an isolated antibody that specifically binds to CD73 (e.g., human, mouse, or cynomolgus CD73), the antibody comprising a light chain constant region comprising the amino acid sequence of SEQ ID NO: 89 or 93.

In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display four fold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild-type heavy chain constant region, wherein the variant heavy chain constant region binds to FcγRIIB with higher affinity than the wild-type heavy chain constant region binds to FcγRIIB In certain embodiments, the variant heavy chain constant region is a variant human heavy chain constant region, e.g., a variant human IgG1, a variant human IgG2, or a variant human IgG4 heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant domain Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A332L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant domain of an IgG$_1$ with an N297Q or N297A amino acid substitution, numbered according to the EU numbering system. In one embodiment, an antibody described herein comprises the constant domain of an IgG$_1$ with a mutation selected from the group consisting of D265A, P329A, and a combination thereof, numbered according to the EU numbering system. In another embodiment, an antibody described herein comprises the constant domain of an IgG$_1$ with a mutation selected from the group consisting of L234A, L235A, and a combination thereof, numbered according to the EU numbering system. In another embodiment, an antibody described herein comprises the constant domain of an IgG$_1$ with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG$_1$ heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG$_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises a modified constant domain of an IgG$_1$, wherein the modification increases the ability of the antibody to mediate antibody dependent cellular cytotoxicity (ADCC). In certain embodiments, 0.1, 1, or 10 µg/ml of the antibody is capable of inducing cell death of at least 20%, 25%, 30%, 35%, 40%, 45%, 50%, 55%, or 60% of CD73-expressing cells within 1, 2, or 3 hours, as assessed by methods described herein and/or known to a person of skill in the art. In certain embodiments, the modified constant domain of an IgG$_1$ comprises S239D and I332E substitutions, numbered according to the EU numbering system. In certain embodiments, the modified constant domain of an IgG$_1$ comprises S239D, A330L, and I332E substitutions, numbered according to the EU numbering system. In certain embodiments, the modified constant domain of an IgG$_1$ comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to CD73 (e.g., human, mouse, or cynomolgus CD73), the antibody comprising a heavy chain constant region comprising the amino acid sequence of SEQ ID NO: 26.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to CD73 (e.g., human, mouse, or cynomolgus CD73), the antibody comprising a heavy chain comprising an amino acid sequence selected from the group consisting of SEQ ID NOs: 63-88. In certain embodiments, the antibody comprises a heavy chain comprising the amino acid sequence set forth in SEQ ID NO: 63. In certain embodiments, the antibody comprises a heavy chain comprising the amino acid sequence set forth in SEQ ID NO: 64. In certain embodiments, the antibody comprises a heavy chain comprising the amino acid sequence set forth in SEQ ID NO: 65. In certain embodiments, the antibody comprises a heavy chain comprising the amino acid sequence set forth in SEQ ID NO: 66. In certain embodiments, the antibody comprises a heavy chain comprising the amino acid sequence set forth in SEQ ID NO: 67. In certain embodiments, the antibody comprises a heavy chain comprising the amino acid sequence set forth in SEQ ID NO: 68. In certain embodiments, the antibody comprises a heavy chain comprising the amino acid sequence set forth in SEQ ID NO: 69. In certain embodiments, the antibody comprises a heavy chain comprising the amino acid sequence set forth in SEQ ID NO: 70. In certain embodiments, the antibody comprises a heavy chain comprising the amino acid sequence set forth in SEQ ID NO: 71. In certain embodiments, the antibody comprises a heavy chain comprising the amino acid sequence set forth in SEQ ID NO: 72. In certain embodiments, the antibody comprises a heavy chain comprising the amino acid sequence set forth in SEQ ID NO: 73. In certain embodiments, the antibody comprises a heavy chain comprising the amino acid sequence set forth in SEQ ID NO: 74. In certain embodiments, the antibody comprises a heavy chain comprising the amino acid sequence set forth in SEQ ID NO: 75. In certain embodiments, the antibody comprises a heavy chain comprising the amino acid sequence set forth in SEQ ID NO: 76. In certain embodiments, the antibody comprises a heavy chain comprising the amino acid sequence set forth in SEQ ID NO: 77. In certain embodiments, the antibody comprises a heavy chain comprising the amino acid sequence set forth in SEQ ID NO: 78. In certain embodiments, the antibody comprises a heavy chain comprising the amino acid sequence set forth in SEQ ID NO: 79. In certain embodiments, the antibody comprises a heavy chain comprising the amino acid sequence set forth in SEQ ID NO: 80. In certain embodiments, the antibody comprises a heavy chain comprising the amino acid sequence set forth in SEQ ID NO: 81. In certain embodiments, the antibody comprises a heavy chain comprising the amino acid sequence set forth in SEQ ID NO: 82. In certain embodiments, the antibody comprises a heavy chain comprising the amino acid sequence set forth in SEQ ID NO: 83. In certain embodiments, the antibody comprises a heavy chain comprising the amino acid sequence set forth in SEQ ID NO: 84. In certain embodiments, the antibody comprises a heavy chain comprising the amino acid sequence set forth in SEQ ID NO: 85. In certain embodiments, the antibody comprises a heavy chain comprising the amino acid sequence set forth in SEQ ID NO: 86. In certain embodiments, the antibody comprises a heavy chain comprising the amino acid sequence set forth in SEQ ID NO: 87. In certain embodiments, the antibody comprises a heavy chain comprising the amino acid sequence set forth in SEQ ID NO: 88.

In certain embodiments, the instant disclosure provides an isolated antibody that specifically binds to CD73 (e.g., human, mouse, or cynomolgus CD73), the antibody comprising a light chain comprising an amino acid sequence selected from the group consisting of SEQ ID NOs: 92-98. In certain embodiments, the antibody comprises a light chain comprising the amino acid sequence set forth in SEQ ID NO: 92. In certain embodiments, the antibody comprises a light chain comprising the amino acid sequence set forth in SEQ ID NO: 93. In certain embodiments, the antibody comprises a light chain comprising the amino acid sequence set forth in SEQ ID NO: 94. In certain embodiments, the antibody comprises a light chain comprising the amino acid sequence set forth in SEQ ID NO: 95. In certain embodiments, the antibody comprises a light chain comprising the amino acid sequence set forth in SEQ ID NO: 96. In certain embodiments, the antibody comprises a light chain comprising the amino acid sequence set forth in SEQ ID NO: 97. In certain embodiments, the antibody comprises a light chain comprising the amino acid sequence set forth in SEQ ID NO: 98.

In certain embodiments, the instant disclosure provides an isolated antibody that specifically binds to CD73 (e.g., human, mouse, or cynomolgus CD73), the antibody comprising a heavy chain comprising an amino acid sequence selected from the group consisting of SEQ ID NOs: 63-88; and a light chain comprising an amino acid sequence selected from the group consisting of SEQ ID NOs: 92-98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 63; and a light chain comprising the amino acid sequence of SEQ ID NO: 92. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 64; and a light chain comprising the amino acid sequence of SEQ ID NO: 92. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 65; and a light chain comprising the amino acid sequence of SEQ ID NO: 94. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 66; and a light chain comprising the amino acid sequence of SEQ ID NO: 94. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 67; and a light chain comprising the amino acid sequence of SEQ ID NO: 95. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 68; and a light chain comprising the amino acid sequence of SEQ ID NO: 95. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 69; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 70; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 71; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 72; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 73; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 74; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 75; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 76; and a light chain comprising the amino acid sequence of SEQ ID NO: 96. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 77; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 78; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 79; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 80; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 77; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 78; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 79; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 80; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 81; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 82; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 83; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 84; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 85; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 86; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 87; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 88; and a light chain comprising the amino acid sequence of SEQ ID NO: 97. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 81; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 82; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 83; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 84; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 85; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 86; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 87; and a light chain comprising the amino acid sequence of SEQ ID NO: 98. In certain embodiments, the instant disclosure provides an isolated antibody that specifically binds to CD73 (e.g., human, mouse, or cynomolgus CD73), the antibody comprising a heavy chain comprising the amino acid sequence of SEQ ID NO: 88; and a light chain comprising the amino acid sequence of SEQ ID NO: 98.

Any antibody format can be used in the antibodies disclosed herein. In certain embodiments, the antibody is a single chain antibody or single-chain Fv (scFv). In certain embodiments, the antibody is a scFv fused with an Fc region (scFv-Fc). In certain embodiments, the antibody is a Fab fragment. In certain embodiments, the antibody is a F(ab')$_2$ fragment.

In certain embodiments, the antibody disclosed herein is a multispecific antibody (e.g., a bispecific antibody) which specifically binds to CD73 (e.g., human, mouse, or cynomolgus CD73) and a second antigen.

In certain embodiments, the antibody disclosed herein is conjugated to a second antibody that specifically binds to a second antigen. In certain embodiments, the antibody disclosed herein is covalently conjugated to a second antibody. In certain embodiments, the antibody disclosed herein is non-covalently conjugated to a second antibody. In certain embodiments, the antibody disclosed herein is cross-linked to a second antibody. In certain embodiments, the second antigen is a tumor-associated antigen (e.g., a polypeptide overexpressed in a tumor, a polypeptide derived from an oncovirus, a polypeptide comprising a post-translational modification specific to a tumor, a polypeptide specifically mutated in a tumor). In certain embodiments, the tumor-associated antigen is EGFR (e.g., human EGFR), optionally wherein the second antibody is cetuximab. In certain embodiments, the tumor-associated antigen is Her2 (e.g., human Her2), optionally wherein the second antibody is trastuzumab. In certain embodiments, the tumor-associated antigen is CD20 (e.g., human CD20).

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. In certain embodiments, the detectable label comprises a fluorescent moiety or a click chemistry handle.

In certain embodiments, the instant disclosure provides an isolated antibody that specifically binds to CD73 (e.g., human, mouse, or cynomolgus CD73) and functions as an antagonist (e.g., decreases or inhibits CD73 activity).

In certain embodiments, the instant disclosure provides an isolated antibody that specifically binds to CD73 (e.g., human, mouse, or cynomolgus CD73) and decreases or inhibits CD73 (e.g., human, mouse, or cynomolgus CD73) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to CD73 (e.g., human, mouse, or cynomolgus CD73) activity without any antibody or with an unrelated antibody (e.g., an antibody that does not specifically bind to CD73 (e.g., human, mouse, or cynomolgus CD73)). In certain embodiments, the instant disclosure provides an isolated antibody that specifically binds to CD73 (e.g., human, mouse, or cynomolgus CD73) and decreases or inhibits CD73 (e.g., human, mouse, or cynomolgus CD73) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to CD73 (e.g., human, mouse, or cynomolgus CD73) activity without any antibody or with an unrelated antibody (e.g., an antibody that does not specifically bind to CD73 (e.g., human CD73)). Non-limiting examples of CD73 (e.g., human, mouse, or cynomolgus CD73) activity can include CD73 (e.g., human, mouse, or cynomolgus CD73) signaling; CD73 (e.g., human, mouse, or cynomolgus CD73) binding to its binding partners and/or substrates (e.g., AMP or an analog or variant thereof); CD73 catalyzing the conversion of at least one of its substrates (e.g., AMP or an analog or variant thereof), facilitation of tumor growth and metastasis, and other known functions (e.g., see Gao et al. (2014) *BioMed Res. Int.* Article ID 460654). In specific embodiments, reduction in a CD73 (e.g., human, mouse, or cynomolgus CD73) activity is assessed as described in the Examples, infra.

In specific embodiments, the instant disclosure provides an isolated antibody that specifically binds to CD73 (e.g., human, mouse, or cynomolgus CD73) and decreases or inhibits CD73 (e.g., human, mouse, or cynomolgus CD73) enzymatic activity (e.g., catalyzing the conversion of AMP into adenosine) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to CD73 (e.g., human, mouse, or cynomolgus CD73) enzymatic activity without any antibody or with an unrelated antibody (e.g., an antibody that does not specifically bind to CD73 (e.g., human, mouse, or cynomolgus CD73)). In specific embodiments, the instant disclosure provides an isolated antibody that specifically binds to CD73 (e.g., human, mouse, cynomolgus CD73) and decreases or inhibits CD73 (e.g., human, mouse, cynomolgus CD73) enzymatic activity (e.g., catalyzing the conversion of AMP into adenosine) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to CD73 (e.g., human CD73) enzymatic activity without any antibody or with an unrelated antibody (e.g., an antibody that does not specifically bind to CD73 (e.g., human, mouse, or cynomolgus CD73)).

In specific embodiments, the instant disclosure provides an isolated antibody that specifically binds to CD73 (e.g., human, mouse, or cynomolgus CD73) and reduces cancer progression (e.g., proliferation and/or metastasis of cells in the microenvironment of a cancer type disclosed herein) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to the cancer progression without any antibody or with an unrelated antibody (e.g., an antibody that does not specifically bind to CD73 (e.g., human, mouse, or cynomolgus CD73)). In specific embodiments, the instant disclosure provides an isolated antibody that specifically binds to CD73 (e.g., human, mouse, or cynomolgus CD73) and reduces cancer progression (e.g., proliferation and/or metastasis of cells in the microenvironment of a cancer type disclosed herein) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein (see the Examples, infra) or known to one of skill in the art, relative to the cancer progression without any antibody or with an unrelated antibody (e.g., an antibody that does not specifically bind to CD73 (e.g., human, mouse, or cynomolgus CD73)).

5.3 Anti-CD73 Antibodies Comprising Ligand Binding Moieties

In one aspect, the instant disclosure provides antibodies that specifically bind to CD73 (e.g., human CD73, cynomolgus CD73, or mouse CD73) and comprise a ligand binding moiety (e.g., a TGFβ-binding moiety or a VEGF-binding moiety).

Anti-CD73 antibodies comprising a ligand binding moiety can comprise an immunoglobulin chain of any anti-CD73 antibody. Exemplary anti-CD73 antibodies are disclosed in Section 5.2 of the instant specification. Additional exemplary anti-CD73 antibodies are disclosed in WO2016055609A1, WO2016075099A1, WO2016081748A2, WO2016131950A1, WO2017064043A1, WO2017100670A1, WO2017118613A1, WO2017152085A1, and U.S. Pat. No. 9,388,249B2, each of which is incorporated herein by reference in its entirety. In certain embodiments, the anti-CD73 antibody comprises a VH and a VL of an anti-CD73 antibody as disclosed in Section 5.2. In certain embodiments, the anti-CD73 antibody comprises a heavy chain and a light chain of an anti-CD73 antibody as disclosed in Section 5.2.

A ligand binding moiety can be linked to any portion of an immunoglobulin chain of an anti-CD73 antibody, including the N- or C-terminal amino acid residue. The ligand binding moiety can be linked (covalently or non-covalently) to the immunoglobulin chain directly or via a linker (e.g., a peptide linker). Covalent linkage can be a chemical linkage or a genetic linkage (i.e., to form a fusion protein). In certain embodiments, the ligand binding moiety is linked (e.g., covalently) to the C-terminal amino acid residue of the immunoglobulin chain. In certain embodiments, the ligand binding moiety is linked to the C-terminal amino acid residue of an immunoglobulin chain without a linker (e.g., via a peptide bond). In certain embodiments, the ligand binding moiety is linked (e.g., covalently) to the C-terminal amino acid residue of the immunoglobulin chain via a linker. In certain embodiments, the linker is a peptide linker. In certain embodiments, the peptide linker has the general formula $(G_4S)_n$, where n is an integer. In certain embodiments, the peptide linker comprises an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker consists of an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker is linked to the immunoglobulin chain via a peptide bond.

In certain embodiments, the ligand binding moiety is linked (e.g., covalently) to a VH of the anti-CD73 antibody. The ligand binding moiety can be linked (e.g., covalently) to any portion of the VH, including the N- or C-terminal amino acid residue. In certain embodiments, the ligand binding moiety is linked (e.g., covalently) to the C-terminal amino acid residue of the VH. In certain embodiments, the ligand binding moiety is linked to the C-terminal amino acid residue of the VH without a linker (e.g., via a peptide bond). In certain embodiments, the ligand binding moiety is linked (e.g., covalently) to the C-terminal amino acid residue of the VH via linker. In certain embodiments, the linker is a peptide linker. In certain embodiments, the peptide linker comprises an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker consists of an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker is linked to the VH via a peptide bond.

In certain embodiments, the ligand binding moiety is linked (e.g., covalently) to a VL of the anti-CD73 antibody. The ligand binding moiety can be linked (e.g., covalently) to any portion of the VL, including the N- or C-terminal amino acid residue. In certain embodiments, the ligand binding moiety is linked (e.g., covalently) to the C-terminal amino acid residue of the VL. In certain embodiments, the ligand binding moiety is linked to the C-terminal amino acid residue of the VL without a linker (e.g., via a peptide bond). In certain embodiments, the ligand binding moiety is linked (e.g., covalently) to the C-terminal amino acid residue of the VL via linker. In certain embodiments, the linker is a peptide linker. In certain embodiments, the peptide linker comprises an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker consists of an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker is linked to the VL via a peptide bond.

In certain embodiments, the ligand binding moiety is linked (e.g., covalently) to a heavy chain constant region of the anti-CD73 antibody. The ligand binding moiety can be linked (e.g., covalently) to any portion of the heavy chain constant region. In certain embodiments, the ligand binding moiety is linked (e.g., covalently) to the C-terminal amino acid residue of the heavy chain constant region. In certain embodiments, the ligand binding moiety is linked to the C-terminal amino acid residue of the heavy chain constant region without a linker (e.g., via a peptide bond). In certain embodiments, the ligand binding moiety is linked (e.g., covalently) to the C-terminal amino acid residue of the heavy chain constant region via linker. In certain embodiments, the linker is a peptide linker. In certain embodiments, the peptide linker comprises an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker consists of an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker is linked to the heavy chain constant region via a peptide bond.

In certain embodiments, the ligand binding moiety is linked (e.g., covalently) to a light chain constant region of the anti-CD73 antibody. The ligand binding moiety can be linked (e.g., covalently) to any portion of the light chain constant region. In certain embodiments, the ligand binding moiety is linked (e.g., covalently) to the C-terminal amino acid residue of the light chain constant region. In certain embodiments, the ligand binding moiety is linked to the C-terminal amino acid residue of the light chain constant region without a linker (e.g., via a peptide bond). In certain embodiments, the ligand binding moiety is linked (e.g., covalently) to the C-terminal amino acid residue of the light chain constant region via linker. In certain embodiments, the linker is a peptide linker. In certain embodiments, the peptide linker comprises an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker consists of an amino acid sequence with at least 60%, 65%, 70%, 75%, 80%, 85%, 90%, 91%, 92%, 93%, 94%, 95%, 96%, 97%, 98%, or 99% identity to SEQ ID NO: 103, 104, 105, 106, 107, or 108. In certain embodiments, the peptide linker is linked to the light chain constant region via a peptide bond.

The ligand binding moiety can be any moiety that has the ability to specifically bind to a target molecule or complex. In certain embodiments, the ligand binding moiety comprises a peptide or polypeptide. In certain embodiments, the peptide or polypeptide is linked to the immunoglobulin chain of the anti-CD73 antibody through a peptide bond. In certain embodiments, the peptide or polypeptide is linked to the immunoglobulin chain of the anti-CD73 antibody via a peptide linker, wherein peptide or polypeptide is linked to the peptide linker through a peptide bond. In certain embodiments, the N-terminal amino acid residue of the peptide or polypeptide is linked to the C-terminal amino acid residue of the immunoglobulin chain or the peptide linker through a peptide bond.

In certain embodiments, the anti-CD73 antibody comprises a polypeptide comprising (a) an immunoglobulin chain, (b) a ligand binding moiety, and optionally (c) a peptide linker as disclosed herein. In certain embodiments, the anti-CD73 antibody comprises a polypeptide comprising from N-terminus to C-terminus the immunoglobulin chain and the binding moiety. In certain embodiments, the anti-CD73 antibody comprises a polypeptide comprising from N-terminus to C-terminus: the immunoglobulin chain, the peptide linker, and the binding moiety. In certain embodiments, the anti-CD73 antibody consists of a polypeptide comprising (a) an immunoglobulin chain, (b) the ligand binding moiety, and optionally (c) a peptide linker as disclosed herein. In certain embodiments, the anti-CD73 antibody consists of a polypeptide comprising from N-terminus to C-terminus the immunoglobulin chain and the binding moiety. In certain embodiments, the anti-CD73 antibody consists of a polypeptide comprising from N-terminus to C-terminus: the immunoglobulin chain, the peptide linker, and the binding moiety. In certain embodiments, the immunoglobulin chain is a full-length heavy chain. In certain embodiments, the immunoglobulin chain comprising is a full-length light chain.

In certain embodiments, the anti-CD73 antibody comprises a binding moiety capable of antagonizing and/or inhibiting TGFβ signaling pathway. In certain embodiments, the anti-CD73 antibody comprises a binding moiety capable of antagonizing and/or inhibiting TGFβ. In certain embodiments, the anti-CD73 antibody comprises a TGFβ-binding moiety. The TGFβ-binding moiety can be any moiety that specifically binds to one or more family members or isoforms of TGFβ. In certain embodiments, the TGFβ-binding moiety specifically binds to TGFβ1 (e.g., human TGFβ1). In certain embodiments, the TGFβ-binding moiety specifically binds to TGFβ2 (e.g., human TGFβ2). In certain embodiments, the TGFβ-binding moiety specifically binds to TGFβ3 (e.g., human TGFβ3). In certain embodiments, the TGFβ-binding moiety specifically binds to at least two of TGFβ1 (e.g., human TGFβ1), TGFβ2 (e.g., human TGFβ2), and TGFβ3 (e.g., human TGFβ3). In certain embodiments, the TGFβ-binding moiety specifically binds to TGFβ1 (e.g., human TGFβ1) and TGFβ3 (e.g., human TGFβ3). In certain embodiments, the TGFβ-binding moiety specifically binds to TGFβ1 (e.g., human TGFβ1), TGFβ2 (e.g., human TGFβ2), and TGFβ3 (e.g., human TGFβ3). The skilled worker will appreciate that a TGFβ-binding moiety that specifically binds to one family member or isoform of TGFβ may bind to one or more other family members or isoforms of TGFβ with similar or higher affinity. Exemplary TGFβ-binding moieties are disclosed in De Crescenzo et al. (2008) Transforming Growth Factor-β in Cancer Therapy, Volume II, Cancer Drug Discovery and Development, Humana Press; Zwaagstra et al. (2012) Mol Cancer Ther. 11(7):1477-87; Ravi et al. (2018) Nat. Commun. 9:741; EP0975771B1, U.S. Pat. Nos. 7,786,261B2, 8,993,524B2, and US20150225483A1, each of which is incorporated herein by reference in its entirety.

In certain embodiments, the TGFβ-binding moiety comprises a domain of a protein that binds to TGFβ1 (e.g., human TGFβ1), TGFβ2 (e.g., human TGFβ2), and/or TGFβ3 (e.g., human TGFβ3), or a variant thereof that has similar or improved TGFβ binding affinity. In certain embodiments, the domain is an extracellular domain of a TGFβ receptor (e.g., a human TGFβ receptor). In certain embodiments, the domain is a TGFβ-binding domain of a TGFβ receptor (e.g., a human TGFβ receptor). In certain embodiments, the TGFβ receptor is selected from the group consisting of TGFβR1 (e.g., human TGFβR1), TGFβR2 (e.g., human TGFβR2), and TGFβR3 (e.g., human TGFβR3). In certain embodiments, the TGFβ-binding moiety comprises an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 109, 110, 111, or 112. In certain embodiments, the TGFβ-binding moiety comprises the amino acid sequence set forth in SEQ ID NO: 109, 110, 111, or 112. In certain embodiments, the TGFβ-binding moiety consists of an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 109, 110, 111, or 112. In certain embodiments, the TGFβ-binding moiety consists of the amino acid sequence set forth in SEQ ID NO: 109, 110, 111, or 112.

In certain embodiments, the anti-CD73 antibody comprises a polypeptide comprising an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 113, 114, 115, 116, 117, 118, 119, 120, or 121. In certain embodiments, the anti-CD73 antibody comprises a polypeptide comprising the amino acid sequence set forth in SEQ ID NO: 113, 114, 115, 116, 117, 118, 119, 120, or 121. In certain embodiments, the anti-CD73 antibody comprises a polypeptide consisting of an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 113, 114, 115, 116, 117, 118, 119, 120, or 121. In certain embodiments, the anti-CD73 antibody comprises a polypeptide consisting of the amino acid sequence set forth in SEQ ID NO: 113, 114, 115, 116, 117, 118, 119, 120, or 121.

In certain embodiments, the anti-CD73 antibody comprising a TGFβ-binding moiety further comprises a polypeptide comprising an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 97, 92, or 128. In certain embodiments, the anti-CD73 antibody comprising a TGFβ-binding moiety further comprises a polypeptide comprising an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 97. In certain embodiments, the anti-CD73 antibody comprising a TGFβ-binding moiety further comprises a polypeptide comprising the amino acid sequence set forth in SEQ ID NO: 97. In certain embodiments, the anti-CD73 antibody comprising a TGFβ-binding moiety further comprises a polypeptide consisting of an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 97. In certain embodiments, the anti-CD73 antibody comprising a TGFβ-binding moiety further comprises a polypeptide consisting of the amino acid sequence set forth in SEQ ID NO: 97.

In certain embodiments, the anti-CD73 antibody comprises a first polypeptide and a second polypeptide, wherein the first and second polypeptides comprise the amino acid sequences set forth in SEQ ID NOs: 113 and 92, 114 and 97, 115 and 97, 116 and 97, 117 and 97, 118 and 97, 119 and 97, 120 and 97, or 121 and 97, respectively. In certain embodiments, the first and second polypeptides consist of the amino acid sequences set forth in SEQ ID NOs: 113 and 92, 114 and 97, 115 and 97, 116 and 97, 117 and 97, 118 and 97, 119 and 97, 120 and 97, or 121 and 97, respectively. In certain embodiments, the anti-CD73 antibody comprises two polypeptides each comprising the amino acid sequence of the first polypeptide, and two polypeptides each comprising the amino acid sequence of the second polypeptide. In certain embodiments, the anti-CD73 antibody comprises two copies of the first polypeptide and two copies of the second polypeptide. In certain embodiments, the anti-CD73 antibody consists of two copies of the first polypeptide and two copies of the second polypeptide.

In certain embodiments, the TGFβ-binding moiety comprises an antibody that specifically binds to TGFβ1 (e.g., human TGFβ1), TGFβ2 (e.g., human TGFβ2), and/or TGFβ3 (e.g., human TGFβ3), or an antigen-binding fragment thereof. Exemplary anti-TGFβ antibodies include fresolumimab and metelimumab, and are described in U.S. Pat. No. 6,492,497B1, U.S. Pat. No. 7,151,169B2, U.S. Pat. No. 7,723,486B2, which are incorporated herein by reference in their entirety.

In certain embodiments, the anti-CD73 antibody comprises a binding moiety capable of antagonizing and/or inhibiting a VEGF signaling pathway. In certain embodiments, the anti-CD73 antibody comprises a binding moiety capable of antagonizing and/or inhibiting VEGF. In certain embodiments, the anti-CD73 antibody comprises a VEGF-binding moiety. The VEGF-binding moiety can be any moiety that specifically binds to one or more family members or isoforms of VEGF. In certain embodiments, the VEGF-binding moiety specifically binds to VEGF-A (e.g., human VEGF-A). In certain embodiments, the VEGF-binding moiety specifically binds to VEGF-B (e.g., human VEGF-B). In certain embodiments, the VEGF-binding moiety specifically binds to VEGF-C (e.g., human VEGF-C). In certain embodiments, the VEGF-binding moiety specifically binds to VEGF-D (e.g., human VEGF-D). In certain embodiments, the VEGF-binding moiety specifically binds to at least two of VEGF-A (e.g., human VEGF-A), VEGF-B (e.g., human VEGF-B), VEGF-C (e.g., human VEGF-C), and VEGF-D (e.g., human VEGF-D). In certain embodiments, the VEGF-binding moiety specifically binds to VEGF-A (e.g., human VEGF-A) and VEGF-B (e.g., human VEGF-B). In certain embodiments, the VEGF-binding moiety specifically binds to VEGF-C (e.g., human VEGF-C) and VEGF-D (e.g., human VEGF-D). In certain embodiments, the VEGF-binding moiety specifically binds to at least three of VEGF-A (e.g., human VEGF-A), VEGF-B (e.g., human VEGF-B), VEGF-C (e.g., human VEGF-C), and VEGF-D (e.g., human VEGF-D). In certain embodiments, the VEGF-binding moiety specifically binds to VEGF-A (e.g., human VEGF-A), VEGF-B (e.g., human VEGF-B), VEGF-C (e.g., human VEGF-C), and VEGF-D (e.g., human VEGF-D). The skilled worker will appreciate that a VEGF-binding moiety that specifically binds to one family member or isoform of VEGF may bind to one or more other family members or isoforms of VEGF with similar or higher affinity. Exemplary VEGF-binding moieties include aflibercept and are disclosed in Holash et al. (2002) PNAS 99 (17): 11393-98; U.S. Pat. No. 7,306,799B2, U.S. Pat. No. 7,608,261B2; and U.S. Pat. No. 7,531,173B2, each of which is incorporated herein by reference in its entirety.

In certain embodiments, the VEGF-binding moiety comprises a domain of a protein that binds to VEGF-A (e.g., human VEGF-A), VEGF-B (e.g., human VEGF-B), VEGF-C (e.g., human VEGF-C), and/or VEGF-D (e.g., human VEGF-D), or a variant thereof that has similar or improved VEGF binding affinity. In certain embodiments, the domain is an extracellular domain of a VEGF receptor (e.g., a human VEGF receptor). In certain embodiments, the domain is a VEGF-binding domain of a VEGF receptor (e.g., a human VEGF receptor). In certain embodiments, the VEGF-binding domain comprises one, two, three, four, five, six, or seven of the immunoglobulin-like domains of a VEGF receptor (e.g., a human VEGF receptor). In certain embodiments, the VEGF-binding domain comprises one or more, two or more, three or more, four or more, five or more, or six or more of the immunoglobulin-like domains of a VEGF receptor (e.g., a human VEGF receptor). In certain embodiments, the VEGF-binding domain comprises at most two, three, four, five, or six of the immunoglobulin-like domains of a VEGF receptor (e.g., a human VEGF receptor). In certain embodiments, the VEGF receptor is selected from the group consisting of VEGFR1 (e.g., human VEGFR1), VEGFR2 (e.g., human VEGFR2), and VEGFR3 (e.g., human VEGFR3). In certain embodiments, the VEGF-binding moiety comprises an extracellular domain of VEGFR1 (e.g., human VEGFR1). In certain embodiments, the VEGF-binding moiety comprises an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 122. In certain embodiments, the VEGF-binding moiety comprises an amino acid sequence set forth in SEQ ID NO: 122. In certain embodiments, the VEGF-binding moiety consists of an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 122. In certain embodiments, the VEGF-binding moiety consists of an amino acid sequence set forth in SEQ ID NO: 122. In certain embodiments, the VEGF-binding moiety comprises an extracellular domain of VEGFR2 (e.g., human VEGFR2). In certain embodiments, the VEGF-binding moiety comprises an extracellular domain of VEGFR3 (e.g., human VEGFR3).

In certain embodiments, the anti-CD73 antibody comprises a polypeptide comprising an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 123, 124, 125, 126, or 127. In certain embodiments, the anti-CD73 antibody comprises a polypeptide comprising the amino acid sequence set forth in SEQ ID NO: 123, 124, 125, 126, or 127. In certain embodiments, the anti-CD73 antibody comprises a polypeptide consisting of an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 123, 124, 125, 126, or 127. In certain embodiments, the anti-CD73 antibody comprises a polypeptide consisting of the amino acid sequence set forth in SEQ ID NO: 123, 124, 125, 126, or 127.

In certain embodiments, the anti-CD73 antibody comprising a VEGF-binding moiety further comprises a polypeptide comprising an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 97, 92, or 128. In certain embodiments, the anti-CD73 antibody comprising a VEGF-binding moiety further comprises a polypeptide comprising an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 97. In certain embodiments, the anti-CD73 antibody comprising a VEGF-binding moiety further comprises a polypeptide comprising the amino acid sequence set forth in SEQ ID NO: 97. In certain embodiments, the anti-CD73 antibody comprising a VEGF-binding moiety further comprises a polypeptide consisting of an amino acid sequence at least 60%, 65%, 70%, 75%, 80%, 85%, 90%, 91%, 92%, 93%, 94%, 95%, 96%, 97%, 98%, or 99% identical to the sequence set forth in SEQ ID NO: 97. In certain embodiments, the anti-CD73 antibody comprising a VEGF-binding moiety further comprises a polypeptide consisting of the amino acid sequence set forth in SEQ ID NO: 97.

In certain embodiments, the anti-CD73 antibody comprises a first polypeptide and a second polypeptide, wherein the first and second polypeptides comprise the amino acid sequences set forth in SEQ ID NOs: 123 and 92, 124 and 128, 125 and 128, 126 and 97, or 127 and 97, respectively. In certain embodiments, the first and second polypeptides consist of the amino acid sequences set forth in SEQ ID NOs: 123 and 92, 124 and 128, 125 and 128, 126 and 97, or 127 and 97, respectively. In certain embodiments, the anti-CD73 antibody comprises two polypeptides each comprising the amino acid sequence of the first polypeptide, and two polypeptides comprising the amino acid sequence of the second polypeptide. In certain embodiments, the anti-CD73 antibody comprises two copies of the first polypeptide and two copies of the second polypeptide. In certain embodiments, the anti-CD73 antibody consists of two copies of the first polypeptide and two copies of the second polypeptide. In certain embodiments, the VEGF-binding moiety comprises an antibody that specifically binds to VEGF-A (e.g., human VEGF-A), VEGF-B (e.g., human VEGF-B), VEGF-C (e.g., human VEGF-C), and/or VEGF-D (e.g., human VEGF-D), or an antigen-binding fragment thereof. Exemplary anti-VEGF antibodies include bevacizumab and ranibizumab, and are described in WO1998045331A2 and WO1998045332A2, which are incorporated herein by reference in their entirety.

5.4 Pharmaceutical Compositions

Provided herein are compositions comprising an anti-CD73 (e.g., human, mouse, or cynomolgus CD73) antibody disclosed herein having the desired degree of purity in a physiologically acceptable carrier, excipient or stabilizer (see, e.g., Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-CD73 (e.g., human. Mouse, or cynomolgus CD73) antibody disclosed herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in decreasing or inhibiting CD73 (e.g., human, mouse, or cynomolgus CD73) activity and treating a condition, such as cancer or an infectious disease. In one embodiment, the present invention relates to a pharmaceutical composition of the present invention comprising an anti-CD73 antibody of the present invention for use as a medicament. In another embodiment, the present invention relates to a pharmaceutical composition of the present invention for use in a method for the treatment of cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising antibody proteins are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-CD73 (e.g., human, mouse, or cynomolgus CD73) antibody disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-CD73 (e.g., human, mouse, or cynomolgus CD73) antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-CD73 (e.g., human, mouse, or cynomolgus CD73) antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

5.5 Methods of Use and Uses

In another aspect, the instant disclosure provides a method of treating a subject using the anti-CD73 (e.g., human, mouse, or cynomolgus CD73) antibodies disclosed herein. Any disease or disorder in a subject that would benefit from decrease of CD73 (e.g., human, mouse, or cynomolgus CD73) function and/or signaling related to TGFβ, VEGF, and/or adenosine can be treated using the anti-CD73 (e.g., human, mouse or cynomolgus CD73) antibodies disclosed herein. In certain embodiments, the disease or disorder is resistant to an immunotherapy, such as a checkpoint targeting agent (e.g., an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD137 antibody, or an agonist anti-OX40 antibody), a TCR T cell therapy, or a chimeric antigen receptor (CAR) T cell therapy (e.g., a CD19 CAR T cell therapy). In certain embodiments, the disease or disorder is recurrent after treatment with an immunotherapy, such as a checkpoint targeting agent (e.g., an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD137 antibody, or an agonist anti-OX40 antibody), a TCR T cell therapy, or a CAR T cell therapy. In certain embodiments, the disease or disorder is resistant to a chemotherapy (e.g., a platinum-based therapy (e.g., cisplatin, carboplatin, or oxaliplatin), a tyrosine kinase (e.g., VEGFR, Raf) inhibitor (e.g., sorafenib), a DNA damage-inducing agent (e.g., gemcitabine), a hypomethylating agent (e.g., azacitidine), and/or a combination of multiple chemotherapies (e.g., a platinum doublet or a FOLFOX regimen (e.g., FOLFIRINOX or mFOLFOX6))). In certain embodiments, the disease or disorder is recurrent after treatment with a chemotherapy (e.g., a platinum-based therapy (e.g., cisplatin, carboplatin, or oxaliplatin), a tyrosine kinase (e.g., VEGFR, Raf) inhibitor (e.g., sorafenib), a DNA damage-inducing agent (e.g., gemcitabine), a hypomethylating agent (e.g., azacitidine), and/or a combination of multiple chemotherapies (e.g., a platinum doublet or a FOLFOX regimen (e.g., FOLFIRINOX or mFOLFOX6))). In certain embodiments, the disease or disorder is resistant to an anti-angiogenic therapy (e.g., bevacizumab). In certain embodiments, the disease or disorder is recurrent after treatment with an anti-angiogenic therapy (e.g., bevacizumab). In certain embodiments, the solid tumor is a measurable disease.

The anti-CD73 (e.g., human CD73) antibodies disclosed herein are particularly useful for inhibiting immune system tolerance to tumors, and accordingly can be used as an immunotherapy for subjects with cancer. For example, in certain embodiments, the instant disclosure provides a method of treating cancer in a subject, the method comprising administering to the subject an effective amount of the antibody, polynucleotide, vector, lipid nanoparticle, or pharmaceutical composition, as disclosed herein.

Cancers that can be treated with the anti-CD73 (e.g., human, mouse, or cynomolgus CD73) antibodies, or pharmaceutical compositions disclosed herein include, without limitation, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas, fibroblastic sarcoma, and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer. In certain embodiments, the cancer is resistant to an immunotherapy, such as a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the cancer is recurrent after treatment with an immunotherapy, such as a checkpoint targeting agent (e.g., an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD137 antibody, or an agonist anti-OX40 antibody).

In one embodiment, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer (e.g., castration-resistant prostate cancer), a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), glioblastoma (GBM), meningioma, endometrial cancer, gastric or stomach cancer, adrenal cancer, anal cancer, gastroesophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In a specific embodiment, the cancer is a cervical cancer.

In one embodiment, the cancer is a hematological cancer, for example, a leukemia, a lymphoma, or a myeloma. In one embodiment, the cancer is a leukemia, for example, acute lymphoblastic leukemia (ALL) (e.g., non-B cell ALL), acute myelogenous leukemia (AML), chronic lymphocytic leukemia (CLL), chronic myelogenous leukemia (CML), chronic myelomonocytic leukemia (CMML), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, extranodal marginal zone lymphoma, or minimal residual disease. In one embodiment the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In one embodiment, the cancer is a lung cancer, e.g., a lung adenocarcinoma, non-small cell lung cancer, or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-CD73 (e.g., human, mouse, or cynomolgus CD73) antibody or pharmaceutical composition disclosed herein, is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an anti-CD73 (e.g., human, mouse, or cynomolgus CD73) antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-CD73 (e.g., human, mouse, or cynomolgus CD73) antibody described herein or a composition thereof is the only active agent administered to a subject. In certain embodiments, an anti-CD73 (e.g., human, mouse, or cynomolgus CD73) antibody described herein or a composition thereof is used in combination with anti-infective interventions (e.g., antivirals, antibacterials, antifungals, or anti-helminthics) for the treatment of infectious diseases. Therefore, in a one embodiment, the present invention relates to an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by anti-CD73 (e.g., human, mouse, or cynomolgus CD73) antibodies or pharmaceutical compositions disclosed herein are caused by infectious agents including but not limited to bacteria, parasites, fungi, protozoa, and viruses. In a specific embodiment, the infectious disease treated and/or prevented by anti-CD73 (e.g., human, mouse, or cynomolgus CD73) antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, Mycobacteria *rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertissus, cholera, plague, diptheria, *chlamydia, S. aureus* and *legionella*.

Protozoal diseases or protozoal infections caused by protozoa that can be prevented and/or treated in accordance with the methods described herein include, but are not limited to, *leishmania, coccidiosis, trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, the anti-CD73 (e.g., human, mouse, or cynomolgus CD73) antibodies or pharmaceutical compositions disclosed herein are administered to the subject as a monotherapy.

In certain embodiments, these methods further comprise administering an additional therapeutic agent to the subject. In certain embodiments, the additional therapeutic agent comprises a chemotherapeutic agent. In certain embodiments, the chemotherapeutic agent comprises a hypomethylating agent (e.g., azacitidine). In certain embodiments, the chemotherapeutic agent comprises a DNA damage-inducing agent (e.g., gemcitabine). In certain embodiments, the chemotherapeutic agent comprises a platinum-based therapy (e.g., cisplatin, carboplatin, or oxaliplatin). In certain embodiments, the chemotherapeutic agent comprises a tyrosine kinase (e.g., VEGFR, Raf) inhibitor (e.g., sorafenib). In certain embodiments, the chemotherapeutic agent comprises a combination of multiple chemotherapies (e.g., a platinum doublet or a FOLFOX regimen (e.g., FOLFIRINOX or mFOLFOX6)). In certain embodiments, the additional therapeutic agent comprises an anti-angiogenic therapy (e.g., bevacizumab). In certain embodiments, the additional therapeutic agent comprises an antibody-drug conjugate. In certain embodiments, the additional therapeutic agent comprises a radiotherapeutic agent. In certain embodiments, the additional therapeutic agent is capable of causing immunogenic cell death (e.g., tumor cell death).

In certain embodiments, the additional therapeutic agent comprises a checkpoint targeting agent. In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-TIGIT antibody, an antagonist anti-VISTA antibody, an antagonist anti-CD96 antibody, an antagonist anti-CEACAM1 antibody, an agonist anti-CD137 antibody, an agonist anti-GITR antibody, and an agonist anti-OX40 antibody. In certain embodiments, the checkpoint targeting agent is selected from the group consisting of an antagonist anti-CTLA-4 antibody, an antagonist anti-PD-L1 antibody, an antagonist anti-PD-L2 antibody, and an antagonist anti-PD-1 antibody, wherein the anti-CD73 (e.g., human, mouse, or cynomolgus CD73) antibodies or pharmaceutical compositions disclosed herein synergize with the checkpoint targeting agent.

In one embodiment, the present invention relates to an antibody and/or pharmaceutical composition of the present invention for use in a method of the present invention, wherein the method further comprises administering an additional therapeutic agent to the subject. In one embodiment, the present invention relates to (a) an antibody and/or pharmaceutical composition of the present invention and (b) an additional therapeutic agent for use as a medicament. In one embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one embodiment, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb.

In certain embodiments, an anti-CD73 (e.g., human, mouse, or cynomolgus CD73) antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in one embodiment, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an anti-CD73 (e.g., human CD73) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, an anti-CD73 (e.g., human, mouse, or cynomolgus CD73) antibody disclosed herein is administered to a subject in combination with a vaccine. The vaccine can be, e.g., a peptide vaccine, a DNA vaccine, or an RNA vaccine. In certain embodiments, the vaccine is a heat shock protein-based tumor vaccine or a heat shock protein-based pathogen vaccine. In a specific embodiment, an anti-CD73 (e.g., human, mouse, or cynomolgus CD73) antibody disclosed herein is administered to a subject in combination with a heat shock protein-based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in one embodiment, the present invention relates to (a) an antibody and/or pharmaceutical composition of the present invention and (b) a vaccine for use as a medicament, for example for use in a method for the treatment of cancer. In one embodiment, the present invention relates to a pharmaceutical composition, kit or kit-of-parts comprising (a) an antibody and/or pharmaceutical composition of the present invention and (b) a vaccine. In one embodiment, the vaccine is a heat shock protein-based tumor vaccine. In one embodiment, the vaccine is a heat shock protein-based pathogen vaccine. In certain embodiments, the vaccine is as described in WO 2016/183486, incorporated herein by reference in its entirety.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-CD73 (e.g., human, mouse, or cynomolgus CD73) antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in one embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In certain embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436, 404, 6,447,780, 6,447,781 and 6,610,659. Examples of HSPPCs include without limitation Prophage™, AutoSynVax™, and PhosphoSynVax™.

In certain embodiments, an anti-CD73 (e.g., human, mouse, or cynomolgus CD73) antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly (U). Combinations of the above adjuvants may also be used. See, e.g., U.S. Pat. Nos. 6,645,495; 7,029,678; and 7,858, 589, all of which are incorporated herein by reference in their entireties. In one embodiment, the adjuvant used herein is QS-21 STIMULON.

In certain embodiments, an anti-CD73 (e.g., human, mouse, or cynomolgus CD73) antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in one embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-CD73 (e.g., human, mouse, or cynomolgus CD73) antibody disclosed herein is administered to a subject in combination with a cell expressing a chimeric antigen receptor (CAR). In certain embodiments, the cell is a T cell. Exemplary CAR T-cell therapies are provided in Pettitt et al. (2017) Molecular Therapy 26(2):342-53, which is incorporated by reference herein in its entirety. In certain embodiments, the CAR T cell therapy comprises a CD19 CAR T cell therapy (e.g., YESCARTA™ and KYMRIAH™). In certain embodiments, the subject has a $CD19^+$ cancer (e.g., a $CD19^+$ hematologic malignancy). In certain embodiments, such $CD19^+$ cancer is resistant to the CAR T cell therapy alone. In certain embodiments, subjects having a tumor or clinical indication in which the response rate to a CAR T cell therapy is no more than 90%, 80%, 70%, 60%, 50%, 40%, 30%, 20%, 10%, or less, are selected for treatment with the antibody and/or pharmaceutical composition disclosed herein, alone or in combination with the CAR T cell therapy. In certain embodiments, a subject having a diffuse large B-cell lymphoma not otherwise specified (DLBCL-nos), primary mediastinal large B cell lymphoma, high grade B cell lymphoma, or DLBCL arising from follicular lymphoma is selected for treatment with the antibody and/or pharmaceutical composition disclosed herein, alone or in combination with a CD19 CAR T cell therapy (e.g., YESCARTA™). In certain embodiments, a subject having B cell precursor ALL is selected for treatment with the antibody and/or pharmaceutical composition disclosed herein, alone or in combination with a CD19 CAR T cell therapy (e.g., KYMRIAH™). In certain embodiments, the subject has had an inadequate response despite exhibiting adequate expansion of infused CAR T cell therapy.

In specific embodiments, the $CD19^+$ cancer is a $CD19^+$ hematologic malignancy. In certain embodiments, the $CD19^+$ hematologic malignancy is a non-B-cell precursor ALL (e.g., diffuse large B-cell lymphoma or mantle cell lymphoma). In certain embodiments, the $CD19^+$ cancer is resistant to or recurrent after treatment with a prior treatment (e.g., a monoclonal anti-CD20 antibody therapy or an anthracycline containing chemotherapy regimen). In certain embodiments, the subject has an inadequate response to at least one infusion of a CD19 CAR T cell therapy (e.g., YESCARTA™ or KYIVIRIAH™). In certain embodiments, the subject has a measurable disease.

In certain embodiments, an anti-CD73 (e.g., human, mouse, or cynomolgus CD73) antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an anti-CD73 (e.g., human, mouse, or cynomolgus CD73) antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), optionally wherein the BiTE and/or DART comprises the VH and VL sequences of cetuximab. In certain embodiments, the tumor-associated antigen is Her2 (e.g., human Her2), optionally wherein the BiTE and/or DART comprises the VH and VL sequences of trastuzumab. In certain embodiments, the tumor-associated antigen is CD20 (e.g., human CD20).

The anti-CD73 (e.g., human, mouse, or cynomolgus CD73) antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-CD73 (e.g., human, mouse, or cynomolgus CD73) antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-CD73 (e.g., human. mouse, or cynomolgus CD73) antibody described herein can also be used to assay CD73 (e.g., human, mouse, or cynomolgus CD73) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}I$, $^{121}I$) carbon ($^{14}C$), sulfur ($^{35}S$), tritium ($^3H$), indium ($^{121}In$), and technetium ($^{99}Tc$); luminescent labels, such as luminol; and fluorescent labels, such as fluorescein and rhodamine, and biotin. Such labels can be used to label an antibody described herein. Alternatively, a second antibody that recognizes an anti-CD73 (e.g., human, mouse, or cynomolgus CD73) antibody described herein can be labeled and used in combination with an anti-CD73 (e.g., human, mouse, or cynomolgus CD73) antibody to detect CD73 (e.g., human, mouse, or cynomolgus CD73) protein levels. Therefore, in one embodiment, the present invention relates to the use of an antibody of the present invention for in vitro detection of CD73 (e.g., human, mouse, or cynomolgus CD73) protein in a biological sample. In a further embodiment, the present invention relates to the use of an anti-CD73 antibody of the invention, for assaying and/or detecting CD73 (e.g., human, mouse, or cynomolgus CD73) protein levels in a biological sample in vitro, optionally wherein the anti-CD73 antibody is conjugated to a radionuclide or detectable label, and/or carries a label described herein, and/or wherein an immunohistological method is used.

Assaying for the expression level of CD73 (e.g., human, mouse, or cynomolgus CD73) protein is intended to include qualitatively or quantitatively measuring or estimating the level of CD73 (e.g., human, mouse, or cynomolgus CD73) protein in a first biological sample either directly (e.g., by determining or estimating absolute protein level) or relatively (e.g., by comparing to the disease associated protein level in a second biological sample). CD73 (e.g., human, mouse, or cynomolgus CD73) polypeptide expression level in the first biological sample can be measured or estimated and compared to a standard CD73 (e.g., human, mouse, or cynomolgus CD73) protein level, the standard being taken, for example, from a second biological sample obtained from an individual not having the disorder or being determined by averaging levels from a population of individuals not having the disorder. As will be appreciated in the art, once the "standard" CD73 (e.g., human, mouse, or cynomolgus CD73) polypeptide level is known, it can be used repeatedly as a standard for comparison. Therefore, in a further embodiment, the present invention relates to an in vitro method for assaying and/or detecting CD73 protein levels, for example human CD73 protein levels, in a biological sample, comprising qualitatively or quantitatively measuring or estimating the level of CD73 protein, for example of human CD73 protein, in a biological sample, by an immunohistological method.

As used herein, the term "biological sample" refers to any biological sample obtained from a subject, cell line, tissue, or other source of cells potentially expressing CD73 (e.g., human, mouse, or cynomolgus CD73). Methods for obtaining tissue biopsies and body fluids from animals (e.g., humans or cynomolgus monkeys) are well known in the art. Biological samples include peripheral mononuclear blood cells.

An anti-CD73 (e.g., human, mouse, or cynomolgus CD73) antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-CD73 antibody and/or pharmaceutical composition of the present invention for use as a diagnostic. In one embodiment, the present invention relates to an anti-CD73 antibody and/or pharmaceutical composition of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-CD73 antibody of the invention, for predicting, diagnosing and/or monitoring of a subject having or suspected to have an immune system-dysfunction and/or with regard to an anticipated or desired immune system response, antigen response or vaccine response by assaying and/or detecting human CD73 protein levels in a biological sample of the subject in vitro.

In one embodiment, an anti-CD73 (e.g., human, mouse, or cynomolgus CD73) antibody can be used in immunohistochemistry of biopsy samples. In one embodiment, the method is an in vitro method. In another embodiment, an anti-CD73 (e.g., human, mouse, or cynomolgus CD73) antibody can be used to detect levels of CD73 (e.g., human, mouse, or cynomolgus CD73), or levels of cells which contain CD73 (e.g., human, mouse, or cynomolgus CD73) on their membrane surface, the levels of which can then be linked to certain disease symptoms. Anti-CD73 (e.g., human, mouse, or cynomolgus CD73) antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-CD73 (e.g., human, mouse, or cynomolgus CD73) antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-CD73 (e.g., human, mouse, or cynomolgus CD73) antibody may carry or may be conjugated to a radioactive label or radionuclide, such as the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-CD73 (e.g., human, mouse, or cynomolgus CD73) antibody to CD73 (e.g., human, mouse, or cynomolgus CD73). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-CD73 (e.g., human, mouse, or cynomolgus CD73) antibody under conditions that allow for the formation of a complex between the antibody and CD73 (e.g., human, mouse, or cynomolgus CD73). Any complexes formed between the antibody and CD73 (e.g., human, mouse, or cynomolgus CD73) are detected and compared in the sample and the control. In light of the specific binding of the antibodies described herein for CD73 (e.g., human, mouse, or cynomolgus CD73), the antibodies can be used to specifically detect CD73 (e.g., human, mouse, or cynomolgus CD73) expression on the surface of cells. The antibodies described herein can also be used to purify CD73 (e.g., human, mouse, or cynomolgus CD73) via immunoaffinity purification. Also included herein is an assay system which may be prepared in the form of a test kit, kit, or kit-of-parts for the quantitative analysis of the extent of the presence of, for instance, CD73 (e.g., human, mouse, or cynomolgus CD73) or CD73 (e.g., human, mouse, or cynomolgus CD73)/CD73 (e.g., human, mouse, or cynomolgus CD73) ligand complexes. The system, test kit, kit or kit-of-parts may comprise a labeled component, e.g., a labeled antibody, and one or more additional immunochemical reagents.

In certain embodiments, the antibodies and pharmaceutical compositions described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In certain embodiments, the application provides a product comprising a compound described herein and an additional therapeutic agent as a combined preparation for simultaneous, separate, or sequential use in therapy, e.g. a method of treating a disease, disorder, or condition that is responsive to CD73 inhibition and/or TGFβ signaling inhibition.

In certain embodiments, the antibodies and pharmaceutical compositions described herein may be used or combined with a DDR2 inhibitor (e.g., dasatinib), optionally in combination with an immune checkpoint inhibitor (e.g., a PD-1 inhibitor).

Targets

In certain embodiments, the antibodies and pharmaceutical compositions described herein may be used or combined with one or more of the additional therapeutic agents. The one or more therapeutic agents include, but are not limited to, an inhibitor, agonist, antagonist, ligand, modulator, stimulator, blocker, activator or suppressor of a gene, ligand, receptor, protein, factor such as: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR8), chemokine (C-X-C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), Fms-like tyrosine kinase-3 ligand (FLT3L), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Mer, Yes, Wee-1 protein kinase, Wilms' tumor antigen 1, Wilms' tumor protein, X-linked inhibitor of apoptosis protein, Zinc finger protein transcription factor or any combination thereof.

Mechanism of Action

The antibodies and pharmaceutical compositions described herein may be used or combined with one or more of the additional therapeutic agents. Therapeutic agents may be categorized by their mechanism of action into, for example, the following groups:

- anti-metabolites/anti-cancer agents, such as pyrimidine analogs floxuridine, capecitabine, cytarabine, CPX-351 (liposomal cytarabine, daunorubicin), and TAS-118;
- purine analogs, folate antagonists (such as pralatrexate), and related inhibitors;
- antiproliferative/antimitotic agents including natural products, such as *vinca* alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);
- DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;
- DNA-hypomethylating agents, such as guadecitabine (SGI-110), ASTX727;
- antibiotics such as dactinomycin, daunorubicin, doxorubicin, idarubicin, anthracyclines, mitoxantrone, bleomycins, plicamycin (mithramycin);
- enzymes such as L-asparaginase which systemically metabolizes L-asparagine and deprives cells which do not have the capacity to synthesize their own asparagine;
- antiplatelet agents;
- DNAi oligonucleotides targeting Bcl-2, such as PNT2258;
- agents that activate or reactivate latent human immunodeficiency virus (HIV), such as panobinostat and romidepsin;
- asparaginase stimulators, such as crisantaspase (Erwinase®) and GRASPA (ERY-001, ERY-ASP), calaspargase pegol;
- pan-Trk, ROS1 and ALK inhibitors, such as entrectinib, TPX-0005;
- anaplastic lymphoma kinase (ALK) inhibitors, such as alectinib, ceritinib;
- antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);
antiproliferative/antimitotic antimetabolites, such as folic acid analogs (methotrexate);
platinum coordination complexes (cisplatin, oxiloplatinim, and carboplatin), procarbazine, hydroxyurea, mitotane, and aminoglutethimide;
hormones, hormone analogs (estrogen, tamoxifen, goserelin, bicalutamide, and nilutamide), and aromatase inhibitors (letrozole and anastrozole);
anticoagulants such as heparin, synthetic heparin salts, and other inhibitors of thrombin;
fibrinolytic agents such as tissue plasminogen activator, streptokinase, urokinase, aspirin, dipyridamole, ticlopidine, and clopidogrel;
antimigratory agents;
antisecretory agents (brefeldin);
immunosuppressives, such as tacrolimus, sirolimus, azathioprine, and mycophenolate;
growth factor inhibitors, and vascular endothelial growth factor inhibitors;
fibroblast growth factor inhibitors, such as FPA14;
anti-VEGFR antibodies, such as IMC-3C5, GNR-011, tanibirumab;
anti-VEGF/DDL4 antibodies, such as ABT-165;
anti-cadherins antibodies, such as HKT-288;
anti-CD70 antibodies, such as AMG-172; anti-leucine-rich repeat containing 15 (LRRC15) antibodies, such as ABBV-085. ARGX-110;
angiotensin receptor blockers, nitric oxide donors;
antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;
DNA interference oligonucleotides, such as PNT2258, AZD-9150;
anti-ANG-2 antibodies, such as MEDI3617, and LY3127804;
anti-ANG-1/ANG-2 antibodies, such as AMG-780;
anti-MET/EGFR antibodies, such as LY3164530;
anti-EGFR antibodies, such as ABT-414, AMG-595, necitumumab, ABBV-221, depatuxizumab mafodotin (ABT-414), tomuzotuximab, ABT-806, vectibix, modotuximab, RM-1929;
anti-CSF1R antibodies, such as emactuzumab, LY3022855, AMG-820, FPA-008 (cabiralizumab);
anti-CD40 antibodies, such as RG7876, SEA-CD40, APX-005M, ABBV-428;
anti-endoglin antibodies, such as TRC105 (carotuximab);
anti-CD45 antibodies, such as 131I-BC8 (lomab-B);
anti-HER3 antibodies, such as LJM716, GSK2849330;
anti-HER2 antibodies, such as margetuximab, MEDI4276, BAT-8001;
anti-HLA-DR antibodies, such as IMMU-114;
anti-IL-3 antibodies, such as JNJ-56022473;
anti-OX40 antibodies, such as MEDI6469, MEDI6383, MEDI0562 (tavolixizumab), MOXR0916, PF-04518600, RG-7888, GSK-3174998, BMS-986178, GBR-8383, ABBV-368;
anti-EphA3 antibodies, such as KB-004;
anti-CD20 antibodies, such as obinutuzumab, IGN-002;
anti-CD20/CD3 antibodies, such as RG7828;
anti-CD37 antibodies, such as AGS67E, otlertuzumab (TRU-016);
anti-ENPP3 antibodies, such as AGS-16C3F;
anti-FGFR-3 antibodies, such as LY3076226, B-701;
anti-FGFR-2 antibodies, such as GAL-F2;
anti-C5 antibodies, such as ALXN-1210;
anti-CD27 antibodies, such as varlilumab (CDX-1127);
anti-TROP-2 antibodies, such as IMMU-132
anti-NKG2a antibodies, such as monalizumab;
anti-VISTA antibodies, such as HMBD-002;
anti-PVRIG antibodies, such as COM-701;
anti-EpCAM antibodies, such as VB4-845;
anti-BCMA antibodies, such as GSK-2857916
anti-CEA antibodies, such as RG-7813;
anti-cluster of differentiation 3 (CD3) antibodies, such as MGD015;
anti-folate receptor alpha antibodies, such as IMGN853;
epha2 inhibitors, such as MM-310;
anti LAG-3 antibodies, such as relatlimab (ONO-4482), LAG-525, MK-4280, REGN-3767;
raf kinase/VEGFR inhibitors, such as RAF-265;
polycomb protein (EED) inhibitors, such as MAK683;
anti-fibroblast activation protein (FAP)/IL-2R antibodies, such as RG7461;
anti-fibroblast activation protein (FAP)/TRAIL-R2 antibodies, such as RG7386;
anti-fucosyl-GM1 antibodies, such as BMS-986012;
p38 MAP kinase inhibitors, such as ralimetinib;
PRMT1 inhibitors, such as MS203;
Sphingosine kinase 2 (SK2) inhibitors, such as opaganib;
FLT3-ITD inhibitors, such as BCI-332;
FLT3-ITD/Mer tyrosine kinase inhibitors, such as MRX-2843;
Nuclear erythroid 2-related factor 2 stimulators, such as omaveloxolone (RTA-408);
Tropomyosin receptor kinase (TRK) inhibitors, such as LOXO-195, ONO-7579;
anti-ICOS antibodies, such as JTX-2011, GSK3359609;
anti-DR5 (TRAIL2) antibodies, such as DS-8273;
anti-GD2 antibodies, such as APN-301;
anti-interleukin-17 (IL-17) antibodies, such as CJM-112;
anti-carbonic anhydrase IX antibodies, such as TX-250;
anti-CD38-attenukine, such as TAK573;
anti-Mucin 1 antibodies, such as gatipotuzumab;
anti-FTL3 antibodies, such as Flysyn, ASP-1235;
anti-FLT3/CD3 BiTE antibodies, such as AMG-427;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
PI3K/Akt/mTOR inhibitors, such as ABTL-0812;
pan-PIM kinase inhibitors, such as INCB-053914;
PIM/FLT3 kinase inhibitors, such as MEN-1703 (SEL-24);
IL-12 gene stimulators, such as EGEN-001, tavokinogene telseplasmid;
Heat shock protein HSP90 inhibitors, such as TAS-116, PEN-866;
VEGF/HGF antagonists, such as MP-0250;
SYK tyrosine kinase/FLT3 tyrosine kinase inhibitors, such as TAK-659 (mivavotinib);
SYK tyrosine kinase/JAK tyrosine kinase inhibitors, such as ASN-002;
JAK3/JAK1/TBK1 kinase inhibitors, such as CS-12912;
FLT3 tyrosine kinases, such as FF-10101, HM-43239, SKI-G-801;
FMS-like tyrosine kinase-3 ligand (FLT3L), such as CDX-301;
EGFR/FLT3/ABL tyrosine kinase inhibitors, such as SKLB-1028;
FLT3/MEK1 inhibitors, such as E-6201;

IL-24 antagonist, such as AD-IL24;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
CCR8 inhibitors, such as I-309, SB-649701, HG-1013, RAP-310;
anti-Mesothelin antibodies, such as SEL-403;
Thymidine kinase stimulators, such as aglatimagene besadenovec;
Polo-like kinase 1 inhibitors, such as PCM-075;
TLR-7 agonists, such as TMX-101 (imiquimod);
NEDD8 inhibitors, such as pevonedistat (MLN-4924), TAS-4464; Pleiotropic pathway modulators, such as avadomide (CC-122);
FoxM1 inhibitors, such as thiostrepton;
Anti-MUC1 antibodies, such as Mab-AR-20.5;
anti-CD38 antibodies, such as isatuximab, MOR-202;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
PD-L1/EGFR inhibitors, such as GNS-1480 (lazertinib);
PD-1/CTLA-4 inhibitors, such as PF-06936308;
Retinoic acid receptor alpha (RARα) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;
CD122 agonists such as NKTR-214;
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as AM-0010;
EGFR/ErbB-2 inhibitors, such as varlitinib;
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
Kit tyrosine kinase/PDGF receptor alpha antagonists such as DCC-2618;
KIT inhibitors, such as PLX-9486;
Exportin 1 inhibitors, such as eltanexor;
EGFR/ErbB2/Ephb4 inhibitors, such as tesevatinib;
anti-CD33 antibodies, such as IMGN-779;
anti-KMA antibodies, such as MDX-1097;
anti-TIM-3 antibodies, such as TSR-022, LY-3321367, MBG-453;
anti-CD55 antibodies, such as PAT-SC1;
anti-PSMA antibodies, such as ATL-101;
anti-CD100 antibodies, such as VX-15;
anti-EPHA3 antibodies, such as fibatuzumab;
anti-Erbb antibodies, such as CDX-3379, HLX-02, seribantumab;
anti-APRIL antibodies, such as BION-1301;
Anti-Tigit antibodies, such as BMS-986207, RG-6058;
CHST15 gene inhibitors, such as STNM-01;
RAS inhibitors, such as NEO-100;
Somatostatin receptor antagonist, such as OPS-201;
CEBPA gene stimulators, such as MTL-501;
DKK3 gene modulators, such as MTG-201;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, and anti-programmed death-ligand 1 (anti-PD-L1) antibodies such as BMS-936559, atezolizumab (MPDL3280A), durvalumab (MEDI-4736), avelumab, CK-301, (MSB0010718C), MEDI-0680, CX-072, CBT-502, PDR-001 (spartalizumab), TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, and MDX1105-01;
PD-L1/VISTA antagonists such as CA-170;
PD-1/PD-L1 inhibitors, such as GS-4416, INCB086550, GS-4224;
anti-PD-L1/TGFβ antibodies, such as M-7824;
anti-transferrin antibodies, such as CX-2029;
anti-IL-8 (Interleukin-8) antibodies, such as HuMax-Inflam;
ATM (ataxia telangiectasia) inhibitors, such as AZD0156;
CHK1 inhibitors, such as GDC-0575, LY2606368 (prexasertib), SRA737, RG7741 (CHK1/2);
CXCR4 antagonists, such as BL-8040, LY2510924, burixafor (TG-0054), X4P-002, X4P-001-IO;
EXH2 inhibitors, such as GSK2816126; HER2 inhibitors, such as neratinib, tucatinib (ONT-380);
KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01);
protein kinase C (PKC) inhibitors, such as LXS-196, sotrastaurin;
Selective estrogen receptor downregulators (SERD), such as fulvestrant (Faslodex®), RG6046, RG6047, elacestrant (RAD-1901) and AZD9496;

Selective estrogen receptor covalent antagonists (SER-CAs), such as H3B-6545;
selective androgen receptor modulator (SARM), such as GTX-024, darolutamide;
transforming growth factor-beta (TGF-beta) kinase antagonists, such as galunisertib;
anti-transforming growth factor-beta (TGF-beta) antibodies, such as LY3022859, NIS793, XOMA 089;
bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APVO436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), and MGD-009 (CD3/B7H3);
Mutant selective EGFR inhibitors, such as PF-06747775, EGF816 (nazartinib), ASP8273, ACEA-0010, BI-1482694;
Anti-GITR (glucocorticoid-induced tumor necrosis factor receptor-related protein) antibodies, such as MEDI1873, FPA-154, TRX-518, BMS-986156, MK-1248, GWN-323;
anti-delta-like protein ligand 3 (DDL3) antibodies, such as rovalpituzumab tesirine;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, Anti-MSLN-MMAE;
anti-sodium phosphate cotransporter 2B (NaP2B) antibodies, such as lifastuzumab
anti-c-Met antibodies, such as ABBV-399;
Adenosine A2A receptor antagonists, such as CPI-444, AZD-4635, preladenant, PBF-509;
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, BAY-1436032;
interleukin-3 receptor (IL-3R) modulators, such as SL-401;
Arginine deiminase stimulators, such as pegargiminase (ADI-PEG-20);
antibody-drug conjugates, such as MLN0264 (anti-GCC, guanylyl cyclase C), T-DM1 (trastuzumab emtansine, Kadcyla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, ABBV-085;
claudin-18 inhibitors, such as claudiximab;
β-catenin inhibitors, such as CWP-291;
anti-CD73 antibodies, such as MEDI-9447 (oleclumab), CPX-006, IPH-53, BMS-986179, NZV-930;
CD73 inhibitors, such as AB-680, PSB-12379, PSB-12441, PSB-12425, CB-708;
CD39/CD73 inhibitors, such as PBF-1662;
chemokine receptor 2 (CCR) inhibitors, such as PF-04136309, CCX-872, BMS-813160 (CCR2/CCR5)
thymidylate synthase inhibitors, such as ONX-0801;
ALK/ROS1 inhibitors, such as lorlatinib;
tankyrase inhibitors, such as G007-LK;
Mdm2 p53-binding protein inhibitors, such as CMG-097, HDM-201;
c-PIM inhibitors, such as PIM447;
BRAF inhibitors, such as dabrafenib, vemurafenib, encorafenib (LGX818), PLX8394;
sphingosine kinase-2 (SK2) inhibitors, such as Yeliva® (ABC294640);
cell cycle inhibitors, such as selumetinib (MEK1/2), and sapacitabine;
AKT inhibitors such as MK-2206, ipatasertib, afuresertib, AZD5363, and ARQ-092, capivasertib, triciribine;
anti-CTLA-4 (cytotoxic T-lymphocyte protein-4) inhibitors, such as tremelimumab, BMS-986218;
c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;
c-Met/VEGFR inhibitors, such as BMS-817378, TAS-115;
c-Met/RON inhibitors, such as BMS-777607;
c-Met/VEGF2/AXL/RON/Mer/FLT3 inhibitors, such as CT-053 (ningetinib);
c-Kit/VEGFR2/PDGFR/VEGFR3/FLT1/FLT3 inhibitors, such as SHR-1020 (famitinib L-malate);
BRAF/EGFR inhibitors, such as BGB-283;
bcr/abl inhibitors, such as rebastinib, asciminib;
MNK1/MNK2 inhibitors, such as eFT-508;
mTOR inhibitor/cytochrome P450 3A4 stimulators, such as TYME-88
lysine-specific demethylase-1 (LSD1) inhibitors, such as CC-90011;
Pan-RAF inhibitors, such as LY3009120, LXH254, TAK-580;
Raf/MEK inhibitors, such as RG7304;
CSF1R/KIT and FLT3 inhibitors, such as pexidartinib (PLX3397);
kinase inhibitors, such as vandetanib;
E selectin antagonists, such as GMI-1271;
differentiation inducers, such as tretinoin;
epidermal growth factor receptor (EGFR) inhibitors, such as osimertinib (AZD-9291);
topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);
corticosteroids, such as cortisone, dexamethasone, hydrocortisone, methylprednisolone, prednisone, prednisolone;
growth factor signal transduction kinase inhibitors;

nucleoside analogs, such as DFP-10917;
Axl inhibitors, such as BGB-324 (bemcentinib), SLC-0211;
BET inhibitors, such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, mivebresib, BI-894999, PLX-2853, PLX-51107, CPI-0610, GS-5829;
PARP inhibitors, such as olaparib, rucaparib, veliparib, talazoparib, ABT-767, BGB-290;
Proteasome inhibitors, such as ixazomib, carfilzomib (Kyprolis®), marizomib;
Glutaminase inhibitors, such as CB-839;
Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01TM, rocapuldencel-T (AGS-003), DCVAC, CVactm, stapuldencel-T, eltrapuldencel-T, SL-701, BSK01TM, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000;
anti-DLL4 (delta like ligand 4) antibodies, such as demcizumab;
STAT-3 inhibitors, such as napabucasin (BBI-608);
ATPase p97 inhibitors, such as CB-5083;
smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;
interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);
interferon gamma ligand modulators, such as interferon gamma (OH-6000, Ogamma 100);
IL-6 receptor modulators, such as tocilizumab, siltuximab, AS-101 (CB-06-02, IVX-Q-101);
Telomerase modulators, such as, tertomotide (GV-1001, HR-2802, Riavax) and imetelstat (GRN-163, JNJ-63935937);
DNA methyltransferases inhibitors, such as temozolomide (CCRG-81045), decitabine, guadecitabine (S-110, SGI-110), KRX-0402, RX-3117, RRx-001, and azacitidine;
DNA gyrase inhibitors, such as pixantrone and sobuzoxane;
Bcl-2 family protein inhibitors, such as ABT-263, venetoclax (ABT-199), ABT-737, and AT-101;
Notch inhibitors, such as LY3039478 (crenigacestat), tarextumab (anti-Notch2/3), BMS-906024;
anti-myostatin inhibitors, such as landogrozumab;
hyaluronidase stimulators, such as PEGPH-20;
Wnt pathway inhibitors, such as SM-04755, PRI-724, WNT-974;
gamma-secretase inhibitors, such as PF-03084014, MK-0752, RO-4929097;
Grb-2 (growth factor receptor bound protein-2) inhibitors, such as BP1001;
TRAIL pathway-inducing compounds, such as ONC201, ABBV-621;
Focal adhesion kinase inhibitors, such as VS-4718, defactinib, GSK2256098;
hedgehog inhibitors, such as saridegib, sonidegib (LDE225), glasdegib and vismodegib;
Aurora kinase inhibitors, such as alisertib (MLN-8237), and AZD-2811, AMG-900, barasertib, ENMD-2076;
HSPB1 modulators (heat shock protein 27, HSP27), such as brivudine, apatorsen;
ATR inhibitors, such as BAY-937, AZD6738, AZD6783, VX-803, VX-970 (berzosertib) and VX-970;
mTOR inhibitors, such as sapanisertib and vistusertib (AZD2014), ME-344;
mTOR/PI3K inhibitors, such as gedatolisib, GSK2141795, omipalisib, RG6114;
Hsp90 inhibitors, such as AUY922, onalespib (AT13387), SNX-2112, SNX5422;
Murine double minute (mdm2) oncogene inhibitors, such as DS-3032b, RG7775, AMG-232, HDM201, and idasanutlin (RG7388);
CD137 agonists, such as urelumab, utomilumab (PF-05082566);
STING agonists, such as ADU-S100 (MIW-815), SB-11285, MK-1454, SR-8291, AdVCA0848, GSK-532, SYN-STING, MSA-1, SR-8291;
FGFR inhibitors, such as FGF-401, INCB-054828, BAY-1163877, AZD4547, JNJ-42756493, LY2874455, Debio-1347;
fatty acid synthase (FASN) inhibitors, such as TVB-2640;
Anti-KIR monoclonal antibodies, such as lirilumab (IPH-2102), IPH-4102;
Antigen CD19 inhibitors, such as MOR208, MEDI-551, AFM-11, inebilizumab;
CD44 binders, such as A6;
protein phosphatease 2A (PP2A) inhibitors, such as LB-100;
CYP17 inhibitors, such as seviteronel (VT-464), ASN-001, ODM-204, CFG920, abiraterone acetate;
RXR agonists, such as IRX4204;
hedgehog/smoothened (hh/Smo) antagonists, such as taladegib, patidegib;
complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLK1);

WEE1 inhibitors, such as AZD-1775 (adavosertib);

Rho kinase (ROCK) inhibitors, such as AT13148, KD025;

ERK inhibitors, such as GDC-0994, LY3214996, MK-8353;

IAP inhibitors, such as ASTX660, debio-1143, birinapant, APG-1387, LCL-161;

RNA polymerase inhibitors, such has lurbinectedin (PM-1183), CX-5461;

Tubulin inhibitors, such as PM-184, BAL-101553 (lisavanbulin), and OXI-4503, fluorapacin (AC-0001), plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, asunercept;

WT1 inhibitors, such as DSP-7888;

splicing factor 3B subunit1 (SF3B1) inhibitors, such as H3B-8800

PDGFR alpha/KIT mutant-specific inhibitors such as BLU-285;

retinoid Z receptor gamma (RORγ) agonists, such as LYC-55716;

Inhibitors of myeloid cell leukemia sequence 1 (MCL1) apoptosis regulator, such as AMG-176, AMG-397, S-64315, AZD-5991, 483-LM, A-1210477, UMI-77, JKY-5-037; and tetrahydronaphthalene derivatives, including those described in WO2016033486, WO2017147410 and WO2018183418.

Inhibitors of protein tyrosine phosphatase, non-receptor type 11 (PTPN11 or SHP2), such as TNO155 (SHP-099), RMC-4550, JAB-3068, RMC-4630; Examples of SHP2 inhibitors include, but are not limited to, those described in WO-2018172984 and WO-2017211303;

Hematopoietic Progenitor Kinase 1 (HPK1) inhibitors; Examples of Hematopoietic Progenitor Kinase 1 (HPK1) inhibitors include, but are not limited to, those described in WO-2018183956, WO-2018183964, WO-2018167147, WO-2018183964, WO-2016205942, WO-2018049214, WO-2018049200, WO-2018049191, WO-2018102366, WO-2018049152 and WO-2016090300;

Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences).

Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315

Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

Cyclin-dependent Kinase (CDK) Inhibitors: CDK inhibitors include inhibitors of CDK 1, 2, 3, 4, 6, 7 and 9, such as abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02.

Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat.

Indoleamine-pyrrole-2,3-dioxygenase (IDO1) inhibitors: Examples of IDO1 inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555), GS-5745 (andecaliximab) and those described in WO 2012/027721 (Gilead Biologics).

Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib.

Phosphatidylinositol 3-kinase (PI3K) Inhibitors: PI3K inhibitors include inhibitors of PI3Kγ, PI3Kδ, PI3Kβ, PI3Kα, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Tyrosine-Kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). TKIs may also target Spleen Tyrosine Kinase (SYK). Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-Like Receptor (TLR) Modulators

In one embodiment, the additional therapeutic agent is a TLR modulator. TLR modulators may include modulators of TLR1, TLR2, TLR3, TLR4, TLR5, TLR6, TLR7, TLR8, TLR9, TLR10, TLR11, TLR12, and TLR13.

In certain embodiments, the antibodies or antigen-binding fragments described herein are combined with a TLR agonist. Examples of TLR agonists include without limitation: vesatolimod (GS-9620), lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod. Additional examples include but are not limited to the compounds described in U.S. Pat. No. 8,367,670 and the compounds described in U.S. Patent Application Publication No. 2016/0289229. In one embodiment, the antibody of the present invention may be combined with TLR7 agonist such as Vesatolimod. In another embodiment, the antibody of the present invention may be combined with TLR8 agonist.

Examples of TLR3 modulators include rintatolimod, poly-ICLC, RIBOXXON®, Apoxxim, RIBOXXIM®, IPH-33, MCT-465, MCT-475, and ND-1.1. Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences). Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventrx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR8 inhibitors include, but are not limited to, E-6887, IMO-4200, IMO-8400, IMO-9200, MCT-465, MEDI-9197, motolimod, resiquimod, GS-9688, VTX-1463, and VTX-763.

Examples of TLR9 inhibitors include, but are not limited to, AST-008, IMO-2055, IMO-2125, lefitolimod, litenimod, MGN-1601, and PUL-042.

Chemotherapeutic Agents i.e. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids or taxanes such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; a FOLFOX (5-fluorouracil, leucovorin, oxaliplatin) regimen (e.g., FOLFOX-4, FOLFOX-6, modified FOLFOX-6 (mFOLFOX-6), FOLFOX-7), FOLFIRI (fluorouracil, leucovorin, and irinotecan); and pharmaceutically acceptable salts, acids, or derivatives of any of the above.

Anti-Hormonal Agents

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

Examples of progesterone receptor antagonists include onapristone.

Anti Angiogenic Agents

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other antiangiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases.

Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

The immunotherapeutic agents include and are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8.

The exemplified therapeutic antibodies may be further labeled or combined with a radioisotope particle such as indium-111, yttrium-90, or iodine-131.

Cancer Gene Therapy and Cell Therapy

Cancer Gene Therapy and Cell Therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Gene Editors

The genome editing system is selected from the group consisting of: a CRISPR/Cas9 system, a zinc finger nuclease system, a TALEN system, a homing endonucleases system, and a meganuclease system.

CAR-T Cell Therapy and TCR-T Cell Therapy

A population of immune effector cells engineered to express a chimeric antigen receptor (CAR), wherein the CAR comprises a tumor antigen-binding domain. The immune effector cell is a T cell or an NK cell. TCR-T cells are engineered to target tumor derived peptides present on the surface of tumor cells. Cells can be autologous or allogeneic.

In some embodiments, the CAR comprises an antigen binding domain, a transmembrane domain, and an intracellular signalling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rib), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 ld, ITGAE, CD103, ITGAL, CD 1 la, LFA-1, ITGAM, CD1 lb, ITGAX, CD1 lc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen. In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (aNeuSAc(2-8)aNeuSAc(2-3)bD-Gaip(1-4)bDGIcp(1-1)Cer); TNF receptor family member B cell maturation (BCMA); Tn antigen ((Tn Ag) or (GaINAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor); carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-1a); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like modulecontaining mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, BMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1(DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

Non limiting examples of cell therapies are: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CART cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005.

In certain embodiments, the cell therapy comprises an agent targeting: Alpha-fetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, and AUTO-2 (APRIL-CAR); Anti-CLL-1 antibodies, such as KITE-796; Anti-PD-L1-CAR tank cell therapy, such as KD-045; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, and IM19 CAR-T; B-lymphocyte antigen CD20, such as ACTR707+Rituximab; B-lymphocyte antigen CD22, such as JCAR-018 (see WO2016090190); NY-ESO-1, such as GSK-3377794 and TBI-1301; Carbonic anhydrase, such as DC-Ad-GMCAIX; Caspase 9 suicide gene, such as CaspaCIDe DLI and BPX-501; CCR5, such as SB-728; CDw123, such as MB-102 and UCART-123; CD20m such as CBM-C20.1; CD22 such as UCART-22; CD4, such as ICG-122; CD30, such as CART30 (CBM-C30.1; CD33, such as CIK-CAR.CD33; CD38, such as T-007, UCART-38; CD40 ligand, such as BPX-201; CEACAM protein 5 modulators, such as MG7-CART; Claudin 6, such as CSG-002; EBV, such as CMD-003; MUC16, such as autologous 4H11-28z/fIL-12/EFGRt T cell; Endonuclease, such as PGN-514 and PGN-201; Epstein-Barr virus specific T-lymphocytes, such as TT-10; Ganglioside (GD2), such as 4SCAR-GD2; Glutamate carboxypeptidase II, such as CIK-CAR.PSMA, CART-PSMA-TGFBRDN, P-PSMA-101; Hemoglobin, such as PGN-236; Hepatocyte growth factor receptor, such as anti-cMet RNA CAR T; Human papillomavirus E7 protein, such as KITE-439; Immunoglobulin gamma Fc receptor III, such as ACTR087; IL-12, such as DC-RTS-IL-12; IL-12 agonist/mucin 16, such as JCAR-020; IL-13 alpha 2, such as MB-101; K-Ras GTPase, such as anti-KRAS G12V mTCR cell therapy; Neural cell adhesion molecule L1 L1CAM (CD171), such as JCAR-023; Latent membrane protein 1/Latent membrane protein 2, such as Ad5f35-LMPd1-2-transduced autologous dendritic cells; Melanoma associated antigen 10, such as MAGE-A10C796T MAGE-A10 TCR; Melanoma associated antigen 3/Melanoma associated antigen 6 (MAGE A3/A6) such as KITE-718; Mesothelin, such as CSG-MESO, TC-210; NKG2D, such as NKR-2; Ntrkr1 tyrosine kinase receptor, such as JCAR-024; PRAME, such as BPX-701; gp100 antigen, such as IMCgp100; Wilms tumor protein, such as JTCR-016 and WT1-CTL.

Types of Cancer

In some embodiments, the cancer is Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the methods of treatment provided may be used to treat cancer at various stages. By way of example, the cancer stage includes but is not limited to early, advanced, locally advanced, remission, refractory, reoccurred after remission and progressive.

Subjects

Any of the methods of treatment provided may be used to treat a subject (e.g., human) who has been diagnosed with or is suspected of having cancer. As used herein, a subject refers to a mammal, including, for example, a human.

In some embodiments, the subject may be a human who exhibits one or more symptoms associated with cancer or hyperproliferative disease. In some embodiments, the subject may be a human who exhibits one or more symptoms associated with cancer. In some embodiments, the subject is at an early stage of a cancer. In other embodiments, the subject is at an advanced stage of cancer.

In certain, the subject may be a human who is at risk, or genetically or otherwise predisposed (e.g., risk factor) to developing cancer or hyperproliferative disease who has or has not been diagnosed. As used herein, an "at risk" subject is a subject who is at risk of developing cancer. The subject may or may not have detectable disease, and may or may not have displayed detectable disease prior to the treatment methods described herein. An at risk subject may have one or more so-called risk factors, which are measurable parameters that correlate with development of cancer, which are described herein. A subject having one or more of these risk factors has a higher probability of developing cancer than an individual without these risk factor(s). These risk factors may include, for example, age, sex, race, diet, history of previous disease, presence of precursor disease, genetic (e.g., hereditary) considerations, and environmental exposure. In some embodiments, the subjects at risk for cancer include, for example, those having relatives who have experienced the disease, and those whose risk is determined by analysis of genetic or biochemical markers.

In addition, the subject may be a human who is undergoing one or more standard therapies, such as chemotherapy, radiotherapy, immunotherapy, surgery, or combination thereof. Accordingly, one or more kinase inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) is in relapse after treatment with chemotherapy, or both (i) and (ii). In some of embodiments, the subject is refractory to at least two, at least three, or at least four chemotherapy treatments (including standard or experimental chemotherapies).

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and predni sone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WHIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R ICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib.

Examples of HDAC inhibitors include, but are not limited to, pracinostat and panobinostat.

Non-limiting examples of tyrosine kinase inhibitors are lestaurtinib, bosutinib, imatinib, gilteritinib, radotinib, and cabozantinib.

Hyperproliferative Disorder Combination Therapy

Gemcitabine, nab-paclitaxel, and gemcitabine/nab-paclitaxel may be used with a CD73 inhibitor and/or TGFβ inhibitor to treat hyperproliferative disorders.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular Carcinoma Combination Therapy

Therapeutic agents used to treat hepatocellular carcinoma include capecitabine, doxorubicin, gemcitabine, sorafenib, and any combinations thereof.

Non-Small Cell Lung Cancer Combination Therapy

Therapeutic agents used to treat non-small cell lung cancer (NSCLC) include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

5.6 Polynucleotides, Vectors and Methods of Producing Anti-CD73 Antibodies

In another aspect, provided herein are polynucleotides comprising a nucleotide sequence encoding an antibody described herein or a fragment thereof (e.g., a light chain variable region and/or heavy chain variable region) that specifically binds to a CD73 (e.g., human, mouse, or cynomolgus CD73) antigen, and vectors, e.g., vectors comprising such polynucleotides for recombinant expression in host cells (e.g., E. coli and mammalian cells). Provided herein are polynucleotides comprising nucleotide sequences encoding a polypeptide (e.g., a heavy and/or light chain) of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a CD73 (e.g., human, mouse, or cynomolgus CD73) polypeptide and comprises an amino acid sequence as described herein, as well as antibodies which compete with such antibodies for binding to a CD73 (e.g., human, mouse, or cynomolgus CD73) polypeptide (e.g., in a dose-dependent manner), or which binds to the same epitope as that of such antibodies.

In certain aspects, provided herein are polynucleotides comprising a nucleotide sequence encoding a polypeptide (e.g., the light chain or heavy chain) of an antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1).

Also provided herein are polynucleotides encoding an anti-CD73 (e.g., human, mouse, or cynomolgus CD73) antibody that are optimized, e.g., by codon/RNA optimization, replacement with heterologous signal sequences, and elimination of mRNA instability elements. Methods to generate optimized nucleic acids encoding an anti-CD73 (e.g., human, mouse, or cynomolgus CD73) antibody or a fragment thereof (e.g., light chain, heavy chain, VH domain, or VL domain, optionally linked to a ligand binding moiety) for recombinant expression by introducing codon changes and/ or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-CD73 (e.g., human, mouse, or cynomolgus CD73) antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-CD73 (e.g., human, mouse, or cynomolgus CD73) antibody encoded by polynucleotides that have not been optimized.

In certain embodiments, an optimized polynucleotide sequence encoding an anti-CD73 (e.g., human, mouse, or cynomolgus CD73) antibody described herein or a fragment thereof (e.g., VL domain and/or VH domain) can hybridize to an antisense (e.g., complementary) polynucleotide of an unoptimized polynucleotide sequence encoding an anti-CD73 (e.g., human, mouse, or cynomolgus CD73) antibody described herein or a fragment thereof (e.g., VL domain and/or VH domain). In specific embodiments, an optimized nucleotide sequence encoding an anti-CD73 (e.g., human, mouse, or cynomolgus CD73) antibody described herein or a fragment hybridizes under high stringency conditions to antisense polynucleotide of an unoptimized polynucleotide sequence encoding an anti-CD73 (e.g., human, mouse, or cynomolgus CD73) antibody described herein or a fragment thereof. In a specific embodiment, an optimized nucleotide sequence encoding an anti-CD73 (e.g., human, mouse, or cynomolgus CD73) antibody described herein or a fragment thereof hybridizes under high stringency, intermediate or lower stringency hybridization conditions to an antisense polynucleotide of an unoptimized nucleotide sequence encoding an anti-CD73 (e.g., human, mouse, or cynomolgus CD73) antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-CD73 (e.g., human, mouse, or cynomolgus CD73) antibodies described herein can be readily isolated and sequenced using conventional procedures (e.g., by using oligonucleotide probes that are capable of binding specifically to genes encoding the heavy and light chains of the anti-CD73 (e.g., human, mouse, or cynomolgus CD73) antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-CD73 (e.g., human, mouse, or cynomolgus CD73) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to CD73 (e.g., human, mouse, or cynomolgus CD73) and related polynucleotides and expression vectors. Provided herein are vectors (e.g., expression vectors) comprising polynucleotides comprising nucleotide sequences encoding anti-CD73 (e.g., human, mouse, or cynomolgus CD73) antibodies or a fragment for recombinant expression in host cells, preferably in mammalian cells (e.g., CHO cells). Also provided herein are host cells comprising such vectors for recombinantly expressing anti-CD73 (e.g., human, mouse, or cynomolgus CD73) antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody optionally comprising a ligand binding moiety described herein) that specifically binds to CD73 (e.g., human, mouse, or cynomolgus CD73) generally involves construction of an expression vector containing a polynucleotide that encodes the antibody. Once a polynucleotide encoding an antibody, a polypeptide (e.g., heavy and/or light chain) of an antibody, or a fragment thereof (e.g., heavy and/or light chain variable regions) described herein has been obtained, the vector for the production of the antibody can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody described herein, a polypeptide (e.g., heavy or light chain) of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464, which are herein incorporated by reference in their entireties) and variable regions of the antibody can be cloned into such a vector for expression of an entire polypeptide (e.g., the entire heavy chain or the entire light chain), or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-CD73 (e.g., human, mouse, or cynomolgus CD73) antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-CD73 (e.g., human, mouse, or cynomolgus CD73) antibody described herein, and a second vector comprising a polynucleotide encoding a heavy chain/heavy chain variable region of an anti-CD73 (e.g., human, mouse, or cynomolgus CD73) antibody described herein.

A variety of host-expression vector systems can be utilized to express antibody described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with, e.g., recombinant bacteriophage DNA, plasmid DNA or cosmid DNA expression vectors containing antibody coding sequences; yeast (e.g., *Saccharomyces Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK-293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, a polypeptide (e.g., the heavy chain and/or light chain) of an antibody produced by a CHO cell may have an N-terminal glutamine or glutamate residue replaced by pyroglutamate. In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody, are used for the expression of a recombinant antibody. For example, mammalian cells such as CHO cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to CD73 (e.g., human, mouse, or cynomolgus CD73) is regulated by a constitutive promoter, inducible promoter or tissue specific promoter.

In bacterial systems, a number of expression vectors can be advantageously selected depending upon the use intended for the antibody being expressed. For example, when a large quantity of such an antibody is to be produced, for the generation of pharmaceutical compositions of an antibody, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) *Methods Enzymol.* 153:516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK-293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-CD73 (e.g., human, mouse, or cynomolgus CD73) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-CD73 (e.g., human, mouse, or cynomolgus CD73) antibody described herein can be engineered. In specific embodiments, a cell provided herein stably expresses a light chain/light chain variable region and a heavy chain/heavy chain variable region which associate to form an antibody described herein, optionally wherein at least one of the light chain/light chain variable region and the heavy chain/heavy chain variable region is linked to a ligand binding moiety.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CD73 (e.g., human, mouse, or cynomolgus CD73) antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, all of which are herein incorporated by reference in their entireties.

The expression levels of an antibody can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain derived polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody optionally linked to a ligand binding moiety as described herein), and a second gene and (e.g., light chain of an antibody optionally linked to a ligand binding moiety as described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to CD73 (e.g., human, mouse, or cynomolgus CD73) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically bind to CD73 (e.g., human, mouse, or cynomolgus CD73) comprising culturing a cell or host cell described herein. In one embodiment, the method is performed in vitro. In a certain aspect, provided herein is a method of making an antibody which specifically bind to CD73 (e.g., human, mouse, or cynomolgus CD73) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing a polypeptide of an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to CD73 (e.g., human, mouse, or cynomolgus CD73) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding domains, each monovalent binding domain capable of binding to an epitope on the antigen. Each monovalent binding domain can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., CD73 (e.g., human, mouse, or cynomolgus CD73)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., CD73 (e.g., human, mouse, or cynomolgus CD73)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against CD73 (e.g., human, mouse, or cynomolgus CD73). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize a specific CD73 (e.g., human, mouse, or cynomolgus CD73), and which can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

In addition, the antibodies described herein can also be generated using specific immunization methods, alone or in a combination with phage display technologies as known in the art. For example, DNA immunization has been recently reported as an efficient strategy for vaccination. See Bolhassani and Yazdi (2009) *Avicenna J Med Biotechnol.* 1:71-88, Liu et al. (2016) *Emerg Microbes Infect.* 5:e33, and van der Woning et al. (2016) *MAbs.* 8:1126-1135, each of which is herein incorporated by reference in its entirety. Immunizing animals with DNA encoding a protein of interest can be performed using the similar methods as traditional animal immunization using the protein itself, and can include similar initial immunization and boosting steps. After DNA immunization, hybridoma cells can be prepared. Alternatively or additionally, nucleic acid molecules (e.g., RNAs) can be isolated from tissues (e.g., spleen) of the immunized animal to generate a phase display library for antibody panning and screening.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is herein incorporated by reference in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a CD73 (e.g., human, mouse, or cynomolgus CD73) antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of CD73 (e.g., human, mouse, or cynomolgus CD73) as an anti-CD73 (e.g., human, mouse, or cynomolgus CD73) antibody described herein, is a human antibody. In particular embodiments, an antibody described herein, which competitively blocks (e.g., in a dose-dependent manner) any one of the antibodies described herein, from binding to CD73 (e.g., human, mouse, or cynomolgus CD73), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., CD73 (e.g., human, mouse, or cynomolgus CD73)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598, all of which are herein incorporated by reference in their entireties. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies that specifically bind to CD73 (e.g., human, mouse, or cynomolgus CD73) can be made by a variety of methods known in the art including the phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., CD73 (e.g., human, mouse, or cynomolgus CD73)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

5.7 Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated CD73 (e.g., human, mouse, or cynomolgus CD73) antigen as a control. In another specific embodiment, the kits described herein further comprise a control antibody which does not react with a CD73 (e.g., human, mouse, or cynomolgus CD73) antigen. In another specific embodiment, kits described herein contain one or more elements for detecting the binding of an antibody to a CD73 (e.g., human, mouse, or cynomolgus CD73) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CD73 (e.g., human, mouse, or cynomolgus CD73) antigen. The CD73 (e.g., human, mouse, or cynomolgus CD73) antigen provided in the kit can also be attached to a solid support. In a more specific embodiment, the detecting means of the above described kit includes a solid support to which a CD73 (e.g., human, mouse, or cynomolgus CD73) antigen is attached. Such a kit can also include a non-attached reporter-labeled anti-human antibody or anti-mouse/rat antibody. In this embodiment, binding of the antibody to the CD73 (e.g., human, mouse, or cynomolgus CD73) antigen can be detected by binding of the said reporter-labeled antibody. In one embodiment, the present invention relates to the use of a kit of the present invention for in vitro assaying and/or detecting CD73 antigen (e.g., human, mouse, or cynomolgus CD73) in a biological sample.

6. EXAMPLES

The examples in this Section (i.e., Section 6) are offered by way of illustration, and not by way of limitation.

6.1 Example 1: Characterization of an Anti-CD73 Antibody

This example describes the generation and characterization of antibodies that bind to CD73 (e.g., human CD73, cynomolgus CD73, or mouse CD73). In particular, this example describes murine and chimeric antibodies that specifically bind to human CD73, inhibit the enzymatic activity of human CD73, and mediate human CD73 internalization upon binding.

6.1.1 Generation of Anti-CD73 Antibodies

Anti-CD73 antibodies were identified by immunizing mice with either recombinant human CD73 protein or DNA encoding human CD73, amplifying nucleic acid sequences (e.g., RNA or complementary DNA sequences) encoding heavy chain variable regions and light chain variable regions from the splenic B cells of the immunized mice, assembling these sequences into vectors to form a proprietary phage display library, and selecting phage clones that produced antibodies having binding affinity to human CD73 (NCBI Reference Sequence: AAH65937, SEQ ID NO: 129, R&D Systems, 5795EN). Three selected antibodies, designated BA010, BA011, and BA012, were further characterized. The heavy chain variable region and light chain variable region amino acid sequences of BA010, BA011, and BA012 are set forth in SEQ ID NOs: 19 and 33; 20 and 34; and 21 and 35, respectively. Constant regions were fused to these variable regions to form the antibodies described herein. For example, the murine antibody BA012 comprises an Igκ light chain (SEQ ID NO: 92) and an IgG2a heavy chain having a N297A substitution (SEQ ID NO: 64), numbered according to the EU numbering system.

Chimeric antibodies were produced by grafting the variable regions of the heavy and light chains of BA010, BA011, and BA012 to the constant region of human $IgG_1$ heavy chain having a N297A substitution, numbered according to the EU numbering system, and the constant region of human Igκ light chain, respectively. The resulting chimeric antibodies originating from BA010, BA011, and BA012 are designated BA013, BA014, and BA015, as set forth in SEQ ID NOs: 65 and 94, 67 and 95, and 70 and 96, respectively, for their heavy and light chains. Similarly, other chimeric antibodies were produced by grafting the variable regions of the heavy and light chains of BA012 to various human constant regions. For example, BA016, as set forth in SEQ ID NOs: 71 (heavy chain) and 96 (light chain), comprises a human $IgG_2$ constant domain. BA017, as set forth in SEQ ID NOs: 73 (heavy chain) and 96 (light chain), comprises a human $IgG_1$-A330S-P331S/$IgG_2$ hybrid constant domain. BA018, as set forth in SEQ ID NOs: 75 (heavy chain) and 96 (light chain), comprises a human $IgG_1$-N297A/$IgG_2$ hybrid constant domain.

6.1.2 Binding of Anti-CD73 Antibodies to Recombinant CD73

Surface plasmon resonance (SPR) was used to determine the affinity of BA013, BA014, and BA015 to recombinant CD73 using the BIAcore® T200 system (GE Healthcare). Specifically, 2 μg/ml of antibodies diluted in a running buffer (10 mM HEPES, 150 mM NaCl, 3 mM EDTA, and 0.05% surfactant P20) were captured on a Series S Sensor Chip Protein A (GE Healthcare Ltd, cat #29-1275-56) using a 15 sec injection at a flow rate of 10 μl/min to reach about 80 resonance units (RUs). Recombinant human, cynomolgus, or mouse CD73 protein fused with a 6×His-tag (R&D Systems, 5795EN; Sino Biological, 90192-C08H; and R&D Systems, 4488EN, respectively) diluted in the running buffer at the concentration of about 0.14 to 33 nM were flowed over the chip surface at a flow rate of 30 μl/min with a 5-min association phase and a 20-min dissociation phase. The sensor chip was regenerated between cycles with a 30-sec injection of 10 mM glycine, pH 1.5. Sensograms were evaluated and fit to a simple Langmuir 1:1 interaction model using the global data analysis option of BiaEvaluation 3.1 software. Data quality was verified by visually inspecting deviations and curve fitting, and by evaluating the parameters of Rmax, Chi2, and Tc. The binding kinetics ($K_a$, $K_d$ and $K_D$) were determined from the sensorgram analyses and are shown in Tables 7 and 8. Two reference anti-CD73 antibodies, named Reference Antibody 1 ("RA001") and Reference Antibody 2 ("RA002"), were used for comparison.

TABLE 7

SPR-based affinity measurements for anti-CD73 antibodies

| | Human CD73 | | | Cynomolgus CD73 | | | Mouse CD73 | | |
|---|---|---|---|---|---|---|---|---|---|
| Clone | $K_a$ (1/Ms) | $K_d$ (1/s) | $K_D$ (nM) | $K_a$ (1/Ms) | $K_d$ (1/s) | $K_D$ (nM) | $K_a$ (1/Ms) | $K_d$ (1/s) | $K_D$ (nM) |
| BA013 | 1.0E+06 | 2.9E−03 | 2.8 | 3.0E+05 | 2.0E−04 | 0.7 | 4.2E+04 | 6.1E−04 | 14.5 |
| BA014 | 4.6E+07 | 4.2E−04 | 0.010 | 5.0E+04 | 3.0E−05 | 0.6 | 2.5E+04 | 2.3E−04 | 9.4 |
| BA015 | 2.8E+07 | 4.1E−04 | 0.015 | 3.1E+05 | 8.7E−05 | 0.3 | 6.1E+04 | 6.0E−04 | 10 |

TABLE 8

Affinity comparison between BA015 and Reference anti-CD73 antibodies

| | Human CD73 | | | Cynomolgus CD73 | | |
|---|---|---|---|---|---|---|
| Clone | $K_a$ (1/Ms) | $K_d$ (1/s) | $K_D$ (nM) | $K_a$ (1/Ms) | $K_d$ (1/s) | $K_D$ (nM) |
| BA015 | 2.27E+06 | 2.00E−04 | 0.088 | 1.14E+06 | 8.30E−05 | 0.07 |
| RA001 | 7.73E+05 | 3.49E−05 | 0.045 | 6.81E+05 | 2.04E−07 | 0.03 |
| RA002 | 1.07E+06 | 1.99E−04 | 0.186 | 4.55E+05 | 1.52E−05 | 0.3 |

6.1.3 Binding of Anti-CD73 Antibodies to CD73-Expressing Cells

The affinity of the anti-CD73 antibodies BA013, BA014, and BA015 for membrane-associated CD73 was determined by assessing their binding to cells ectopically expressing full-length human, cynomolgus, or mouse CD73. Briefly, Chinese hamster ovarian (CHO) cells were transduced with lentiviral vectors comprising a mouse, cynomolgus, or human CD73 coding sequence under the control of a CMV promoter, and stable CHO-CD73 cells were generated by antibiotic selection. Expression of CD73 was verified by flow cytometry using positive control antibodies. The stable CHO-CD73 cells were grown in suspension culture in RPMI media supplemented with 10% heat-inactivated FBS at 37° C. and 5% $CO_2$. For binding analysis, the stable CHO-CD73 cells were incubated for 30 minutes at 4° C. with an eight-point dose titration of a test or isotype control antibody from 0.005 to 10 μg/ml diluted in FACS buffer (PBS, 2 mM EDTA, 0.5% BSA, pH 7.2). RA001, which has an Igλ light chain, was used for comparison. The cells were washed twice in FACS buffer and incubated with FITC-conjugated mouse anti-human kappa detection antibody (for BA013, BA014, and BA015; Life Technologies, HP6062, 1:100 dilution in FACS buffer) or FITC-conjugated goat-anti-human lambda detection antibody (for Reference Antibody 1; BD Biosciences, 644139, 1:100 dilution in FACS buffer) for 30 minutes at 4° C. The cells were then washed twice and analyzed using the LSRFortessa™ flow cytometer (BD Biosciences). FACS data were analyzed using FACS DIVA and WEHI Weasel software, and were plotted with Graphpad Prism software.

Figure 1:
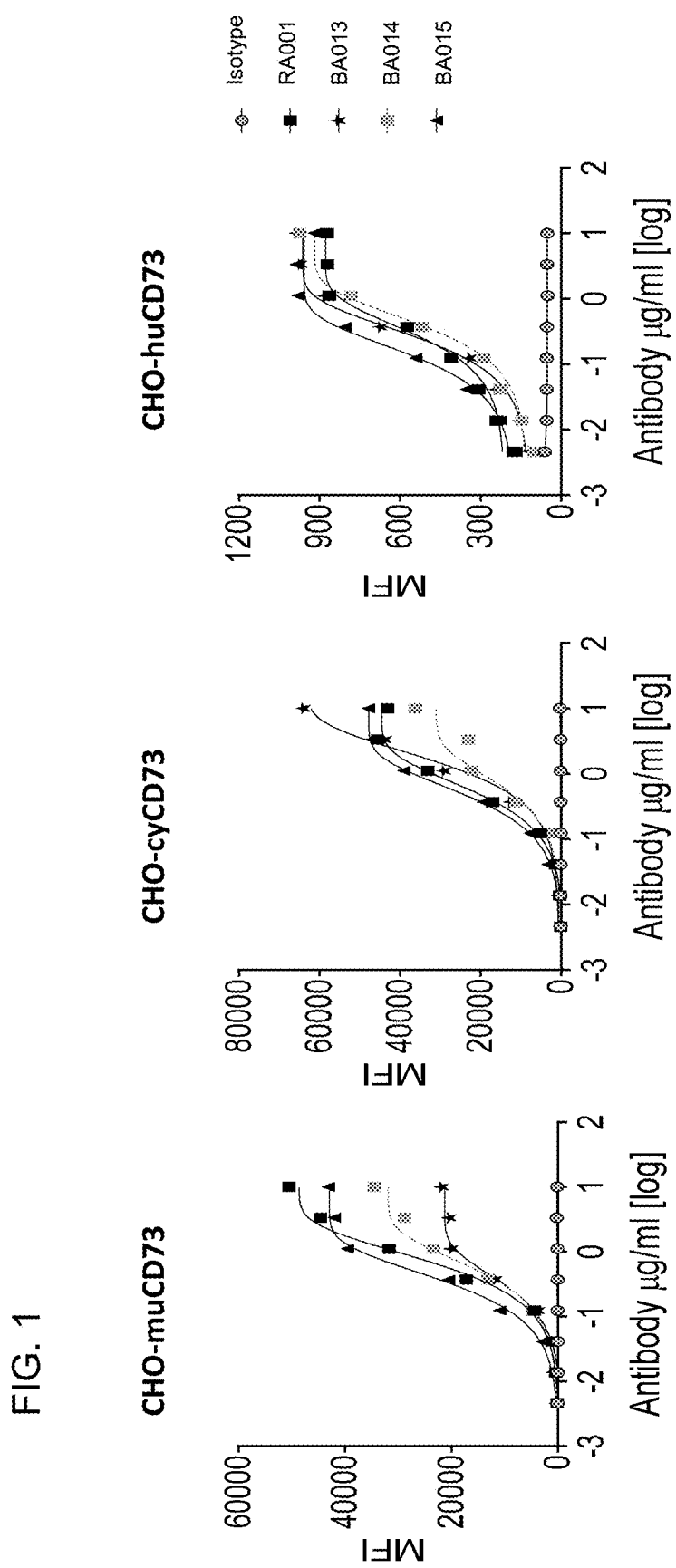

As shown in FIG. 1, BA013, BA014, BA015, and RA001 each exhibited dose-dependent binding to mouse, cynomolgus, and human CD73.

6.1.4 Inhibition of CD73 Enzymatic Activity by Anti-CD73 Antibodies

The ability of the anti-CD73 antibodies to inhibit the enzymatic activity of CD73 was assessed on live cells ectopically expressing human CD73. Briefly, Jurkat cells or CHO cells were transduced with lentiviral vectors comprising a human CD73 coding sequence under the control of an EF1a promoter. Stable cell lines were generated by fluorescence activated cell sorting (FACS ARIA Fusion), and the expression of CD73 was verified by flow cytometry using a positive control anti-CD73 antibody RA001. Cells were grown in suspension culture in RPMI media supplemented with 10% heat-inactivated FBS at 37° C. and 5% $CO_2$. For enzymatic activity analysis, the CHO or Jurkat cells were plated in flat-bottom tissue culture plates at a density of $5\times10^4$ cells per well. An eight-point dose titration of an anti-CD73 antibody or isotype control antibody from 0.005 to 10 µg/ml was added to the cells to reach a final volume of 50 µl/well. After a one-hour incubation, 25 µl of 300 µM adenosine monophosphate (AMP) was added to each well to allow hydrolysis of AMP by CD73 for 20 minutes at 37° C. and 5% $CO_2$. The cells were then pelleted, and approximately 75 µl of supernatant was mixed with 25 µl of 12 µM adenosine triphosphate (ATP) in a white flat-bottom tissue culture plate. 100 µl of reconstituted CellTiter Glo® (Promega) was added to each well immediately afterwards, and luminescence was recorded using Envision instrument (Perkin Elmer) after 5 minutes.

Figure 2A:
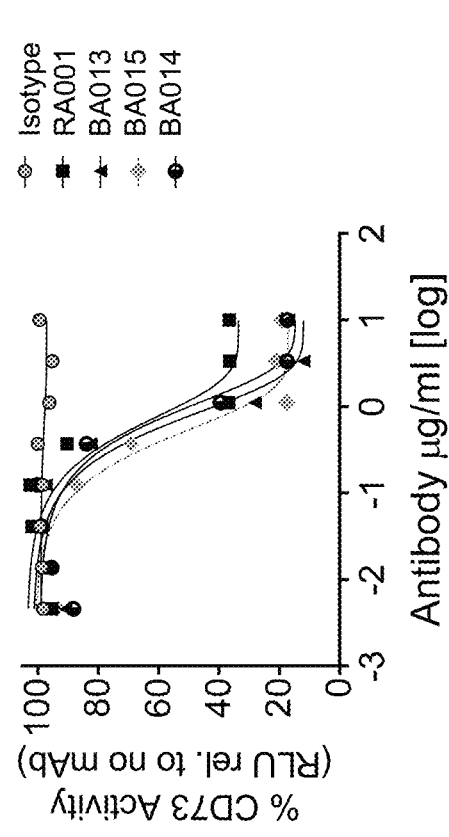
Figure 2B:
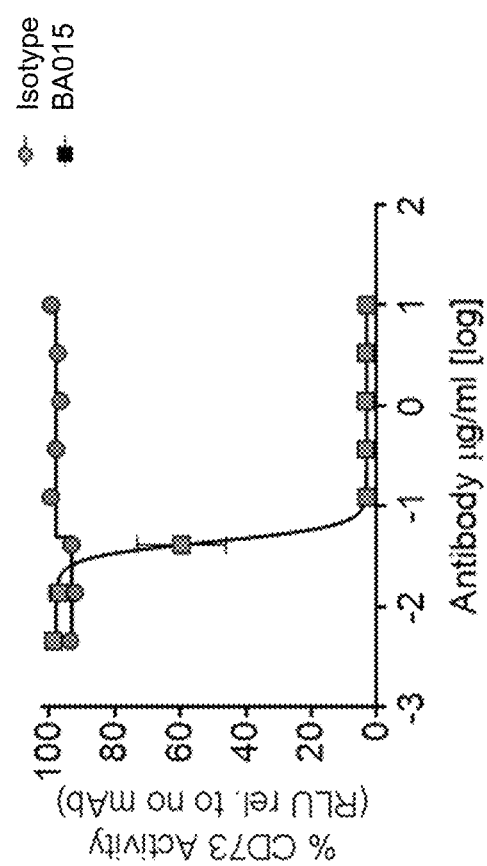

The luminescence levels correlate with the CD73 activity in each sample, because AMP inhibits the luciferase reaction, and hydrolysis of AMP by CD73 relieves the inhibition. Thus, as shown in FIG. 2A, BA013, BA014, BA015, and RA001 each inhibited the enzymatic activity of CD73 expressed on Jurkat cells. The calculated area under the curve (AUC) values for anti-CD73 antibodies in FIG. 2A are presented in Table 9. Similar inhibition by BA015 was observed using CD73-expressing CHO cells (FIG. 2B).

TABLE 9

AUC values for anti-CD73 antibodies in FIG. 2A

| Antibody | AUC |
|---|---|
| BA013 | 215.2 |
| BA015 | 239 |
| BA014 | 260 |
| RA001 | 407.9 |

6.1.5 Internalization of Anti-CD73 Antibodies Upon CD73 Binding

The internalization of anti-CD73 antibodies into cells was analyzed using a cell toxicity assay, and antibody-mediated internalization of CD73 was assessed using a live-cell imaging method.

The cell toxicity assay employed an antibody-drug conjugate αHFc-NC-MMAE (anti-human IgG Fc antibody conjugated to monomethyl auristatin E (MMAE), with a non-cleavable linker, Moradec LLC), which could transport the cytotoxic payload MMAE into the cytoplasm upon internalization. Briefly, a Jurkat cell line ectopically expressing human CD73, as described in Section 6.1.4, was plated in white flat-bottom tissue culture plates at a density of $2\times10^4$ per well. An eight-point dose titration of an anti-CD73 antibody or isotype control antibody from 0.005 to 10 µg/ml, along with αHFc-NC-MMAE at the same concentration as the antibody, was added to the cells to reach a final volume of 100 µl/well. Following a 72-hour incubation at 37° C. and 5% $CO_2$, 90 µl of reconstituted CellTiter Glo® (Promega) was added to each well, and luminescence, representing cell viability, was recorded using Envision instrument (Perkin Elmer) after 5 minutes.

Figure 3A:
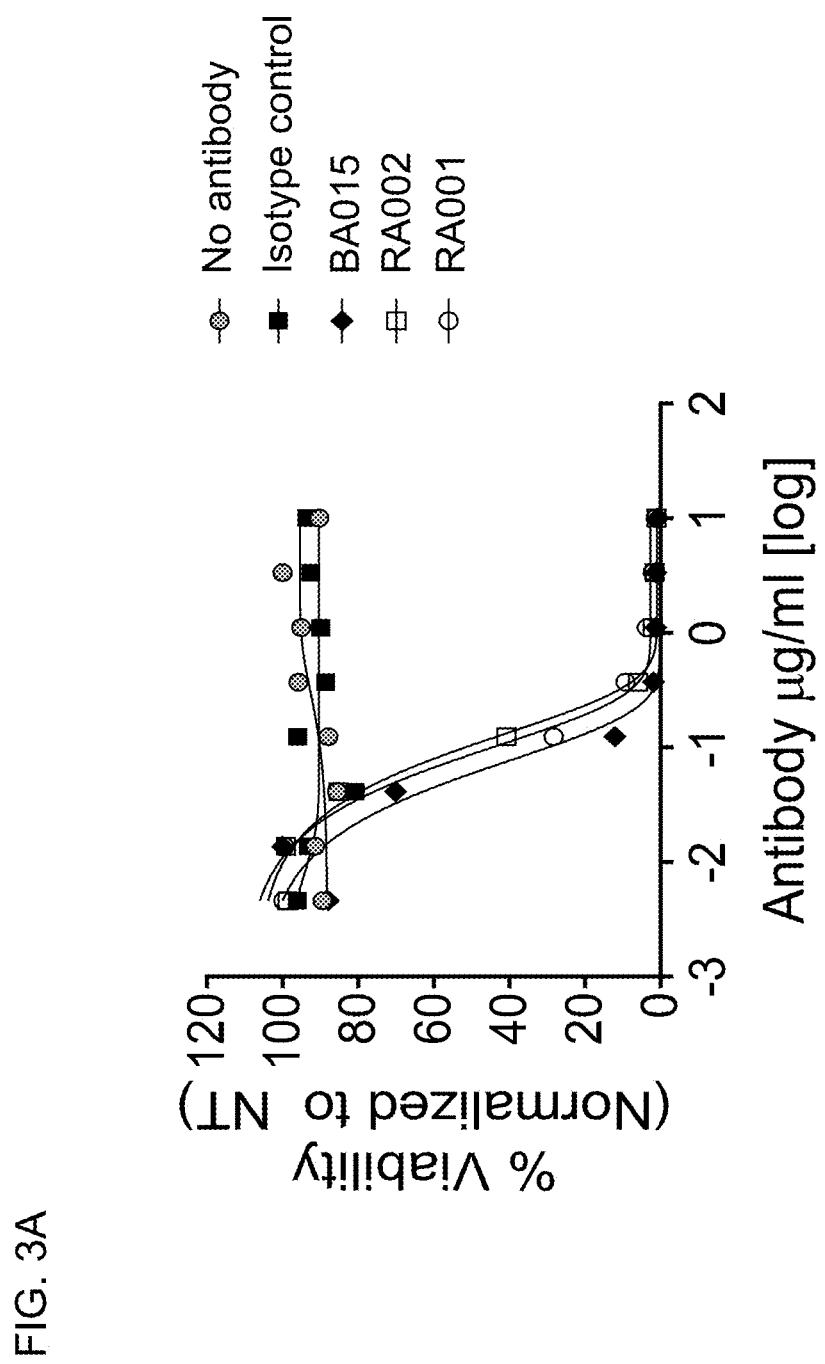

As shown in FIG. 3A, incubation with BA015, RA001, or RA002, along with αHFc-NC-MMAE, caused cell death of CD73-expressing Jurkat cells in a dose-dependent manner. The calculated AUC values for anti-CD73 antibodies in FIG. 3A are presented in Table 10. This result suggested that BA015, RA001, and RA002 were internalized upon CD73 binding.

TABLE 10

AUC values for anti-CD73 antibodies in FIG. 3A

| Antibody | AUC |
|---|---|
| BA015 | 20.81 |
| RA002 | 30.92 |
| RA001 | 35.98 |

Imaging by confocal fluorescence microscopy of live cells revealed internalization of CD73. Specifically, Jurkat cells ectopically expressing a HaloTag®-CD73 fusion protein, generated by a similar method as described in Section 6.1.4, were first incubated with 1 µM CellTrace Far Red Cell Proliferation Dye (Life Technologies) for 30 minutes at 37° C. and 5% CO2 to label the cell bodies. The cells were then washed in PBS and stained with a membrane-impermeable HaloTag® Alexa Fluor™ 488 ligand (Promega, 1 µM) for 15 minutes at 37° C. and 5% $CO_2$ to label the HaloTag®-CD73 fusion protein on the cell surface. The labeled cells were resuspended in fresh culture media at the density of 15,000 cells per well in a 384-well microscopy plate, and were incubated with 10 µg/ml of an anti-CD73 antibody or isotype control antibody. Live images were collected using an ImageXpress Micro Confocal High-Content microscope (Molecular Devices) at 37° C. and 5% CO2, and images were acquired in the Cy5 channel (CellTrace Far Red Cell Proliferation Dye) and FITC channel (HaloTag® Alexa Fluor™ 488) every hour over a course of 6 hours. In total, for each condition at each time point, four images (40× magnification) were acquired resulting in analysis of an average of 648 cells (±87 cells, standard deviation). Image analysis to quantify the amount of internalized CD73 was performed using MetaXpress analysis software (Molecular Devices).

Figure 3B:
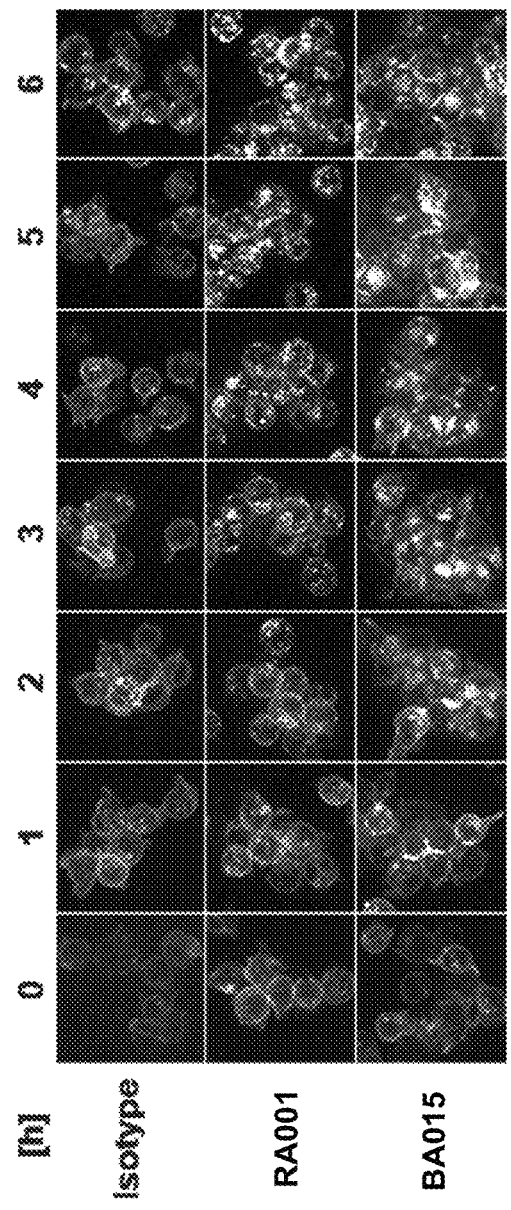
Figure 3C:
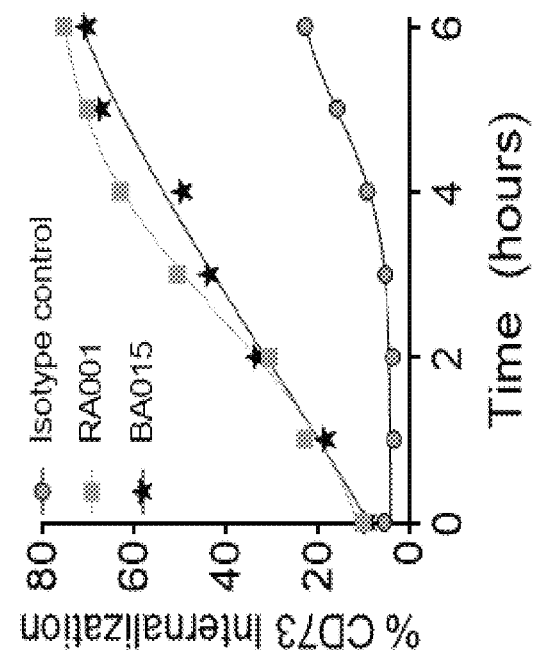

As shown in FIGS. 3B (representative images) and 3C (quantification of imaging data), BA015 and RA001 each promoted rapid CD73 internalization, as demonstrated by the fluorescence of Alexa Fluor™ 488 in the cytosol.

6.2 Example 2: Generation and Characterization of Humanized Anti-CD73 Antibodies This example describes the generation and characterization of humanized antibodies that specifically bind to CD73 (e.g., human CD73, cynomolgus CD73, and mouse CD73).

6.2.1 Generation of Humanized Anti-CD73 Antibodies

Humanized variants of BA012 were generated by grafting the heavy chain and light chain CDR sequences of BA012 into human antibody framework regions. An exemplary humanized variant, BA019, comprises a heavy chain comprising the amino acid sequence of SEQ ID NO: 77 and a light chain comprising the amino acid sequence of SEQ ID NO: 97. Variants incorporated amino acid substitutions G24A/R98S in the heavy chain variable region ($V_H$), and/or F71Y in the light chain variable region ($V_L$), in the human framework regions. In addition, variants incorporated amino acid substitutions in the CDRs, such as N55S/N61S or N55A/N61A in CDRH2, and N31I/Y32S in CDRL1. The sequences of the humanized antibodies BA019-BA034 are disclosed in Tables 1-4. In particular, a humanized anti-CD73 antibody designated BA020 comprises a heavy chain comprising the amino acid sequence of SEQ ID NO: 79 and a light chain comprising the amino acid sequence of SEQ ID NO: 97. Another humanized anti-CD73 antibody designated BA025 comprises a heavy chain comprising the amino acid sequence of SEQ ID NO: 85 and a light chain comprising the amino acid sequence of SEQ ID NO: 97.

6.2.2 Binding of Humanized and Chimeric Anti-CD73 Antibodies to Recombinant CD73

The affinity of some humanized anti-CD73 antibodies (BA019-BA022 and BA024-BA030) to human or cynomolgus CD73 were determined by SPR using the method as described in Section 6.1.2. BA012, RA001, and RA002 were used as controls. The binding kinetics ($K_a$, $K_d$ and $K_D$) determined from the binding curves are shown in Table 11.

TABLE 11

Affinity of anti-CD73 antibodies to CD73 as measured by SPR

| | Human CD73 | | | Cynomolgus CD73 | | |
|---|---|---|---|---|---|---|
| Clone | $K_a$ (1/Ms) | $K_d$ (1/s) | $K_D$ (nM) | $K_a$ (1/Ms) | $K_d$ (1/s) | $K_D$ (nM) |
| RA001 | 7.39E+05 | 1.24E−05 | 0.02 | 3.38E+05 | 2.96E−05 | 0.09 |
| RA002 | 4.14E+05 | 7.19E−05 | 0.17 | 3.57E+05 | 7.49E−05 | 0.21 |
| BA012 | 1.46E+06 | 6.17E−05 | 0.04 | 1.47E+06 | 7.23E−05 | 0.05 |
| BA019 | 1.21E+06 | 1.21E−04 | 0.1 | 9.88E+05 | 1.28E−04 | 0.13 |
| BA020 | 1.12E+06 | 7.35E−05 | 0.06 | 1.06E+06 | 9.83E−05 | 0.09 |
| BA021 | 9.82E+05 | 1.66E−04 | 0.17 | 9.38E+05 | 1.82E−04 | 0.19 |
| BA022 | 1.07E+06 | 8.57E−05 | 0.08 | 1.01E+06 | 1.05E−04 | 0.1 |
| BA024 | 1.09E+06 | 7.43E−04 | 0.68 | 9.20E+05 | 6.45E−04 | 0.7 |
| BA025 | 1.22E+06 | 2.29E−04 | 0.19 | 1.14E+06 | 2.60E−04 | 0.23 |
| BA026 | 1.13E+06 | 1.85E−04 | 0.17 | 1.05E+06 | 2.16E−04 | 0.21 |
| BA027 | 1.23E+06 | 9.40E−04 | 0.76 | 1.16E+06 | 9.83E−04 | 0.85 |
| BA028 | 1.13E+06 | 1.20E−03 | 1.1 | 1.06E+06 | 1.29E−03 | 1.2 |
| BA029 | 1.20E+06 | 4.42E−04 | 0.37 | 1.13E+06 | 4.70E−04 | 0.42 |
| BA030 | 1.08E+06 | 3.63E−04 | 0.34 | 1.02E+06 | 3.95E−04 | 0.39 |

Similarly, the binding kinetics for chimeric (murine variable domain+human constant domain) antibodies BA016 and BA018 are shown in Table 12. Specifically, different Fc variants for RA001 and RA002, as well as murine antibody BA012, were used for comparison.

TABLE 12

Affinity comparison between anti-CD73 antibodies with different Fc regions

| | | Human CD73 | | | Cynomolgus CD73 | | | Mouse CD73 | | |
|---|---|---|---|---|---|---|---|---|---|---|
| Clone | Fc | $K_a$ (1/Ms) | $K_d$ (1/s) | $K_D$ (nM) | $K_a$ (1/Ms) | $K_d$ (1/s) | $K_D$ (nM) | $K_a$ (1/Ms) | $K_d$ (1/s) | $K_D$ (nM) |
| BA012 | IgG1-N297A | 1.47E+06 | 8.11E−05 | 0.06 | 1.36E+06 | 9.46E−05 | 0.07 | 8.90E+06 | 7.07E−03 | 0.79 |
| BA016 | IgG2 | 1.33E+06 | 3.38E−04 | 0.25 | 1.29E+06 | 3.27E−04 | 0.25 | 3.15E+06 | 7.85E−03 | 2.50 |
| BA018 | IgG1/IgG2 hybrid | 1.40E+06 | 1.51E−04 | 0.10 | 1.41E+06 | 1.65E−04 | 0.01 | 8.37E+06 | 1.58E−02 | 1.90 |
| RA001 | IgG1-N297A | 3.16E+05 | 1.89E−05 | 0.06 | 2.95E+05 | 1.66E−05 | 0.06 | 8.88E+04 | 2.19E−05 | 0.25 |
| | IgG2 | 4.17E+05 | 8.85E−05 | 0.21 | 3.39E+05 | 1.09E−04 | 0.32 | 1.50E+05 | 9.95E−05 | 0.70 |
| | IgG1/IgG2 hybrid | 3.25E+05 | 1.30E−05 | 0.04 | 3.08E+05 | 2.48E−05 | 0.09 | 1.40E+05 | 4.36E−06 | 0.03 |
| RA002 | IgG1-N297A | 3.71E+05 | 7.37E−05 | 0.20 | 3.89E+05 | 8.19E−05 | 0.21 | NB | NB | NB |
| | IgG4-S228P | 4.14E+05 | 7.19E−05 | 0.17 | 3.57E+05 | 7.49E−05 | 0.21 | NB | NB | NB |

NB: no binding

6.2.3 Binding of Humanized Anti-CD73 Antibodies to CD73-Expressing Cells

The affinities of the humanized anti-CD73 antibodies to membrane-associated CD73 were determined. Specifically, CHO cells ectopically expressing full-length human or cynomolgus CD73 were generated, and the binding of the antibodies to the cells were examined, using the method as described in Example 6.1.3. BA015, RA001, and RA002 were also examined for comparison.

As shown in FIGS. 4A-4P and 5A-5P, each of the tested humanized antibodies, BA019-BA030, as well as chimeric antibody BA015 and the two reference antibodies, but not the isotype control, exhibited dose-dependent binding to cynomolgus CD73 (FIGS. 4A-4P) and human CD73 (FIGS. 5A-5P). The calculated AUC values for anti-CD73 antibodies in FIGS. 4B-4P and FIGS. 5B-5P are presented in Table 13 and Table 14, respectively.

TABLE 13

AUC values for anti-CD73 antibodies in FIGS. 4B-4P

| Antibody | AUC |
|---|---|
| RA001 | 1848 |
| BA026 | 1881 |
| BA030 | 1920 |
| RA002 | 2054 |
| BA028 | 2178 |
| BA021 | 2196 |
| BA027 | 2212 |
| BA029 | 2267 |
| BA023 | 2285 |
| BA024 | 2340 |
| BA022 | 2386 |
| BA019 | 2421 |
| BA015 | 2441 |
| BA020 | 2486 |
| BA025 | 2827 |

TABLE 14

AUC values for anti-CD73 antibodies in FIGS. 5B-5P

| Antibody | AUC |
|---|---|
| RA002 | 61111 |
| BA030 | 68786 |
| BA026 | 72777 |
| RA001 | 77155 |
| BA028 | 90740 |
| BA023 | 97165 |
| BA029 | 97805 |
| BA024 | 99898 |
| BA027 | 101503 |
| BA019 | 102780 |
| BA025 | 103903 |
| BA021 | 108065 |
| BA015 | 112756 |
| BA020 | 113013 |
| BA022 | 123732 |

6.2.4 Inhibition of CD73 Enzymatic Activity by Anti-CD73 Antibodies

The ability of the humanized anti-CD73 antibodies to inhibit the enzymatic activity of CD73 was assessed using the same method as described in Example 6.1.4. BA015, RA001, and RA002 were also examined for comparison.

Figures 6A, 6B, 6C, 6D, 6E, 6F, 6G, 6H:
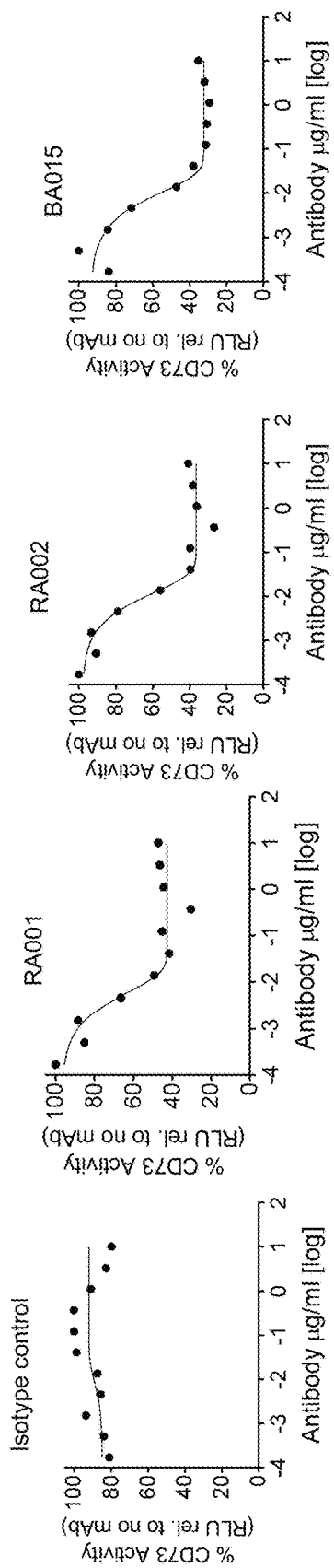

As shown in FIGS. 6A-6P, each of the tested humanized antibodies, BA019-BA030, as well as chimeric antibody BA015 and the two reference antibodies, but not the isotype control, inhibited the enzymatic activity of CD73 expressed on Jurkat cells. The calculated AUC values for anti-CD73 antibodies in FIGS. 6B-6P are presented in Table 15.

TABLE 15

AUC values for anti-CD73 antibodies in FIGS. 6B-6P

| Antibody | AUC |
|---|---|
| BA021 | 301.6 |
| BA025 | 317.5 |
| BA015 | 327.5 |
| BA019 | 329.2 |
| BA024 | 360.8 |
| BA028 | 368.4 |
| BA020 | 377.8 |
| RA002 | 384.4 |
| BA022 | 385.8 |
| BA026 | 386.6 |
| BA023 | 386.7 |
| BA030 | 396.9 |
| BA029 | 400.5 |
| RA001 | 436.4 |
| BA027 | 442.2 |

Additionally, the ability of the humanized antibodies to inhibit CD73 enzymatic activity was assessed using a biochemical assay. Specifically, a recombinant human CD73 fused with a 6×His-tag (R&D Systems, 5795EN) was cross-linked to white nickel-coated 96-well plates overnight at 4° C. in an assay buffer (25 mM Tris, pH 7.5, 5 mM $MgCl_2$, and 0.005% Tween-20). The wells were gently washed twice, and an eight-point dose titration of an anti-CD73 antibody or isotype control antibody from 0.005 to 10 µg/ml was added at a final volume of 50 µl/well. The samples were incubated for 1 hour at 37° C. and 5% $CO_2$, and 50 µl of 200 µM AMP and 6 µM ATP was added to each well. Following a 20-minute incubation at 37° C. and 5% $CO_2$, 100 µl of reconstituted CellTiter Glo® (Promega) was added to each well, and luminescence was recorded using Envision instrument (Perkin Elmer) after 5 minutes. BA015, RA001, and RA002 were also examined for comparison.

Similar to the cell-based assay described above, in this biochemical assay, the luminescence levels correlate with the CD73 activity in each sample, because AMP inhibits the luciferase reaction, and hydrolysis of AMP by CD73 relieves the inhibition. Thus, as shown in FIGS. 7A-7P, each of the tested humanized antibodies, BA019-BA030, as well as chimeric antibody BA015 and the two reference anti-CD73 antibodies, but not the isotype control, inhibited the enzymatic activity of recombinant CD73. The calculated AUC values for anti-CD73 antibodies in FIGS. 7B-7P are presented in Table 16.

TABLE 16

AUC values for anti-CD73 antibodies in FIGS. 7B-7P

| Antibody | AUC |
|---|---|
| BA025 | 66.11 |
| BA021 | 71.93 |
| BA022 | 82.64 |
| RA001 | 85.1 |
| BA027 | 85.87 |
| BA029 | 88.63 |
| BA015 | 91.2 |
| BA026 | 95.04 |
| BA020 | 95.3 |
| BA019 | 98.11 |
| BA024 | 110.8 |
| BA023 | 116 |
| BA030 | 116.1 |

TABLE 16-continued

AUC values for anti-CD73 antibodies in FIGS. 7B-7P

| Antibody | AUC |
|---|---|
| BA028 | 124.5 |
| RA002 | 171.3 |

6.2.5 Anti-CD73 Antibodies Mediating CD73 Internalization

Internalization of humanized anti-CD73 antibodies into cells was analyzed using the cell toxicity assay as described in Section 6.1.5.

As shown in FIGS. 8A-8M, incubation with each of BA019-BA027 and BA030, along with αHFc-NC-MMAE, caused cell death of CD73-expressing Jurkat cells in a dose-dependent manner. This result suggested dose-dependent internalization of these anti-CD73 antibodies upon CD73 binding.

6.3 Example 3: Generation and Characterization of Anti-CD73-TGFβ Trap Fusion Proteins This example describes the generation and characterization of antibodies comprising a CD73-binding portion and a TGFβ-binding portion ("TGFβ trap"). These antibodies are also referred to as anti-CD73-TGFβ trap fusion proteins in this Example and Example 4.

6.3.1 Generation of Anti-CD73-TGFβ Trap Fusion Proteins

Exemplary anti-CD73-TGFβ trap fusion proteins comprise a first polypeptide comprising, from the N-terminus to the C-terminus, a heavy chain of an anti-CD73 antibody described herein, a peptide linker, and an extracellular domain of TGFβR2; and a second polypeptide comprising a light chain of the anti-CD73 antibody. The sequences of exemplary peptide linkers, the "TGFβ trap" portion, and anti-CD73-TGFβ trap fusion proteins are disclosed in Table 6.

In particular, an anti-CD73-TGFβ trap fusion protein designated BA035 comprises a heavy chain comprising the amino acid sequence of SEQ ID NO: 113 and a light chain comprising the amino acid sequence of SEQ ID NO: 92. Another anti-CD73-TGFβ trap fusion protein designated BA036 comprises a heavy chain comprising the amino acid sequence of SEQ ID NO: 114 and a light chain comprising the amino acid sequence of SEQ ID NO: 97. A third exemplary anti-CD73-TGFβ trap fusion protein designated BA037 comprises a heavy chain comprising the amino acid sequence of SEQ ID NO: 115 and a light chain comprising the amino acid sequence of SEQ ID NO: 97. BA035 and BA037 were examined in this Example and Example 4. In the following experiments, two additional antibodies were used for comparison: (i) BA012, an anti-CD73 antibody having the same sequences as the anti-CD73 portion of BA035, was used to represent the activity of the CD73-binding portion of BA035; and (ii) isotype-TGFβ trap, an isotype control antibody comprising the peptide linker and the extracellular domain of TGFβR2, was used to represent the activity of the TGFβ-binding portions of BA035 and BA037. An isotype control antibody without the peptide linker or the extracellular domain of TGFβ R2 was used to represent the baseline. BA035 and corresponding isotype controls were in the mouse IgG2a format with a N297A substitution in the heavy chain constant region. BA037 and corresponding controls were humanized antibodies in a human IgG1 format with N297A mutation.

6.3.2 Binding of Anti-CD73-TGFβ Trap Fusions Protein to CD73

The binding affinity of BA037 for recombinant CD73 was determined by surface plasmon resonance (SPR) using the BIAcore® T200 system (GE Healthcare). BA037 (human anti-CD73-TGFβ trap fusion protein), BA025 (an anti-CD73 antibody having the same sequences as the anti-CD73 portion of BA037), or an isotype-TGFβ trap were captured on a CM5 sensor chip (GE Healthcare, Series Sensor Chip CM5, 29-1496-03) using chip-immobilized mouse anti-human IgG (GE Healthcare, Human Antibody Capture Kit, BR100839). Specifically, antibodies diluted in a running buffer (10 mM HEPES, 150 mM NaCl, 3 mM EDTA, and 0.05% surfactant P20) were captured using a 30-sec injection at a flow rate of 10 µl/min to reach capture levels optimal for kinetic analysis (about 55 RU for BA025 and about 60 RU for BA037 and isotype-TGFβ trap). The concentration of antibody to reach the optimal capture level was determined separately for each experiment. Recombinant human, cynomolgus, or mouse CD73 protein (R&D Systems, 5795EN; Sino Biological, 90192-C08H; and Sino Biological, 50231-M08H, respectively), diluted in the running buffer at the concentration of about 0.098 to 100 nM, were applied to the chip surface at a flow rate of 100 µl/min with a 3-min association phase and a 20-min dissociation phase. The sensor chip was regenerated between cycles with two 30-sec injections of 3M $MgCl_2$. Kinetic parameters were determined using a Langmuir 1:1 binding model using BIAcore® T200 Evaluation software v3.0 (GE Healthcare). The analysis assumed that each Fab arm of the antibody interacted with one dimeric CD73 molecule. Data quality was verified by visually inspecting deviations and curve fitting, and by evaluating the parameters of U-value, Rmax, Chi2, and Tc. The binding kinetics ($K_a$, $K_d$ and $K_D$) were determined from the sensorgram analyses and are shown in Table 17. Values are the geometric mean of three experiments. No measurable binding was observed for mouse CD73 to either BA037 or BA025. No measurable binding was observed for CD73 to isotype-TGFβ trap.

TABLE 17

SPR-based affinity measurements for BA025 and BA037 binding to CD73

| | Human CD73 | | | Cynomolgus CD73 | | |
|---|---|---|---|---|---|---|
| Clone | $K_a$ (1/Ms) | $K_d$ (1/s) | $K_D$ (nM) | $K_a$ (1/Ms) | $K_d$ (1/s) | $K_D$ (nM) |
| BA037 | 4.79E+06 | 3.31E-04 | 0.069 | 1.97E+06 | 2.40E-04 | 0.122 |
| BA025 | 3.87E+06 | 3.23E-04 | 0.083 | 1.64E+06 | 2.33E-04 | 0.143 |

6.3.3 Binding of Anti-CD73-TGFβ Trap Fusions Protein to TGFβ

The binding affinity of BA037 for recombinant TGFβ was determined by surface plasmon resonance (SPR) using the BIAcore® T200 system (GE Healthcare). BA037, BA025, or an isotype-TGFβ trap were captured on a CM5 sensor chip (GE Healthcare, Series Sensor Chip CM5, 29-1496-03) using chip-immobilized mouse anti-human IgG (GE Healthcare, Human Antibody Capture Kit, BR100839). Specifically, antibodies diluted in a running buffer (10 mM HEPES, 150 mM NaCl, 3 mM EDTA, and 0.05% surfactant P20) were captured using a 30-sec injection at a flow rate of 10 µl/min to reach capture levels optimal for kinetic analysis (about 110 RU for BA025 and about 120 RU for BA037 and isotype-TGFβ trap). The concentration of antibody to reach the optimal capture level was determined separately for each experiment. Recombinant human TGFβ1, TGFβ2, or TGFβ3 protein (Peprotech, AF-100-21C; Peprotech, 100-35B; Peprotech, AF-100-36E, respectively) were used in this example. Each TGFβ was diluted in the running buffer at concentrations of 0.0312 to 32 nM and were flowed over the chip surface at a flow rate of 100 μl/min with a 3-min association phase and a 20-min dissociation phase. The sensor chip was regenerated between cycles with two 30-sec injections of 3M $MgCl_2$. Kinetic parameters were determined using a Langmuir 1:1 binding model using BIAcore® T200 Evaluation software v3.0 (GE Healthcare). Data quality was verified by visually inspecting deviations and curve fitting, and by evaluating the parameters of U-value, Rmax, Chi2, and Tc. The binding kinetics ($K_a$, $K_d$ and $K_D$) were determined from the sensorgram analyses and are shown in Table 18. Values are the geometric mean of three experiments.

TABLE 18

SPR-based affinity measurements for BA037 and BA025 binding to TGFβ

| Clone | Human TGFβ1 | | | Human TGFβ2 | | | Human TGFβ3 | | |
|---|---|---|---|---|---|---|---|---|---|
| | $K_a$ (1/Ms) | $K_d$ (1/s) | $K_D$ | $K_a$ (1/Ms) | $K_d$ (1/s) | $K_D$ | $K_a$ (1/Ms) | $K_d$ (1/s) | $K_D$ |
| BA037 | 9.66E+07 | 2.05E−04 | 2.1 pM | 5.54E+07 | 8.85E−02 | 1.6 nM | 5.00E+07 | 2.09E−04 | 4.2 pM |
| isotype-TGFβ trap | 7.01E+07 | 9.63E−05 | 1.4 pM | 5.67E+07 | 1.78E−01 | 1.5 nM | 6.16E+07 | 1.40E−04 | 2.3 pM |

6.3.4 Binding of Anti-CD73-TGFβ Trap Fusion Proteins to CD73-Expressing Cells

The affinity of BA035 for membrane-associated CD73 was assessed. Specifically, CHO cells were transduced with lentiviral vectors comprising a full-length mouse CD73 coding sequence under the control of a CMV promoter, and stable CHO-muCD73 cells were generated by antibiotic selection. Expression of mouse CD73 was verified by flow cytometry using positive control antibodies. The stable CHO-muCD73 cells were grown in suspension culture in RPMI media supplemented with 10% heat-inactivated FBS at 37° C. and 5% $CO_2$. For binding analysis, the stable CHO-muCD73 cells were incubated for 30 minutes at 4° C. with an eight-point dose titration of BA035, BA012, isotype-TGFβ trap, or isotype control antibody from 0.005 to 10 μg/ml diluted in FACS buffer (PBS, 2 mM EDTA, 0.5% BSA, pH 7.2). The cells were washed twice in FACS buffer and incubated with FITC-conjugated mouse anti-human kappa detection antibody (Life Technologies, HP6062, 1:100 dilution in FACS buffer) for 30 minutes at 4° C. The cells were then washed twice and analyzed using the LSR-Fortessa™ flow cytometer (BD Biosciences). FACS data were analyzed using FACS DIVA and WEHI Weasel software, and were plotted with Graphpad Prism software.

As shown in FIG. 9A, BA035 retained its ability to bind to CD73, suggesting that fusion with the TGFβ trap did not abrogate the CD73-binding ability of anti-CD73 antibodies.

The binding affinity of BA035 to CD73 was further assessed in the presence of TGFβ. Specifically, a ten-point dose titration of recombinant human TGFβ1 (Peprotech) from 0.002 to 40 μg/ml were added to stable CHO-muCD73 cells in concert with 10 μg/ml of BA035, BA012, or isotype control antibody. After a 30-minute incubation at 37° C. and 5% $CO_2$, the cells were washed twice in FACS buffer and incubated with FITC-conjugated mouse anti-human kappa detection antibody (Life Technologies, HP6062, 1:100 dilution in FACS buffer) for 30 minutes at 4° C. The cells were then washed twice and analyzed using the LSRFortessa™ flow cytometer (BD Biosciences). FACS data were analyzed using FACS DIVA and WEHI Weasel software, and were plotted with Graphpad Prism software.

As shown in FIG. 9B, BA035 retained its ability to bind to CD73 in the presence of TGFβ1.

In a separate experiment, the affinity of BA037 for membrane-associated CD73 from primary human, cynomolgus monkey, or mouse CD8⁺ T cells was analyzed (for the mouse cells, expression of mouse CD73 was verified by flow cytometry using positive control antibodies). Specifically, cryopreserved PBMCs and splenocytes were thawed in RPMI-1640 media. For binding analysis, PBMCs or splenocytes were incubated for 30 minutes at 4° C. with a twelve-point dose titration of BA037, BA025, isotype-TGFβ trap, or isotype control antibody, each conjugated to PE, from 0.004 to 666 nM diluted in assay buffer (PBS, 0.5% BSA, 1:100 Trustain FcX™). Cells also were stained with Zombie NIR™, fluorescently labeled anti-CD3, and fluorescently labeled anti-CD8 to identify viable CD8⁺ T cells. The cells were then washed twice and analyzed using the LSRFortessa™ flow cytometer (BD Biosciences). FACS data were analyzed using WEASEL software, and were plotted with Graphpad Prism software. FIGS. 13A and 13B show the human and cynomolgus monkey T cell binding data obtained from this experiment.

As shown in FIGS. 13A and 13B, BA037 demonstrated dose-dependent binding to human and cynomolgus monkey CD8⁺ T cells, which was broadly similar to that observed for BA025 (the anti-CD73 component of BA037). BA037 binding curves to human and cynomolgus monkey CD8⁺ T cells were comparable to each other with average cellular $EC_{50}$ values of 2.57 and 9.67 nM respectively. In contrast, no binding was observed with isotype control antibodies (with or without a TGFβRII trap fusion). No binding of BA037 to mouse CD8⁺ T cells was observed (data not shown).

6.3.5 Inhibition of CD73 Enzymatic Activity by Anti-CD73-TGFβ Trap Fusion Proteins The ability of BA035 to inhibit CD73 enzymatic activity was assessed using a biochemical assay. Specifically, 0.3 μg/ml of recombinant human, cynomolgus, or mouse CD73 protein fused with a 6×His-tag (R&D Systems, 5795EN; Sino Biological, 90192-C08H; or R&D Systems, 4488EN, respectively) was mixed with an eight-point dose titration of BA035, BA012, isotype-TGFβ trap, or isotype control antibody from 0.005 to 10 μg/ml in an assay buffer (25 mM Tris pH 7.5, 5 mM $MgCl_2$, and 0.005% Tween-20) to reach a final volume of 50 μl/well in a white tissue-culture treated plate. The samples were incubated for 30 minutes at 37° C. and 5% $CO_2$, and 50 μl of 200 μM AMP and 6 μM ATP was added to each well. Following a 20-minute incubation at 37° C. and 5% $CO_2$, 100 μl of reconstituted CellTiter Glo® (Promega) was added to each well, and luminescence was recorded using Envision instrument (Perkin Elmer) after 5 minutes. The data were plotted with Graphpad Prism software.

As shown in FIGS. 9C and 9D, BA035 retained its ability to inhibit CD73 activity, suggesting that fusion with the TGFβ trap did not abrogate the CD73-inhibiting function of anti-CD73 antibodies.

The ability of BA035 to inhibit CD73 activity was further assessed in the presence of TGFβ. Specifically, 40 μg/ml of recombinant human TGFβ1 (Peprotech) was mixed with 0.3 μg/ml of recombinant mouse CD73 protein and an eight-point dose titration of BA035, BA012, isotype-TGFβ trap, or isotype control antibody from 0.009 to 6.6 μg/ml to reach a final volume of 50 μl (final TGFβ1 concentration to be 20 μg/ml). The samples were incubated for 30 minutes at 37° C. and 5% CO2, and 50 μl of 200 μM AMP and 6 μM ATP was added to each well. Following a 20-minute incubation at 37° C. and 5% CO2, 100 μl of reconstituted CellTiter Glo® (Promega) was added to each well, and luminescence was recorded using Envision instrument (Perkin Elmer) after 5 minutes. The data were plotted with Graphpad Prism software.

As shown in FIG. 9E, BA035 retained its ability to inhibit CD73 activity in the presence of TGFβ1.

In a separate experiment, the ability of BA037 to inhibit plate-bound CD73 enzymatic activity was also assessed. Specifically, 50 μL of 300 ng/ml recombinant human, cynomolgus, or mouse CD73 protein fused with a 6×His-tag (R&D Systems, 5795EN; Sino Biological, 90192-C08H; or, Sino Biological, 50231-M08H, respectively) was incubated in each well of a Ni-coated white flat-bottom 96-well plate for 2 hours at 37° C. After washing twice, 50 μL/well of BA037, BA025, isotype-TGFβ trap, or isotype control antibody were added to each well. For human and cynomolgus monkey CD73, a ten-point concentration curve from 0.001 to 20 nM of antibody in an assay buffer was used. For mouse CD73, an eight-point concentration curve from 0.01 to 20 nM of antibody in an assay buffer was used. The samples were incubated for 60 minutes at 37° C. and 5% $CO_2$, and 50 μL of 200 μM AMP and 6 μM ATP was added to each well. Following a 20-minute incubation at 37° C. and 5% $CO_2$, 100 μl of reconstituted CellTiter Glo® (Promega) was added to each well, and luminescence was recorded using EnVision instrument (Perkin Elmer) after 5 minutes. The data were plotted with Graphpad Prism software.

The ability of BA037 to inhibit soluble CD73 enzymatic activity was assessed using a biochemical assay. Specifically, 0.3 μg/ml of recombinant human, cynomolgus, or mouse CD73 protein fused with a 6×His-tag (R&D Systems, 5795EN; Sino Biological, 90192-C08H; or, Sino Biological, 50231-M08H, respectively) was mixed with an eleven-point dose titration of BA037, BA025, isotype-TGFβ trap, or isotype control antibody from 0.005 to 100 nM in an assay buffer (25 mM Tris pH 7.5, 5 mM $MgCl_2$) to reach a final volume of 50 μl/well in a white tissue-culture treated plate. The samples were incubated for 60 minutes at 37° C. and 5% $CO_2$, and 50 μl of 200 μM AMP and 6 μM ATP was added to each well. Following a 20-minute incubation at 37° C. and 5% $CO_2$, 100 μl of reconstituted CellTiter Glo® (Promega) was added to each well, and luminescence was recorded using EnVision instrument (Perkin Elmer) after 5 minutes. The data were plotted with Graphpad Prism software.

The ability of BA037 to inhibit cell-expressed CD73 enzymatic activity was also assessed. Jurkat cells expressing human CD73 (or control cells not expressing CD73) were used in this experiment. Cells at a concentration of $1\times10^6$ cells/mL were plated in a flat bottom clear 96-well cell culture plate in a volume of 50 μL/well. 50 μL/well of BA037, BA025, isotype-TGFβ trap, or isotype control antibody were then added to each well in a ten-point concentration curve from 0.001 to 20 nM of antibody in an assay buffer. The samples were incubated for 60 minutes at 37° C. and 5% $CO_2$, and 50 μL of 200 μM AMP and 6 μM ATP was added to each well. Following a 20-minute incubation at 37° C. and 5% $CO_2$, 100 μl of reconstituted CellTiter Glo® (Promega) was added to each well, and luminescence was recorded using EnVision instrument (Perkin Elmer) after 5 minutes. The data were plotted with Graphpad Prism software.

As shown in FIGS. 14A, 14B, 15A and 15B, BA037 demonstrated dose-dependent inhibition of the enzymatic activity of both human and cynomolgus monkey recombinant CD73 in plate-bound format with average $IC_{50}$ values of 0.518 nM and 0.707 nM, respectively. BA025 similarly inhibited CD73 enzymatic activity across species, whereas the isotype control antibody and the isotype-TGFβ trap fusion protein did not, thereby confirming that the inhibition effected by BA037 was entirely due to the anti-CD73 portion of the molecule. As expected, BA037 did not block the enzymatic activity of mouse recombinant CD73 (data not shown), because of its low affinity for mouse CD73. In contrast, an anti-mouse CD73 antibody (Clone TY/11.8) inhibited recombinant mouse CD73 activity in a dose-dependent manner (data not shown).

As shown in FIGS. 14C, 14D, 15C and 15D, BA037 demonstrated dose-dependent inhibition of the enzymatic activity of both human and cynomolgus monkey recombinant CD73 in soluble form, with average $IC_{50}$ values of 0.99 nM and 0.623 nM, respectively.

As shown in FIGS. 16A and 16B, BA037 also inhibited the enzymatic activity of human CD73 produced by Jurkat cells engineered to overexpress human CD73, with an average $IC_{50}$ value of 0.235 nM.

6.3.6 Neutralization of TGFβ Signaling and Mesenchymal Antigen Expression by Anti-CD73-TGFβ Trap Fusion Proteins The ability of BA035 to impair TGFβ-induced signaling was evaluated using an ectopically expressed reporter system and an endogenous reporter system.

The ectopically expressed reporter was a vector comprising a luciferase coding sequence under control of a SMAD binding element (SBE) in a commercial HEK293 cell line (BPS Biosciences). Briefly, HEK293 cells were transfected with the vector, thereby generating HEK293-SMAD reporter cells. The HEK293-SMAD reporter cells were plated at the density of $3.5\times10^4$ cells/well and cultured overnight in 100 μl of growth medium (MEM medium supplemented with 10% FBS) in white flat-bottom tissue culture plate at 37° C. and 5% $CO_2$. The growth media was replaced with assay media (MEM medium supplemented with 0.5% FBS), and the cells were cultured for 4.5 hours at 37° C. and 5% $CO_2$. An eight-point dose titration of BA035, BA012, isotype-TGFβ trap, or isotype control antibody from 0.009 to 20 μg/ml was added to the cells in concert with 20 ng/ml of recombinant human TGFβ (Peprotech), and the cells were incubated overnight at 37° C. and 5% $CO_2$. To detect TGFβ-induced luciferase activity, 100 μl of reconstituted Bio-Glo™ (Promega) was added to each well, and luminescence was recorded using an Envision instrument (Perkin Elmer) after 5 minutes.

As shown in FIG. 10A, both BA035 and isotype-TGFβ trap, but not BA012, showed a dose-dependent inhibition of the TGFβ-induced luciferase expression in the HEK293-SMAD reporter cells.

In a separate experiment, an eleven-point dose titration of BA037, BA025, isotype-TGFβ trap, or isotype control antibody from 0.0003 to 20 nM was conducted separately for TGFβ1, TGFβ2, and TGFβ3 isoforms. Otherwise the same protocol was used as above. As shown in FIGS. 17A-17C, both BA037 and isotype-TGFβ trap, but not BA025, showed a dose-dependent inhibition of the TGFβ-induced luciferase expression for the β1 and β3 isoforms, but not the β2 isoform, in the HEK293-SMAD reporter cells.

To determine the effect of these molecules on epithelial-to-mesenchymal transition (EMT) in a tumor cell line, a red fluorescent protein (RFP) coding sequence was inserted at the 3' end of the endogenous open reading frame of the vimentin gene in the genome of lung carcinoma A549 cells (ATCC® CCL-185EMT™). This A549-Vimentin-RFP cell reporter system allowed detection of TGFβ-induced expression of vimentin, a marker of EMT, by measuring fluorescence from RFP fused to the C-terminus of the Vimentin protein. Briefly, A549-Vimentin-RFP cells were grown in suspension culture in F-12K media supplemented with 10% heat-inactivated FBS at 37° C. and 5% $CO_2$, and were incubated with 10 μg/ml BA035, BA012, isotype-TGFβ trap, or isotype control antibody in the presence or absence of 2.5 ng/ml TGFβ1 for 48 hours. The cells were washed twice in FACS buffer (PBS, 2 mM EDTA, 0.5% BSA, pH 7.2) and analyzed using the LSRFortessa™ flow cytometer (BD Biosciences). FACS data were analyzed using FACS DIVA and WEHI Weasel software and were plotted with Graphpad Prism software.

As shown in FIG. 10B, BA035 and isotype-TGFβ trap, but not BA012 or isotype control, inhibited TGFβ1-induced upregulation of vimentin expression levels.

Figure 18G:
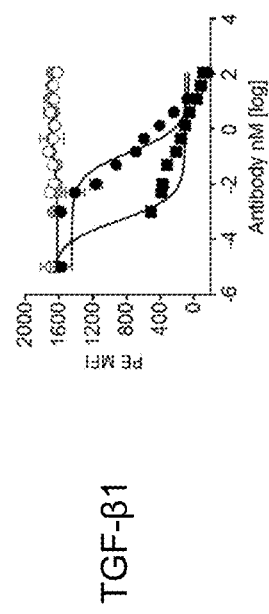
Figure 18H:
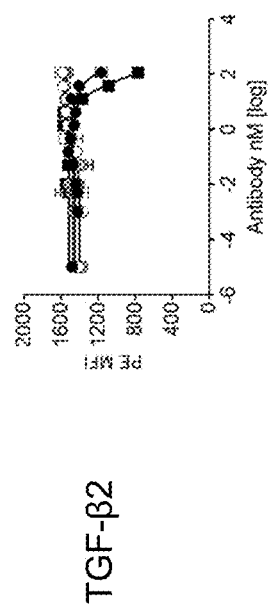
Figure 18I:
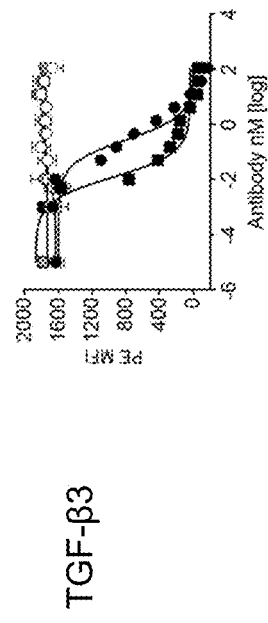

In a separate set of experiments, an eleven-point dose titration of BA037, BA025, isotype-TGFβ trap, or isotype control antibody from 0.0028 to 165 nM was conducted separately for TGFβ1, TGFβ2, and TGFβ3 isoforms. A549-Vimentin-RFP cells were grown and prepared as described above. TGFβ was preincubated with antibodies for 20 minutes at room temperature (FIG. 18A-18F) or 30 minutes at 37° C. (FIG. 18G-18I). The antibody and TGFβ were then added to cells and incubated for 24 hours at 37° C. Cells were washed with PBS and analyzed by flow cytometry using the BD FACSCanto II™ flow cytometer. FACS data were analyzed using FACS DIVA software and were plotted with Graphpad Prism software. As shown in FIGS. 18A-18I, BA037 and isotype-TGFβ trap, but not BA025 or isotype control, inhibited TGFβ1- and TGFβ3-induced upregulation of vimentin expression levels.

6.3.7 Internalization of Anti-CD73-TGFβ Trap Fusion Proteins Upon CD73 Binding

Internalization of the anti-CD73-TGFβ trap, BA037, or control antibodies into cells expressing CD73 was analyzed using a cell toxicity assay. The cell toxicity assay employed an antibody-drug conjugate αHFc-NC-DM1 (anti-human IgG Fc antibody conjugated to maytansinoid DM1 (DM1), with a non-cleavable linker, Moradec LLC), which could transport the cytotoxic payload DM1 into the cytoplasm upon internalization. Briefly, a Jurkat cell line ectopically expressing human CD73, as described in Section 6.1.4, was plated in white flat-bottom tissue culture plates at a density of $1 \times 10^4$ per well. A seven-point dose titration of an anti-CD73 antibody or isotype control antibody from 0.03 to 20 nM, along with αHFc-NC-DM1 at the same concentration as the antibody, was added to the cells to reach a final volume of 100 μl/well. Following a 72-hour incubation at 37° C. and 5% $CO_2$, 100 μl of reconstituted CellTiter Glo® (Promega) was added to each well. After 5 minutes, luminescence, representing cell viability, was recorded using Envision instrument (Perkin Elmer).

Figures 19A, 19B, 19C, 19D:
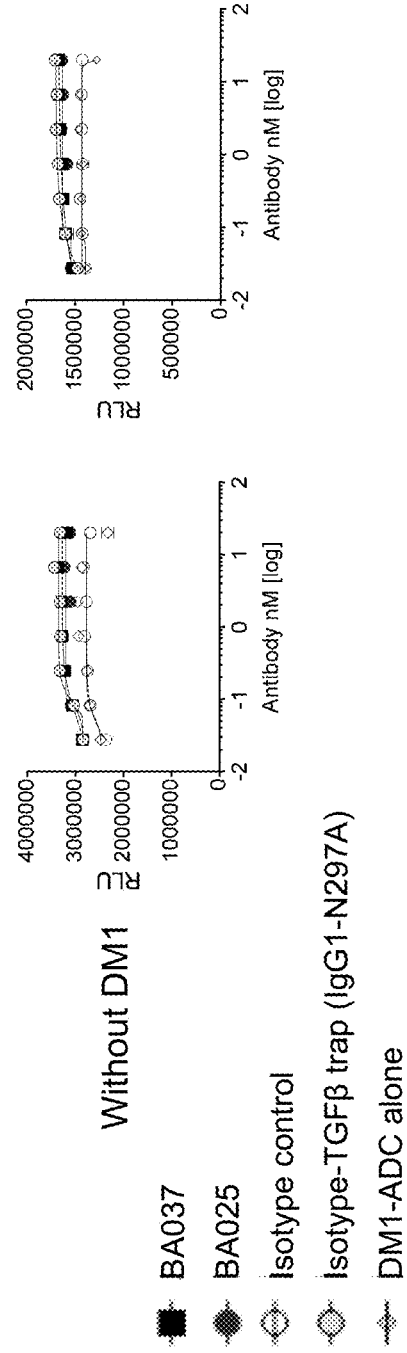

As shown in FIGS. 19A and 19B, incubation with BA025 or BA037, along with αHFc-NC-DM1, caused cell death of CD73-expressing Jurkat cells in a dose-dependent manner. As shown in FIGS. 19C and 19D, control experiments without αHFc-NC-DM1 did not result in cell death. This result showed that the presence of a TGFβ cytokine trap moiety in BA037 did not affect its CD73-mediated internalization.

6.3.8 Anti-CD73-TGFβ Trap Fusion Proteins do not Activate FcγR

Activation of the high-affinity allotypes FcγRIIA (H131) or FcγRIIIA (V158) by anti-CD73-TGFβ trap fusion protein (BA037) or control antibodies was measured, in the presence of cells expressing CD73, using Jurkat reporter cell lines engineered to express either FcγRIIA (H131) or FcγRIIIA (V158) together with a downstream luciferase 2 (luc2) reporter gene driven by an NFAT promoter. Briefly, 25 μL of CHO cells expressing CD73 (CHO-CD73, at $2.4 \times 10^6$ cells/mL) were dispensed into the wells of a 96-well, flat-bottom, white assay plate, resulting in $6.0 \times 10^4$ cells per well. A ten-point dose titration (from 0.0005 to 10 nM) of BA037, BA025, an Fc-competent anti-CD73, isotype-TGFβ trap or isotype control antibody was added to the cells. Next, 25 μL of either the Jurkat FcγRIIA (H131) or Jurkat FcγRIIIA (V158) reporter cell suspension (at $6 \times 10^6$ cells/mL, resulting in $1.5 \times 10^5$ cells/well) was added to the wells. Following a 20-hour incubation at 37° C. and 5% $CO_2$, 75 μL of reconstituted CellTiter Glo® (Promega) was added to each well, and luminescence, representing cell viability, was recorded using Envision instrument (Perkin Elmer) after 5 minutes.

In these experiments, BA037 and BA025 showed no appreciable activation of high affinity FcγRIIA (H131) or FcγRIIIA (V158) signaling upon target engagement (FIGS. 20A and 20B, dark circles and squares). By contrast, an Fc-competent anti-CD73 antibody (human IgG1λ) induced robust reporter gene activation (FIGS. 20A and 20B, dark diamonds). These findings are consistent with BA037 lacking associated Fc-mediated effector cell activity.

6.4 Example 4: In Vivo Activities of Anti-CD73 Antibodies

This example describes the anti-tumor activities of anti-CD73 antibodies, including anti-CD73-TGFβ trap fusion proteins, in various models of tumor growth and metastasis.

6.4.1 Anti-CD73 Antibodies Impairs Tumor Growth and Metastasis

The anti-tumor function of anti-CD73 antibodies was tested in animal models of colon cancer and tumor metastasis.

In the colon cancer model, 6-8 week old female Balb/c mice were injected with $5 \times 10^4$ CT26 tumor cells subcutaneously on day 0, and treated intraperitoneally with 200 μg of BA012, an antibody comprising the variable domain of RA001 and a murine $IgG_2a$ constant domain comprising an N297A mutation (designated RA001-$IgG_2$a-N207A), or an isotype control antibody, on days 5, 9, and 14. Tumor growth was monitored bi-weekly using a digital caliper. Tumor volume was calculated using the formula of volume=height×width×width×0.52.

As shown in FIG. 11A, BA012 inhibited tumor growth more potently than the chimeric variant of RA001.

In the tumor metastasis model, 6-8 week old female Balb/c mice were injected intravenously on day 0 with $2 \times 10^4$ EMT6 breast carcinoma cells, which expressed high levels of endogenous CD73. 200 μg of BA012 or isotype control antibody were administered intraperitoneally on the same day (day 0) and on day 3. The mice were euthanized on day 14, and metastatic nodules in the lungs were evaluated by washing the tissues in PBS, staining for contrast using 4% India ink, and fixing at room temperature using Fekete's solution (aqueous solution of ethanol, formaldehyde, and acetic acid). White metastatic nodules were counted manually and plotted with Graphpad Prism software.

As shown in FIG. 11B, BA012 inhibited invasion of the EMT6 tumor cells into the lungs relative to the isotype control, suggesting that the anti-CD73 antibody inhibited tumor metastasis.

In a parallel experiment, 6-8 week old female Balb/c mice were injected intravenously on day 0 with $2 \times 10^4$ EMT6 breast carcinoma cells. 400 μg of BA012, 400 μg isotype control antibody or 492 μg (equimolar to BA012 and isotype control) of BA035 were administered intraperitoneally on the same day (day 0) and on day 3. The mice were euthanized on day 14, and metastatic nodules in the lungs were evaluated by washing the tissues in PBS, staining for contrast using 4% India ink, and fixing at room temperature using Fekete's solution (aqueous solution of ethanol, formaldehyde, and acetic acid). White metastatic nodules were counted manually and plotted with Graphpad Prism software.

As shown in FIG. 21, BA035 inhibited invasion of the EMT6 tumor cells into the lungs relative to BA012 and the isotype control, demonstrating that the anti-CD73-TGFβ trap fusion protein is capable of inhibiting tumor metastasis.

6.4.2 Anti-CD73-TGFβ Trap Fusion Proteins Show Synergy Between CD73 Antagonism and TGFβ Neutralization in Tumor Inhibition The functions of anti-CD73-TGFβ trap fusion proteins were tested in two animal models of tumor growth.

In the first model, 6-8 week old female C57BL/6 mice were injected with $2 \times 10^5$ HPV16-E6/7$^+$ c-Ha-ras$^+$ TC1 mouse lung cancer cells subcutaneously on day 0. The tumor-bearing mice were randomized on day 5, and were treated intraperitoneally with 200 μg of BA012 or isotype control antibody, or 246 μg of BA035 or isotype-TGFβ trap on days 5, 8, and 11. Tumor growth was monitored bi-weekly using a digital caliper. Tumor volume was calculated using the formula of volume=height×width×width×0.52, and the data were plotted with Graphpad Prism software.

As shown in FIG. 12A, BA035, but not BA012 or isotype-TGFβ trap alone, inhibited tumor growth.

In a second model, of LLC Lewis lung cancer, wildtype female C57BL/6 mice were implanted with $0.5 \times 10^6$ LLC tumor cells (ATCC no. CRL-1642). Dosing started when tumors reached 75-100 mm$^3$, which occurred on day 4. Mice were administered 200 μg isotype control antibody, 246 μg of BA035, 200 μg of BA012, or 246 μg of isotype-TGFβ trap on days 4, 7, and 11. Tumor growth was monitored bi-weekly using a digital caliper. Tumor volume was calculated using the formula of volume=height×width×width×0.52, and the data were plotted with Graphpad Prism software.

As shown in FIG. 22, BA035 was more effective than BA012 or isotype-TGFβ trap fusion protein alone at inhibiting tumor growth.

In a third model, a Detroit562 mouse xenograft model that is known to be sensitive to TGFβ inhibition was employed (see Koopman et al., Cancer Res. 68, 561-569 (2008)). Specifically, Detroit562 tumor cells were administered subcutaneously to 6-8 week old female nude (Foxn1$^{nu}$) mice ($1 \times 10^6$ cell/mouse). Tumor-bearing mice (n=8-10 mice/group) were treated intraperitoneally (i.p.) with 246 μg of BA035, 200 μg of BA012, 246 μg of isotype-TGFβ trap, a combination of 200 μg of BA012 and 246 μg of isotype-TGFβ trap, or 200 μg of isotype control on days 8, 11, and 15 post-tumor implantation. Tumor growth was monitored bi-weekly using a digital caliper. Tumor volume was calculated using the formula volume=height×width×width×0.52, and the data were plotted with Graphpad Prism software.

As shown in FIG. 23, all treatments comprising a TGFβ trap moiety were effective in this model.

In a fourth model, 6-8 week old female Balb/c mice were injected with $4 \times 10^5$ EMT6 tumor cell subcutaneously on day 0. The tumor-bearing mice were randomized and treated intraperitoneally with 246 μg of BA035, 200 μg of BA012, 246 μg of isotype-TGFβ trap, a combination of 200 μg of BA012 and 246 μg of isotype-TGFβ trap, or 200 μg of isotype control antibody on days 5, 8, and 11. Tumor growth was monitored bi-weekly using a digital caliper. Tumor volume was calculated using the formula of volume=height×width×width×0.52, and the data were plotted with Graphpad Prism software.

As shown in FIG. 12B, each of the antibody treatments, except for the isotype control antibody, inhibited tumor growth. BA035 showed stronger anti-tumor activity compared to the combination of BA012 and isotype-TGFβ trap, indicating synergy between CD73 antagonism and TGFβ neutralization when the two activities are provided in a single complex.

6.4.3 Anti-CD73-TGFβ Trap Fusion Proteins Effectively Combine with Other Cancer Treatments The ability of anti-CD73-TGFβ trap fusion proteins to enhance the efficacy of other cancer treatment was tested in two animal models of tumor growth.

Using the EMT6 model described above, groups of mice were treated with BA012, isotype control, BA035, isotype-TGFβ trap, or BA012 plus isotype-TGFβ trap. Antibodies were dosed on days 7, 10, 14 and 17. Mice were then treated with either doxorubicin or an anti-PD-1 antibody. A control group did not receive combination treatment. Doxorubicin was administered intravenously on days 7 and 14 at 400 μg per injection. Anti-PD-1 antibody (clone RMP1-14, BioXcell) was administered at 200 μg per injection at the same time points as the other antibodies.

As shown in FIGS. 24A-24D, all treatments demonstrated some effect at inhibiting tumor growth relative to isotype control. Notably, the combination of BA035 with an anti-PD-1 antibody was more effective at inhibiting tumor growth than the combination of anti-PD-1 antibody with either BA012 or an isotype-TGFβ trap, as shown in FIG. 24B. Similarly, as shown in FIGS. 24C and 24D, the combination of BA035 with doxorubicin was more effective at inhibiting tumor growth than the combination of doxorubicin with either BA012 or an isotype-TGFβ trap.

In a colon cancer model, 6-8 week old female Balb/cJ mice were injected with $5 \times 10^4$ CT26 tumor cells subcutaneously on day 0. Once tumors reached an average size of 75-100 mm$^3$, mice were treated intraperitoneally with 200 μg BA012, 200 μg of an isotype control antibody, 246 μg of an isotype-TGFβ trap, 246 µg BA035, or 200 µg BA012 plus 200 µg of an isotype-TGFβ trap, on days 13, 17, and 20 after injection of the CT26 cells. Mice were also injected with 800 µg of etoposide intraperitoneally on days 12 and 19. Tumor growth was monitored twice weekly using a digital caliper. Tumor volume was calculated using the formula of volume=height×width×width×0.52. Mice were euthanized once tumors reached 1000 mm$^3$.

As shown in FIG. 25, the combination of BA035 and etoposide was more effective at inhibiting tumor growth than etoposide alone, a combination of etoposide and BA012, or a combination of etoposide and either of the isotype controls. The fusion protein BA035 was also more effective in combination with etoposide than was the combination of BA012 and an isotype-TGFβ trap in combination with etoposide.

6.5 Example 5: Epitope Mapping

This example describes the portions of CD73 bound by BA037.

6.5.1 Epitope Mapping by HDX

The interaction of human CD73 with the Fab fragment of BA037 (BA037-Fab) was studied by HDX mass spectrometry. These data were used to identify epitope regions bound by BA037-Fab on human CD73. The interaction of CD73 with BA037-Fab were evaluated using the methods below.

CD73 Interaction with Anti-Human CD73 Fab

20 µL recombinant human CD73 (8 µg; R&D Systems, Cat. No. 5795-EN) or 20 µL recombinant human CD73 and BA037-Fab mixture (8 µg:24 µg) was incubated with 110 µL deuterium oxide labeling buffer (50 mM sodium phosphate, 100 mM sodium chloride at pD 7.4) for 0 sec, 10 sec, 60 sec, 600 sec, or 3600 sec at 20° C. Hydrogen/deuterium exchange was quenched by adding 130 µL of 4 M guanidine hydrochloride, 0.85 M TCEP buffer (final pH 2.5) and incubating the mixture for 3 min at 20° C. Subsequently, the quenched samples were subjected to on column pepsin/protease XIII digestion and LC-MS analysis, as described below. The mass spectra were recorded in MS only mode.

Pepsin/Protease XIII Digestion and LC-MS

Each CD73 or CD73:BA037-Fab mixture was subjected to on-column pepsin/protease XIII digestion using an in-house packed pepsin/protease XIII (w/w, 1:1) column, and the resultant peptides were analyzed using an UPLC-MS system comprised of a Waters Acquity UPLC coupled to a Q Exactive™ Hybrid Quadrupole-Orbitrap Mass Spectrometer (Thermo). The peptides were separated on a 50 mm×1 mm C8 column with a 16.5 min gradient from 2-30% Solvent B (0.2% formic acid in acentonitrile) in Solvent A (0.2% formic acid in water). Peptide identification was performed by searching MS/MS data against the human CD73 sequence with Mascot. The mass tolerance for the precursor and product ions was 7 ppm and 0.02 Da, respectively.

HDX Data Analysis

Raw MS data was processed using HDX WorkBench software for the analysis of H/D exchange MS data. The deuterium levels were calculated using the average mass difference between the deuterated peptide and its native form ($t_0$). For the calculation of deuterium incorporation, the mass spectra for a given peptide were combined across the extracted ion chromatogram peak and the weighted average m/z was calculated. The mass increase from the mass of the native peptide (0 minute) to the weighted averaged mass corresponds to the level of deuterium incorporation.

Epitope Binding of Anti-Human CD73 Fab

Residues contributing to the epitope were identified by protection from deuterium exchange when BA037-Fab was bound to CD73. All the residues in this paragraph are numbered according to SEQ ID NO: 99. One region consisting of residues 144-170 (IKAKGPLASQISG-LYLPYKVLPVGDEV, SEQ ID NO: 90), experienced strong deuterium protection when human CD73 was bound to BA037-Fab. Thus, this region corresponds to an epitope or portion thereof of BA037 on CD73. Another region consisting of residues 195-213 (DEITALQPE-VDKLKTLNVN, SEQ ID NO: 91) also experienced strong deuterium protection when human CD73 was bound to BA037-Fab. Thus, this region also corresponds to an epitope or portion thereof of BA037 on CD73. Both regions (residues 144-170 and 195-213 of SEQ ID NO: 129) may also be collectively considered an epitope or portion thereof of BA037 on CD73.

6.5.2 Epitope Mapping by Mutation of CD73

The binding of BA037 and RA001 to human and mouse CD73 were further studied using a series of CD73 mutants, as described in Table 19 and Table 20. CD73 residues were selected for mutagenesis based on differences between human and mouse CD73 sequence or based on consideration of the human CD73 crystal structure (PDB reference No. 4H2F).

The affinity of BA037 and the reference anti-CD73 antibody, RA001, to recombinant CD73 proteins was determined by SPR using the BIAcore® T200 system (GE Healthcare). BA037, RA001, or an isotype control-TGFβ trap fusion protein were captured on a CM5 sensor chip (GE Healthcare, Series Sensor Chip CM5, 29-1496-03) using chip-immobilized mouse anti-human IgG (GE Healthcare, Human Antibody Capture Kit, BR100839). Specifically, antibodies diluted in a running buffer (10 mM HEPES, 150 mM NaCl, and 0.05% surfactant P20) were captured using a flow rate of 10 µl/min to reach capture levels optimal for kinetic analysis. The concentration of antibody to reach the optimal capture level was fixed to 1.5 µg/ml. Recombinant CD73 used in this example was produced in house. Binding to human wild-type CD73 was similar for the internal CD73 and a commercial recombinant CD73 (Sino Biological Cat. No. 10904-H08H) (data not shown). CD73 was serially diluted and each mutant was flowed over the chip surface at a flow rate of 50 µl/min with a 2-min association phase and a 10-min dissociation phase. The sensor chip was regenerated between cycles with one 90-sec injection of 3M MgCl$_2$. Kinetic parameters were determined using a Langmuir 1:1 binding model using BIAcore® T200 Evaluation software v3.0 (GE Healthcare).

The effect of CD73 mutations on maximal binding of BA037 and RA001 is shown in Table 19. Maximal binding was measured at 60 nM. Y161A showed a partial loss of BA037 binding, as did a quadruple human-to-mouse mutation (Y158F, Y161S, P165S, D168G). When the same four residues were mutated to alanine (Y158A, Y161A, P165A, D168A), additional BA037 binding was lost. In contrast, RA001 bound at similar levels to all CD73 mutants tested.

Consistent with prior observations, no significant binding was observed to wild-type mouse CD73 for BA037. However, mutation of residues 163, 167, and 170 in mouse CD73 to the corresponding human residues (i.e., the mouse-to-human mutations S163Y, S167P, G170D) resulted in restoration of BA037 binding (as shown in Table 19) or partial restoration of binding affinity (as shown in Table 20). Furthermore, mutation of residues 109, 111, 154, 160, 163, 167, 170, 200, 298, and 299 in mouse CD73 to the corresponding human residues (i.e., the mouse-to-human mutations I109A, G111R, H154S, F160Y, S163Y, S167P, G170D, S200T, D298E, K299R) resulted in restoration of both binding (as shown in Table 19) and binding affinity (as shown in Table 20). RA001 bound to mouse CD73 at similar levels to human CD73.

TABLE 19

Effect of CD73 mutations on maximal BA037 and RA001 binding

| CD73 Variant | SEQ ID NO: | BA037 | RA001 |
|---|---|---|---|
| Human WT | 99 | + | + |
| Y158A | 59 | + | + |
| Y161A | 60 | +/− | + |
| T198A | 61 | + | + |
| K274A | 62 | + | + |
| S269A | 132 | + | + |
| Y158A, Y161A, P165A, D168A | 133 | − | + |
| Y158F, Y161S, P165S, D168G (human to mouse) | 134 | +/− | + |
| S152H, Y158F, Y161S (human to mouse) | 135 | + | + |
| P165S, D168G (human to mouse) | 136 | + | + |
| Mouse WT | 102 | − | + |
| I109A, G111R, H154S, F160Y, S163Y, S167P, G170D, S200T, D298E, K299R (mouse to human) | 137 | + | + |
| S163Y, S167P, G170D (mouse to human) | 138 | + | + |

+: at least 70% relative to maximal binding to human wild-type CD73
+/−: less than 70% and at least 20% relative to maximal binding to human wild-type CD73
−: less than 20% relative to maximal binding to human wild-type CD73

The effect of the foregoing CD73 mutations on the $K_A$ (binding affinity) of BA037 and RA001 binding is shown in Table 20. In this experiment, the $K_A$ values for BA037 and RA001 binding to wild-type human CD73 were determined to be $7.35 \times 10^9$ M$^{-1}$ and $3.21 \times 10^9$ M$^{-1}$, respectively.

TABLE 20

Effect of CD73 mutations on $K_A$ of BA037 and RA001 binding

| CD73 Variant | SEQ ID NO: | BA037 | RA001 |
|---|---|---|---|
| Human WT | 99 | + | + |
| Y158A | 59 | +/− | + |
| Y161A | 60 | − | + |
| T198A | 61 | + | + |
| K274A | 62 | + | + |
| S269A | 132 | + | + |
| Y158A, Y161A, P165A, D168A (human to mouse) | 133 | − | + |
| Y158F, Y161S, P165S, D168G (human to mouse) | 134 | − | + |
| S152H, Y158F, Y161S (human to mouse) | 135 | − | + |
| P165S, D168G (human to mouse) | 136 | − | + |
| Mouse WT | 102 | − | + |
| I109A, G111R, H154S, F160Y, S163Y, S167P, G170D, S200T, D298E, K299R (mouse to human) | 137 | + | + |
| S163Y, S167P, G170D (mouse to human) | 138 | +/− | + |

+: no more than 4 times lower affinity relative to affinity to human wild-type CD73
+/−: between 4 and 10 times lower affinity relative to affinity to human wild-type CD73
−: at least 10 times lower affinity relative to affinity to human wild-type CD73

As shown in Tables 19 and 20, mutation of one or more of residues Y158, Y161, P165, and/or D168 reduced maximal binding and affinity of BA037 to human CD73. BA037 was not sensitive to single mutation of residues T198, S269 or K274. Binding of RA001 was not affected by any mutation tested. These results indicate that BA037 binds to human CD73 via an epitope (or epitopes) comprising residues Y158, Y161, P165, and/or D168. These results also indicate that the epitope of BA037 is different from the epitope of the reference antibody RA001.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody that specifically binds to human CD73, comprising a heavy chain variable region (VH) and a light chain variable region (VL), wherein the VH comprises the CDRH1, CDRH2, and CDRH3 amino acid sequences of the VH amino acid sequence of SEQ ID NO: 27, and the VL comprises the CDRL1, CDRL2, and CDRL3 amino acid sequences of the VL amino acid sequence of SEQ ID NO: 37.

2. The isolated antibody of claim 1 wherein the CDRH1, CDRH2, CDRH3, CDRL1, CDRL2, and CDRL3 comprise the amino acid sequences of SEQ ID NOs: 2, 5, 7, 8, 10, and 12, respectively.

3. The isolated antibody of claim 1, wherein:
(a) the VH comprises an amino acid sequence that is at least 95% identical to the amino acid sequence of SEQ ID NO: 27; and/or
(b) the VL comprises an amino acid sequence that is at least 95% identical to the amino acid sequence of SEQ ID NO: 37.

4. The isolated antibody of claim 1, wherein:
(a) the VH comprises the amino acid sequence of SEQ ID NO: 25 or 27; and/or
(b) the VL comprises the amino acid sequence of SEQ ID NO: 37.

5. The isolated antibody of claim 1, wherein the antibody comprises:
(a) (i) a heavy chain constant region selected from the group consisting of human IgG$_1$, IgG$_2$, IgG$_3$, IgG$_4$, IgA$_1$, and IgA$_2$,
(ii) an IgG$_1$ heavy chain constant region comprising an N297A mutation, numbered according to the EU numbering system,
(iii) a heavy chain constant region comprising an amino acid sequence selected from the group consisting of SEQ ID NOs: 47-58, or
(iv) a heavy chain comprising an amino acid sequence selected from the group consisting of SEQ ID NOs: 81, 82, 85, 86, 115, 117, 119, 121, and 127;
(b) (i) a light chain constant region selected from the group consisting of human kappa light chain and human lambda light chain,
(ii) a light chain constant region comprising the amino acid sequence of SEQ ID NO: 93, or
(iii) a light chain comprising the amino acid sequence of SEQ ID NO: 97; or
(c) a heavy chain and a light chain comprising the amino acid sequences selected from the group consisting of SEQ ID NOs: 81 and 97; 82 and 97; 85 and 97; 86 and 97; 115 and 97; 117 and 97; 119 and 97; 121 and 97; and 127 and 97, respectively.

6. The isolated antibody of claim 1, wherein the antibody further comprises a TGFβ-binding moiety selected from the group consisting of:
(i) an extracellular domain of a human TGFβ receptor; and
(ii) an antibody that specifically binds to TGFβ.

7. The isolated antibody of claim 6, wherein the extracellular domain of the human TGFβ receptor comprises an amino acid sequence selected from the group consisting of SEQ ID NOs: 109-112.

8. The isolated antibody of claim 6, wherein the extracellular domain of the human TGFβ receptor comprises the amino acid sequence of SEQ ID NO: 111.

9. The isolated antibody of claim 6, wherein the TGFβ-binding moiety is linked to a peptide linker.

10. The isolated antibody of claim 9, wherein the peptide linker comprises an amino acid sequence that is at least 95% identical to an amino acid sequence selected from the group consisting of SEQ ID NOs: 103-108.

11. The isolated antibody of claim 9, wherein the peptide linker comprises the amino acid sequence of SEQ ID NO: 103.

12. The isolated antibody of claim 1, wherein the antibody comprises a heavy chain comprising an amino acid sequence that is at least 95% identical to an amino acid sequence selected from the group consisting of SEQ ID NOs: 115, 117, 119, and 121, and/or a light chain comprising an amino acid sequence that is at least 95% identical to the amino acid sequence of SEQ ID NO: 97.

13. The isolated antibody of claim 1, wherein the antibody further comprises a VEGF-binding moiety selected from the group consisting of:
(i) an extracellular domain of a human VEGF receptor; and
(ii) an antibody that specifically binds to VEGF.

14. The isolated antibody of claim 13, wherein the extracellular domain of the human VEGF receptor comprises the amino acid sequence of SEQ ID NO: 122.

15. The isolated antibody of claim 13, wherein the VEGF-binding moiety is linked to a peptide linker.

16. The isolated antibody of claim 15, wherein the peptide linker comprises an amino acid sequence that is at least 95% identical to an amino acid sequence selected from the group consisting of SEQ ID NOs: 103-108.

17. The isolated antibody of claim 15, wherein the peptide linker comprises the amino acid sequence of SEQ ID NO: 103.

18. The isolated antibody of claim 1, wherein the antibody comprises a heavy chain comprising the amino acid sequence of SEQ ID NO: 127, and/or a light chain comprising the amino acid sequence of SEQ ID NO: 97.

19. A pharmaceutical composition comprising the antibody of claim 1.

20. The isolated antibody of claim 1, wherein the antibody comprises: a VH comprising the amino acid sequence of SEQ ID NO: 27; and a VL comprising the amino acid sequence of SEQ ID NO: 37.

21. The isolated antibody of claim 20, wherein the antibody comprises: a heavy chain comprising the amino acid sequence of SEQ ID NO: 85; and a light chain comprising the amino acid sequence of SEQ ID NO: 97.

22. The isolated antibody of claim 1, wherein the antibody comprises: a heavy chain comprising the amino acid sequence of SEQ ID NO: 115, and a light chain comprising the amino acid sequence of SEQ ID NO: 97.

* * * * *